(12) United States Patent
Crawford et al.

(10) Patent No.: US 10,844,398 B2
(45) Date of Patent: Nov. 24, 2020

(54) METHODS AND COMPOSITIONS FOR PLANT PEST CONTROL

(71) Applicant: Monsanto Technology LLC, St. Louis, MO (US)

(72) Inventors: Michael J. Crawford, St. Louis, MO (US); Xiangqian Li, St. Louis, MO (US); Barry J. Shortt, St. Louis, MO (US); Deryck Jeremy Williams, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/100,852

(22) Filed: Aug. 10, 2018

(65) Prior Publication Data

US 2019/0040410 A1 Feb. 7, 2019

Related U.S. Application Data

(62) Division of application No. 14/435,939, filed as application No. PCT/US2013/065561 on Oct. 18, 2013, now Pat. No. 10,077,451.

(60) Provisional application No. 61/715,549, filed on Oct. 18, 2012.

(51) Int. Cl.
*C12N 15/82* (2006.01)
*C12N 15/113* (2010.01)

(52) U.S. Cl.
CPC ........ *C12N 15/8282* (2013.01); *C12N 15/113* (2013.01); *C12N 15/8218* (2013.01); *C12N 15/8285* (2013.01); *C12N 2310/11* (2013.01); *Y02A 40/164* (2018.01)

(58) Field of Classification Search
None
See application file for complete search history.

(56) References Cited

U.S. PATENT DOCUMENTS

| | | |
|---|---|---|
| 3,687,808 A | 8/1972 | Alice De et al. |
| 3,850,752 A | 11/1974 | Schuurs et al. |
| 3,935,074 A | 1/1976 | Rubenstein et al. |
| 4,023,525 A | 5/1977 | Weber |
| 4,079,696 A | 3/1978 | Weber |
| 4,476,301 A | 10/1984 | Imbach et al. |
| 4,535,060 A | 8/1985 | Comai |
| 4,581,847 A | 4/1986 | Hibberd et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,971,908 A | 11/1990 | Kishore et al. |
| 5,004,863 A | 4/1991 | Umbeck |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,562 A | 11/1993 | Matteucci |
| 5,264,564 A | 11/1993 | Matteucci |
| 5,304,732 A | 4/1994 | Anderson et al. |
| 5,310,667 A | 5/1994 | Eichholtz et al. |
| 5,312,910 A | 5/1994 | Kishore et al. |
| 5,331,107 A | 7/1994 | Anderson et al. |
| 5,378,824 A | 1/1995 | Bedbrook et al. |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,463,174 A | 10/1995 | Moloney et al. |
| 5,463,175 A | 10/1995 | Barry et al. |
| 5,470,967 A | 11/1995 | Huie et al. |
| 5,476,925 A | 12/1995 | Letsinger et al. |

(Continued)

FOREIGN PATENT DOCUMENTS

| | | |
|---|---|---|
| CN | 101914540 A | 12/2010 |
| EP | 1416049 A1 | 5/2004 |

(Continued)

OTHER PUBLICATIONS

Bai et al (MPMI(2008), vol. 21(1), pp. 30-39.*
Momentive Performance Materials Inc. Marketing Bulleting for Silwet L-77* Ag spray adjuvant DA Performance Additives, 2011, pp. 1-4.
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).

(Continued)

*Primary Examiner* — Medina A Ibrahim
(74) *Attorney, Agent, or Firm* — Thompson Coburn LLP; William A. Holtz; Amanda J. Carmany-Rampey

(57) ABSTRACT

The present invention provides methods and compositions to improve fungal disease resistance and/or nematode resistance in various crop plants. The present invention also provides for combinations of compositions and methods to improve fungal disease resistance and/or nematode resistance in various crop plants.

19 Claims, 6 Drawing Sheets

Specification includes a Sequence Listing.

(56) References Cited

U.S. PATENT DOCUMENTS

| | | |
|---|---|---|
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,866,775 A | 2/1999 | Eichholtz et al. |
| 5,874,265 A | 2/1999 | Adams et al. |
| 5,876,739 A | 3/1999 | Turnblad et al. |
| 5,879,903 A | 3/1999 | Strauch et al. |
| 5,891,246 A | 4/1999 | Lund |
| 5,914,451 A | 6/1999 | Martinell et al. |
| 5,919,675 A | 7/1999 | Adams et al. |
| 5,922,602 A | 7/1999 | Kumagai et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,225,105 B1 | 5/2001 | Sathasivan et al. |
| 6,225,114 B1 | 5/2001 | Eichholtz et al. |
| 6,245,968 B1 | 6/2001 | Boudec et al. |
| 6,248,876 B1 | 6/2001 | Barry et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,453,609 B1 | 9/2002 | Soll et al. |
| 6,506,559 B1 | 1/2003 | Fire et al. |
| 6,582,516 B1 | 6/2003 | Carlson |
| 6,635,805 B1 | 10/2003 | Baulcombe et al. |
| 6,644,341 B1 | 11/2003 | Chemo et al. |
| 6,768,044 B1 | 7/2004 | Boudec et al. |
| 6,791,007 B1 | 9/2004 | Schulze-Lefert et al. |
| 6,800,748 B2 | 10/2004 | Holzberg et al. |
| 6,870,075 B1 | 3/2005 | Beetham et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,122,719 B2 | 10/2006 | Hakimi et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,405,347 B2 | 7/2008 | Hammer et al. |
| 7,406,981 B2 | 8/2008 | Hemo et al. |
| 7,485,777 B2 | 2/2009 | Nakajima et al. |
| 7,525,013 B2 | 4/2009 | Hildebrand et al. |
| 7,622,301 B2 | 11/2009 | Ren et al. |
| 7,671,254 B2 | 3/2010 | Tranel et al. |
| 7,714,188 B2 | 5/2010 | Castle et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,143,480 B2 | 3/2012 | Axtell et al. |
| 8,642,505 B2 | 2/2014 | Kohn |
| 9,121,022 B2 | 9/2015 | Sammons et al. |
| 9,422,557 B2 | 8/2016 | Ader et al. |
| 9,840,715 B1 | 12/2017 | Deikman et al. |
| 2001/0042257 A1 | 11/2001 | Connor-Ward et al. |
| 2002/0114784 A1 | 8/2002 | Li et al. |
| 2003/0150017 A1 | 8/2003 | Mesa et al. |
| 2003/0167537 A1 | 9/2003 | Jiang |
| 2003/0235916 A1 | 12/2003 | Monahan et al. |
| 2004/0053289 A1 | 3/2004 | Christian et al. |
| 2004/0055041 A1 | 3/2004 | Labate et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0244075 A1 | 12/2004 | Cai et al. |
| 2005/0026290 A1 | 2/2005 | Ciardi et al. |
| 2005/0239728 A1 | 10/2005 | Pachuk et al. |
| 2006/0021087 A1 | 1/2006 | Baum et al. |
| 2006/0064775 A1 | 3/2006 | Frank et al. |
| 2006/0111241 A1 | 5/2006 | Gerwick et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |

(56) References Cited

U.S. PATENT DOCUMENTS

| | | |
|---|---|---|
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0098614 A1 | 4/2009 | Zamore et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0188005 A1 | 7/2009 | Boukharov et al. |
| 2009/0205079 A1 | 8/2009 | Kumar et al. |
| 2009/0293148 A1 | 11/2009 | Ren et al. |
| 2009/0307803 A1 | 12/2009 | Baum et al. |
| 2010/0005551 A1 | 1/2010 | Roberts et al. |
| 2010/0068172 A1 | 3/2010 | Van De Craen |
| 2010/0071088 A1 | 3/2010 | Sela et al. |
| 2010/0100988 A1 | 4/2010 | Tranel et al. |
| 2010/0122381 A1 | 5/2010 | Buehler et al. |
| 2010/0154083 A1 | 6/2010 | Ross et al. |
| 2010/0192254 A1 | 7/2010 | Frank et al. |
| 2010/0247578 A1 | 9/2010 | Salama |
| 2010/0306875 A1 | 12/2010 | Rikkerink et al. |
| 2011/0035836 A1 | 2/2011 | Eudes et al. |
| 2011/0098180 A1 | 4/2011 | Michel et al. |
| 2011/0105327 A1 | 5/2011 | Nelson |
| 2011/0126310 A1 | 5/2011 | Feng et al. |
| 2011/0126311 A1 | 5/2011 | Velcheva et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0137387 A1 | 5/2012 | Baum et al. |
| 2012/0156784 A1 | 6/2012 | Adams, Jr. et al. |
| 2012/0159672 A1 | 6/2012 | Alexandrov et al. |
| 2012/0164205 A1 | 6/2012 | Baum et al. |
| 2012/0185967 A1 | 7/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0067618 A1 | 3/2013 | Ader et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1* | 11/2013 | Avniel ............... C12N 15/8279 800/285 |
| 2013/0318658 A1 | 11/2013 | Ader et al. |
| 2013/0326731 A1 | 12/2013 | Ader et al. |
| 2013/0333061 A1 | 12/2013 | Wu et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0215656 A1 | 7/2014 | Crawford et al. |
| 2014/0230090 A1 | 8/2014 | Avniel et al. |
| 2014/0274712 A1 | 9/2014 | Finnessy et al. |
| 2014/0283211 A1 | 9/2014 | Crawford et al. |
| 2014/0296503 A1 | 10/2014 | Avniel et al. |
| 2015/0247153 A1 | 9/2015 | Fillatti et al. |

FOREIGN PATENT DOCUMENTS

| | | |
|---|---|---|
| EP | 2530159 A1 | 12/2012 |
| JP | 2006343473 A | 12/2006 |
| WO | 1989/11789 A1 | 12/1989 |
| WO | 94/03607 A1 | 2/1994 |
| WO | 1996/005721 A1 | 2/1996 |
| WO | 1996/033270 A1 | 10/1996 |
| WO | 1996/038567 A2 | 12/1996 |
| WO | 1996/040964 A2 | 12/1996 |
| WO | 1999/024585 A1 | 5/1999 |
| WO | 99/32619 A1 | 7/1999 |
| WO | 1999/32619 A1 | 7/1999 |
| WO | 99/67367 A1 | 12/1999 |
| WO | 1999/61631 A1 | 12/1999 |
| WO | 00/32757 A2 | 6/2000 |
| WO | 2000/044914 A1 | 8/2000 |
| WO | 2002/14472 A2 | 2/2002 |
| WO | 2003/106636 A2 | 12/2003 |
| WO | 2004/005485 A2 | 1/2004 |
| WO | 2004/009761 A2 | 1/2004 |
| WO | 2004/022771 A2 | 3/2004 |
| WO | 2004/074443 A2 | 9/2004 |
| WO | 2005/003362 A2 | 1/2005 |
| WO | 2005/007860 A1 | 1/2005 |
| WO | 2005/107437 A2 | 11/2005 |
| WO | 2005/110068 A2 | 11/2005 |
| WO | 2006/074400 A2 | 7/2006 |
| WO | 2006/138638 A1 | 12/2006 |
| WO | 2007/007316 A1 | 1/2007 |
| WO | 2007/035650 A2 | 3/2007 |
| WO | 2007/039454 A1 | 4/2007 |
| WO | 2007/051462 A2 | 5/2007 |
| WO | 2007/070389 A2 | 6/2007 |
| WO | 2007/074405 A2 | 7/2007 |
| WO | 2007/080126 A2 | 7/2007 |
| WO | 2007/080127 A2 | 7/2007 |
| WO | 2008/007100 A2 | 1/2008 |
| WO | 2008/063203 A2 | 5/2008 |
| WO | 2008/148223 A1 | 12/2008 |
| WO | 2009/046384 A1 | 4/2009 |
| WO | 2009/116558 A1 | 9/2009 |
| WO | 2009/125401 A2 | 10/2009 |
| WO | 2010/078912 A1 | 7/2010 |
| WO | 2010/083179 A2 | 7/2010 |
| WO | 2010/104217 A1 | 9/2010 |
| WO | 2010/108611 A1 | 9/2010 |
| WO | 2010/112826 A2 | 10/2010 |
| WO | 2010/116122 A2 | 10/2010 |
| WO | 2010/119906 A1 | 10/2010 |
| WO | 2010/130970 A1 | 11/2010 |
| WO | 2011/001434 A1 | 1/2011 |
| WO | 2011/003776 A2 | 1/2011 |
| WO | 2011/067745 A2 | 6/2011 |
| WO | 2011/080674 A2 | 7/2011 |
| WO | 2011/112570 A1 | 9/2011 |
| WO | 2011/132127 A1 | 10/2011 |
| WO | 2012/001626 A1 | 1/2012 |
| WO | 2012/056401 A1 | 5/2012 |
| WO | 2012/092580 A2 | 7/2012 |
| WO | 2013/010691 A1 | 1/2013 |
| WO | 2013/025670 A1 | 2/2013 |
| WO | 2013/039990 A1 | 3/2013 |
| WO | 2013/040005 A1 | 3/2013 |
| WO | 2013/040021 A1 | 3/2013 |
| WO | 2013/040033 A1 | 3/2013 |
| WO | 2013/040049 A1 | 3/2013 |
| WO | 2013/040057 A1 | 3/2013 |
| WO | 2013/040116 A9 | 3/2013 |
| WO | 2013/040117 A1 | 3/2013 |
| WO | 2013/040117 A9 | 6/2013 |
| WO | 2013/175480 A1 | 11/2013 |
| WO | 2014/106837 A2 | 7/2014 |
| WO | 2014/106838 A2 | 7/2014 |

(56) References Cited

FOREIGN PATENT DOCUMENTS

| WO | 2014/151255 A1 | 9/2014 |
|---|---|---|
| WO | 2014/164761 A1 | 10/2014 |
| WO | 2014/164797 A1 | 10/2014 |
| WO | 2015/010026 A2 | 1/2015 |

OTHER PUBLICATIONS

Morrissey et al., "Potent and persistent in vivo anti-HBV activity of chemically modified siRNAs," Nat Biotechnol. 23(8):1002-1007 (2005).
Moser et al., "Sequence—Specific Cleavage of Double Helical DNA by Triple Helix Formation," Science, 238:645-646 (1987).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated May 15, 2015, in U.S. Appl. No. 14/608,951.
Non-Final Office Action dated May 22, 2015, in U.S. Appl. No. 13/612,985.
Nowak et al., "A new and efficient method for inhibition of RNA viruses by DNA interference", The FEBS Journal, 2009, pp. 4372-4380, vol. 276.
Office Action dated Feb. 17, 2014, in Mexican Patent Application No. MX/a/2012/010479.
Office Action for NZ Application 601784 dated Apr. 23, 2013.
Office Action for UA Application No. 201211548 dated Jul. 23, 2015.
Office Action for U.S. Appl. No. 13/612,985 dated Nov. 10, 2015.
Office Action for U.S. Appl. No. 13/619,980 dated Apr. 7, 2016.
Office Action for U.S. Appl. No. 13/619,980, filed Apr. 7, 2016.
Office Action dated Jan. 6, 2015, in Japanese Patent Application No. 2012-557165.
Office Action dated Nov. 19, 2014, in Eurasian Patent Application No. 201201264/28.
Office Action dated Nov. 3, 2014, in Chinese Patent Application No. 201180012795.2.
Office Action dated Oct. 8, 2014, in Mexican Patent Application MX/a/2012/010479.
Orbovic et al., "Foliar-Applied Surfactants and Urea Temporarily Reduce Carbon Assimilation of Grapefruit Leaves", Journal of the American Society for Horticultural Science, 2001, pp. 486-490, vol. 126(4).
Paddison et al., "Stable suppression of gene expression by RNAi in mammalian cells," Proc. Natl Acad. Sci. USA, 99(3):1443-1448 (2002).
Palauqui et al., "Activation of systemic acquired silencing by localised introduction of DNA," Current Biology, 9:59-66 (1999).
Panstruga., "Serpentine Plant MLO Proteins as Entry Portals for Powdery Mildew Fungi", Biochemical Society Transactions, Apr. 1, 2005, pp. 389-392, vol. 33 No. 2.
Parera et al., "Dehydration Rate after Solid Matrix Priming Alters Seed Performance of Shrunken-2 Corn," J. Amer. Soc. Hort. Sci., 119(3):629-635 (1994).
Paungfoo-Lonhienne et al., "DNA Is Taken Up by Root Hairs and Pollen, and Stimulates Root and Pollen Tube Growth", Plant Physiology, 2010, pp. 799-805, vol. 153.

Paungfoo-Lonhienne et al., "DNA uptake by *Arabidopsis* induces changes in the expression of CLE peptides which control root morphology", Plant Signaling & Behavior, 2010, pp. 1112-1114, vol. 5 No. 9.
Pei et al., "On the Art of Identifying Effective and Specific siRNAs", Nature Methods, Sep. 2006, pp. 670-676, vol. 3 No. 9.
Peretz et al., "A Universal Expression/Silencing Vector in Plants," Plant Physiology, 145:1251-1263 (2007).
Piffanelli et al., "A Barely Cultivation-Associated Polymorphism Conveys Resistance to Powdery Mildew", Nature, 2004, pp. 887-891, vol. 430.
Piffanelli et al., "The Barely MLO Modulator of Defense and Cell Death is Responsive to Biotic and Abiotic Stress Stimuli", Plant Physiology, Jul. 1, 2002, pp. 1076-1085, vol. 129.
Pomprom et al., "Glutamine synthetase mutation conferring target-site-based resistance to glufosinate in soybean cell selections," Pest Manag Sci, 2009; 65(2):216-222 (2009).
Pratt et al., "Amaranthus Rudis and A. Tuberculatus, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Qiwei,"Progress in DNA interference," Progress in Veterinary Medicine, 30(1):71-75 (2009).
Rajur et al., "Covalent Protein-Oligonucleotide Conjugates for Efficient Delivery of Antisense Molecules," Bioconjug Chem., 8:935-940 (1997).
Reddy et al., "Aminomethylphosphonic Acid Accumulation in Plant Species Treated with Glyphosate," J. Agric. Food Chem., 56(6):2125-2130 (2008).
Reddy et al., "Organosilicone Adjuvants Increased the Efficacy of Glyphosate for Control of Weeds in Citrus (*Citrus* spp.)", HortScience, 1992, pp. 1003-1005, vol. 27 No. 9.
Reither et al., "Specificity of DNA triple helix formation analyzed by a FRET assay," BMC Biochemistry, 3:27 (2002).
Reynolds et al., "Rational siRNA Design for RNA Interference", Nature Biotechnology, Mar. 2004, pp. 326-330, vol. 22 No. 3.
Riggins et al., "Characterization of De Nova Transcriptome for Waterhemp (*Amaranthus tuberculalus*) Using Gs-Flx 454 Pyrosequeneing and Its Application for Studies of Herbicide Target-Site Genes," Pest Manag. Sci., 66:1042-1052 (2010).
Roberts, Michael R., "Fast-track applications: The potential for direct delivery of proteins and nucleic acids to plant cells for the discovery of gene function", Plant Methods, 2005, vol. 1 No. 12.
Rose et al., "Functional Polarity Is Introduced by Dicer Processing of Short Substrate RNAs," Nucleic Acids Research, 33(13):4140-4156 (2005).
Ryabov et al., "Cell-to-Cell, but Not Long-Distance, Spread of RNA Silencing That Is Induced in Individual Epidermal Cells", Journal of Virology, Mar. 2004, pp. 3149-3154, vol. 78 No. 6.
Gressel et al., "A Strategy to Provide Long-Term Control of Weedy Rice While Mitigating Herbicide Resistance Transgene Flow, and Its Potential Use for Other Crops with Related Weeds", Pest Management Science, 2009, pp. 723-731, vol. 65.
Gutensohn et al., "Functional analysis of the two *Arabidopsis* homologues of Toc34, a component of the chloroplast protein import apparatus," The Plant Journal, 23(6):771-783 (2000).
Haigh, "The Priming of Seeds: Investigation into a method of priming large quantities of seeds using salt solutions," Thesis submitted to Macquarie University (1983).
Hamilton et al., "Two Classes of Short Interfering RNA in RNA Silencing", The European Molecular Biology Organization Journal, 2002, pp. 4671-4679, vol. 21, No. 17.
Han et al., "Molecular Basis for the Recognition of Primary microRNAs by the Drosha-DGCR8 Complex," Cell, 125(5):887-901 (2006).
Hannon, Gregory J., "RNA interference", Nature, 2002, pp. 244-251, vol. 418.
Hardegree, "Drying and storage effects on germination of primed grass seeds," Journal of Range Management, 47(3):196-199 (1994).

(56) References Cited

OTHER PUBLICATIONS

Herman et al., "A three-component dicamba O-demethylase from Pseudomonas maltophilia, strain DI-6: gene isolation, characterization, and heterologous expression," J. Biol. Chem., 280: 24759-24767 (2005).

Hewezi et al., "Local infiltration of high- and low-molecular-weight RNA from silenced sunflower (*Helianthus annuus* L.) plants triggers post-transcriptional gene silencing in non-silenced plants", Plant Biotechnology Journal, 2005, pp. 81-89, vol. 3.

Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).

Himber et al., "Transitivity-dependent and -independent Cell-to-Cell Movement of RNA Silencing", The European Molecular Biology Organization Journal, 2003, pp. 4523-4533, vol. 22 No. 17.

Hirschberg et al., "Molecular Basis of Herbicide Resistance in Amaranthus hybridus," Science, 222:1346-1349 (1983).

Hoekema et al., "A binary plant vector strategy based on separation of vir- and T-region of the Agrobacterium tumefaciens Ti-plasmid," Nature, 303:179-180 (1983).

Hofgen et al., "Repression of Acetolactate Synthase Activity through Antisense Inhibition: Molecular and Biochemical Analysis of Transgenic Potato (*Solanum tuberosum* L. cv Desiree) Plants," Plant Physiol., 107(2):469-477 (1995).

Hsieh et al., "A library of siRNA duplexes targeting the phosphoinositide 3-kinase pathway: determinants of gene silencing for use in cell-based screens," Nucleic Acids Res., 32(3):893-901 (2004).

Hu et al., "High Efficiency Transport of Quantum Dots into Plant Roots with the Aid of Silwet L-77", Plant Physiology and Biochemistry, Aug. 2010, pp. 703-709, vol. 48, Issue 8.

Huckelhoven et al., "Overexpression of Barley BAX Inhibitor 1 Induces Breakdown of mlo-Mediated Penetration Resistance to Blumeria Graminis", Proceedings of the National Academy of Sciences, Apr. 29, 2003, pp. 5555-5560, vol. 100 No. 9.

Huesken et al., "Design of a genome-wide siRNA library using an artificial neural network," Nature Biotechnology, 23(8): 995-1001 (2005).

Humphry et al., "Durable Broad-Spectrum Powdery Mildew Resistance in Pea ER1 Plants is Conferred by Natrual Loss-of-Function Mutations in PsMLO1", Molecular Plant Pathology, 2011, pp. 866-878, vol. 12, No. 9.

Hunter, Wayne B., "RNA Interference Strategies to Suppress Psyllids", International Plant and Animal Genome XIX, Jan. 15-19, 2011.

Ichihara et al., "Thermodynamic instability of siRNA duplex is a prerequisite for dependable prediction of siRNA activities," Nucleic Acids Res., 35(18):e123 (2007).

International Preliminary Report on Patentability (Chapter II) dated Jul. 24, 2015, in International Application No. PCT/US2014/047204.

International Preliminary Report on Patentability for PCT/US2011/027528 dated Sep. 11, 2012.

International Preliminary Report on Patentability dated Sep. 11, 2014, in International Application No. PCT/IL13/50447.

International Search Report and the Written Opinion dated Feb. 25, 2013, in International Application No. PCT/US12/54883.

International Search Report and the Written Opinion dated Feb. 27, 2013, in International Application No. PCT/US12/54814.

International Search Report and the Written Opinion dated Feb. 27, 2013, in International Application No. PCT/US12/54842.

International Search Report and the Written Opinion dated Feb. 27, 2013, in International Application No. PCT/US12/54862.

International Search Report and the Written Opinion dated Feb. 27, 2013, in International Application No. PCT/US12/54894.

International Search Report and the Written Opinion dated Feb. 27, 2013, in International Application No. PCT/US12/54974.

International Search Report and the Written Opinion dated Feb. 27, 2013, in International Application No. PCT/US12/54980.

International Search Report and the Written Opinion dated Jul. 15, 2014, in International Application No. PCT/US2014/025305.

International Search Report and the Written Opinion dated Jul. 22, 2014, in International Application No. PCT/IL2013/051083.

International Search Report and the Written Opinion dated Jul. 22, 2014, in International Application No. PCT/IL2013/051085.

International Search Report and the Written Opinion dated Jul. 24, 2014, in International Application No. PCT/US2014/026036.

International Search Report and the Written Opinion dated Oct. 1, 2013, in International Application No. PCT/IL2013/050447.

International Search Report and Written Opinion dated Aug. 25, 2014, in International Application No. PCT/US2014/023503.

International Search Report and Written Opinion dated Aug. 27, 2014, in International Application No. PCT/US2014/023409.

International Search Report and Written Opinion for PCT/US2011/27528 dated May 10, 2011.

International Search Report and Written Opinion issued in PCT/US13/61475, dated Apr. 8, 2014.

International Search Report and Written Opinion dated Jul. 8, 2015 in International Application No. PCT/US2015/011408.

International Search Report and Written Opinion dated Mar. 26, 2015, in International Application No. PCT/US2014/069353.

International Search Report dated Mar. 12, 2013 in International Application No. PCT/US 12/54789.

Isaacs et al., "Engineered riboregulators enable post-transcriptional control of gene expression," Nature Biotechnology, 22(7):841-847 (2004).

Ji et al., "Regulation of small RNA stability: methylation and beyond," Cell Research, 22:624-636 (2012).

Jofre-Garfias El Al., "Agrobacterium—Mediated Transformation of Amaranthus Hypochondriacus: Light- And Tissue-Specific Expression of a Pea Chlorophyll A/B—Binding Protein Promoter," Plant Cell Reports, 16:847-852 (1997).

Jones-Rhoades et al., "MicroRNAs and Their Regulatory Roles in Plants", Annual Review of Plant Biology, 2006, pp. 19-53, vol. 57.

Josse et al., "A DELLA in Disguise: SPATULA Restrains the Growth of the Developing *Arabidopsis* Seedling," Plant Cell, 23:1337-1351 (2011).

Kam et al., "Nanotube Molecular Transporters:? Internalization of Carbon Nanotube?Protein Conjugates into Mammalian Cells," J. Am. Chem. Soc., 126(22):6850-6851 (2004).

Katoh et al., "Specific residues at every third position of siRNA shape its efficient RNAi activity," Nucleic Acids Res., 35(4): e27 (2007).

Schmutz et al., "Genome Sequence of the Palaeopolyploid Soybean", Nature, Jan. 14, 2010, pp. 178-183, vol. 463.

Xu et al., "Computational Estimation and Experimental Verification of Off-Target Silencing During Posttranscriptional Gene Silencing in Plants", Plant Physiology, 2006, pp. 429-440, vol. 142.

Colbourne et al., "The Ecoresponsive Genome of Daphnia pulex," Science, 331(6017):555-561 (2011).

Colombian Office Action dated Aug. 2, 2013 in Application No. 12 152898.

Colombian Office Action issued Feb. 21, 2014 in Application No. 12 152898.

Communication pursuant to Article 94(3) EPC dated Jun. 26, 2015, as received in European Patent Application No. 11 753 916.3.

Concise Descriptions of Relevance filed by a third party on Nov. 29, 2012 in U.S. Appl. No. 13/042,856.

Consonni et al., "Conserved Requirement for a Plant Host Cell Protein in Powdery Mildew Pathogenesis", Nature Genetics, 2006, pp. 716-720, vol. 38, No. 6.

Cost Action FA0806 progress report, "Plant virus control employing RNA-based vaccines: A novel non-transgenic strategy", 2010.

Dalakouras et al., "Induction of Silencing in Plants by High-Pressure Spraying of In vitro-Synthesized Small RNAs", Frontiers in Plant Science, Aug. 2016, pp. 1-5, vol. 7, No. 1327.

Dalakouras et al., "Induction of Silencing in Plants by High-Pressure Spraying of In vitro-Sythesized Small RNAs", Frontiers in Plant Science, Aug. 2016, pp. 1-5, vol. 7, No. 1327.

Dalmay et al., "An RNA-Dependent RNA Polymerase Gene in *Arabidopsis* Is Required for Posttranscriptional Gene Silencing Mediated by a Transgene but Not by a Virus," Cell, 101:543-553 (2000).

Datebase EMBL CBIB Daphnia—XP-002732239 (2011).

(56) References Cited

OTHER PUBLICATIONS

Davidson et al., "Engineering regulatory RNAs," TRENDS in Biotechnology, 23(3):109-112 (2005).
De Block, et al. "Engineering herbicide resistance in plants by expression of a detoxifying enzyme," EMBO J. 6(9):2513-2519 (1987).
De Framond, "MINI-Ti: A New Vector Strategy for Plant Genetic Engineering," Nature Biotechnology, 1:262-269 (1983).
Della-Cioppa et al., "Import of a precursor protein into chloroplasts is inhibited by the herbicide glyphosate," The EMBO Journal, 7(5):1299-1305 (1988).
Devgen, "The mini-Monsanto", KBC Securities, 2006.
Diallo et al., "Long Endogenous dsRNAs Can Induce Complete Gene Silencing in Mammalian Cells and Primary Cultures," Oligonucleotides, 13:381-392 (2003).
Du et al., "A Systematic Analysis of the Silencing Effects of an Active siRNA at All Single-nucleotide Mismatched Target Sites", Nucleic Acids Research, 2005, pp. 1671-1677, vol. 33 No. 5.
Dunoyer et al., "Small RNA Duplexes Function as Mobile Silencing Signals Between Plant Cells", Science, 2010, pp. 912-916, vol. 328.
Eichmann et al., "BAX Inhibitor-1 Is Required for Full Susceptibility of Barley to Powdery Mildew", Molecular Plant-Microbe Interactions, 2010, pp. 1217-1227, vol. 23 No. 9.
Eichmann et al., "The Barley Apoptosis Suppressor Homologue BAX Inhibitor-1 Compromises Nonhost Penetration Resistance of Barley to the Inappropriate Pathogen *Blumeria graminis* F. Sp. *Tritici*", Molecular Plant-Microbe Interactions, 2004, pp. 484-490, vol. 17, No. 5.
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
Eurasian Office Action dated Feb. 24, 2014, in Application No. 201201264.
European Cooperation in the field of Scientific and Technical Research, Memorandum of Understanding for COST Action FA0806, 2008.
European Supplemental Search Report dated Oct. 8, 2013 in Application No. 11753916.3.
Extended European Search Report dated Jun. 29, 2015, in European Patent Application No. 12831494.5.
Farooq et al., "Rice seed priming," IPRN, 30(2):45-48 (2005).
Final Office Action dated Nov. 7, 2013, in U.S. Appl. No. 13/042,856.
Fire et al., "Potent and specific genetic interference by double-stranded RNA in Caenorhabditis elegans," Nature, 391:806-811 (1998).
First Examination Report issued for New Zealand Application No. 601784 dated Apr. 23, 2013.
First Examination Report dated Jul. 28, 2014, in New Zealand Patent Application No. 627060.
First Office Action dated May 27, 2015, in Chinese Patent Application No. 201280054179.8.
Fraley et al., "Liposome-mediated delivery of tobacco mosaic virus RNA into tobacco protoplasts: A sensitive assay for monitoring liposome-protoplast interactions", Proceedings of the National Academy of Sciences, 1982, pp. 1859-1863, vol. 79.
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Further Examination Report issued in New Zealand Patent Application No. 601784 dated May 16, 2014.
Gaines et al., "Gene Amplification Confers Glyphosate Resistance in Amaranthus Palmeri", PNAS, 2010, pp. 1029-1034, vol. 107 No. 3.

Gan et al., "Bacterially Expressed dsRNA Protects Maize Against SCMV Infection", Plant Cell Reports, published online Aug. 24, 2010.
Gao et al., "Nonviral Methods for siRNA Delivery", Molecular Pharmaceutics, 2008, pp. 651-658, vol. 6 No. 3.
Ge et al., "Rapid vacuolar sequestration: the horseweed glyphosate resistance mechanism," Pest Management Sci., 66:345-348 (2010).
Gelvin, "Agrobacterium-Mediated Plant Transformation: The Biology Behind the "Gene-Jockeying" Tool", Microbiology and Molecular Biology Reviews, Mar. 2003, p. 16-37, vol. 67 No. 1.
GenBank Accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the Internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. GI:186478573, published Jan. 22, 2014.
GenEmbl FJ861243, published Feb. 3, 2010.
Gong et al., "Silencing of Rieske iron-sulfur protein using chemically synthesised siRNA as a potential biopesticide against Plutella xylostella", Pest Management Science, 2011, pp. 514-520, vol. 67.
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Töpfer et al., "Uptake and Transient Expression of Chimeric Genes in Seed-Derived Embryos," Plant Cell, 1:133-139 (1989).
Ui-Tei et al., "Guidelines for the selection of highly effective siRNA sequences for mammalian and chick RNA interference," Nucleic Acids Res., 32(3): 936-948 (2004).
Unnamalai et al., "Cationic oligopeptide-mediated delivery of dsRNA for post-transcriptional gene silencing in plant cells", FEBS Letters, 2004, pp. 307-310, vol. 566.
Urayama et al., "Knock-down of OsDCL2 in Rice Negatively Affects Maintenance of the Endogenous dsRNA Virus, Oryza sativa Endornavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Varallyay et al., "Virus-Induced Gene Silencing of Mlo Genes Induces Powdery Mildew Resistance in Triticum aestivum", Archives of Virology: Official Journal of the Virology Division of the International Union of Micobiological Societies, 2012, pp. 1345-1350, vol. 157, No. 7.
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, Hervé, "Post-transcriptional Small RNA Pathways in Plants: Mechanisms and Regulations", Genes & Development, 2006, pp. 759-771, vol. 20.
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The Contributions of dsRNA Structure to Dicer Specificity and Efficiency," RNA, 11 (5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants Is Initiated by Localized Introduction of Ectopic Promoterless DNA", Cell, 1998, pp. 177-187, vol. 95.
Wakelin et al., "A target-site mutation is present in a glyphosate-resistant Lolium rigidum population," Weed Res. (Oxford), 46(5):432-440 (2006).

(56) References Cited

OTHER PUBLICATIONS

Walton et al., "Prediction of antisense oligonucleotide binding affinity to a structured RNA target," Biotechnol Bioeng 65 (1):1-9 (1999).
Wan et al., "Generation of Large Numbers of Independently Transformed Fertile Barley Plants," Plant Physiol., 104:37-48 (1994).
Wang et al., "A Web-Based Design Center for Vector-Based siRNA and siRNA Cassette", BioInformatic Applications Note, 2004, pp. 1818-1820, vol. 20 No. 11.
Wardell, William L., "Floral Activity in Solutions of Deoxyribonucleic Acid Extracted from Tobacco Stems", Plant Physiology, 1976, pp. 855-861, vol. 57.
Wardell, William L., "Floral Induction of Vegetative Plants Supplied a Purified Fraction of Deoxyribonucleic Acid from Stems of Flowering Plants", Plant Physiology, 1977, pp. 885-891, vol. 60.
Warnasooriya et al., "Using transgenic modulation of protein synthesis and accumulation to probe protein signaling networks in *Arabidopsis thaliana*" Plant Signaling & Behavior, 6(9):1312-1321 (2011).
Waterhouse et al., "Exploring Plant Genomes by RNA-Induced Gene Silencing", Nature Reviews, Genetics, 2003, pp. 29-38, vol. 4.
Waterhouse et al., "Virus resistance and gene silencing in plants can be induced by simultaneous expression of sense and antisense RNA," Proc Natl Acad Sci USA, 95:13959-13964 (1998).
Welch et al., "Expression of ribozymes in gene transfer systems to modulate target RNA levels," Curr Opin Biotechnol. 9(5):486-496 (1998).
Written Opinion dated May 8, 2014, in International Application No. PCT/IL2013/050447.
Written Opinion dated Sep. 4, 2014, in Singapore Patent Application No. 201206152-9.
Yan et al., "Sprout Vacuum-Infiltration: A Simple and Efficient Agroinoculation Method for Viru-Induced Gene Silencingin Diverse Solanaceous Species", Plant Cell Reports, Sep. 2012, pp. 1713-1722, vol. 31 Issue 9.
Yan et al., "Sprout Vacuum-Infiltration: A Simple and Efficient Agroinoculation Method for Virus-Induced Gene Silencingin Diverse Solanaceous Species", Plant Cell Reports, 2012, pp. 1713-1722, vol. 31.
YouTube video by General Electric Company "Silwet Surfactants," screen shot taken on Jan. 11, 2012 of video of www.youtube_com/watch?v=WBw7nXMqHk8 (uploaded Jul. 13, 2009).
Yuan et al., "A High Throughput Barley Strip Mosaic Virus Vector for Virus Induced Gene Silencing in Monocots and Dicots", PLOS One, Oct. 21, 2011, pp. 1-16, vol. 6 Issue 10 e26468.
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhai et al., "Establishing RNA Interference as a Reverse-Genetic Approach for Gene Functional Analysis in Protoplasts" Plant Physiology, 149:642-652 (2009).
Zhang et al., "A novel rice gene, NRR responds to macronutrient deficiency and regulates root growth," Mol Plant, 5 (1):63-72 (2012).
Zhang et al., "Agrobacterium-mediated Transformation of *Arabidopsis thaliana* Using the Floral Dip Method", Nature Protocols, 2006, pp. 1-6, vol. 1 No. 2.
Zhang et al., "Cationic Lipids and Polymers Mediated Vectors for Delivery of siRNA", Journal of Controlled Release, Oct. 18, 2007, pp. 1-10, vol. 123 Issue. 1.
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).

Zhao et al., "Phyllotreta striolata (Coleoptera: Chrysomelidae): Arginine kinase cloning and RNAi-based pest control", European Journal of Entomology, 2008, pp. 815-822, vol. 105.
Zhu et al., "Ingested RNA interference for managing the populations of the Colorado potato beetle, *Leptinotarsa decemlineata*", Pest Management Science, 2010, pp. 175-182, vol. 67.
Kertbundit et al., "In vivo random ß-glucuronidase gene fusions in *Arabidopsis thaliana*," Proc. Natl. Acad. Sci. U S A., 88:5212-5216 (1991).
Khachigian, "DNAzymes: Cutting a path to a new class of therapeutics," Curr Opin Mol Ther 4(2):119-121 (2002).
Khan et al., "Matriconditioning of Vegetable Seeds to Improve Stand Establishment in Early Field Plantings," .1 Amer. Soc. Hon. Sci., 1 17(1):41-47 (1992).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Kim et al., "Calmodulin Interacts with MLO Protein to Regulate Defence Against Mildew in Barley", Nature, Mar. 28, 2002, pp. 447-450, vol. 416.
Kim et al., "Optimization of Conditions for Transient Agrobacterium-Mediated Gene Expression Assays in *Arabidopsis*", Plant Cell Reproduction, 2009, pp. 1159-1167, vol. 28.
Kim et al., "Synthetic dsRNA Dicer substrates enhance RNAi potency and efficacy," Nature Biotechnology, 23 (2):222-226 (2005).
Kirkwood, "Herbicides and Plants", Botanical Journal of Scotland, Jan. 1, 1993, pp. 447-462, vol. 46 Issue 3.
Kirkwood, Ralph C., "Use and Mode of Action of Adjuvants for Herbicides: A Review of some Current Work", Pesticide Science, 1993, pp. 93-102, vol. 38.
Klahre et al., "High molecular weight RNAs and small interfering RNAs induce systemic posttranscriptional gene silencing in plants", PNAS, 2002, pp. 11981-11986, vol. 99 No. 18.
Kozomara et al., "miRBase: Annotating High Confidence MicroRNAs Using Deep Sequencing Data", Nucleic Acids Research, 2014, p. D68-D73, vol. 42.
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Kusaba et al., "Low glutelin content1: A Dominant Mutation That Supresses the Glutelin Multigene Family via RNA Silencing in Rice", The Plant Cell, 2003, pp. 1455-1467, vol. 15.
Kusaba, "RNA interference in crop plants", Current Opinion in Biotechnology, 2004, pp. 139-143, vol. 15, No. 2.
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Leopold et al., "Chapter 4: Moisture as a Regulator of Physiological Reaction in Seeds," Seed Moisture, CSSA Special Publication No. 14, pp. 51-69 (1989).
Li et al., "Establishment of a highly efficient transformation system for pepper (*Capsicum annuum* L.)," Plant Cell Reports, 21: 785-788 (2003).
Li et al., "The FAST technique: a simplified Agrobacterium-based transformation method for transient gene expression analysis in seedlings of *Arabidopsis* and other plant species", Plant Methods, 2009, vol. 5 No. 6.
Liu et al., "Carbon Nanotubes as Molecular Transporters for Walled Plant Cells," Nano Letters, 9(3):1007-1010 (2009).
Liu et al., "Comparative study on the interaction of DNA with three different kinds of surfactants and the formation of multilayer films", Bioelectrochemistry, 2007, pp. 301-307, vol. 70.
Liu et al., "DNAzyme-mediated recovery of small recombinant RNAs from a 5S rRNA-derived chimera expressed in *Escherichia coli*," BMC Biotechnology, 10:85 (2010).
Liu et al., "Insecticidal Activity of Surfactants and Oils Against Silverleaf Whitefly (*Bemisia Argentifolii*) Nymphs (Homoptera: Aleyrodidae) on Collards and Tomato", Pest Management Science, 2000, pp. 861-866, vol. 56.

(56) References Cited

OTHER PUBLICATIONS

Llave et al., "Endogenous and Silencing-Associated Small RNAs in Plants," The Plant Cell, 14:1605-1619 (2002).
Lu et al., "Novel and Mechanical Stress-Responsive MicroRNAs in Populus Trichocarpa That Are Absent from *Arabidopsis*", The Plant Cell, Aug. 2005, pp. 2186-2203, vol. 17.
Lu et al., "OligoWalk: an online siRNA design tool utilizing hybridization thermodynamics," Nucleic Acids Research, 36: W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).
Maas et al., "Mechanism and optimized conditions for PEG mediated DNA transfection into plant protoplasts", Plant Cell Reports, 1989, pp. 148-151, vol. 8.
Mackenzie et al., "Transgenic Nicotiana Debneyii Expressing Viral Coat Protein Are Resistant to Potato Virus S Infection," Journal of General Virology, 71:2167-2170 (1990).
Maher III et al., "Inhibition of DNA binding proteins by oligonucleotide-directed triple helix formation," Science, 245(4919):725-730 (1989).
Mallory et al., "MicroRNA Control of PHABULOSA in Leaf Development: Importance of Pairing to the MicroRNA 5' Region", The EMBO Journal, 2004, pp. 3356-3364, vol. 23 No. 16.
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews | Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Mansoor et al., "Engineering Novel Traits in Plants Through RNA Interference", Trends in Plant Science, 2006, pp. 559-565, vol. 11, No. 11.
Masoud et al., "Constitutive expression of an inducible ß-1,3-glucanase in alfalfa reduces disease severity caused by the oomycete pathogen *Phytophthora megasperma* f. sp medicaginis, but does not reduce disease severity of chitincontaining fungi," Transgenic Research, 5:313-323 (1996).
Matveeva et al., "Prediction of antisense oligonucleotide efficacy by in vitro methods," Nature Biotechnology, 16:1374-1375 (1998).
McMullen et al., "Effects of Application Parameters on Control of Fusarium Head Blight with Fungicides", 2000 National Fusarium Head Blight Forum, Dec. 10-12, 2000, 4 pages.
Meinke, et al., "Identifying essential genes in *Arabidopsis thaliana*," Trends Plant Sci., 13(9):483-491 (2008).
Meins, Jr. et al., "RNA Silencing Systems and Their Relevance to Plant Development", Annual Review of Cell and Developmental Biology, 2005, pp. 297-318, vol. 21.
Melnyk et al., "Intercellular and systemic movement of RNA silencing signals", The EMBO Journal, 2011, pp. 3553-3563, vol. 30.
Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (1994).
Misawa et al., "Functional expression of the Erwinia uredovora carotenoid biosynthesis gene crtI in transgenic plants showing an increase of ?-carotene biosynthesis activity and resistance to the bleaching herbicide norflurazon," The Plant Journal, 4(5):833-840 (1993).
Miura et al., "The Balance between Protein Synthesis and Degradation in Chloroplasts Determined Leaf Variegation in *Arabidopsis* yellow variegated Mutants," The Plant Cell, 19:1313-1328 (2007).
Molin-Cano et al., "Mildew-Resistant Mutants Induced in North American Two-and six-rowed Malting Barley Cultivars," Theor Appl. Genet, Jul. 30, 2003, pp. 1278-1287, vol. 107.
Molina et al., "Inhibition of Protoporphyrinogen Oxidase Expression in *Arabidopsis* Causes a Lesion-Mimic Phenotype That Induces Systemic Acquired Resistance," The Plant Journal, 1 7(6):667-678 (1999).
Molina-Cano et al., "Mildew-Resistant Mutants Induced in North America Two- and Six- Rowed Malting Barley Cultivars", Theoretical and Applied Genetics, 2003, pp. 1278-1287, vol. 107.
Molnar et al., "Plant Virus-Derived Small Interfering RNAs Originate Predominantly from Highly Structured Single-Stranded Viral RNAs," Journal of Virology, 79(12):7812-7818 (2005).
Molnar et al., "Small Silencing RNAs in Plants Are Mobile and Direct Epigenetic Modification in Recipient Cells", Science, 2010, pp. 872-875, vol. 328.
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Sato et al., "Development of 5006 Full-Length CDNAs in Barley: A Tool for Accessing Cereal Genomics Resources", DNA Research, Jan. 15, 2009, pp. 81-98, vol. 16.
Schwab et al., "RNA silencing amplification in plants: Size matters," PNAS, 107(34):14945-14946 (2010).
Schweizer et al., "Double-Stranded RNA Interferes with Gene Function at the Single Cell Level in Cereals", The Plant Journal, 2000, pp. 895-903, vol. 24, No. 6, Blackwell Scientific Publications, Oxford, GB.
Schwember et al., "Drying Rates following Priming Affect Temperature Sensitivity of Germination and Longevity of Lettuce Seeds," HortScience, 40(3):778-781 (2005).
Second Chinese Office Action issued in Chinese Patent Application No. 201180012795.2, dated Jun. 10, 2014.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. *Aggregatum*) and carrot (*Daucus carota*)," Journal of Agricultural Technology, 7(3):857-867 (2011).
Senthil-Kumar et al., "A Systematic Study to Determine the Extent of Gene Silencing in Nicotiana Benthamiana and Other Solanaccac Species When Heterologous Gene Sequences Are Used for Virus-Induced Gene Silencing", New Phylologist, 176:782-791 (2007).
Senthil-Kumar et al., "RNAi in Plants: Recent Developments and Applications in Agriculture", Gene Silencing: Theory, Techniques and Applications, Oct. 1, 2010, p. 185, Retrieved from the Internet: URL: https://www.researchgate.net/profile/Senthil-Kumar_Muthappa/publication/216017213_RNAi_in_Plants_Recent_Developments_and_Applications_in_Agriculture/links/097fe5ffe6c103ae5cc028f6.pdf, Retrieved on Feb. 14, 2017.
Sharma et al., "A simple and efficient Agrobacterium-mediated procedure for transformation of tomato," J. Biosci., 34 (3):423 433 (2009).
Shen et al., "Genome-Scale Identification of MLO Domain-Containing Genes in Soybean (*Glycine max* L. *Merr.*)", Genes and Genetic Systems, Apr. 2012, pp. 89-98, vol. 87, No. 2.
Showalter, "Structure and Function of Plant Cell Wall Proteins", The Plant Cell, Jan. 1993, pp. 9-23, vol. 5.
Sijen et al., "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc., 2003.
Singh et al., "Absorption and translocation of glyphosate with conventional and organosilicone adjuvants," Weed Biology and Management, 8:104-111 (2008).
Snead et al., "Molecular Basis for Improved Gene Silencing by Dicer Substrate Interfering RNA Compared With Other siRNA Variants," Nucleic Acids Research, 41(12):6209-6221 (2013).
Solano et al., "Isolation and Characterization of Strain MMB-1 (CECT 4803), a Novel Melanogenic Marine Bacterium," Appl. Environ. Microbiol., 1997, pp. 3499, vol. 63 No. 9.
Somerville et al., "Plant Functional Genomics" Science, 285:380-383 (1999).

(56) References Cited

OTHER PUBLICATIONS

Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—SilWet® Organosilicone Surfactants Have Physical and Physiological Properties Which Enhance the Performance of Sprays", Proceedings of the 9th Australian Weeds Conference, 1990, pp. 327-331.
Stevens, "Organosilicone Surfactants as Adjuvants for Agrochemicals", Pesticide Science, 1993, pp. 103-122, vol. 38.
Stock et al., "Possible Mechanisms for Surfactant-Induced Foliar Uptake of Agrochemicals", Pesticide Science, 1993, pp. 165-177, vol. 38.
Strat et al., "Specific and nontoxic silencing in mammalian cells with expressed long dsRNAs," Nucleic Acids Research, 34(13):3803-3810 (2006).
Street, "Why is DNA (and not RNA) a Stable Storage Form for Genetic Information?," Biochemistry Revisited, pp. 1-4 (2008).
Sudarsan et al., "Metabolite-binding RNA domains are present in the genes of eukaryotes," RNA, 9:644-647 (2003).
Sun et al., "A Highly efficient Transformation Protocol for Micro-Tom, a Model Cultivar for Tomato Functional Genomics," Plant Cell Physiol., 47(3):426-431 (2006).
Sun et al., "Antisense Oligodeoxynucleotide Inhibition as a Potent Strategy in Plant Biology: Identification of SUSIBA2 as a Transcriptional Activator in Plant Sugar Signalling", The Plant Journal, 2005, pp. 128-138, vol. 44.
Sun et al., "Sweet delivery—sugar translocators as ports of entry for antisense oligodeoxynucleotides in plant cells", The Plant Journal, 2007, pp. 1192-1198, vol. 52.
Supplementary European Search Report for EP 12831567.8 dated Jan. 29, 2015.
Supplementary European Search Report for EP 12832415.9 dated Jan. 21, 2015.
Sutton et al., "Activity of Mesotrione on Resistant Weeds in Maize," Pest Manag. Sci., 58:981-984 (2002).
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing", Plant Science, 2006, pp. 375-381, vol. 171.
Tank Mixing Chemicals Applied to Peanut Crops: Are the Chemicals. Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Templeton et al., "Improved DNA: liposome complexes for increased systemic delivery and gene expression," Nature Biotechnology, 15:647-652 (1997).
Tenllado et al., "Crude Extracts of Bacterially Expressed dsRNA can be used to Protect Plants Against Virus Infection" BMC Biotechnology, 2003, pp. 1-11, vol. 3 No. 3.
Tenllado et al., "Double-Stranded RNA-Mediated Interference with Plant Virus Infection", Journal of Virology, 2001, pp. 12288-12297, vol. 75 No. 24.
Tenllado, et al., "RNA interference as a new biotechnological tool for the control of virus diseases in plants", Virus Research, 2004, pp. 85-96, vol. 102.
Tepfer, "Risk assessment of virus resistant transgenic plants," Annual Review of Phytopathology, 40:467-491 (2002).
The Seed Biology Place, Website Gerhard Leubner Lab Royal Holloway, University of London, http://www.seedbiology.de/seedtechnology.asp, last updated May 2, 2012.
Thomas et al., "Size Constraints for Targeting Post-Transcriptional Gene Silencing and for RNA-Directed Methylation in Nicotiana Benthamiana using a Potato Virus X Vector", The Plant Journal, 2001, pp. 417-425, vol. 25 No. 4.
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Timmons et al., "Specific interference by ingested dsRNA," Nature, 395:854 (1998).
Tomari et al., "Perspective: Machines for RNAi", Genes & Development, 2005, pp. 517-529, vol. 19.
Toriyama et al., "Transgenic Rice Plants After Direct Gene Transfer Into Protoplasts", Biotechnology, 1988, pp. 1072-1074, vol. 6.
Tran et al., "Control of specific gene expression in mammalian cells by co-expression of long complementary RNAs," FEBS Lett.;573(1-3):127-134 (2004).
Tranel et al., "Resistance of Weeds to ALS-Inhibiting Herbicides: What Have We Learned?," Weed Science, 50:700-712 (2002).
"Agricultural Chemical Usage 2006 Vegetables Summary", Agricultural Statistics Board, Jul. 2007, pp. 1-372.
AccuStandard, Inc., "Pesticide Standards Reference Guide", 2010, 116 pages.
Agrios, Plant Pathology (Second Edition), 2:466-470 (1978).
Al-Kaff et al., "Plants rendered herbicide-susceptible by cauliflower mosaic virus-elicited suppression of a 35S promoter-regulated transgene", Nature Biotechnology, 2000, pp. 995-999, vol. 18.
Alarcón-Reverte et al., "Resistance to ACCase-inhibiting herbicides in the weed Lolium multiflorum," Comm. Appl. Biol. Sci., 73(4):899-902 (2008).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
An et al., "Transient RNAi Induction against Endogenous Genes in *Arabidopsis* Protoplasts Using in Vitro-Prepared Double-Stranded RNA", Bioscience Biotechnology and Biochemistry, 2005, pp. 415-418, vol. 69 No. 2.
Anonymous, "A handbook for high-level expression and purification of 6xHis-tagged proteins," The QIAexpressionist, (2003).
Anonymous, "Do Monsanto Have the Next Big Thing?" Australian Herbicide Resistance Initiative (AHRI), retreived on Jan. 19, 2015, XP007922963.
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).
Artymovich, Katherine A., "Using RNA interference to increase crop yield and decrease pest damage", MMG 445 Basic Biotechnology, 2009, pp. 7-12, vol. 5.
Austrailian Government, Grains Research & Development Corporation, "Adjuvants: Oils, Surfactants and other Additives for Farm Chemicals", 2012, 52 pages.
Australian Patent Examination report No. 1 dated Nov. 11, 2013, in Australian Application No. 2011224570.
Axtell et al., "A Two-Hit Trigger for siRNA Biogenesis in Plants," Cell, 127:565?577 (2006).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al., "Naturally Occuring Broad-Spectrum Powdery Mildew Resistance in Central American Tomato Accession Is Caused by Loss of Mlo Function", Molecular Plant-Microbe Interactions, 2008, pp. 30-39, vol. 21, No. 1.
Balcombe et al., "RNA Silencing and Heritable Epigenetic Effects in Tomato and *Arabidopsis*", Abstract 13th Annual Fall Symposium, Plant Genomes to Phenomes, Donal Danforth Plant Science, Sep. 28-30, 2011.
Banerjee et al., "Efficient production of transgenic potato (*S. tuberosum* L. ssp. *andigena*) plants via Agrobacterium tumefaciens-mediated transformation," Plant Sci., 170:732 738 (2006).
Bart et al., "A novel system for gene silencing using siRNAs in rice leaf and stem-derived protoplasts", Plant Methods, 2006, vol. 2 No. 13.

(56) References Cited

OTHER PUBLICATIONS

Basu et al., "Weed genomics: new tools to understand weed biology", TRENDS in Plant Science, 2004, pp. 391-398, vol. 9 No. 8.
Baulcombe et al., "RNA Silencing and Heritable Epigenetic Effects in Tomato and *Arabidopsis*", Abstract 13th Annual Fall Symposium, Plant Genomes to Phenomes, Donald Danforth Plant Science, Sep. 28-30, 2011.
Baulcombe, David, "RNA Silencing and Heritable Epigenetic Effects in Tomato and *Arabidopsis*", Abstract 13th Annual Fall Symposium, Plant Genomes to Phenomes, Donald Danforth Plant Science Center, Sep. 28-30, 2011.
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5 (2):299-307 (1994).
Bhargava et al., "Long double-stranded RNA-mediated RNA interference as a tool to achieve site-specific silencing of hypothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera* virgifera LeConte)," PLoS One 7(10):e47534 (2012).
Bolter et al., "A chloroplastic inner envelope membrane protease is essential for plant development," FEBS Letters, 580:789-794 (2006).
Bourgeois et al., "Field and Producer Survey of Accase Resistant Wild Oat in Manitoba," Canadian Journal of Plant Science, 709-7 15 (1997).
Breaker et al., "A DNA enzyme with Mg2+-dependent RNA phosphoesterase activity," Chemistry and Biology, 2:655-660 (1995).
Brodersen et al., "The Diversity of RNA Silencing Pathways in Plants", TRENDS in Genetics, May 2006, pp. 268-280, vol. 22 No. 5.
Brugière et al., "Glutamine Synthetase in the Phloem Plays a Major Role in Controlling Proline Production," The Plant Cell, 11:1995-2011(1999).
Busch et al., "RNAi for discovery of novel crop protection products", Pflanzenschutz-Nachrichten Bayer, 2005, pp. 34-50, vol. 58 No. 1.
Busi et al., "Gene Flow Increases the Initial Frequency of Herbicide Resistance Alleles in Unselected Lolium Rigidum Populations", Agriculture, Ecosystems and Environments, 2011, pp. 403-409, vol. 142.
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Cellular Internalization of Fluorescent Proteins via Arginine-Rich Intracellular Delivery Peptide in Plant Cells", Plant Cell Physiology, 2005, pp. 482-488, vol. 46.
Chee et al., "Transformation of Soybean (*Glycine max*) by Infecting Germinating Seeds with Agrobacterium tumefaciens," Plant Physiol., 91:1212-1218 (1989).
Chen et al., "In Vivo Analysis of the Role of atTic20 in Protein Import into Chloroplasts," The Plant Cell, 14:641-654 (2002).
Chen et al., "Transfection and Expression of Plasmid DNA in Plant Cells by Arginine-Rich Intracellular Delivery Peptide Without Protoplast Preparation", Federation of European Biochemical Societies Letters, 2007, pp. 1891-1897, vol. 581.
Cheng et al., "Production of fertile transgenic peanut (*Arachis hypogaea* L.) plants using Agrobacterium tumefaciens," Plant Cell Reports, 15:653-657 (1996).
Chi et al., "The Function of RH22, a Dead RNA Helicase, in the Biogenesis of the 50S Ribosomal Subunits of Arabidopsis Chloroplasts," Plant Physiology, 158:693-707 (2012).
Chinese Office Action dated Aug. 28, 2013 in Chinese Application No. 201180012795.2.
Chupp et al., "Chapter 8: White Rust," Vegetable Diseases and Their Control, The Ronald Press Company, New York, pp. 267-269 (1960).
Clough et al., "Floral dip: a simplified method for Agrobacterium-mediated transformation of *Arabidopsis thaliana*", The Plant Journal, 1998, pp. 735-743, vol. 16 No. 6.

\* cited by examiner

SEQUENCE LISTING

<160> NUMBER OF SEQ ID NOS: 213

<210> SEQ ID NO 1
<211> LENGTH: 544
<212> TYPE: PRT
<213> ORGANISM: Hordeum vulgaris
<220> FEATURE:
<223> OTHER INFORMATION: Sequence listing for 58633.

<400> SEQUENCE: 1

Met Ala Gly Pro Ala Gly Gly Arg Glu Leu Ser Asp Thr Pro Thr Trp
1               5                   10                  15

Ala Val Ala Val Val Cys Ala Val Met Ile Leu Val Ser Val Ala Met
            20                  25                  30

Glu His Ala Leu His Lys Leu Gly His Trp Phe His Lys Trp Arg Lys
        35                  40                  45

Lys Ala Leu Gly Glu Ala Leu Glu Lys Met Lys Ala Glu Leu Met Leu
    50                  55                  60

Val Gly Phe Ile Ser Leu Leu Ile Val Thr Gln Asp Pro Val Ser
65                  70                  75                  80

Arg Ile Cys Ile Ser Lys Glu Ala Gly Glu Lys Met Leu Pro Cys Lys
                85                  90                  95

Pro Tyr Asp Gly Ala Gly Gly Lys Gly Lys Asp Asn His Arg Arg
            100                 105                 110

Leu Leu Trp Leu Gln Gly Glu Ser Glu Thr His Arg Arg Phe Leu Ala
        115                 120                 125

Ala Pro Ala Gly Val Asp Val Cys Ala Lys Gln Gly Lys Val Ala Leu
    130                 135                 140

Met Ser Ala Gly Ser Met His Gln Leu His Ile Phe Ile Phe Val Leu
145                 150                 155                 160

Ala Val Phe His Val Leu Tyr Ser Val Val Thr Met Thr Leu Ser Arg
                165                 170                 175

Leu Lys Met Lys Gln Trp Lys Lys Trp Glu Ser Glu Thr Ala Ser Leu
            180                 185                 190

Glu Tyr Gln Phe Ala Asn Asp Pro Ser Arg Cys Arg Phe Thr His Gln
        195                 200                 205

Thr Thr Leu Val Arg Arg His Leu Gly Leu Ser Ser Thr Pro Gly Val
    210                 215                 220

Arg Trp Val Val Ala Phe Phe Arg Gln Phe Phe Thr Ser Val Thr Lys
225                 230                 235                 240

Val Asp Tyr Leu Thr Leu Arg Gln Gly Phe Ile Asn Ala His Leu Ser
                245                 250                 255

Gln Gly Asn Arg Phe Asp Phe His Lys Tyr Ile Lys Arg Ser Leu Glu
            260                 265                 270

Asp Asp Phe Lys Val Val Val Arg Ile Ser Leu Lys Leu Trp Phe Val
        275                 280                 285

Ala Val Leu Ile Leu Phe Leu Asp Phe Asp Gly Ile Gly Thr Leu Leu
    290                 295                 300

Trp Met Ser Val Val Pro Leu Val Ile Leu Leu Trp Val Gly Thr Lys
305                 310                 315                 320

Leu Glu Met Val Ile Met Glu Met Ala Gln Glu Ile His Asp Arg Glu
                325                 330                 335

Ser Val Val Lys Gly Ala Pro Ala Val Glu Pro Ser Asn Lys Tyr Phe
            340                 345                 350

Trp Phe Asn Arg Pro Asp Trp Val Leu Phe Leu Met His Leu Thr Leu

|   |   |   | 355 |   |   |   | 360 |   |   |   | 365 |   |   |

Phe Gln Asn Ala Phe Gln Met Ala His Phe Val Trp Thr Val Ala Thr
                370                 375                 380

Pro Gly Leu Lys Lys Cys Tyr His Glu Lys Met Ala Met Ser Ile Ala
385                 390                 395                 400

Lys Val Val Leu Gly Val Ala Ala Gln Ile Leu Cys Ser Tyr Ile Thr
                405                 410                 415

Phe Pro Leu Tyr Ala Leu Val Thr Gln Met Gly Ser His Met Lys Arg
                420                 425                 430

Ser Ile Phe Asp Glu Gln Thr Ala Lys Ala Leu Thr Asn Trp Arg Lys
            435                 440                 445

Met Ala Lys Glu Lys Lys Ala Arg Asp Ala Ala Met Leu Met Ala
450                 455                 460

Gln Met Gly Gly Gly Ala Thr Pro Ser Val Gly Ser Ser Pro Val His
465                 470                 475                 480

Leu Leu His Lys Ala Gly Ala Arg Ser Asp Asp Pro Gln Ser Val Pro
                485                 490                 495

Ala Ser Pro Arg Ala Glu Lys Glu Gly Gly Gly Val Gln His Pro Ala
                500                 505                 510

Arg Lys Val Pro Pro Cys Asp Gly Trp Arg Ser Ala Ser Ser Pro Ala
            515                 520                 525

Leu Asp Ala His Ile Pro Gly Ala Asp Phe Gly Phe Ser Thr Gln Arg
530                 535                 540

<210> SEQ ID NO 2
<211> LENGTH: 572
<212> TYPE: PRT
<213> ORGANISM: Sorghum bicolor
<220> FEATURE:
<223> OTHER INFORMATION: Sequence listing for 58633.

<400> SEQUENCE: 2

Met Gly Gly Asp Gly Asp Gly Thr Arg Ala Leu Asp Gln Thr Pro Thr
1               5                   10                  15

Trp Ala Val Ala Ala Val Cys Ala Val Ile Val Ala Ala Ser Ile Leu
                20                  25                  30

Leu Glu Gly Leu Leu His His Leu Gly Gln Leu Leu Asn Lys Lys Arg
            35                  40                  45

Lys Ile Ala Leu Phe Asp Ala Leu Glu Lys Val Lys Ser Glu Leu Met
        50                  55                  60

Thr Leu Gly Phe Ile Ser Leu Leu Leu Thr Val Thr Gly Arg Tyr Ile
65                  70                  75                  80

Ala His Ile Cys Ile Pro Glu Gly Ala Ala Asn Thr Met Leu Pro Cys
                85                  90                  95

Arg Arg Gln Ser Gly His Ser Glu Ala Glu Glu Pro Glu Asp His Gly
                100                 105                 110

Arg Arg His Leu Ser Glu Asp Pro Thr Asn Leu Phe Ser Cys Pro Lys
            115                 120                 125

Gly Met Val Ser Leu Val Ser Ala Asp Gly Met His Gln Leu His Ile
130                 135                 140

Phe Val Phe Phe Leu Ala Val Phe His Val Thr Phe Ser Phe Phe Thr
145                 150                 155                 160

Met Ser Leu Gly Arg Ala Lys Thr Arg Ile Trp Lys Val Trp Glu Lys
                165                 170                 175

Glu Thr Cys Ser Pro Glu Tyr Asn Tyr Leu Asn Asp Pro Ser Lys Phe

```
                180                 185                 190
Arg Leu Thr His Gln Thr Ser Phe Val Arg Gln His Ala Ser Cys Trp
            195                 200                 205

Ser Lys Ser Thr Ile Thr Leu Tyr Phe Val Ser Phe Phe Arg Gln Phe
210                 215                 220

Phe Arg Ser Val Arg Arg Thr Asp Tyr Leu Thr Leu Arg His Gly Phe
225                 230                 235                 240

Ile Ser Ala His Leu Ser Pro Gly Thr Arg Phe Asn Phe Arg Lys Tyr
                245                 250                 255

Ile Lys Arg Ser Leu Glu Asp Asp Phe Lys Thr Val Val Gly Ile Ser
            260                 265                 270

Pro Pro Leu Trp Ala Ser Ala Leu Ala Val Met Leu Phe Asn Val His
        275                 280                 285

Gly Trp His Asn Leu Phe Trp Phe Ser Thr Ile Pro Leu Val Val Ile
    290                 295                 300

Leu Ala Val Gly Thr Lys Leu Gln Ala Ile Ile Ala Met Met Ala Ile
305                 310                 315                 320

Glu Ile Thr Glu Arg His Thr Val Ile Gln Gly Met Pro Val Val Lys
                325                 330                 335

Leu Ser Asp Asp His Phe Trp Phe Gly Lys Pro Arg Leu Val Leu His
            340                 345                 350

Leu Ile His Phe Ala Ser Phe Gln Asn Ala Phe Glu Ile Thr Tyr Phe
        355                 360                 365

Phe Trp Ile Trp Tyr Glu Phe Gly Leu Arg Ser Cys Phe His Asp Asn
370                 375                 380

Phe Glu Leu Ile Ile Ala Arg Val Cys Leu Gly Ala Ile Val Gln Phe
385                 390                 395                 400

Met Cys Ser Tyr Ile Thr Leu Pro Leu Tyr Ala Leu Val Ser Gln Met
                405                 410                 415

Gly Ser Gln Met Lys Arg Thr Ile Phe Asp Glu Gln Thr Ala Lys Ala
            420                 425                 430

Leu Lys Lys Trp His Lys Ala Val Val Lys Lys Lys His His Asn Lys
        435                 440                 445

Gly Ser Ser His Asp Ser Ser Glu Thr Pro Ser Thr Asp Thr Ala Thr
    450                 455                 460

Pro Ala Arg Glu Ala Gly Glu Trp Gln Arg Leu His Asp Val Pro Val
465                 470                 475                 480

Arg His Leu His Arg Tyr Lys Thr Ile Ala His Val Gly Gly Ala Arg
                485                 490                 495

Ser Pro Leu Ser Asp Ser Asp Tyr Ser Asp Thr Asp Thr Glu Pro
            500                 505                 510

Leu Ser Ser Ser Gln Thr Arg His Leu Ile Pro Pro Ala Lys Gln Arg
        515                 520                 525

Ser Leu Asp Thr Glu Arg Ala Glu Val Arg Val Asp Val Val Glu Thr
    530                 535                 540

Val Ala Ala Val Ala Pro Arg Asp Val Leu Gln Asp Ser Phe Ser Phe
545                 550                 555                 560

Pro Arg Leu Leu Pro Arg His Val Pro Asp Lys
                565                 570

<210> SEQ ID NO 3
<211> LENGTH: 515
<212> TYPE: PRT
<213> ORGANISM: Zea mays
```

<220> FEATURE:
<223> OTHER INFORMATION: Sequence listing for 58633.

<400> SEQUENCE: 3

Met Gly Gly Gly Gly Gly Gly Asn Ser Arg Glu Leu Asp Gln Thr
1               5                   10                  15

Pro Thr Trp Ala Val Ala Ser Val Cys Gly Val Ile Val Leu Ile Ser
            20                  25                  30

Ile Leu Leu Glu Lys Gly Leu His His Val Gly Glu Phe Phe Ser His
                35                  40                  45

Arg Lys Lys Lys Ala Met Val Glu Ala Leu Glu Lys Val Lys Ala Glu
50                  55                  60

Leu Met Val Leu Gly Phe Ile Ser Leu Leu Val Phe Gly Gln Asn
65                  70                  75                  80

Tyr Ile Ile Lys Val Cys Ile Ser Asn His Ala Ala Asn Thr Met Leu
                85                  90                  95

Pro Cys Lys Leu Glu Ala Ala Val Glu Gly Lys Asp Gly His Gly
                100                 105                 110

Lys Glu Ala Ala Ala Val Val Ala Gly Lys Lys Val Ala Val Ala
            115                 120                 125

Val Pro Gly Lys Lys Lys Lys Ala Ala Ala Ala Asp His Leu
130                 135                 140

Gly Gly Val Val Asp Trp Pro Pro Tyr Tyr Ala His Asn Ala Arg
145                 150                 155                 160

Met Leu Ala Glu Ala Ser Met Ala Thr Lys Cys Pro Glu Gly Lys Val
                165                 170                 175

Pro Leu Ile Ser Ile Asn Ala Leu His Gln Leu His Ile Phe Ile Phe
                180                 185                 190

Phe Leu Ala Val Phe His Val Ser Tyr Ser Ala Ile Thr Met Ala Leu
                195                 200                 205

Gly Arg Ala Lys Ile Arg Ala Trp Lys Glu Trp Glu Lys Glu Ala Ala
210                 215                 220

Gly Gln Asp Tyr Glu Phe Ser His Asp Pro Thr Arg Phe Arg Phe Thr
225                 230                 235                 240

His Glu Thr Ser Phe Val Arg Gln His Met Asn Val Leu Asn Lys Phe
                245                 250                 255

Pro Ala Ser Phe Tyr Ile Ser Asn Phe Phe Arg Gln Phe Phe Arg Ser
                260                 265                 270

Val Arg Gln Ala Asp Tyr Cys Ala Leu Arg His Ser Phe Val Asn Val
            275                 280                 285

His Leu Ala Pro Gly Ser Lys Phe Asp Phe Gln Lys Tyr Ile Lys Arg
290                 295                 300

Ser Leu Glu Asp Asp Phe Lys Val Ile Val Gly Ile Ser Pro Pro Leu
305                 310                 315                 320

Trp Ala Ser Ala Leu Ile Phe Leu Phe Leu Asn Val Asn Gly Trp His
                325                 330                 335

Thr Met Leu Trp Ile Ser Ile Met Pro Val Val Ile Ile Leu Ser Val
                340                 345                 350

Gly Thr Lys Leu Gln Gly Ile Ile Cys Arg Met Ala Ile Asp Ile Thr
            355                 360                 365

Glu Arg His Ala Val Ile Gln Gly Ile Pro Met Val Gln Val Ser Asp
                370                 375                 380

Ser Tyr Phe Trp Phe Ala Arg Pro Thr Phe Val Leu Phe Leu Ile His
385                 390                 395                 400

-continued

```
Phe Thr Leu Phe Gln Asn Gly Phe Gln Ile Ile Tyr Phe Leu Trp Ile
                405                 410                 415
Leu Tyr Glu Tyr Gly Met Asp Ser Cys Phe Asn Asp Ser Glu Glu Phe
            420                 425                 430
Val Phe Ala Arg Leu Cys Leu Gly Val Val Gln Val Leu Cys Ser
        435                 440                 445
Tyr Val Thr Leu Pro Leu Tyr Ala Leu Val Ser Gln Met Gly Ser Thr
450                 455                 460
Met Lys Gln Ser Ile Phe Asp Glu Gln Thr Ser Lys Ala Leu Lys Asn
465                 470                 475                 480
Trp Arg Ala Gly Ala Lys Lys Ala Pro Thr Gly Gly Ser Lys His
                485                 490                 495
Gly Gly Gly Gly Ser Pro Thr Ala Gly Gly Ser Pro Thr Lys Ala Asp
            500                 505                 510
Gly Asp Ala
        515

<210> SEQ ID NO 4
<211> LENGTH: 574
<212> TYPE: PRT
<213> ORGANISM: Gossypium hirsutum
<220> FEATURE:
<223> OTHER INFORMATION: Sequence listing for 58633.

<400> SEQUENCE: 4

Met Lys Gly Val Leu Leu Trp Tyr Cys Ser Trp Val Trp Leu Thr Met
1               5                   10                  15
Glu Gly Gly Lys Val Met Gly Ala Thr Glu Ser Ser Gly Glu Arg Lys
                20                  25                  30
Leu Asp Gln Thr Pro Thr Trp Ala Val Ala Gly Val Cys Ala Val Ile
            35                  40                  45
Ile Ile Ile Ser Ile Val Leu Glu Thr Val Leu Asn Lys Leu Gly Thr
        50                  55                  60
Trp Phe Thr Glu Arg His Lys Ser Ala Leu Phe Glu Ala Leu Asp Lys
65                  70                  75                  80
Val Lys Ala Glu Leu Met Val Leu Gly Phe Ile Ser Leu Leu Leu Thr
                85                  90                  95
Phe Gly Gln Ser Tyr Ile Ala Arg Ile Cys Ile Pro Ile Asp Val Ala
            100                 105                 110
Asn Thr Met Leu Pro Cys Lys Ser Asp Ser Glu Lys Asp Thr Ser Glu
        115                 120                 125
Ser Ser Glu Glu Glu His Arg Arg Arg Leu Leu Trp Phe Asp Arg Arg
130                 135                 140
Ser Leu Ser Thr Ile Ser Thr Ala Pro Lys Cys Lys Glu Gly His Glu
145                 150                 155                 160
Pro Leu Ile Ser Val Glu Gly Leu His Glu Leu His Ile Leu Ile Phe
                165                 170                 175
Phe Leu Ala Val Phe His Val Leu Tyr Ser Phe Val Thr Met Met Leu
            180                 185                 190
Gly Arg Leu Lys Ile Arg Gly Trp Lys Val Trp Glu Gln Glu Thr Leu
        195                 200                 205
Ser His Asp Tyr Glu Phe Ser Asn Asp Pro Ser Arg Phe Arg Leu Thr
    210                 215                 220
His Glu Thr Ser Phe Val Lys Ala His Thr Ser Phe Trp Thr Arg Ile
225                 230                 235                 240
```

```
Pro Phe Phe Phe Tyr Ile Gly Cys Phe Phe Arg Gln Phe Phe Arg Ser
            245                 250                 255

Val Gly Arg Val Asp Tyr Leu Thr Leu Arg Asn Gly Phe Ile Asn Val
            260                 265                 270

His Leu Ala Pro Gly Ser Lys Phe Asn Phe Gln Lys Tyr Ile Lys Arg
            275                 280                 285

Ser Leu Glu Asp Asp Phe Lys Ile Val Val Gly Val Ser Pro Val Leu
            290                 295                 300

Trp Ala Ser Phe Val Val Tyr Leu Leu Leu Asn Val Arg Gly Trp His
305                 310                 315                 320

Ala Leu Phe Trp Ala Ser Leu Val Pro Val Ile Ile Leu Ala Val
            325                 330                 335

Gly Thr Lys Leu Gln Ala Ile Leu Thr Lys Met Ala Leu Glu Ile Thr
            340                 345                 350

Glu Arg His Ala Val Val Gln Gly Met Pro Leu Val Gln Ala Ser Asp
            355                 360                 365

Gln Tyr Phe Trp Phe Gly Arg Pro Gln Leu Val Leu His Leu Ile His
            370                 375                 380

Phe Ala Leu Phe Gln Asn Ala Phe Gln Ile Thr Tyr Phe Leu Trp Ile
385                 390                 395                 400

Trp Tyr Ala Phe Gly Ile Lys Ser Cys Phe His Ala Asp Phe Thr Leu
            405                 410                 415

Ala Ile Ile Lys Val Ser Leu Gly Val Gly Val Leu Cys Leu Cys Ser
            420                 425                 430

Tyr Ile Thr Leu Pro Leu Tyr Ala Leu Val Thr Gln Met Gly Leu Arg
            435                 440                 445

Met Lys Lys Ser Ile Phe Asp Glu Gln Thr Ser Lys Ala Leu Lys Lys
            450                 455                 460

Trp His Met Ala Ala Lys Lys Arg Gly Asn Ala Arg Lys Ser Pro Thr
465                 470                 475                 480

Arg Ala Leu Gly Gly Ser Thr Ser Pro Ser Ser Thr Leu His Ser Thr
            485                 490                 495

Gly His Ser Leu His Arg Tyr Lys Thr Thr Gly His Ser Thr His Ser
            500                 505                 510

Ser Tyr Asn Tyr Glu Asp Arg Asp Met Ser Asp Leu Glu Ala Glu Pro
            515                 520                 525

Leu Thr Pro Thr Ser Thr Asn Leu Ile Ile Arg Val Asp His Asp Glu
            530                 535                 540

Gln Ala Thr Glu Ile Thr Glu Thr Tyr His Thr Glu Ala Arg Asn Glu
545                 550                 555                 560

Asp Asp Phe Ser Phe Ala Lys Pro Ala Pro Lys Glu Pro
            565                 570

<210> SEQ ID NO 5
<211> LENGTH: 598
<212> TYPE: PRT
<213> ORGANISM: Glycine max
<220> FEATURE:
<223> OTHER INFORMATION: Sequence listing for 58633.

<400> SEQUENCE: 5

Met Tyr Ser Ser Lys Phe Arg Lys Leu Phe Cys Ser Val Leu Phe Ser
1               5                   10                  15

Trp Leu Cys Phe Gly Gly Leu Ala Met Ala Ala Gly Glu Ser Ser Ser
            20                  25                  30
```

-continued

```
Ser Ser Arg Asp Leu Asp Gln Thr Pro Thr Trp Ala Val Ala Val
        35                  40                  45

Cys Thr Val Phe Ile Leu Val Ser Ile Ala Leu Glu Lys Ser Leu His
    50                  55                  60

Lys Val Gly Thr Trp Leu Gly Gln Lys Lys Lys Ala Leu Leu Glu
65                  70                  75                  80

Ala Leu Glu Lys Val Lys Ala Glu Leu Met Ile Leu Gly Phe Ile Ser
                85                  90                  95

Leu Leu Leu Thr Phe Gly Gln Ser Tyr Ile Val Arg Ile Cys Ile Pro
            100                 105                 110

Glu Lys Leu Ala Asp Asn Met Leu Pro Cys Pro Tyr Lys Tyr Lys Glu
            115                 120                 125

Asp Lys Lys Ala Ser Asp Ser Glu Glu Glu His Arg Arg Lys Leu Leu
130                 135                 140

Ser Tyr Glu Arg Arg Tyr Leu Ala Ala Asp Thr Thr Ser Phe Lys Cys
145                 150                 155                 160

Ser Arg Glu Gly His Glu Pro Leu Leu Ser Val Asn Gly Leu His Gln
                165                 170                 175

Leu His Ile Leu Val Phe Phe Leu Ala Val Ile His Val Leu Tyr Ser
            180                 185                 190

Ala Ile Thr Met Met Leu Gly Arg Leu Lys Ile Arg Gly Trp Lys Ala
            195                 200                 205

Trp Glu Ala Glu Thr Ser Thr His Asn Tyr Glu Phe Ala Asn Ala Ala
        210                 215                 220

Ser Arg Phe Arg Leu Thr His Glu Thr Ser Phe Val Arg Ala His Ser
225                 230                 235                 240

Ser Phe Leu Thr Arg Ile Pro Ile Phe Phe Tyr Ile Arg Cys Phe Phe
                245                 250                 255

Arg Gln Phe Tyr Arg Ser Val Asn Lys Thr Asp Tyr Leu Thr Leu Arg
            260                 265                 270

Asn Gly Phe Ile Thr Val His Leu Ala Pro Gly Ser Lys Phe Asn Phe
            275                 280                 285

Gln Lys Tyr Ile Lys Arg Ser Leu Glu Asp Asp Phe Lys Val Val Val
        290                 295                 300

Gly Val Ser Pro Ile Leu Trp Ala Ser Val Val Tyr Leu Leu Ile
305                 310                 315                 320

Asn Val Asn Gly Trp His Thr Val Leu Trp Ala Ala Leu Ile Pro Val
                325                 330                 335

Val Ile Ile Leu Ala Val Gly Thr Lys Leu Gln Ala Ile Leu Ala Asn
            340                 345                 350

Met Ala Leu Glu Ile Thr Glu Arg His Ala Val Gln Gly Met Pro
            355                 360                 365

Leu Val Gln Gly Ser Asp Lys Tyr Phe Trp Phe Gly Gln Pro Gln Leu
        370                 375                 380

Val Leu His Leu Ile His Phe Ala Leu Phe Gln Asn Ala Phe Gln Ile
385                 390                 395                 400

Thr Tyr Ile Leu Trp Ile Trp Tyr Ser Phe Gly Leu Arg Asn Cys Phe
                405                 410                 415

Arg Thr Asp Tyr Lys Leu Ala Val Val Lys Val Ala Leu Gly Ile Leu
            420                 425                 430

Met Leu Cys Leu Cys Ser Tyr Ile Thr Leu Pro Leu Tyr Ala Leu Val
            435                 440                 445
```

```
Thr Gln Met Gly Ser Arg Met Lys Thr Ala Ile Phe Asp Glu Gln Thr
    450                 455                 460

Asn Lys Ala Leu Lys Lys Trp His Met Ala Ala Lys Lys Lys Gln Gly
465                 470                 475                 480

Gly Ala Val Thr Leu Gly Lys Ser Ser Ala Arg Ile Met Asp Gly Ser
                485                 490                 495

Pro Ile Gly Asn Ser Ser Thr Val His Ser Thr Gly Pro Thr Leu His
            500                 505                 510

Arg Phe Lys Thr Thr Gly His Ser Thr Arg Ser Ser Thr Ala Tyr
        515                 520                 525

Glu Asp Gln Asp Gln Asp His Glu Tyr Glu Ser Asp Gly Val Glu Leu
530                 535                 540

Ser Pro Leu Ala Ser Gln Thr Thr Ser Phe Ile Val Arg Val Asp His
545                 550                 555                 560

Gly Asp Gln Gln Gln Ala Glu His Arg Gln Asp Ser Glu Gly Glu Thr
                565                 570                 575

Asn Ser Ser Glu Gly Glu Phe Ser Phe Val Lys Pro Asp Pro Val
            580                 585                 590

Glu Ile Arg Thr Thr Thr
        595
```

<210> SEQ ID NO 6
<211> LENGTH: 599
<212> TYPE: PRT
<213> ORGANISM: Glycine max
<220> FEATURE:
<223> OTHER INFORMATION: Sequence listing for 58633.

<400> SEQUENCE: 6

```
Met Tyr Ser Ser Lys Phe Arg Lys Leu Phe Cys Ser Val Leu Phe Ser
1               5                   10                  15

Trp Leu Cys Phe Gly Gly Leu Ala Met Ala Ala Gly Glu Ser Ser Ser
            20                  25                  30

Ser Ser Arg Asp Leu Asp Gln Thr Pro Thr Trp Ala Val Ala Ala Val
        35                  40                  45

Cys Thr Val Phe Ile Leu Val Ser Ile Ala Leu Glu Lys Ser Leu His
    50                  55                  60

Lys Val Gly Thr Trp Leu Gly Gln Lys Lys Lys Ala Leu Leu Glu
65                  70                  75                  80

Ala Leu Glu Lys Val Lys Ala Glu Leu Met Ile Leu Gly Phe Ile Ser
                85                  90                  95

Leu Leu Leu Thr Phe Gly Gln Ser Tyr Ile Val Arg Ile Cys Ile Pro
            100                 105                 110

Glu Lys Leu Ala Asp Asn Met Leu Pro Cys Pro Tyr Lys Tyr Lys Glu
        115                 120                 125

Asp Lys Lys Ala Ser Asp Ser Glu Glu Glu His Arg Arg Lys Leu Leu
130                 135                 140

Ser Tyr Glu Arg Arg Tyr Leu Ala Ala Asp Thr Thr Ser Phe Lys Cys
145                 150                 155                 160

Ser Arg Glu Gly His Glu Pro Leu Leu Ser Val Asn Gly Leu His Gln
                165                 170                 175

Leu His Ile Leu Val Phe Phe Leu Ala Ser His Ile His Val Leu Tyr
            180                 185                 190

Ser Ala Ile Thr Met Met Leu Gly Arg Leu Lys Ile Arg Gly Trp Lys
        195                 200                 205
```

```
Ala Trp Glu Ala Glu Thr Ser Thr His Asn Tyr Glu Phe Ala Asn Ala
            210                 215                 220

Ala Ser Arg Phe Arg Leu Thr His Glu Thr Ser Phe Val Arg Ala His
225                 230                 235                 240

Ser Ser Phe Leu Thr Arg Ile Pro Ile Phe Phe Tyr Ile Arg Cys Phe
                245                 250                 255

Phe Arg Gln Phe Tyr Arg Ser Val Asn Lys Thr Asp Tyr Leu Thr Leu
            260                 265                 270

Arg Asn Gly Phe Ile Thr Val His Leu Ala Pro Gly Ser Lys Phe Asn
                275                 280                 285

Phe Gln Lys Tyr Ile Lys Arg Ser Leu Glu Asp Asp Phe Lys Val Val
290                 295                 300

Val Gly Val Ser Pro Ile Leu Trp Ala Ser Val Val Tyr Leu Leu
305                 310                 315                 320

Ile Asn Val Asn Gly Trp His Thr Val Leu Trp Ala Ala Leu Ile Pro
                325                 330                 335

Val Val Ile Ile Leu Ala Val Gly Thr Lys Leu Gln Ala Ile Leu Ala
                340                 345                 350

Asn Met Ala Leu Glu Ile Thr Glu Arg His Ala Val Val Gln Gly Met
            355                 360                 365

Pro Leu Val Gln Gly Ser Asp Lys Tyr Phe Trp Phe Gly Gln Pro Gln
370                 375                 380

Leu Val Leu His Leu Ile His Phe Ala Leu Phe Gln Asn Ala Phe Gln
385                 390                 395                 400

Ile Thr Tyr Ile Leu Trp Ile Trp Tyr Ser Phe Gly Leu Arg Asn Cys
                405                 410                 415

Phe Arg Thr Asp Tyr Lys Leu Ala Val Val Lys Val Ala Leu Gly Ile
            420                 425                 430

Leu Met Leu Cys Leu Cys Ser Tyr Ile Thr Leu Pro Leu Tyr Ala Leu
            435                 440                 445

Val Thr Gln Met Gly Ser Arg Met Lys Thr Ala Ile Phe Asp Glu Gln
            450                 455                 460

Thr Asn Lys Ala Leu Lys Lys Trp His Met Ala Ala Lys Lys Lys Gln
465                 470                 475                 480

Gly Gly Ala Val Thr Leu Gly Lys Ser Ser Ala Arg Ile Met Asp Gly
                485                 490                 495

Ser Pro Ile Gly Asn Ser Ser Thr Val His Ser Thr Gly Pro Thr Leu
                500                 505                 510

His Arg Phe Lys Thr Thr Gly His Ser Thr Arg Ser Ser Thr Ala
                515                 520                 525

Tyr Glu Asp Gln Asp Gln Asp His Glu Tyr Glu Ser Asp Gly Val Glu
            530                 535                 540

Leu Ser Pro Leu Ala Ser Gln Thr Thr Ser Phe Ile Val Arg Val Asp
545                 550                 555                 560

His Gly Asp Gln Gln Ala Glu His Arg Gly Asp Ser Glu Gly Glu
                565                 570                 575

Thr Asn Ser Ser Ser Glu Gly Glu Phe Ser Phe Val Lys Pro Asp Pro
            580                 585                 590

Val Glu Ile Arg Thr Thr Thr
                595

<210> SEQ ID NO 7
<211> LENGTH: 569
<212> TYPE: PRT
```

<213> ORGANISM: Cucumis sativus
<220> FEATURE:
<223> OTHER INFORMATION: Sequence listing for 58633.

<400> SEQUENCE: 7

```
Met Ser Val Phe Cys Leu Cys Phe Cys Leu Leu Leu Thr Gly Ala Ala
1               5                   10                  15

Ala Ser Gly Gly Asp Gly Ser His Ser Arg Asp Leu Asp Asn Thr
            20                  25                  30

Pro Thr Trp Ala Val Ala Ala Val Cys Phe Phe Val Leu Ile Ser
        35                  40                  45

Ile Val Leu Glu Asn Val Ile His Lys Leu Gly Thr Trp Leu Thr Lys
50                  55                  60

Lys His Lys Ser Ser Leu Tyr Glu Ala Leu Glu Lys Val Lys Ala Glu
65                  70                  75                  80

Leu Met Ile Leu Gly Phe Ile Ser Leu Leu Leu Thr Phe Ala Gln Ala
                85                  90                  95

Tyr Ile Val Gln Ile Cys Ile Pro Pro Ala Ile Ala Asn Ser Met Leu
            100                 105                 110

Pro Cys Arg Arg Glu Glu Lys Asn Ala Ser Thr Asp Glu Asp Glu His
        115                 120                 125

His Arg Arg Leu Gln Trp Leu Ile Arg Arg Ser Leu Ala Gly Gly His
130                 135                 140

Asn Val Val Ser Cys Glu Asp Gly Lys Val Ser Leu Ile Ser Ile Asp
145                 150                 155                 160

Gly Leu His Gln Leu His Ile Leu Ile Phe Phe Leu Ala Val Phe His
                165                 170                 175

Val Leu Phe Ser Val Ile Thr Met Thr Leu Gly Arg Ile Lys Ile Arg
            180                 185                 190

Gly Trp Lys Glu Trp Glu Gln Glu Thr Ser Thr His Asn Tyr Glu Phe
        195                 200                 205

Phe Asn Asp Pro Ala Arg Phe Arg Leu Thr His Glu Thr Ser Phe Val
210                 215                 220

Lys Ala His Thr Ser Phe Trp Thr Arg Leu Pro Phe Phe Phe Tyr Ile
225                 230                 235                 240

Ser Cys Phe Phe Arg Gln Phe Tyr Gly Ser Val Ser Lys Ala Asp Tyr
                245                 250                 255

Leu Thr Leu Arg Asn Gly Phe Ile Thr Val His Leu Ala Pro Gly Ser
            260                 265                 270

Lys Phe Asn Phe Gln Arg Tyr Ile Lys Arg Ser Leu Glu Asp Asp Phe
        275                 280                 285

Lys Val Val Val Gly Val Ser Pro Phe Leu Trp Ser Ser Phe Val Ile
290                 295                 300

Phe Leu Leu Leu Asn Leu Ser Gly Trp His Thr Leu Phe Trp Ala Ser
305                 310                 315                 320

Phe Ile Pro Leu Leu Ile Leu Ala Val Gly Ser Lys Leu Gln Ala
                325                 330                 335

Ile Leu Thr Arg Met Ala Leu Glu Ile Ser Glu Lys His Ala Val Val
            340                 345                 350

Gln Gly Ile Pro Leu Val Gln Gly Ser Asp Lys Tyr Phe Trp Phe Gly
        355                 360                 365

Arg Pro Gln Leu Ile Leu His Leu Met His Phe Ser Leu Phe Gln Asn
370                 375                 380

Ala Phe Gln Thr Thr Tyr Ile Leu Ser Thr Leu Tyr Ser Phe Gly Leu
```

```
                385                 390                 395                 400
Asn Ser Cys Phe Phe Asp Gly His Ile Leu Thr Ile Ile Lys Val Gly
                    405                 410                 415

Leu Gly Val Val Ala Leu Phe Leu Cys Ser Tyr Val Thr Leu Pro Ile
                420                 425                 430

Tyr Ala Leu Val Asn Gln Met Gly Ser Gly Met Lys Arg Ser Ile Phe
                435                 440                 445

Asp Glu Gln Thr Ser Lys Ala Leu Met Lys Trp Gln Glu Thr Ala Lys
            450                 455                 460

Lys Lys Arg Ala Lys Arg Ala Ser Ala Thr Lys Thr Leu Gly Gly Ser
465                 470                 475                 480

Ser Asn Ala Ser Pro Leu His Ser Leu Arg Arg Phe Lys Thr Thr Gly
                    485                 490                 495

His Ser Ile Arg Val Pro Thr Tyr Glu Asp Leu Glu Ser Asp Tyr
                500                 505                 510

Glu Gly Asp Pro Leu Ala Thr Pro Thr Gln Ala Ser Thr Ser Glu Ser
                515                 520                 525

Ile Asn Val Asp Val Lys Asp Gly Asp Glu Ile Gln Gln Ile Ala Glu
            530                 535                 540

Thr Glu Gln Pro His Ser Thr Ile Gln Thr Lys Gly Asp Glu Phe
545                 550                 555                 560

Ser Phe Ile Lys Pro Ala Thr Leu Gly
                    565

<210> SEQ ID NO 8
<211> LENGTH: 532
<212> TYPE: PRT
<213> ORGANISM: Cucumis sativus
<220> FEATURE:
<223> OTHER INFORMATION: Sequence listing for 58633.

<400> SEQUENCE: 8

Met Gly Gly Gly Ala Gly Ala Gly Gly Pro Ser Arg Glu Leu Asp Gln
1               5                   10                  15

Thr Pro Thr Trp Ala Val Ala Ala Val Cys Ala Val Ile Ile Leu Ile
                20                  25                  30

Ser Ile Ile Leu Glu Lys Val Leu His Met Val Gly Glu Ile Phe Gln
                35                  40                  45

Lys Arg Lys Lys Lys Ala Leu Tyr Glu Ala Leu Glu Lys Val Lys Gly
            50                  55                  60

Glu Leu Met Val Leu Gly Phe Ile Ser Leu Leu Leu Thr Phe Gly Gln
65              70                  75                  80

Asn Tyr Ile Ala Lys Val Cys Ile Pro Ser Lys Tyr Glu Asn Thr Met
                85                  90                  95

Leu Pro Cys Pro Phe Arg Gly Ser Ser Thr Thr Leu Pro Lys Ser Ser
                    100                 105                 110

His His Ala Glu Pro Asp Asp Asp Glu Glu Thr Ser Asp His His Arg
                115                 120                 125

Arg Leu Leu Trp Tyr Glu His Arg Arg Leu Gly Gly Gly Ser Val
            130                 135                 140

Glu Gly Cys Lys Pro Gly Tyr Thr Gln Leu Ile Ser Leu Asn Gly Leu
145                 150                 155                 160

His Gln Ile His Ile Phe Ile Phe Leu Ala Val Leu His Val Val
                    165                 170                 175

Phe Ser Ala Ile Thr Met Thr Leu Gly Arg Leu Lys Ile Arg Ala Trp
```

```
                180             185             190
Lys Val Trp Glu Arg Gln Thr Glu Gln Glu His Asp Ala Met Asn Asp
            195                 200                 205

Pro Thr Arg Phe Arg Leu Thr His Glu Thr Ser Phe Val Arg Asp His
        210                 215                 220

Ser Ser Phe Trp Thr Lys Thr Pro Leu Ser Phe Tyr Phe Val Cys Phe
225                 230                 235                 240

Trp Arg Gln Phe Phe Arg Ser Val Ser Arg Pro Asp Tyr Leu Ser Leu
                245                 250                 255

Arg His Gly Phe Val Thr Val His Leu Ala Pro Gly Ser Lys Phe Asp
                260                 265                 270

Phe Gln Lys Tyr Ile Lys Arg Ser Leu Glu Asp Phe Lys Val Val
        275                 280                 285

Val Gly Ile Ser Pro Leu Leu Trp Ala Ser Met Val Leu Phe Leu Leu
        290                 295                 300

Leu Asn Val Asn Gly Trp Gln Val Met Phe Trp Val Ser Ile Phe Pro
305                 310                 315                 320

Leu Val Val Ile Leu Ala Val Gly Thr Lys Leu Gln Gly Ile Ile Thr
                325                 330                 335

Gln Met Ala Leu Glu Ile Lys Glu Arg His Ala Val Val Gln Gly Ile
                340                 345                 350

Pro Leu Val Gln Val Ser Asp Arg His Phe Trp Phe Ser Trp Pro Ile
            355                 360                 365

Leu Val Leu Tyr Leu Ile His Tyr Val Leu Phe Gln Tyr Glu Phe Gly
        370                 375                 380

Leu Arg Ser Cys Phe His Asp Asn Phe Asp Leu Ile Ile Ala Arg Val
385                 390                 395                 400

Gly Leu Gly Val Gly Val Gln Ile Leu Cys Ser Tyr Ile Thr Leu Pro
                405                 410                 415

Leu Tyr Ala Leu Val Thr Gln Met Gly Ser Thr Met Lys Lys Ser Ile
            420                 425                 430

Phe Asp Glu Gln Thr Ser Lys Ala Leu Lys Gln Trp His Arg Ser Ala
        435                 440                 445

Leu Lys Lys Lys Asn Glu Gly Gly Lys Pro Glu Pro Thr Pro Met Arg
        450                 455                 460

Thr Leu Gly Gly Ala Val Val Gly Gly Ser Pro Pro Glu Ser Pro
465                 470                 475                 480

Ile Gln Gln Pro Leu His Asp Gln Phe Gln His Gln Thr Met Thr Gln
                485                 490                 495

Ser Ser Pro Thr Asp Val Glu Ala Ser Ala Val Pro Ser Val Asn Ile
            500                 505                 510

Met Thr Thr Val Asp Leu His Gln Gln Gln Asn Tyr Ser Asn Arg
            515                 520                 525

Asp Leu Leu Arg
    530
```

<210> SEQ ID NO 9
<211> LENGTH: 560
<212> TYPE: PRT
<213> ORGANISM: Cucumis sativus
<220> FEATURE:
<223> OTHER INFORMATION: Sequence listing for 58633.

<400> SEQUENCE: 9

Met Leu Leu Val Val Tyr Tyr Leu Cys Leu Ser Leu Leu Trp Gly Lys

-continued

```
1               5                   10                  15
Ser Trp Gly Ala Pro Ala Ser Asp Gly Thr Thr Arg Glu Leu Asp Gln
                20                  25                  30
Thr Pro Thr Trp Ala Val Ala Gly Val Cys Ala Ile Ile Ile Leu Ile
            35                  40                  45
Ser Ile Ala Leu Glu Lys Leu Leu His Lys Ala Gly Thr Trp Leu Thr
        50                  55                  60
Glu Lys His Lys Arg Ala Leu Phe Glu Ala Leu Glu Lys Val Lys Ala
65                  70                  75                  80
Glu Leu Met Ile Leu Gly Phe Ile Ser Leu Leu Thr Phe Gly Gln
                85                  90                  95
Asn Tyr Ile Ile Lys Ile Cys Ile Pro Thr Lys Val Ala Asn Thr Met
                100                 105                 110
Leu Pro Cys Ala Ala Lys Glu Asp Lys Leu Glu Lys Gly Asp Glu Gly
            115                 120                 125
Glu His His Arg Arg Leu Leu Met Tyr Glu Arg Arg Phe Leu Ala Ala
        130                 135                 140
Ala Gly Gly Ala Val Ser Cys Lys Glu Gly His Val Pro Leu Ile Ser
145                 150                 155                 160
Ile Ser Gly Leu His Gln Leu His Leu Phe Ile Phe Phe Leu Ala Val
                165                 170                 175
Phe His Val Val Tyr Ser Ala Ile Thr Met Met Leu Gly Arg Leu Lys
                180                 185                 190
Ile Arg Gly Trp Lys Ala Trp Glu Glu Glu Thr Ser Thr His Asn Tyr
            195                 200                 205
Glu Phe Ser Asn Asp Asn Ala Arg Phe Arg Leu Thr His Glu Thr Ser
        210                 215                 220
Phe Val Lys Ala His Thr Ser Phe Trp Thr Lys Leu Pro Val Phe Phe
225                 230                 235                 240
Tyr Ile Gly Cys Phe Phe Arg Gln Phe Lys Ser Val Gly Lys Ala
                245                 250                 255
Asp Tyr Leu Ala Leu Arg Asn Gly Phe Ile Ala Val His Leu Ala Pro
            260                 265                 270
Gly Ser Lys Phe Asp Phe Gln Lys Tyr Ile Lys Arg Ser Leu Glu Asp
        275                 280                 285
Asp Phe Lys Ile Ile Val Gly Val Ser Pro Val Leu Trp Thr Ser Phe
290                 295                 300
Val Val Phe Leu Leu Ile Asn Val Tyr Gly Trp Gln Ala Leu Phe Trp
305                 310                 315                 320
Ser Ser Leu Val Pro Val Ile Ile Leu Ala Val Gly Thr Lys Leu
            325                 330                 335
Gln Gly Val Met Thr Lys Met Ala Leu Glu Ile Thr Glu Arg His Ala
        340                 345                 350
Val Val Gln Gly Ile Pro Leu Val Gln Ala Ser Asp Lys Tyr Phe Trp
            355                 360                 365
Phe Gly Lys Pro Gln Leu Val Leu Tyr Leu Ile His Phe Ala Leu Phe
        370                 375                 380
Ser Asn Ala Phe Gln Ile Thr Tyr Phe Phe Trp Ile Trp Tyr Ser Phe
385                 390                 395                 400
Gly Leu Lys Ser Cys Phe His Thr Asp Phe Lys Leu Ala Ile Ile Lys
            405                 410                 415
Val Gly Leu Gly Val Gly Val Leu Cys Leu Cys Ser Tyr Ile Thr Leu
            420                 425                 430
```

-continued

```
Pro Leu Tyr Ala Leu Val Thr Gln Met Gly Thr Arg Met Lys Lys Ser
        435                 440                 445

Ile Phe Asp Glu Gln Thr Ser Lys Ala Leu Lys Lys Trp His Met Ala
    450                 455                 460

Val Lys Lys Arg His Gly Lys Ser Pro Thr Arg Lys Leu Gly Ser Pro
465                 470                 475                 480

Ser Ser Ser Pro Ile His Pro Ser Ser Gly Tyr Ala Leu His Arg Phe
                    485                 490                 495

Lys Thr Thr Gly His Ser Asn Arg Ser Ser Met Tyr Asp Glu Asn Asp
                500                 505                 510

Ala Ser Asp Tyr Glu Val Asp Thr Pro Asn Phe Thr Val Arg Ile Asp
                515                 520                 525

His Gly Asp Glu His Gln Ala Glu Ile Ile Glu Pro Gln His Thr Glu
                530                 535                 540

Lys Arg Asn Glu Asp Asp Phe Ser Phe Val Lys Pro Gly Pro Thr Lys
545                 550                 555                 560

<210> SEQ ID NO 10
<211> LENGTH: 530
<212> TYPE: PRT
<213> ORGANISM: Cucumis sativus
<220> FEATURE:
<223> OTHER INFORMATION: Sequence listing for 58633.

<400> SEQUENCE: 10

Met Ser Val Phe Cys Leu Cys Phe Cys Leu Leu Thr Gly Ala Ala
1               5                   10                  15

Ala Ser Gly Gly Asp Gly Gly Ser His Ser Arg Asp Leu Asp Asn Thr
                20                  25                  30

Pro Thr Trp Ala Val Ala Ala Val Cys Phe Phe Phe Val Leu Ile Ser
            35                  40                  45

Ile Val Leu Glu Asn Val Ile His Lys Leu Gly Thr Trp Leu Thr Lys
        50                  55                  60

Lys His Lys Ser Ser Leu Tyr Glu Ala Leu Glu Lys Val Lys Ala Glu
65                  70                  75                  80

Leu Met Ile Leu Gly Phe Ile Ser Leu Leu Leu Thr Phe Ala Gln Ala
                85                  90                  95

Tyr Ile Val Gln Ile Cys Ile Pro Pro Ala Ile Ala Asn Ser Met Leu
                100                 105                 110

Pro Cys Arg Arg Glu Glu Lys Asn Ala Ser Thr Asp Glu Asp Glu His
            115                 120                 125

His Arg Arg Leu Gln Trp Leu Ile Arg Arg Ser Leu Ala Gly Gly His
        130                 135                 140

Asn Val Val Ser Cys Glu Asp Ile Arg Gly Trp Lys Glu Trp Glu Gln
145                 150                 155                 160

Glu Thr Ser Thr His Asn Tyr Glu Phe Phe Asn Asp Pro Ala Arg Phe
                165                 170                 175

Arg Leu Thr His Glu Thr Ser Phe Val Lys Ala His Thr Ser Phe Trp
            180                 185                 190

Thr Arg Leu Pro Phe Phe Phe Tyr Ile Ser Cys Phe Phe Arg Gln Phe
        195                 200                 205

Tyr Gly Ser Val Ser Lys Ala Asp Tyr Leu Thr Leu Arg Asn Gly Phe
    210                 215                 220

Ile Thr Val His Leu Ala Pro Gly Ser Lys Phe Asn Phe Gln Arg Tyr
225                 230                 235                 240
```

-continued

```
Ile Lys Arg Ser Leu Glu Asp Phe Lys Val Val Gly Val Ser
            245                 250                 255

Pro Phe Leu Trp Ser Ser Phe Val Ile Phe Leu Leu Asn Leu Ser
            260                 265                 270

Gly Trp His Thr Leu Phe Trp Ala Ser Phe Ile Pro Leu Leu Ile Ile
            275                 280                 285

Leu Ala Val Gly Ser Lys Leu Gln Ala Ile Leu Thr Arg Met Ala Leu
            290                 295                 300

Glu Ile Ser Glu Lys His Ala Val Val Gln Gly Ile Pro Leu Val Gln
305                 310                 315                 320

Gly Ser Asp Lys Tyr Phe Trp Phe Gly Arg Pro Gln Leu Ile Leu His
            325                 330                 335

Leu Met His Phe Ser Leu Phe Gln Asn Ala Phe Gln Thr Thr Tyr Ile
            340                 345                 350

Leu Ser Thr Leu Tyr Ser Phe Gly Leu Asn Ser Cys Phe Phe Asp Gly
            355                 360                 365

His Ile Leu Thr Ile Ile Lys Val Gly Leu Gly Val Val Ala Leu Phe
            370                 375                 380

Leu Cys Ser Tyr Val Thr Leu Pro Ile Tyr Ala Leu Val Asn Gln Met
385                 390                 395                 400

Gly Ser Gly Met Lys Arg Ser Ile Phe Asp Glu Gln Thr Ser Lys Ala
            405                 410                 415

Leu Met Lys Trp Gln Glu Thr Ala Lys Lys Arg Ala Lys Arg Ala
            420                 425                 430

Ser Ala Thr Lys Thr Leu Gly Gly Ser Ser Asn Ala Ser Pro Leu His
            435                 440                 445

Ser Leu Arg Arg Phe Lys Thr Thr Gly His Ser Ile Arg Val Pro Thr
450                 455                 460

Tyr Glu Asp Leu Glu Ser Ser Asp Tyr Glu Gly Asp Pro Leu Ala Thr
465                 470                 475                 480

Pro Thr Gln Ala Ser Thr Ser Glu Ser Ile Asn Val Asp Val Lys Asp
            485                 490                 495

Gly Asp Glu Ile Gln Gln Ile Ala Glu Thr Gln Pro His Ser Thr
            500                 505                 510

Ile Gln Thr Lys Glu Gly Asp Glu Phe Ser Phe Ile Lys Pro Ala Thr
            515                 520                 525

Leu Gly
530

<210> SEQ ID NO 11
<211> LENGTH: 482
<212> TYPE: PRT
<213> ORGANISM: Vitis vinifera
<220> FEATURE:
<223> OTHER INFORMATION: Sequence listing for 58633.

<400> SEQUENCE: 11

Met Ser Gly Gly Gly Ala Glu Glu Thr Thr Leu Glu Tyr Thr Pro
1               5                   10                  15

Thr Trp Val Val Ala Val Val Cys Thr Val Ile Val Ala Ile Ser Leu
            20                  25                  30

Ala Val Glu Arg Phe Leu His Phe Leu Gly Lys Tyr Leu Lys Lys Lys
            35                  40                  45

Asn Gln Asn Pro Leu Phe Gln Ala Leu Gln Lys Val Lys Glu Glu Leu
50                  55                  60
```

```
Met Leu Leu Gly Phe Ile Ser Leu Leu Leu Thr Val Phe Gln Asn Leu
 65                  70                  75                  80

Ile Thr Lys Phe Cys Val Pro Lys His Val Ser His Leu Leu Pro
                 85                  90                  95

Cys Lys Leu Pro Glu Lys His Ala Thr Gln Ser Leu Ser His Trp
                100                 105                 110

Ala Leu Gly Arg His Leu Leu Ser Ser Ala Pro Ser Ser Cys Ser Asn
                115                 120                 125

Glu Lys Val Pro Phe Leu Ser Leu Glu Ala Leu His His Leu His Ile
            130                 135                 140

Phe Ile Phe Val Leu Ala Ile Val His Val Thr Phe Cys Val Leu Thr
145                 150                 155                 160

Ile Ile Phe Gly Gly Ala Lys Ile His Gln Trp Lys Leu Trp Glu Asp
                165                 170                 175

Ser Ile Ala Lys Asp Asn Tyr Asp Thr Glu Glu Val Leu Lys Lys Lys
                180                 185                 190

Ile Thr His Val His Asp His Ala Phe Ile Lys Asp Arg Phe Leu Gly
            195                 200                 205

Ile Gly Lys Asn Ser Ala Val Met Ser Trp Val His Ser Phe Lys
                210                 215                 220

Gln Phe Tyr Ala Ser Val Thr Lys Ser Asp Tyr Leu Thr Leu Arg Leu
225                 230                 235                 240

Gly Phe Ile Met Met His Cys Arg Gln Asn Arg Lys Phe Asn Phe His
                245                 250                 255

Lys Tyr Met Val Arg Ala Leu Glu Asp Asp Phe Lys Lys Val Val Gly
                260                 265                 270

Ile Ser Trp Tyr Leu Trp Ile Phe Val Val Phe Leu Leu Asn
                275                 280                 285

Val Asp Gly Trp His Thr Tyr Phe Trp Ile Ala Phe Ile Pro Phe Ile
            290                 295                 300

Leu Leu Leu Ala Val Gly Ala Lys Leu Glu His Val Ile Ser Gln Leu
305                 310                 315                 320

Ala His Glu Val Ala Glu Lys His Ala Ala Ile Glu Gly Glu Leu Val
                325                 330                 335

Val Gln Pro Ser Asp Asp His Phe Trp Phe His Arg Pro Arg Ile Val
                340                 345                 350

Leu Phe Leu Ile His Ile Ile Leu Phe Gln Asn Ser Phe Glu Met Ala
            355                 360                 365

Phe Phe Phe Trp Ile Leu Phe Thr Tyr Gly Phe Asp Ser Cys Ile Met
            370                 375                 380

Gly Lys Val Gln Tyr Ile Ile Pro Arg Leu Val Ile Gly Val Ile Ile
385                 390                 395                 400

Gln Val Leu Cys Ser Tyr Ser Thr Leu Pro Leu Tyr Ala Ile Val Thr
                405                 410                 415

Gln Met Gly Thr His Phe Lys Lys Ala Ile Phe Asp Glu His Val Gln
                420                 425                 430

Ala Gly Leu Val Gly Trp Ala Gln Lys Ala Arg Lys Lys Thr Thr Thr
                435                 440                 445

Gly Asn Ala Asn Arg Gly Pro Thr Ile Gln Leu Gly Arg Val Val Arg
            450                 455                 460

Ser Glu Asn Ala Lys Glu Glu Ile Thr Leu Thr Gly Ala Ala Glu Glu
465                 470                 475                 480
```

Asn Lys

```
<210> SEQ ID NO 12
<211> LENGTH: 506
<212> TYPE: PRT
<213> ORGANISM: Vitis vinifera
<220> FEATURE:
<223> OTHER INFORMATION: Sequence listing for 58633.
<220> FEATURE:
<221> NAME/KEY: unsure
<222> LOCATION: (1)..(506)
<223> OTHER INFORMATION: unsure at all Xaa locations
<220> FEATURE:
<221> NAME/KEY: unsure
<222> LOCATION: (1)..(506)
<223> OTHER INFORMATION: unsure at all Xaa locations

<400> SEQUENCE: 12
```

Met Ala Val Ala Gly Glu Thr Thr Leu Glu Tyr Thr Pro Thr Trp Val
1               5                   10                  15

Val Ala Val Cys Thr Val Ile Val Gly Ile Ser Leu Gly Ala Glu
            20                  25                  30

Arg Ile Leu His Tyr Ala Gly Lys Tyr Leu Lys Lys Asp Gln Lys
            35                  40                  45

Pro Leu Phe Glu Ala Leu Leu Lys Ile Lys Glu Glu Leu Met Leu Leu
    50                  55                  60

Gly Phe Ile Ser Leu Leu Leu Thr Val Phe Gln Asp Thr Ile Ala Lys
65                  70                  75                  80

Ile Cys Ile Pro Lys Arg Tyr Ser Asp Asp Trp Leu Pro Cys Lys Lys
                85                  90                  95

Lys Lys Glu Asp Ser Ser Ser Glu Glu Ser Thr Ser His Phe Gln
            100                 105                 110

Thr Phe Tyr His Phe Thr Ser Gly Gly Ala Arg Arg Leu Leu Ala Glu
                115                 120                 125

His Ser Ala Ser Pro Ser Tyr Cys Ala Lys Arg Gly Lys Asp Pro Leu
    130                 135                 140

Leu Ser Thr Thr Ala Leu His His Leu His Ile Phe Ile Phe Val Leu
145                 150                 155                 160

Ala Val Val His Val Ile Phe Cys Val Leu Thr Ile Ile Phe Gly Gly
                165                 170                 175

Ala Lys Ile Arg Gln Trp Lys Arg Trp Glu Asp Ala Ile Ser Lys Lys
            180                 185                 190

Glu Tyr Asp Pro Glu Glu Val Leu Lys Phe Thr Asn Val Arg Glu His
        195                 200                 205

Asp Phe Ile Lys Asp Arg Tyr Arg Gly Val Gly Lys Ile Gly Asn Leu
    210                 215                 220

Arg Gly Trp Val Arg Ser Phe Lys Gln Phe Tyr Ala Ser Val Thr
225                 230                 235                 240

Arg Ser Asp Tyr Val Thr Met Arg Met Gly Phe Ile Met Thr His Cys
                245                 250                 255

Arg Gly Asn Pro Lys Phe Asn Phe His Lys Tyr Met Ile Arg Ala Leu
            260                 265                 270

Glu Ala Asp Phe Lys Arg Val Val Gly Ile Ser Trp Tyr Leu Trp Ile
        275                 280                 285

Phe Val Val Val Phe Leu Leu Leu Asn Val Lys Gly Trp His Ala Tyr
    290                 295                 300

Phe Trp Ile Ala Phe Ile Pro Phe Ile Leu Leu Leu Leu Val Gly Thr
305                 310                 315                 320

Lys Leu Glu His Val Thr Thr Gln Leu Ala His Val Ala Glu Lys
                325                 330                 335

His Val Ala Ile Glu Gly Asp Leu Val Val Arg Pro Ser Asp Asp His
            340                 345                 350

Phe Trp Phe His Arg Pro Gln Ile Val Leu Phe Leu Ile Gln Ile Ile
        355                 360                 365

Leu Phe Gln Asn Ser Phe Glu Leu Ala Phe Phe Trp Ile Trp Val
370                 375                 380

Gln Tyr Gly Phe Asp Ser Cys Ile Met Gly Gln Leu Gly Phe Ile Ile
385                 390                 395                 400

Pro Arg Leu Phe Ile Gly Ala Phe Val Gln Phe Leu Cys Ser Tyr Ser
                405                 410                 415

Thr Leu Pro Leu Tyr Ala Ile Val Ala Gln Met Gly Ser Ser Phe Lys
            420                 425                 430

Arg Ser Ile Phe Glu Glu His Ile Gln His Gly Leu Val Glu Trp Ala
        435                 440                 445

His Lys Ala Lys Leu Lys Thr Gly Phe Lys Lys Asn Ala Asn Gly Pro
    450                 455                 460

Ser Gln Val Gly Pro Lys Glu Val Pro Pro Xaa Ala Val Gln Leu Ala
465                 470                 475                 480

Glu Val Val Lys Glu Ser Ala Glu Glu Lys Gly Asn Val Gly Glu Ile
                485                 490                 495

His Pro Ala Thr Gly Ser Gly Gly Ser Lys
            500                 505

<210> SEQ ID NO 13
<211> LENGTH: 508
<212> TYPE: PRT
<213> ORGANISM: Arabidopsis thaliana
<220> FEATURE:
<223> OTHER INFORMATION: Sequence listing for 58633.

<400> SEQUENCE: 13

Met Thr Asp Lys Glu Glu Ser Asn His Ser Ser Glu Val Gly Ala Val
1               5                   10                  15

Arg Ser Leu Gln Glu Thr Pro Thr Trp Ala Leu Ala Thr Val Cys Phe
            20                  25                  30

Phe Phe Ile Ala Val Ser Ile Cys Leu Glu Arg Leu Ile Asn Leu Leu
        35                  40                  45

Ser Thr Arg Leu Lys Lys Asn Arg Lys Thr Ser Leu Leu Glu Ala Val
    50                  55                  60

Glu Lys Leu Lys Ser Val Leu Met Val Leu Gly Phe Met Ser Leu Met
65                  70                  75                  80

Leu Asn Val Thr Glu Gly Glu Val Ser Lys Ile Cys Ile Pro Ile Lys
                85                  90                  95

Tyr Ala Asn Arg Met Leu Pro Cys Arg Lys Thr Ile Lys Ser His Asn
            100                 105                 110

Asp Val Ser Glu Asp Asp Asp Asp Gly Asp Asn His Asp Asn
        115                 120                 125

Ser Phe Phe His Gln Cys Ser Ser Lys Gly Lys Thr Ser Leu Ile Ser
    130                 135                 140

Glu Glu Gly Leu Thr Gln Leu Ser Tyr Phe Phe Val Leu Ala Cys
145                 150                 155                 160

Met His Ile Leu Cys Asn Leu Ala Ile Leu Leu Leu Gly Met Ala Lys
                165                 170                 175

```
Met Arg Lys Trp Asn Ser Trp Glu Lys Glu Thr Gln Thr Val Glu Tyr
            180                 185                 190

Leu Ala Ala Asn Asp Pro Asn Arg Phe Arg Ile Thr Arg Asp Thr Thr
        195                 200                 205

Phe Ala Arg Arg His Leu Ser Ser Trp Thr Glu Thr Ser Phe Gln Leu
    210                 215                 220

Trp Ile Lys Cys Phe Phe Arg Gln Phe Tyr Asn Ser Val Ala Lys Val
225                 230                 235                 240

Asp Tyr Leu Thr Leu Arg His Gly Phe Ile Phe Ala His Val Ser Ser
                245                 250                 255

Asn Asn Ala Phe Asn Phe Gln Asn Tyr Ile Gln Arg Ser Leu His Glu
            260                 265                 270

Asp Phe Lys Thr Val Val Gly Ile Ser Pro Leu Met Trp Leu Thr Val
        275                 280                 285

Val Ile Phe Met Leu Leu Asp Val Ser Gly Trp Arg Val Tyr Phe Tyr
    290                 295                 300

Met Ser Phe Val Pro Leu Ile Ile Val Leu Val Ile Gly Thr Lys Leu
305                 310                 315                 320

Glu Met Ile Val Ala Lys Met Ala Val Thr Ile Lys Glu Asn Asn Ser
                325                 330                 335

Val Ile Arg Gly Thr Pro Leu Val Glu Ser Asn Asp Thr His Phe Trp
            340                 345                 350

Phe Ser Asn Pro Arg Phe Leu Leu Ser Ile Leu His Tyr Thr Leu Phe
        355                 360                 365

Leu Asn Thr Phe Glu Met Ala Phe Ile Val Trp Ile Thr Trp Gln Phe
    370                 375                 380

Gly Ile Asn Ser Cys Tyr His Asp Asn Gln Gly Ile Ile Ile Thr Arg
385                 390                 395                 400

Leu Val Leu Ala Val Thr Val Gln Phe Leu Ser Ser Tyr Ile Thr Leu
                405                 410                 415

Pro Leu Tyr Ala Ile Val Thr Gln Met Gly Ser Ser Tyr Lys Arg Ala
            420                 425                 430

Ile Leu Glu Glu Gln Leu Ala Asn Val Leu Arg His Trp Gln Gly Met
        435                 440                 445

Val Arg Asp Lys Lys Lys Thr Ile Gln Thr Pro Asp Thr Asp Asn Asn
    450                 455                 460

Ser Asn Asn Asn Asn Gly Asp Ile Asp Ser Gly Glu Ser Pro Val Gln
465                 470                 475                 480

Thr Glu Val Ala Ser Glu Phe Arg Phe Ser Gly Arg Gln Ser Pro Ile
                485                 490                 495

Leu Gln Glu Ile Gln Ile Gln Glu Lys Thr Glu Arg
            500                 505

<210> SEQ ID NO 14
<211> LENGTH: 460
<212> TYPE: PRT
<213> ORGANISM: Arabidopsis thaliana
<220> FEATURE:
<223> OTHER INFORMATION: Sequence listing for 58633.

<400> SEQUENCE: 14

Met Ala Gly Gly Gly Gly Gly Gly Gly Glu Gly Pro Arg Gln Leu
1               5                   10                  15

Asp Gln Thr Pro Thr Trp Ala Val Ser Thr Val Cys Gly Val Ile Ile
            20                  25                  30
```

-continued

```
Leu Ile Ser Ile Ile Leu Glu Leu Ile Ile His Lys Val Gly Glu Val
            35                  40                  45

Phe Glu Arg Lys Lys Lys Ala Leu Phe Glu Ala Leu Glu Lys Ile
 50                  55                  60

Lys Asn Glu Leu Met Val Leu Gly Phe Ile Ser Leu Leu Leu Thr Phe
 65                  70                  75                  80

Gly Gln Asn Tyr Ile Ala Ser Ile Cys Val Pro Ser Arg Tyr Gly His
                    85                  90                  95

Ala Met Ser Phe Cys Gly Pro Tyr Asp Gly Pro Ser Glu Asp Asp Arg
                100                 105                 110

Lys Lys Leu Lys Lys Thr Asp His Ala Met Arg Ile Leu Tyr Ser Val
            115                 120                 125

Gln Arg Arg Ser Leu Ala Asp Ala Pro Pro Val Asn Cys Lys Lys Asp
130                 135                 140

Tyr Val Ala Leu Ile Ser Leu Asn Ala Leu His Gln Val His Ile Phe
145                 150                 155                 160

Ile Phe Phe Leu Ala Val Phe His Val Ile Tyr Ser Ala Ile Thr Met
                165                 170                 175

Met Leu Gly Arg Ala Lys Ile Arg Gly Trp Lys Val Trp Glu Gln Glu
                180                 185                 190

Val Ile His Glu Gln Glu Met Met Asn Asp Pro Ser Arg Phe Arg Leu
                195                 200                 205

Thr His Glu Thr Ser Phe Val Arg Glu His Val Asn Ser Trp Ala Ser
                210                 215                 220

Asn Lys Phe Phe Phe Tyr Val Met Cys Phe Phe Arg Gln Ile Leu Arg
225                 230                 235                 240

Ser Val Arg Lys Ser Asp Tyr Leu Thr Met Arg His Gly Phe Ile Ser
                245                 250                 255

Val His Leu Ala Pro Gly Met Lys Phe Asp Phe Gln Lys Tyr Ile Lys
                260                 265                 270

Arg Ser Leu Glu Asp Asp Phe Lys Val Val Gly Ile Arg Pro Glu
            275                 280                 285

Leu Trp Ala Phe Val Met Leu Phe Leu Leu Phe Asp Val His Gly Trp
            290                 295                 300

Tyr Val Thr Ala Val Ile Thr Met Ile Pro Pro Leu Leu Thr Leu Ala
305                 310                 315                 320

Ile Gly Thr Lys Leu Gln Ala Ile Ile Ser Tyr Met Ala Leu Glu Ile
                325                 330                 335

Gln Glu Arg His Ala Val Ile Gln Gly Met Pro Val Val Asn Val Ser
                340                 345                 350

Asp Gln His Phe Trp Phe Glu Lys Pro Asp Leu Val Leu His Met Ile
                355                 360                 365

His Phe Val Leu Phe Gln Asn Ala Phe Glu Ile Thr Tyr Phe Phe Trp
            370                 375                 380

Ile Trp Tyr Glu Phe Gly Leu Arg Ser Cys Phe His His Phe Gly
385                 390                 395                 400

Leu Ile Ile Ile Arg Val Cys Leu Gly Val Gly Val Gln Phe Leu Cys
                405                 410                 415

Ser Tyr Ile Thr Leu Pro Leu Tyr Ala Leu Val Thr Gln Met Gly Ser
                420                 425                 430

Thr Met Lys Arg Ser Val Phe Asp Glu Gln Thr Ser Lys Ala Leu Glu
            435                 440                 445
```

```
Gln Trp His Lys Lys Ala Arg Lys Lys Asn Glu Lys
    450                 455                 460

<210> SEQ ID NO 15
<211> LENGTH: 573
<212> TYPE: PRT
<213> ORGANISM: Arabidopsis thaliana
<220> FEATURE:
<223> OTHER INFORMATION: Sequence listing for 58633.

<400> SEQUENCE: 15

Met Glu His Met Met Lys Glu Gly Arg Ser Leu Ala Glu Thr Pro Thr
1               5                   10                  15

Tyr Ser Val Ala Ser Val Val Thr Val Leu Val Phe Val Cys Phe Leu
            20                  25                  30

Val Glu Arg Ala Ile Tyr Arg Phe Gly Lys Trp Leu Lys Lys Thr Arg
        35                  40                  45

Arg Lys Ala Leu Phe Thr Ser Leu Glu Lys Met Lys Glu Glu Leu Met
    50                  55                  60

Leu Leu Gly Leu Ile Ser Leu Leu Leu Ser Gln Ser Ala Arg Trp Ile
65                  70                  75                  80

Ser Glu Ile Cys Val Asn Ser Ser Leu Phe Asn Ser Lys Phe Tyr Ile
                85                  90                  95

Cys Ser Glu Glu Asp Tyr Gly Ile His Lys Lys Val Leu Leu Glu His
            100                 105                 110

Thr Ser Ser Thr Asn Gln Ser Ser Leu Pro His His Gly Ile His Glu
        115                 120                 125

Ala Ser His Gln Cys Gly His Gly Arg Glu Pro Phe Val Ser Tyr Glu
    130                 135                 140

Gly Leu Glu Gln Leu Leu Arg Phe Leu Phe Val Leu Gly Ile Thr His
145                 150                 155                 160

Val Leu Tyr Ser Gly Ile Ala Ile Gly Leu Ala Met Ser Lys Ile Tyr
                165                 170                 175

Ser Trp Arg Lys Trp Glu Ala Gln Ala Ile Ile Met Ala Glu Ser Asp
            180                 185                 190

Ile His Ala Lys Lys Thr Lys Val Met Lys Arg Gln Ser Thr Phe Val
        195                 200                 205

Phe His His Ala Ser His Pro Trp Ser Asn Asn Arg Phe Leu Ile Trp
    210                 215                 220

Met Leu Cys Phe Leu Arg Gln Phe Arg Gly Ser Ile Arg Lys Ser Asp
225                 230                 235                 240

Tyr Phe Ala Leu Arg Leu Gly Phe Leu Thr Lys His Asn Leu Pro Phe
                245                 250                 255

Thr Tyr Asn Phe His Met Tyr Met Val Arg Thr Met Glu Asp Glu Phe
            260                 265                 270

His Gly Ile Val Gly Ile Ser Trp Pro Leu Trp Val Tyr Ala Ile Val
        275                 280                 285

Cys Ile Cys Ile Asn Val His Gly Leu Asn Met Tyr Phe Trp Ile Ser
    290                 295                 300

Phe Val Pro Ala Ile Leu Val Met Leu Val Gly Thr Lys Leu Glu His
305                 310                 315                 320

Val Val Ser Lys Leu Ala Leu Glu Val Lys Glu Gln Thr Gly Thr
                325                 330                 335

Ser Asn Gly Ala Gln Val Lys Pro Arg Asp Gly Leu Phe Trp Phe Gly
            340                 345                 350
```

```
Lys Pro Glu Ile Leu Leu Arg Leu Ile Gln Phe Ile Ile Phe Gln Asn
            355                 360                 365

Ala Phe Glu Met Ala Thr Phe Ile Trp Phe Leu Trp Gly Ile Lys Glu
    370                 375                 380

Arg Ser Cys Phe Met Lys Asn His Val Met Ile Ser Ser Arg Leu Ile
385                 390                 395                 400

Ser Gly Val Leu Val Gln Phe Trp Cys Ser Tyr Gly Thr Val Pro Leu
                405                 410                 415

Asn Val Ile Val Thr Gln Met Gly Ser Arg His Lys Lys Ala Val Ile
            420                 425                 430

Ala Glu Ser Val Arg Asp Ser Leu His Ser Trp Cys Lys Arg Val Lys
    435                 440                 445

Glu Arg Ser Lys His Thr Arg Ser Val Cys Ser Leu Asp Thr Ala Thr
450                 455                 460

Ile Asp Glu Arg Asp Glu Met Thr Val Gly Thr Leu Ser Arg Ser Ser
465                 470                 475                 480

Ser Met Thr Ser Leu Asn Gln Ile Thr Ile Asn Ser Ile Asp Gln Ala
                485                 490                 495

Glu Ser Ile Phe Gly Ala Ala Ala Ser Ser Ser Ser Pro Gln Asp Gly
            500                 505                 510

Tyr Thr Ser Arg Val Glu Glu Tyr Leu Ser Glu Thr Tyr Asn Asn Ile
        515                 520                 525

Gly Ser Ile Pro Pro Leu Asn Asp Glu Ile Glu Ile Glu Ile Glu Gly
            530                 535                 540

Glu Glu Asp Asn Gly Gly Arg Gly Ser Gly Ser Asp Glu Asn Asn Gly
545                 550                 555                 560

Asp Ala Gly Glu Thr Leu Leu Glu Leu Phe Arg Arg Thr
                565                 570

<210> SEQ ID NO 16
<211> LENGTH: 593
<212> TYPE: PRT
<213> ORGANISM: Arabidopsis thaliana
<220> FEATURE:
<223> OTHER INFORMATION: Sequence listing for 58633.

<400> SEQUENCE: 16

Met Gly Ile Ile Asp Gly Ser Leu Leu Arg Arg Leu Ile Cys Leu Cys
1               5                   10                  15

Leu Trp Cys Leu Leu Gly Gly Val Thr Val Val Thr Ala Glu Asp
            20                  25                  30

Glu Lys Lys Val Val His Lys Gln Leu Asn Gln Thr Pro Thr Trp Ala
        35                  40                  45

Val Ala Ala Val Cys Thr Phe Phe Ile Val Val Ser Val Leu Leu Glu
    50                  55                  60

Lys Leu Leu His Lys Val Gly Lys Val Leu Trp Asp Arg His Lys Thr
65                  70                  75                  80

Ala Leu Leu Asp Ala Leu Glu Lys Ile Lys Ala Glu Leu Met Val Leu
                85                  90                  95

Gly Phe Ile Ser Leu Leu Leu Thr Phe Gly Gln Thr Tyr Ile Leu Asp
            100                 105                 110

Ile Cys Ile Pro Ser His Val Ala Arg Thr Met Leu Pro Cys Pro Ala
        115                 120                 125

Pro Asn Leu Lys Lys Glu Asp Asp Asn Gly Glu Ser His Arg Arg
    130                 135                 140
```

```
Leu Leu Ser Phe Glu His Arg Phe Leu Ser Gly Glu Ala Ser Pro
145                 150                 155                 160

Thr Lys Cys Thr Lys Glu Gly Tyr Val Glu Leu Ile Ser Ala Glu Ala
                165                 170                 175

Leu His Gln Leu His Ile Leu Ile Phe Phe Leu Ala Ile Phe His Val
            180                 185                 190

Leu Tyr Ser Phe Leu Thr Met Met Leu Gly Arg Leu Lys Ile Arg Gly
            195                 200                 205

Trp Lys His Trp Glu Asn Glu Thr Ser Ser His Asn Tyr Glu Phe Ser
        210                 215                 220

Thr Asp Thr Ser Arg Phe Arg Leu Thr His Glu Thr Ser Phe Val Arg
225                 230                 235                 240

Ala His Thr Ser Phe Trp Thr Arg Ile Pro Phe Phe Tyr Val Gly
                245                 250                 255

Cys Phe Phe Arg Gln Phe Phe Arg Ser Val Gly Arg Thr Asp Tyr Leu
                260                 265                 270

Thr Leu Arg Asn Gly Phe Ile Ala Val His Leu Ala Pro Gly Ser Gln
            275                 280                 285

Phe Asn Phe Gln Lys Tyr Ile Lys Arg Ser Leu Glu Asp Asp Phe Lys
        290                 295                 300

Val Val Val Gly Val Ser Pro Val Leu Trp Gly Ser Phe Val Leu Phe
305                 310                 315                 320

Leu Leu Leu Asn Ile Asp Gly Phe Lys Met Met Phe Ile Gly Thr Ala
                325                 330                 335

Ile Pro Val Ile Ile Ile Leu Ala Val Gly Thr Lys Leu Gln Ala Ile
            340                 345                 350

Met Thr Arg Met Ala Leu Gly Ile Thr Asp Arg His Ala Val Val Gln
            355                 360                 365

Gly Met Pro Leu Val Gln Gly Asn Asp Glu Tyr Phe Trp Phe Gly Arg
        370                 375                 380

Pro His Leu Ile Leu His Leu Met His Phe Ala Leu Phe Gln Asn Ala
385                 390                 395                 400

Phe Gln Ile Thr Tyr Phe Phe Trp Ile Trp Tyr Ser Phe Gly Ser Asp
                405                 410                 415

Ser Cys Tyr His Pro Asn Phe Lys Ile Ala Leu Val Lys Val Ala Ile
            420                 425                 430

Ala Leu Gly Val Leu Cys Leu Cys Ser Tyr Ile Thr Leu Pro Leu Tyr
        435                 440                 445

Ala Leu Val Thr Gln Met Gly Ser Arg Met Lys Lys Ser Val Phe Asp
450                 455                 460

Glu Gln Thr Ser Lys Ala Leu Lys Lys Trp Arg Met Ala Val Lys Lys
465                 470                 475                 480

Lys Lys Gly Val Lys Ala Thr Thr Lys Arg Leu Gly Gly Asp Gly Ser
                485                 490                 495

Ala Ser Pro Thr Ala Ser Thr Val Arg Ser Thr Ser Ser Val Arg Ser
            500                 505                 510

Leu Gln Arg Tyr Lys Thr Thr Pro His Ser Met Arg Tyr Glu Gly Leu
            515                 520                 525

Asp Pro Glu Thr Ser Asp Leu Asp Thr Asp Asn Glu Ala Leu Thr Pro
        530                 535                 540

Pro Lys Ser Pro Pro Ser Phe Glu Leu Val Val Lys Val Glu Pro Asn
545                 550                 555                 560

Lys Thr Asn Thr Gly Glu Thr Ser Arg Asp Thr Glu Thr Asp Ser Lys
```

-continued

```
                565                 570                 575
Glu Phe Ser Phe Val Lys Pro Ala Pro Ser Asn Glu Ser Ser Gln Asp
                580                 585                 590
Arg

<210> SEQ ID NO 17
<211> LENGTH: 542
<212> TYPE: PRT
<213> ORGANISM: Arabidopsis thaliana
<220> FEATURE:
<223> OTHER INFORMATION: Sequence listing for 58633.

<400> SEQUENCE: 17

Met Ile Thr Arg Ser Arg Cys Arg Arg Ser Leu Leu Trp Phe Leu Val
1               5                   10                  15

Phe His Gly Gly Ala Thr Ala Thr Gly Ala Pro Ser Gly Gly Lys Glu
                20                  25                  30

Leu Ser Gln Thr Pro Thr Trp Ala Val Ala Val Val Cys Thr Phe Leu
            35                  40                  45

Ile Leu Ile Ser His Leu Leu Glu Lys Gly Leu Gln Arg Leu Ala Asn
        50                  55                  60

Trp Leu Trp Lys Lys His Lys Asn Ser Leu Leu Glu Ala Leu Glu Lys
65                  70                  75                  80

Ile Lys Ala Glu Leu Met Ile Leu Gly Phe Ile Ser Leu Leu Leu Thr
                85                  90                  95

Phe Gly Glu Pro Tyr Ile Leu Lys Ile Cys Val Pro Arg Lys Ala Ala
                100                 105                 110

Leu Ser Met Leu Pro Cys Leu Ser Glu Asp Thr Val Leu Phe Gln Lys
            115                 120                 125

Leu Ala Pro Ser Ser Leu Ser Arg His Leu Leu Ala Ala Gly Asp Thr
        130                 135                 140

Ser Ile Asn Cys Lys Gln Gly Ser Glu Pro Leu Ile Thr Leu Lys Gly
145                 150                 155                 160

Leu His Gln Leu His Ile Leu Leu Phe Phe Leu Ala Ile Phe His Ile
                165                 170                 175

Val Tyr Ser Leu Ile Thr Met Met Leu Ser Arg Leu Lys Ile Arg Gly
                180                 185                 190

Trp Lys Lys Trp Glu Gln Glu Thr Leu Ser Asn Asp Tyr Glu Phe Ser
            195                 200                 205

Ile Asp His Ser Arg Leu Arg Leu Thr His Glu Thr Ser Phe Val Arg
        210                 215                 220

Glu His Thr Ser Phe Trp Thr Thr Pro Phe Phe Tyr Val Gly
225                 230                 235                 240

Cys Phe Phe Arg Gln Phe Phe Val Ser Val Glu Arg Thr Asp Tyr Leu
                245                 250                 255

Thr Leu Arg His Gly Phe Ile Ser Ala His Leu Ala Pro Gly Arg Lys
                260                 265                 270

Phe Asn Phe Gln Arg Tyr Ile Lys Arg Ser Leu Glu Asp Asp Phe Lys
            275                 280                 285

Leu Val Val Gly Ile Ser Pro Val Leu Trp Ala Ser Phe Val Ile Phe
        290                 295                 300

Leu Leu Phe Asn Val Asn Gly Trp Arg Thr Leu Phe Trp Ala Ser Ile
305                 310                 315                 320

Pro Pro Leu Leu Ile Ile Leu Ala Val Gly Thr Lys Leu Gln Ala Ile
                325                 330                 335
```

-continued

Met Ala Thr Met Ala Leu Glu Ile Val Glu Thr His Ala Val Val Gln
                340                 345                 350

Gly Met Pro Leu Val Gln Gly Ser Asp Arg Tyr Phe Trp Phe Asp Cys
            355                 360                 365

Pro Gln Leu Leu Leu His Leu Ile His Phe Ala Leu Phe Gln Asn Ala
        370                 375                 380

Phe Gln Ile Thr His Phe Phe Trp Ile Trp Tyr Ser Phe Gly Leu Lys
385                 390                 395                 400

Ser Cys Phe His Lys Asp Phe Asn Leu Val Val Ser Lys Leu Phe Leu
                405                 410                 415

Cys Leu Gly Ala Leu Ile Leu Cys Ser Tyr Ile Thr Leu Pro Leu Tyr
            420                 425                 430

Ala Leu Val Thr Gln Met Gly Ser His Met Lys Lys Ala Val Phe Asp
        435                 440                 445

Glu Gln Met Ala Lys Ala Leu Lys Lys Trp His Lys Asp Ile Lys Leu
    450                 455                 460

Lys Lys Gly Lys Ala Arg Lys Leu Pro Ser Lys Thr Leu Gly Val Ser
465                 470                 475                 480

Glu Ser Phe Ser Leu Ser Ser Ser Ser Ala Thr Thr Leu His Arg
                485                 490                 495

Ser Lys Thr Thr Gly His Ser Ser Asn Ile Ile Tyr Tyr Lys Gln Glu
            500                 505                 510

Asp Glu Glu Asp Glu Met Ser Asp Leu Glu Ala Gly Ala Glu Asp Ala
        515                 520                 525

Ile Asp Arg Ile Gln Gln Gln Glu Met Gln Phe His Asn Ser
    530                 535                 540

<210> SEQ ID NO 18
<211> LENGTH: 573
<212> TYPE: PRT
<213> ORGANISM: Arabidopsis thaliana
<220> FEATURE:
<223> OTHER INFORMATION: Sequence listing for 58633.

<400> SEQUENCE: 18

Met Ala Asp Gln Val Lys Glu Arg Thr Leu Glu Glu Thr Ser Thr Trp
1               5                   10                  15

Ala Val Ala Val Val Cys Phe Val Leu Leu Phe Ile Ser Ile Val Leu
                20                  25                  30

Glu His Ser Ile His Lys Ile Gly Thr Trp Phe Lys Lys Lys His Lys
            35                  40                  45

Gln Ala Leu Phe Glu Ala Leu Glu Lys Val Lys Ala Glu Leu Met Leu
        50                  55                  60

Leu Gly Phe Ile Ser Leu Leu Thr Ile Gly Gln Thr Pro Ile Ser
65                  70                  75                  80

Asn Ile Cys Ile Ser Gln Lys Val Ala Ser Thr Met His Pro Cys Ser
                85                  90                  95

Ala Ala Glu Glu Ala Lys Lys Tyr Gly Lys Lys Asp Ala Gly Lys Lys
            100                 105                 110

Asp Asp Gly Asp Gly Asp Lys Pro Gly Arg Leu Leu Leu Glu Leu
        115                 120                 125

Ala Glu Ser Tyr Ile His Arg Arg Ser Leu Ala Thr Lys Gly Tyr Asp
    130                 135                 140

Lys Cys Ala Glu Lys Gly Lys Val Ala Phe Val Ser Ala Tyr Gly Ile
145                 150                 155                 160

His Gln Leu His Ile Phe Ile Phe Val Leu Ala Val His Val Val
                165                 170                 175

Tyr Cys Ile Val Thr Tyr Ala Phe Gly Lys Ile Lys Met Arg Thr Trp
            180                 185                 190

Lys Ser Trp Glu Glu Thr Lys Thr Ile Glu Tyr Gln Tyr Ser Asn
                195                 200                 205

Asp Pro Glu Arg Phe Arg Phe Ala Arg Asp Thr Ser Phe Gly Arg Arg
            210                 215                 220

His Leu Asn Phe Trp Ser Lys Thr Arg Val Thr Leu Trp Ile Val Cys
225                 230                 235                 240

Phe Phe Arg Gln Phe Phe Gly Ser Val Thr Lys Val Asp Tyr Leu Ala
                245                 250                 255

Leu Arg His Gly Phe Ile Met Ala His Phe Ala Pro Gly Asn Glu Ser
            260                 265                 270

Arg Phe Asp Phe Arg Lys Tyr Ile Gln Arg Ser Leu Glu Lys Asp Phe
            275                 280                 285

Lys Thr Val Val Glu Ile Ser Pro Val Ile Trp Phe Val Ala Val Leu
            290                 295                 300

Phe Leu Leu Thr Asn Ser Tyr Gly Leu Arg Ser Tyr Leu Trp Leu Pro
305                 310                 315                 320

Phe Ile Pro Leu Val Val Ile Leu Ile Val Gly Thr Lys Leu Glu Val
                325                 330                 335

Ile Ile Thr Lys Leu Gly Leu Arg Ile Gln Glu Lys Gly Asp Val Val
            340                 345                 350

Arg Gly Ala Pro Val Val Gln Pro Gly Asp Asp Leu Phe Trp Phe Gly
            355                 360                 365

Lys Pro Arg Phe Ile Leu Phe Leu Ile His Leu Val Leu Phe Thr Asn
370                 375                 380

Ala Phe Gln Leu Ala Phe Phe Ala Trp Ser Thr Tyr Glu Phe Asn Leu
385                 390                 395                 400

Asn Asn Cys Phe His Glu Ser Thr Ala Asp Val Val Ile Arg Leu Val
                405                 410                 415

Val Gly Ala Val Val Gln Ile Leu Cys Ser Tyr Val Thr Leu Pro Leu
            420                 425                 430

Tyr Ala Leu Val Thr Gln Met Gly Ser Lys Met Lys Pro Thr Val Phe
            435                 440                 445

Asn Asp Arg Val Ala Thr Ala Leu Lys Lys Trp His His Thr Ala Lys
450                 455                 460

Asn Glu Thr Lys His Gly Arg His Ser Gly Ser Asn Thr Pro Phe Ser
465                 470                 475                 480

Ser Arg Pro Thr Thr Pro Thr His Gly Ser Ser Pro Ile His Leu Leu
                485                 490                 495

His Asn Phe Asn Asn Arg Ser Val Glu Asn Tyr Pro Ser Ser Pro Ser
            500                 505                 510

Pro Arg Tyr Ser Gly His Gly His Glu His Gln Phe Trp Asp Pro
            515                 520                 525

Glu Ser Gln His Gln Glu Ala Glu Thr Ser Thr His His Ser Leu Ala
530                 535                 540

His Glu Ser Ser Glu Pro Val Leu Ala Ser Val Glu Leu Pro Pro Ile
545                 550                 555                 560

Arg Thr Ser Lys Ser Leu Arg Asp Phe Ser Phe Lys Lys
                565                 570

```
<210> SEQ ID NO 19
<211> LENGTH: 569
<212> TYPE: PRT
<213> ORGANISM: Arabidopsis thaliana
<220> FEATURE:
<223> OTHER INFORMATION: Sequence listing for 58633.

<400> SEQUENCE: 19

Met Ala Thr Arg Cys Phe Trp Cys Trp Thr Thr Leu Leu Phe Cys Ser
1               5                   10                  15

Gln Leu Leu Thr Gly Phe Ala Arg Ala Ser Ser Ala Gly Gly Ala Lys
            20                  25                  30

Glu Lys Gly Leu Ser Gln Thr Pro Thr Trp Ala Val Ala Leu Val Cys
        35                  40                  45

Thr Phe Phe Ile Leu Val Ser Val Leu Leu Glu Lys Ala Leu His Arg
    50                  55                  60

Val Ala Thr Trp Leu Trp Glu Lys His Lys Asn Ser Leu Leu Glu Ala
65                  70                  75                  80

Leu Glu Lys Ile Lys Ala Glu Leu Met Ile Leu Gly Phe Ile Ser Leu
                85                  90                  95

Leu Leu Thr Phe Gly Glu Gln Tyr Ile Leu Lys Ile Cys Ile Pro Glu
            100                 105                 110

Lys Ala Ala Ser Met Leu Pro Cys Pro Ala Pro Ser Thr His Asp
        115                 120                 125

Gln Asp Lys Thr His Arg Arg Leu Ala Ala Thr Thr Ser Ser
    130                 135                 140

Arg Cys Asp Glu Gly His Glu Pro Leu Ile Pro Ala Thr Gly Leu His
145                 150                 155                 160

Gln Leu His Ile Leu Leu Phe Phe Met Ala Ala Phe His Ile Leu Tyr
                165                 170                 175

Ser Phe Ile Thr Met Met Leu Gly Arg Leu Lys Ile Arg Gly Trp Lys
            180                 185                 190

Lys Trp Glu Gln Glu Thr Cys Ser His Asp Tyr Glu Phe Ser Ile Asp
        195                 200                 205

Pro Ser Arg Phe Arg Leu Thr His Glu Thr Ser Phe Val Arg Gln His
    210                 215                 220

Ser Ser Phe Trp Thr Lys Ile Pro Phe Phe Tyr Ala Gly Cys Phe
225                 230                 235                 240

Leu Gln Gln Phe Phe Arg Ser Val Gly Arg Thr Asp Tyr Leu Thr Leu
                245                 250                 255

Arg His Gly Phe Ile Ala Ala His Leu Ala Pro Gly Arg Lys Phe Asp
            260                 265                 270

Phe Gln Lys Tyr Ile Lys Arg Ser Leu Glu Asp Asp Phe Lys Val Val
        275                 280                 285

Val Gly Ile Ser Pro Leu Leu Trp Ala Ser Phe Val Ile Phe Leu Leu
    290                 295                 300

Leu Asn Val Asn Gly Trp Glu Ala Leu Phe Trp Ala Ser Ile Leu Pro
305                 310                 315                 320

Val Leu Ile Ile Leu Ala Val Ser Thr Lys Leu Gln Ala Ile Leu Thr
                325                 330                 335

Arg Met Ala Leu Gly Ile Thr Glu Arg His Ala Val Val Gln Gly Ile
            340                 345                 350

Pro Leu Val His Gly Ser Asp Lys Tyr Phe Trp Phe Asn Arg Pro Gln
        355                 360                 365
```

```
Leu Leu Leu His Leu Leu His Phe Ala Leu Phe Gln Asn Ala Phe Gln
        370             375                 380

Leu Thr Tyr Phe Phe Trp Val Trp Tyr Ser Phe Gly Leu Lys Ser Cys
385                 390                 395                 400

Phe His Thr Asp Phe Lys Leu Val Ile Val Lys Leu Ser Leu Gly Val
                405                 410                 415

Gly Ala Leu Ile Leu Cys Ser Tyr Ile Thr Leu Pro Leu Tyr Ala Leu
                420                 425                 430

Val Thr Gln Met Gly Ser Asn Met Lys Lys Ala Val Phe Asp Glu Gln
                435                 440                 445

Met Ala Lys Ala Leu Lys Lys Trp His Met Thr Val Lys Lys Lys
450                 455                 460

Gly Lys Ala Arg Lys Pro Pro Thr Glu Thr Leu Gly Val Ser Asp Thr
465                 470                 475                 480

Val Ser Thr Ser Thr Ser Ser Phe His Ala Ser Gly Ala Thr Leu Leu
                485                 490                 495

Arg Ser Lys Thr Thr Gly His Ser Thr Ala Ser Tyr Met Ser Asn Phe
                500                 505                 510

Glu Asp Gln Ser Met Ser Asp Leu Glu Ala Glu Pro Leu Ser Pro Glu
                515                 520                 525

Pro Ile Glu Gly His Thr Leu Val Arg Val Gly Asp Gln Asn Thr Glu
530                 535                 540

Ile Glu Tyr Thr Gly Asp Ile Ser Pro Gly Asn Gln Phe Ser Phe Val
545                 550                 555                 560

Lys Asn Val Pro Ala Asn Asp Ile Asp
                565

<210> SEQ ID NO 20
<211> LENGTH: 573
<212> TYPE: PRT
<213> ORGANISM: Arabidopsis thaliana
<220> FEATURE:
<223> OTHER INFORMATION: Sequence listing for 58633.

<400> SEQUENCE: 20

Met Gly Glu Gly Glu Asn Gly Asn Glu Ala Asp Ser Asn Glu Arg
1               5                   10                  15

Ser Leu Ala Leu Ser Pro Thr Trp Ser Val Ala Ile Val Leu Thr Val
                20                  25                  30

Phe Val Val Ser Leu Ile Val Glu Arg Ser Ile Tyr Arg Leu Ser
            35                  40                  45

Thr Trp Leu Arg Lys Thr Lys Arg Lys Pro Met Phe Ala Ala Leu Glu
50                  55                  60

Lys Met Lys Glu Glu Leu Met Leu Leu Gly Phe Ile Ser Leu Leu Leu
65                  70                  75                  80

Thr Ala Thr Ser Ser Thr Ile Ala Asn Ile Cys Val Pro Ser Ser Phe
                85                  90                  95

Tyr Asn Asp Arg Phe Leu Pro Cys Thr Arg Ser Glu Ile Gln Glu Glu
                100                 105                 110

Leu Glu Ser Gly Ser Thr Val Lys Arg Asn Leu Leu Thr Lys Ser Leu
                115                 120                 125

Phe Phe Asn Ile Phe Arg Arg Leu Asp Val Ile Lys Arg Thr Thr
            130                 135                 140

Cys Ser Glu Gly His Glu Pro Phe Val Ser Tyr Glu Gly Leu Glu Gln
145                 150                 155                 160
```

```
Leu His Arg Phe Ile Phe Ile Met Ala Val Thr His Val Thr Tyr Ser
                165                 170                 175
Cys Leu Thr Met Leu Leu Ala Ile Val Lys Ile His Ser Trp Arg Ile
            180                 185                 190
Trp Glu Asp Val Ala Arg Leu Asp Arg His Asp Cys Leu Thr Ala Val
        195                 200                 205
Ala Arg Glu Lys Ile Phe Arg Arg Gln Thr Thr Phe Val Gln Tyr His
    210                 215                 220
Thr Ser Ala Pro Leu Ala Lys Asn Arg Ile Leu Ile Trp Val Thr Cys
225                 230                 235                 240
Phe Phe Arg Gln Phe Gly Arg Ser Val Asp Arg Ser Asp Tyr Leu Thr
                245                 250                 255
Leu Arg Lys Gly Phe Ile Val Asn His His Leu Thr Leu Lys Tyr Asp
            260                 265                 270
Phe His Ser Tyr Met Ile Arg Ser Met Glu Glu Phe Gln Arg Ile
        275                 280                 285
Val Gly Val Ser Gly Pro Leu Trp Gly Phe Val Ala Phe Met Leu
    290                 295                 300
Phe Asn Ile Lys Gly Ser Asn Leu Tyr Phe Trp Ile Ala Ile Pro
305                 310                 315                 320
Val Thr Leu Val Leu Leu Val Gly Ala Lys Leu Gln His Val Ile Ala
                325                 330                 335
Thr Leu Ala Leu Glu Asn Ala Gly Leu Thr Glu Tyr Pro Ser Gly Val
            340                 345                 350
Lys Leu Arg Pro Arg Asp Glu Leu Phe Trp Phe Asn Lys Pro Glu Leu
        355                 360                 365
Leu Leu Ser Leu Ile His Phe Ile Leu Phe Gln Asn Ser Phe Glu Leu
    370                 375                 380
Ala Ser Phe Phe Trp Phe Trp Trp Gln Phe Gly Tyr Ser Ser Cys Phe
385                 390                 395                 400
Leu Lys Asn His Tyr Leu Val Tyr Phe Arg Leu Leu Leu Gly Phe Ala
                405                 410                 415
Gly Gln Phe Leu Cys Ser Tyr Ser Thr Leu Pro Leu Tyr Ala Leu Val
            420                 425                 430
Thr Gln Met Gly Thr Asn Tyr Lys Ala Ala Leu Ile Pro Gln Arg Ile
        435                 440                 445
Arg Glu Thr Ile Arg Gly Trp Gly Lys Ala Thr Arg Arg Lys Arg Arg
    450                 455                 460
His Gly Leu Tyr Gly Asp Asp Ser Thr Val Arg Thr Glu Thr Ser Thr
465                 470                 475                 480
Ile Ala Ser Leu Glu Glu Tyr Asp His Gln Val Leu Asp Val Thr Glu
                485                 490                 495
Thr Ser Phe Glu Gln Gln Arg Lys Gln Gln Glu Gln Gly Thr Thr Glu
            500                 505                 510
Leu Glu Leu Gln Pro Ile Gln Pro Arg Asn Asp Cys Val Pro Asn Asp
        515                 520                 525
Thr Ser Ser Arg Val Gly Thr Pro Leu Leu Arg Pro Trp Leu Ser Ile
530                 535                 540
Ser Ser Pro Thr Thr Thr Ile Glu Leu Arg Ser Glu Pro Met Glu Thr
545                 550                 555                 560
Leu Ser Arg Ser Ser Ser Leu Pro Ser Glu Lys Arg Val
                565                 570
```

<210> SEQ ID NO 21
<211> LENGTH: 583
<212> TYPE: PRT
<213> ORGANISM: Arabidopsis thaliana
<220> FEATURE:
<223> OTHER INFORMATION: Sequence listing for 58633.

<400> SEQUENCE: 21

```
Met Ala Asp Gln Val Lys Glu Lys Thr Leu Glu Glu Thr Ser Thr Trp
1               5                   10                  15

Ala Val Ala Val Val Cys Phe Val Leu Leu Ile Ser Ile Val Ile
            20                  25                  30

Glu Lys Leu Ile His Lys Ile Gly Ser Trp Phe Lys Lys Lys Asn Lys
        35                  40                  45

Lys Ala Leu Tyr Glu Ala Leu Glu Lys Val Lys Ala Glu Leu Met Leu
    50                  55                  60

Met Gly Phe Ile Ser Leu Leu Thr Ile Gly Gln Gly Tyr Ile Ser
65                  70                  75                  80

Asn Ile Cys Ile Pro Lys Asn Ile Ala Ala Ser Met His Pro Cys Ser
                85                  90                  95

Ala Ser Glu Glu Ala Arg Lys Tyr Gly Lys Lys Asp Val Pro Lys Glu
            100                 105                 110

Asp Glu Glu Glu Asn Leu Arg Arg Lys Leu Leu Gln Leu Val Asp Ser
        115                 120                 125

Leu Ile Pro Arg Arg Ser Leu Ala Thr Lys Gly Tyr Asp Lys Cys Ala
    130                 135                 140

Glu Lys Gly Lys Val Ala Phe Val Ser Ala Tyr Gly Met His Gln Leu
145                 150                 155                 160

His Ile Phe Ile Phe Val Leu Ala Val Cys His Val Ile Tyr Cys Ile
                165                 170                 175

Val Thr Tyr Ala Leu Gly Lys Thr Lys Met Arg Arg Trp Lys Lys Trp
            180                 185                 190

Glu Glu Glu Thr Lys Thr Ile Glu Tyr Gln Tyr Ser His Asp Pro Glu
        195                 200                 205

Arg Phe Arg Phe Ala Arg Asp Thr Ser Phe Gly Arg Arg His Leu Ser
    210                 215                 220

Phe Trp Ser Lys Ser Thr Ile Thr Leu Trp Ile Val Cys Phe Phe Arg
225                 230                 235                 240

Gln Phe Phe Arg Ser Val Thr Lys Val Asp Tyr Leu Thr Leu Arg His
                245                 250                 255

Gly Phe Ile Met Ala His Leu Ala Pro Gly Ser Asp Ala Arg Phe Asp
            260                 265                 270

Phe Arg Lys Tyr Ile Gln Arg Ser Leu Glu Glu Asp Phe Lys Thr Ile
        275                 280                 285

Val Glu Ile Asn Pro Val Ile Trp Phe Ile Ala Val Leu Phe Leu Leu
    290                 295                 300

Thr Asn Thr Asn Gly Leu Asn Ser Tyr Leu Trp Leu Pro Phe Ile Pro
305                 310                 315                 320

Phe Ile Val Ile Leu Ile Val Gly Thr Lys Leu Gln Val Ile Ile Thr
                325                 330                 335

Lys Leu Gly Leu Arg Ile Gln Glu Lys Gly Asp Val Lys Gly Thr
            340                 345                 350

Pro Leu Val Gln Pro Gly Asp His Phe Phe Trp Phe Gly Arg Pro Arg
        355                 360                 365

Phe Ile Leu Phe Leu Ile His Leu Val Leu Phe Thr Asn Ala Phe Gln
```

```
                370                 375                 380
Leu Ala Phe Phe Val Trp Ser Thr Tyr Glu Phe Gly Leu Lys Asn Cys
385                 390                 395                 400

Phe His Glu Ser Arg Val Asp Val Ile Ile Arg Ile Ser Ile Gly Leu
                405                 410                 415

Leu Val Gln Ile Leu Cys Ser Tyr Val Thr Leu Pro Leu Tyr Ala Leu
            420                 425                 430

Val Thr Gln Met Gly Ser Lys Met Lys Pro Thr Val Phe Asn Glu Arg
            435                 440                 445

Val Ala Thr Ala Leu Lys Ser Trp His His Thr Ala Lys Lys Asn Ile
        450                 455                 460

Lys His Gly Arg Thr Ser Glu Ser Thr Thr Pro Phe Ser Ser Arg Pro
465                 470                 475                 480

Thr Thr Pro Thr His Gly Ser Ser Pro Ile His Leu Leu Arg Asn Ala
                485                 490                 495

Pro His Lys Arg Ser Arg Ser Val Asp Glu Ser Phe Ala Asn Ser Phe
                500                 505                 510

Ser Pro Arg Asn Ser Asp Phe Asp Ser Trp Asp Pro Glu Ser Gln His
                515                 520                 525

Glu Thr Ala Glu Thr Ser Asn Ser Asn His Arg Ser Arg Phe Gly Glu
        530                 535                 540

Glu Glu Ser Glu Lys Lys Phe Val Ser Ser Val Glu Leu Pro Pro
545                 550                 555                 560

Gly Pro Gly Gln Ile Arg Thr Gln His Glu Ile Ser Thr Ile Ser Leu
                565                 570                 575

Arg Asp Phe Ser Phe Lys Arg
                580

<210> SEQ ID NO 22
<211> LENGTH: 478
<212> TYPE: PRT
<213> ORGANISM: Arabidopsis thaliana
<220> FEATURE:
<223> OTHER INFORMATION: Sequence listing for 58633.

<400> SEQUENCE: 22

Met Ala Glu Ala Arg Ser Gly Ser Leu Glu Tyr Thr Pro Thr Trp Val
1               5                  10                  15

Val Ala Phe Ile Cys Phe Ile Ile Val Leu Ser Leu Leu Ala Glu
            20                  25                  30

Arg Gly Leu His His Leu Gly Lys Cys Leu Lys Arg Arg Gln Gln Asp
        35                  40                  45

Ala Leu Phe Glu Ala Leu Gln Lys Leu Lys Glu Glu Leu Met Leu Leu
    50                  55                  60

Gly Phe Ile Ser Leu Met Leu Thr Val Ser Gln Ala Ala Ile Arg His
65                  70                  75                  80

Ile Cys Val Pro Pro Ala Leu Val Asn Asn Met Phe Pro Cys Lys Lys
                85                  90                  95

Pro Leu Glu Glu His His Ala Pro Lys Ser Ser His Ser Ile Ile Asn
            100                 105                 110

Asn Ala Arg His Leu Leu Ser Thr Gly Glu Ser Pro Asp His Cys Ala
        115                 120                 125

Ala Lys Gly Gln Val Pro Leu Val Ser Val Glu Ala Leu His Gln Leu
    130                 135                 140

His Ile Phe Ile Phe Val Leu Ala Val Phe His Val Ile Phe Cys Ala
```

```
            145                 150                 155                 160
Ser Thr Met Val Leu Gly Gly Ala Arg Ile Gln Gln Trp Lys His Trp
                165                 170                 175

Glu Asp Trp Phe Lys Lys Arg Pro Ser Gln Lys Gly Thr Thr Arg Arg
            180                 185                 190

Gly His His Ala His Ala His Glu Leu Phe Ser Ala Asn His Glu Phe
        195                 200                 205

Phe Glu Met His Ala Gly Gly Phe Trp Arg Arg Ser Val Val Ile Ser
    210                 215                 220

Trp Val Arg Ser Phe Phe Lys Gln Phe Tyr Gly Ser Val Thr Lys Ser
225                 230                 235                 240

Glu Tyr Ile Ala Leu Arg Gln Ala Phe Ile Met Ser His Cys Arg Thr
                245                 250                 255

Asn Pro Ser Phe Asp Phe His Lys Tyr Met Leu Arg Thr Leu Glu Ile
            260                 265                 270

Asp Phe Lys Lys Val Val Ser Ile Ser Trp Tyr Leu Trp Leu Phe Val
        275                 280                 285

Val Val Phe Leu Leu Leu Asn Val Gly Gly Trp Asn Thr Tyr Phe Trp
    290                 295                 300

Leu Ser Phe Leu Pro Leu Ile Leu Leu Leu Met Val Gly Ala Lys Leu
305                 310                 315                 320

Glu Tyr Ile Ile Ser Ser Leu Ala Leu Asp Val Ser Glu Lys Arg Ser
                325                 330                 335

Arg Ala Glu Glu Ala Val Ile Thr Pro Ser Asp Glu Leu Phe Trp Phe
            340                 345                 350

His Arg Pro Gly Ile Val Leu Gln Leu Ile His Phe Ile Leu Phe Gln
        355                 360                 365

Asn Ser Phe Glu Ile Ala Phe Phe Trp Ile Leu Phe Thr Tyr Gly
    370                 375                 380

Ile His Ser Cys Ile Met Glu Lys Leu Gly Tyr Leu Ile Pro Arg Leu
385                 390                 395                 400

Val Met Gly Val Leu Val Gln Val Leu Cys Ser Tyr Ser Thr Leu Pro
                405                 410                 415

Leu Tyr Ala Leu Val Thr Gln Met Gly Ser Lys Phe Lys Lys Gly Ile
            420                 425                 430

Phe Asp Asn Val Val Gln Ser Thr Leu Glu Gly Trp Leu Glu Asp Thr
        435                 440                 445

Arg Asn Arg Gly Glu Ser Thr Ser Glu Ala His Arg Ile Glu Met Gln
    450                 455                 460

Pro Thr Thr Pro Glu Ser Tyr Asn Val Gln Ser Glu Asn Pro
465                 470                 475

<210> SEQ ID NO 23
<211> LENGTH: 554
<212> TYPE: PRT
<213> ORGANISM: Arabidopsis thaliana
<220> FEATURE:
<223> OTHER INFORMATION: Sequence listing for 58633.

<400> SEQUENCE: 23

Met Arg Glu Glu Thr Glu Pro Ser Glu Arg Thr Leu Gly Leu Thr Pro
1               5                   10                  15

Thr Trp Ser Val Ala Thr Val Leu Thr Ile Phe Val Phe Val Ser Leu
                20                  25                  30

Ile Val Glu Arg Ser Ile His Arg Leu Ser Asn Trp Leu Gln Lys Thr
```

```
                35                  40                  45
Lys Arg Lys Pro Leu Phe Ala Ala Leu Glu Lys Met Lys Glu Glu Leu
 50                  55                  60
Met Leu Leu Gly Phe Ile Ser Leu Leu Leu Thr Ala Thr Ser Ser Thr
 65                  70                  75                  80
Ile Ala Asn Ile Cys Val Ser Ser Phe His Asn Asp Arg Phe Val
                 85                  90                  95
Pro Cys Thr Pro Ser Glu Ile Asn Glu Glu Leu Glu Ser Thr Ile Ser
                100                 105                 110
Thr Val Lys Arg Thr Gln Leu Thr Arg Ser Leu Phe Leu His Thr Leu
            115                 120                 125
Arg Arg Arg Leu Ser Gly Ile Gly Glu Asp Thr Cys Ser Glu Gly His
130                 135                 140
Glu Pro Phe Leu Ser Tyr Glu Gly Met Glu Gln Leu His Arg Phe Ile
145                 150                 155                 160
Phe Ile Met Ala Val Thr His Val Thr Tyr Ser Cys Leu Thr Met Leu
                165                 170                 175
Leu Ala Ile Val Lys Ile His Arg Trp Arg Ile Trp Glu Asp Glu Val
                180                 185                 190
His Met Asp Arg Asn Asp Cys Leu Thr Val Val Ala Arg Glu Lys Ile
            195                 200                 205
Phe Arg Arg Gln Thr Thr Phe Val Gln Tyr His Thr Ser Ala Pro Leu
210                 215                 220
Val Lys Asn Arg Leu Leu Ile Trp Val Ile Cys Phe Phe Arg Gln Phe
225                 230                 235                 240
Gly His Ser Val Val Arg Ser Asp Tyr Leu Thr Leu Arg Lys Gly Phe
                245                 250                 255
Ile Met Asn His His Leu Thr Leu Thr Tyr Asp Phe His Ser Tyr Met
                260                 265                 270
Ile Arg Ser Met Glu Glu Glu Phe Gln Lys Ile Val Gly Val Ser Gly
            275                 280                 285
Pro Leu Trp Gly Phe Val Val Gly Phe Met Leu Phe Asn Ile Lys Gly
290                 295                 300
Ser Asn Leu Tyr Phe Trp Leu Ala Ile Ile Pro Ile Thr Leu Val Leu
305                 310                 315                 320
Leu Val Gly Ala Lys Leu Gln His Val Ile Ala Thr Leu Ala Leu Glu
                325                 330                 335
Asn Ala Ser Ile Thr Glu Tyr Ala Ser Gly Ile Lys Leu Arg Pro Arg
                340                 345                 350
Asp Glu Leu Phe Trp Phe Lys Lys Pro Glu Leu Leu Leu Ser Leu Ile
            355                 360                 365
His Phe Ile Gln Phe Gln Asn Ala Phe Glu Leu Ala Ser Phe Phe Trp
            370                 375                 380
Phe Trp Trp Gln Phe Gly Tyr Asn Ser Cys Phe Leu Arg Asn His Leu
385                 390                 395                 400
Leu Val Tyr Leu Arg Leu Ile Leu Gly Phe Ser Gly Gln Phe Leu Cys
                405                 410                 415
Ser Tyr Ser Thr Leu Pro Leu Tyr Ala Leu Val Thr Gln Met Gly Thr
                420                 425                 430
Asn Tyr Lys Ala Ala Leu Leu Pro Gln Arg Val Arg Glu Thr Ile Asn
            435                 440                 445
Gly Trp Gly Lys Ala Thr Arg Arg Lys Arg His Gly Leu Tyr Gly
450                 455                 460
```

```
Asp Asp Ser Thr Ile Arg Thr Glu Thr Ser Thr Ile Ala Ser Val Asp
465                 470                 475                 480

Glu Tyr Asn Asp Gln Val Leu Asp Val Ser Glu Thr Ser Pro Val Gln
                485                 490                 495

Asp Asn Glu Leu Glu Leu Gln Leu Ile Arg Gly Ala Cys Gly Asn Ser
            500                 505                 510

Ser Ser Val Glu Thr Pro Ile Leu Arg Pro Cys Ala Ser Ile Ser Ser
        515                 520                 525

Thr Thr Phe Ser Arg Leu Gln Thr Glu Thr Thr Asp Ser Leu Ser Arg
    530                 535                 540

Ser Ser Ser Leu Pro Met Arg Arg Glu Cys
545                 550

<210> SEQ ID NO 24
<211> LENGTH: 576
<212> TYPE: PRT
<213> ORGANISM: Arabidopsis thaliana
<220> FEATURE:
<223> OTHER INFORMATION: Sequence listing for 58633.

<400> SEQUENCE: 24

Met Ala Ile Lys Glu Arg Ser Leu Glu Glu Thr Pro Thr Trp Ala Val
1               5                   10                  15

Ala Val Val Cys Phe Val Leu Leu Phe Ile Ser Ile Met Ile Glu Tyr
            20                  25                  30

Phe Leu His Phe Ile Gly His Trp Phe Lys Lys Lys His Lys Lys Ala
        35                  40                  45

Leu Ser Glu Ala Leu Glu Lys Val Lys Ala Glu Leu Met Leu Leu Gly
    50                  55                  60

Phe Ile Ser Leu Leu Leu Val Val Leu Gln Thr Pro Val Ser Glu Ile
65                  70                  75                  80

Cys Ile Pro Arg Asn Ile Ala Ala Thr Trp His Pro Cys Ser Asn His
                85                  90                  95

Gln Glu Ile Ala Lys Tyr Gly Lys Asp Tyr Ile Asp Asp Gly Arg Lys
            100                 105                 110

Ile Leu Glu Asp Phe Asp Ser Asn Asp Phe Tyr Ser Pro Arg Arg Asn
        115                 120                 125

Leu Ala Thr Lys Gly Tyr Asp Lys Cys Ala Glu Lys Gly Lys Val Ala
    130                 135                 140

Leu Val Ser Ala Tyr Gly Ile His Gln Leu His Ile Phe Ile Phe Val
145                 150                 155                 160

Leu Ala Val Phe His Val Leu Tyr Cys Ile Ile Thr Tyr Ala Leu Gly
                165                 170                 175

Lys Thr Lys Met Lys Lys Trp Lys Ser Trp Glu Arg Glu Thr Lys Thr
            180                 185                 190

Ile Glu Tyr Gln Tyr Ala Asn Asp Pro Glu Arg Phe Arg Phe Ala Arg
        195                 200                 205

Asp Thr Ser Phe Gly Arg Arg His Leu Asn Ile Trp Ser Lys Ser Thr
    210                 215                 220

Phe Thr Leu Trp Ile Thr Cys Phe Phe Arg Gln Phe Gly Ser Val
225                 230                 235                 240

Thr Lys Val Asp Tyr Leu Thr Leu Arg His Gly Phe Ile Met Ala His
                245                 250                 255

Leu Pro Ala Gly Ser Ala Ala Arg Phe Asp Phe Gln Lys Tyr Ile Glu
            260                 265                 270
```

Arg Ser Leu Glu Gln Asp Phe Thr Val Val Gly Ile Ser Pro Leu
         275                 280                 285

Ile Trp Cys Ile Ala Val Leu Phe Ile Leu Thr Asn Thr His Gly Trp
290                 295                 300

Asp Ser Tyr Leu Trp Leu Pro Phe Leu Pro Leu Ile Val Ile Leu Ile
305                 310                 315                 320

Val Gly Ala Lys Leu Gln Met Ile Ile Ser Lys Leu Gly Leu Arg Ile
                 325                 330                 335

Gln Glu Lys Gly Asp Val Val Lys Gly Ala Pro Val Val Glu Pro Gly
             340                 345                 350

Asp Asp Leu Phe Trp Phe Gly Arg Pro Arg Phe Ile Leu Phe Leu Ile
             355                 360                 365

His Leu Val Leu Phe Thr Asn Ala Phe Gln Leu Ala Phe Phe Val Trp
         370                 375                 380

Ser Thr Tyr Glu Phe Thr Leu Lys Asn Cys Phe His His Lys Thr Glu
385                 390                 395                 400

Asp Ile Ala Ile Arg Ile Thr Met Gly Val Leu Ile Gln Val Leu Cys
                 405                 410                 415

Ser Tyr Ile Thr Leu Pro Leu Tyr Ala Leu Val Thr Gln Met Gly Thr
             420                 425                 430

Ser Met Arg Pro Thr Ile Phe Asn Asp Arg Val Ala Asn Ala Leu Lys
         435                 440                 445

Lys Trp His His Thr Ala Lys Lys Gln Thr Lys His Gly His Ser Gly
         450                 455                 460

Ser Asn Thr Pro His Ser Arg Pro Thr Thr Pro Thr His Gly Met
465                 470                 475                 480

Ser Pro Val His Leu Leu His Asn Tyr Asn Asn Arg Ser Leu Asp Gln
                 485                 490                 495

Gln Thr Ser Phe Thr Ala Ser Pro Ser Pro Arg Phe Ser Asp Tyr
             500                 505                 510

Ser Gly Gln Gly His Gly His Gln His Phe Phe Asp Pro Glu Ser Gln
         515                 520                 525

Asn His Ser Tyr Gln Arg Glu Ile Thr Asp Ser Glu Phe Ser Asn Ser
         530                 535                 540

His His Pro Gln Val Asp Met Ala Ser Pro Val Arg Glu Glu Lys Glu
545                 550                 555                 560

Ile Val Glu His Val Lys Val Asp Leu Ser Glu Phe Thr Phe Lys Lys
                 565                 570                 575

<210> SEQ ID NO 25
<211> LENGTH: 526
<212> TYPE: PRT
<213> ORGANISM: Arabidopsis thaliana
<220> FEATURE:
<223> OTHER INFORMATION: Sequence listing for 58633.

<400> SEQUENCE: 25

Met Gly His Gly Gly Glu Gly Met Ser Leu Glu Phe Thr Pro Thr Trp
1               5                   10                  15

Val Val Ala Gly Val Cys Thr Val Ile Val Ala Ile Ser Leu Ala Val
                20                  25                  30

Glu Arg Leu Leu His Tyr Phe Gly Thr Val Leu Lys Lys Lys Lys Gln
            35                  40                  45

Lys Pro Leu Tyr Glu Ala Leu Gln Lys Val Lys Glu Glu Leu Met Leu
        50                  55                  60

```
Leu Gly Phe Ile Ser Leu Leu Thr Val Phe Gln Gly Leu Ile Ser
 65                  70                  75                  80

Lys Phe Cys Val Lys Glu Asn Val Leu Met His Met Leu Pro Cys Ser
                 85                  90                  95

Leu Asp Ser Arg Arg Glu Ala Gly Ala Ser Glu His Lys Asn Val Thr
            100                 105                 110

Ala Lys Glu His Phe Gln Thr Phe Leu Pro Ile Val Gly Thr Thr Arg
        115                 120                 125

Arg Leu Leu Ala Glu His Ala Ala Val Gln Val Gly Tyr Cys Ser Glu
    130                 135                 140

Lys Gly Lys Val Pro Leu Leu Ser Leu Glu Ala Leu His His Leu His
145                 150                 155                 160

Ile Phe Ile Phe Val Leu Ala Ile Ser His Val Thr Phe Cys Val Leu
                165                 170                 175

Thr Val Ile Phe Gly Ser Thr Arg Ile His Gln Trp Lys Lys Trp Glu
            180                 185                 190

Asp Ser Ile Ala Asp Glu Lys Phe Asp Pro Glu Thr Ala Leu Arg Lys
        195                 200                 205

Arg Arg Val Thr His Val His Asn His Ala Phe Ile Lys Glu His Phe
210                 215                 220

Leu Gly Ile Gly Lys Asp Ser Val Ile Leu Gly Trp Thr Gln Ser Phe
225                 230                 235                 240

Leu Lys Gln Phe Tyr Asp Ser Val Thr Lys Ser Asp Tyr Val Thr Leu
                245                 250                 255

Arg Leu Gly Phe Ile Met Thr His Cys Lys Gly Asn Pro Lys Leu Asn
            260                 265                 270

Phe His Lys Tyr Met Met Arg Ala Leu Glu Asp Asp Phe Lys Gln Val
        275                 280                 285

Val Gly Ile Ser Trp Tyr Leu Trp Ile Phe Val Val Ile Phe Leu Leu
    290                 295                 300

Leu Asn Val Asn Gly Trp His Thr Tyr Phe Trp Ile Ala Phe Ile Pro
305                 310                 315                 320

Phe Ala Leu Leu Leu Ala Val Gly Thr Lys Leu Glu His Val Ile Ala
                325                 330                 335

Gln Leu Ala His Glu Val Ala Glu Lys His Val Ala Ile Glu Gly Asp
            340                 345                 350

Leu Val Val Lys Pro Ser Asp Glu His Phe Trp Phe Ser Lys Pro Gln
        355                 360                 365

Ile Val Leu Tyr Leu Ile His Phe Ile Leu Phe Gln Asn Ala Phe Glu
    370                 375                 380

Ile Ala Phe Phe Phe Trp Ile Trp Val Thr Tyr Gly Phe Asp Ser Cys
385                 390                 395                 400

Ile Met Gly Gln Val Arg Tyr Ile Val Pro Arg Leu Val Ile Gly Val
                405                 410                 415

Phe Ile Gln Val Leu Cys Ser Tyr Ser Thr Leu Pro Leu Tyr Ala Ile
            420                 425                 430

Val Ser Gln Met Gly Ser Ser Phe Lys Lys Ala Ile Phe Glu Glu Asn
        435                 440                 445

Val Gln Val Gly Leu Val Gly Trp Ala Gln Lys Val Lys Gln Lys Arg
    450                 455                 460

Asp Leu Lys Ala Ala Ala Ser Asn Gly Asp Glu Gly Ser Ser Gln Ala
465                 470                 475                 480
```

```
Gly Pro Gly Pro Asp Ser Gly Ser Gly Ser Ala Pro Ala Ala Gly Pro
                485                 490                 495
Gly Ala Gly Phe Ala Gly Ile Gln Leu Ser Arg Val Thr Arg Asn Asn
            500                 505                 510
Ala Gly Asp Thr Asn Asn Glu Ile Thr Pro Asp His Asn Asn
        515                 520                 525

<210> SEQ ID NO 26
<211> LENGTH: 496
<212> TYPE: PRT
<213> ORGANISM: Arabidopsis thaliana
<220> FEATURE:
<223> OTHER INFORMATION: Sequence listing for 58633.

<400> SEQUENCE: 26

Met Ala Gly Gly Gly Thr Thr Leu Glu Tyr Thr Pro Thr Trp Val Val
1               5                   10                  15
Ala Leu Val Cys Ser Val Ile Val Ser Ile Ser Phe Ala Val Glu Arg
                20                  25                  30
Leu Ile His Arg Ala Gly Lys His Phe Lys Asn Asn Asp Gln Lys Gln
            35                  40                  45
Leu Phe Gly Ala Leu Gln Lys Ile Lys Glu Glu Leu Met Leu Val Gly
        50                  55                  60
Phe Ile Ser Leu Leu Ser Val Gly Gln Ser Lys Ile Ala Lys Ile
65                  70                  75                  80
Cys Ile Ser Lys Glu Leu Ser Glu Lys Phe Leu Pro Cys Thr Lys Pro
                85                  90                  95
Ala Gly Ala Glu Lys Ser Leu Lys Asp Ser Ser His Phe Gln Phe Ser
            100                 105                 110
Phe Thr Gly Arg His Leu Leu Ala Gly Asp Ala Pro Ala Gly Asp Tyr
        115                 120                 125
Cys Ser Leu Lys Gly Lys Val Pro Ile Met Ser Leu Ser Ala Leu His
    130                 135                 140
Glu Leu His Ile Phe Ile Phe Val Leu Ala Val Ala His Ile Ile Phe
145                 150                 155                 160
Cys Leu Leu Thr Ile Val Phe Gly Thr Met Lys Ile Lys Gln Trp Lys
                165                 170                 175
Lys Trp Glu Asp Lys Val Leu Glu Lys Asp Phe Asp Thr Asp Gln Ser
            180                 185                 190
Ile Lys Lys Phe Thr His Val Gln Glu His Glu Phe Ile Arg Ser Arg
        195                 200                 205
Phe Leu Gly Val Gly Lys Ala Asp Ala Ser Leu Gly Trp Val Gln Ser
    210                 215                 220
Phe Met Lys Gln Phe Leu Ala Ser Val Asn Glu Ser Asp Tyr Ile Thr
225                 230                 235                 240
Met Arg Leu Gly Phe Val Thr Thr His Cys Lys Thr Asn Pro Lys Phe
                245                 250                 255
Asn Phe His Lys Tyr Leu Met Arg Ala Leu Asn Ser Asp Phe Lys Lys
            260                 265                 270
Val Val Gly Ile Ser Trp Tyr Leu Trp Val Phe Val Val Leu Phe Leu
        275                 280                 285
Leu Leu Asn Ile Val Ala Trp His Val Tyr Phe Trp Leu Ala Phe Ile
    290                 295                 300
Pro Leu Ile Leu Leu Leu Ala Val Gly Thr Lys Leu Glu His Ile Ile
305                 310                 315                 320
```

```
Thr Asp Leu Ala His Glu Val Ala Glu Lys His Ile Ala Val Glu Gly
            325                 330                 335

Asp Leu Val Val Arg Pro Ser Asp Asp Leu Phe Trp Phe Gln Ser Pro
        340                 345                 350

Arg Leu Val Leu Phe Leu Ile His Phe Ile Leu Phe Gln Asn Ser Phe
        355                 360                 365

Glu Ile Ala Tyr Phe Phe Phe Ile Leu Phe Gln Phe Gly Trp Asp Ser
    370                 375                 380

Cys Ile Met Asp His Val Lys Phe Val Ile Pro Arg Leu Val Ile Gly
385                 390                 395                 400

Val Ile Ile Gln Leu Leu Cys Ser Tyr Ser Thr Leu Pro Leu Tyr Ala
                405                 410                 415

Leu Val Thr Gln Met Gly Ser Ser Phe Lys Gly Ala Ile Phe Asn Glu
            420                 425                 430

Gln Thr Gln Glu His Leu Val Gly Trp Ala Lys Met Ala Lys Arg Gly
        435                 440                 445

Val Lys Lys Gly Ala Thr Gln Val Gly Thr Ser His Asp Ala Thr Ser
    450                 455                 460

Pro Arg Pro Ser Ile Gln Leu Asn Ser Leu Leu Gly Lys Gly Ser Ser
465                 470                 475                 480

Gln Gln Asn Gln Asn Pro Lys Glu Lys Ser Glu Ile Ala His His Asp
                485                 490                 495

<210> SEQ ID NO 27
<211> LENGTH: 501
<212> TYPE: PRT
<213> ORGANISM: Arabidopsis thaliana
<220> FEATURE:
<223> OTHER INFORMATION: Sequence listing for 58633.

<400> SEQUENCE: 27

Met Ala Gly Gly Gly Gly Ser Thr Ser Gly Glu Gly Pro Arg Glu
1               5                   10                  15

Leu Asp Gln Thr Pro Thr Trp Ala Val Ser Thr Val Cys Gly Val Ile
            20                  25                  30

Ile Leu Ile Ser Ile Val Leu Glu Leu Met Ile His Lys Ile Gly Glu
        35                  40                  45

Val Phe Thr Glu Arg Arg Lys Lys Ala Leu Tyr Glu Ala Leu Gln Lys
    50                  55                  60

Ile Lys Asn Glu Leu Met Val Leu Gly Phe Ile Ser Leu Leu Leu Thr
65                  70                  75                  80

Phe Gly Gln Asn Tyr Ile Ala Ser Leu Cys Val Ala Ser Arg Tyr Gly
                85                  90                  95

His Ala Met Ser Phe Cys Gly Pro Tyr Asp Gly Pro Ser Gly Glu Ser
            100                 105                 110

Lys Lys Pro Lys Thr Thr Glu His Leu Glu Arg Arg Val Leu Ala Asp
        115                 120                 125

Ala Ala Pro Ala Gln Cys Lys Lys Gly Tyr Val Pro Leu Ile Ser Leu
    130                 135                 140

Asn Ala Leu His Gln Val His Ile Phe Ile Phe Phe Leu Ala Val Phe
145                 150                 155                 160

His Val Ile Tyr Ser Ala Ile Thr Met Met Leu Gly Arg Ala Lys Ile
                165                 170                 175

Arg Gly Trp Lys Val Trp Glu Glu Glu Val Ile Asn Asp His Glu Met
            180                 185                 190
```

```
Met Asn Asp Pro Ser Arg Phe Arg Leu Thr His Glu Thr Ser Phe Val
            195                 200                 205

Arg Glu His Val Asn Pro Trp Ala Lys Asn Arg Phe Ser Phe Tyr Val
        210                 215                 220

Met Cys Phe Phe Arg Gln Met Leu Arg Ser Val Arg Lys Ser Asp Tyr
225                 230                 235                 240

Leu Thr Met Arg His Gly Phe Ile Ser Val His Leu Ala Pro Gly Met
                245                 250                 255

Lys Phe Asn Phe Gln Lys Tyr Ile Lys Arg Ser Leu Glu Asp Asp Phe
                260                 265                 270

Lys Val Val Gly Ile Ser Pro Glu Leu Trp Ala Phe Val Met Leu
        275                 280                 285

Phe Leu Leu Phe Asp Val His Gly Trp Tyr Val Thr Ala Val Ile Thr
        290                 295                 300

Met Ile Pro Pro Leu Leu Thr Leu Ala Ile Gly Thr Lys Leu Gln Ala
305                 310                 315                 320

Ile Ile Ser Asp Met Ala Leu Glu Ile Gln Glu Arg His Ala Val Ile
                325                 330                 335

Gln Gly Met Pro Leu Val Asn Val Ser Asp Arg His Phe Trp Phe Ser
                340                 345                 350

Arg Pro Ala Leu Val Leu His Ile Ile His Phe Ile Leu Phe Gln Asn
        355                 360                 365

Ala Phe Glu Ile Thr Tyr Phe Phe Trp Ile Trp Tyr Glu Phe Gly Leu
        370                 375                 380

Arg Ser Cys Phe His His His Phe Ala Leu Ile Ile Ile Arg Val Ala
385                 390                 395                 400

Leu Gly Val Gly Val Gln Phe Leu Cys Ser Tyr Ile Thr Leu Pro Leu
                405                 410                 415

Tyr Ala Leu Val Thr Gln Met Gly Ser Thr Met Lys Arg Ser Val Phe
                420                 425                 430

Asp Asp Gln Thr Ser Lys Ala Leu Lys Asn Trp His Lys Asn Ala Lys
        435                 440                 445

Lys Lys Ser Glu Thr Pro Gly Gln Thr Gln Pro Pro Leu Pro Asn Leu
450                 455                 460

Arg Pro Lys Thr Gly Gly Asp Ile Glu Ser Ala Ser Pro Ala Asn Ile
465                 470                 475                 480

Thr Ala Ser Val Asp Val Lys Glu Ser Asp Gln Ser Gln Ser Arg Asp
                485                 490                 495

Leu Leu Ser Gly Pro
            500

<210> SEQ ID NO 28
<211> LENGTH: 533
<212> TYPE: PRT
<213> ORGANISM: Hordeum vulgare
<220> FEATURE:
<223> OTHER INFORMATION: Sequence listing for 58633.

<400> SEQUENCE: 28

Met Ser Asp Lys Lys Gly Val Pro Ala Arg Glu Leu Pro Glu Thr Pro
1               5                   10                  15

Ser Trp Ala Val Ala Val Val Phe Ala Ala Met Val Leu Val Ser Val
            20                  25                  30

Leu Met Glu His Gly Leu His Lys Leu Gly His Trp Phe Gln His Arg
        35                  40                  45
```

-continued

```
His Lys Lys Ala Leu Trp Glu Ala Leu Glu Lys Met Lys Ala Glu Leu
 50                  55                  60

Met Leu Val Gly Phe Ile Ser Leu Leu Ile Val Thr Gln Asp Pro
 65                  70                  75                  80

Ile Ile Ala Lys Ile Cys Ile Ser Glu Asp Ala Ala Asp Val Met Trp
                 85                  90                  95

Pro Cys Lys Arg Gly Thr Glu Gly Arg Lys Pro Ser Lys Tyr Val Asp
                100                 105                 110

Tyr Cys Pro Glu Gly Lys Val Ala Leu Met Ser Thr Gly Ser Leu His
            115                 120                 125

Gln Leu His Val Phe Ile Phe Val Leu Ala Val Phe His Val Thr Tyr
130                 135                 140

Ser Val Ile Thr Ile Ala Leu Ser Arg Leu Lys Met Arg Thr Trp Lys
145                 150                 155                 160

Lys Trp Glu Thr Glu Thr Thr Ser Leu Glu Tyr Gln Phe Ala Asn Asp
                165                 170                 175

Pro Ala Arg Phe Arg Phe Thr His Gln Thr Ser Phe Val Lys Arg His
                180                 185                 190

Leu Gly Leu Ser Ser Thr Pro Gly Ile Arg Trp Val Val Ala Phe Phe
            195                 200                 205

Arg Gln Phe Phe Arg Ser Val Thr Lys Val Asp Tyr Leu Thr Leu Arg
210                 215                 220

Ala Gly Phe Ile Asn Ala His Leu Ser Gln Asn Ser Lys Phe Asp Phe
225                 230                 235                 240

His Lys Tyr Ile Lys Arg Ser Met Glu Asp Asp Phe Lys Val Val Val
                245                 250                 255

Gly Ile Ser Leu Pro Leu Trp Gly Val Ala Ile Leu Thr Leu Phe Leu
            260                 265                 270

Asp Ile Asn Gly Val Gly Thr Leu Ile Trp Ile Ser Phe Ile Pro Leu
            275                 280                 285

Val Ile Leu Leu Cys Val Gly Thr Lys Leu Glu Met Ile Ile Met Glu
290                 295                 300

Met Ala Leu Glu Ile Gln Asp Arg Ala Ser Val Ile Lys Gly Ala Pro
305                 310                 315                 320

Val Val Glu Pro Ser Asn Lys Phe Phe Trp Phe His Arg Pro Asp Trp
                325                 330                 335

Val Leu Phe Phe Ile His Leu Thr Leu Phe Gln Asn Ala Phe Gln Met
            340                 345                 350

Ala His Phe Val Trp Thr Val Ala Thr Pro Gly Leu Lys Lys Cys Tyr
            355                 360                 365

His Thr Gln Ile Gly Leu Ser Ile Met Lys Val Val Gly Leu Ala
370                 375                 380

Leu Gln Phe Leu Cys Ser Tyr Met Thr Phe Pro Leu Tyr Ala Leu Val
385                 390                 395                 400

Thr Gln Met Gly Ser Asn Met Lys Arg Ser Ile Phe Asp Glu Gln Thr
                405                 410                 415

Ser Lys Ala Leu Thr Asn Trp Arg Asn Thr Ala Lys Glu Lys Lys Lys
            420                 425                 430

Val Arg Asp Thr Asp Met Leu Met Ala Gln Met Ile Gly Asp Ala Thr
            435                 440                 445

Pro Ser Arg Gly Ser Ser Pro Met Pro Ser Arg Gly Ser Ser Pro Val
450                 455                 460

His Leu Leu His Lys Gly Met Gly Arg Ser Asp Asp Pro Gln Ser Ala
```

Pro Thr Ser Asp Asn Ala Gln Gln Glu Ala Arg Asp Met Tyr Pro Val
465                 470                 475                 480
                        485                         490                 495

Val Val Ala His Pro Val His Arg Leu Asn Pro Asn Asp Arg Arg Arg
                500                         505                 510

Ser Ala Ser Ser Ala Leu Glu Ala Asp Ile Pro Ser Ala Asp Phe
            515                 520                 525

Ser Phe Ser Gln Gly
    530

<210> SEQ ID NO 29
<211> LENGTH: 1906
<212> TYPE: DNA
<213> ORGANISM: Hordeum vulgare
<220> FEATURE:
<223> OTHER INFORMATION: Sequence listing for 58633.

<400> SEQUENCE: 29

| | | | | | |
|---|---|---|---|---|---|
| ggcctcggct | gctccgccag | caaaccagac | acacagcagc | gtacctgcgt | acgtagcgtg | 60 |
| cgctttcttt | ttttcctttc | gcctctcttg | cttgctccgg | ccggccacgg | ccaggcacct | 120 |
| cgcggttgcg | tcgcgtgcat | ctgcgtgtgc | gtacctggta | gaggcggccg | tctgcttgct | 180 |
| ccgggcaagg | aaggaggttg | cggcggtcga | ccgatgtcgg | acaaaaaagg | ggtgccggcg | 240 |
| cgggagctgc | cggagacgcc | gtcgtgggcg | gtggcggtgg | tcttcgccgc | catggtgctc | 300 |
| gtgtccgtcc | tcatggagca | cggcctccac | aagctcggcc | attggttcca | gcaccggcac | 360 |
| aagaaggccc | tgtgggaggc | gctggagaag | atgaaggcgg | agctcatgct | ggtgggcttc | 420 |
| atatccctgc | tcctcatcgt | cacgcaggac | cccatcatcg | ccaagatatg | catctccgag | 480 |
| gatgccgccg | acgtcatgtg | gccctgcaag | cgcggcaccg | agggccgcaa | gcccagcaag | 540 |
| tacgttgact | actgcccgga | gggcaaggtg | gcgctcatgt | ccacgggcag | cttgcaccag | 600 |
| ctgcacgtct | tcatcttcgt | gctcgcggtc | ttccatgtca | cctacagcgt | catcaccata | 660 |
| gctctaagcc | gtctcaaaat | gagaacatgg | aagaaatggg | agacagagac | cacctccttg | 720 |
| gaataccagt | tcgcaaatga | tcctgcacgg | ttccggttca | cgcaccagac | gtcgttcgtg | 780 |
| aagcgccacc | tgggcctctc | cagcacccct | ggcatcagat | gggtggtggc | cttcttcagg | 840 |
| cagttcttca | ggtcagtcac | caaggtggac | tacctgacct | tgagggcagg | cttcatcaac | 900 |
| gcgcatttgt | cgcaaaacag | caagttcgac | ttccacaagt | acatcaagag | gtcgatggag | 960 |
| gacgacttca | aggtcgtcgt | cggcatcagc | ctcccgctgt | ggggtgtggc | gatcctcacc | 1020 |
| ctcttccttg | acatcaatgg | ggttggcacg | ctcatctgga | tttctttcat | ccctctcgtg | 1080 |
| atcctcttgt | gtgttggaac | caagctggag | atgatcatca | tggagatggc | cctggagatc | 1140 |
| caggaccggg | cgagcgtcat | caagggggcc | cccgtggtcg | agcccagcaa | caagttcttc | 1200 |
| tggttccacc | gccccgactg | ggtcctcttc | ttcatacacc | tgacgttgtt | ccagaacgcg | 1260 |
| tttcagatgg | cgcattttgt | gtggacagtg | gccacgcccg | gcttgaagaa | atgctaccac | 1320 |
| acgcagatcg | ggctgagcat | catgaaggta | gtggtggggc | tagctctcca | gttcctctgc | 1380 |
| agctatatga | ccttccccct | ctacgcgctc | gtcacacaga | tgggatcaaa | catgaagagg | 1440 |
| tccatcttcg | acgagcagac | gtccaaggcg | ctcaccaact | ggcggaacac | ggccaaggag | 1500 |
| aagaagaaag | tccgagacac | ggacatgctg | atggctcaga | tgatcggcga | cgcaacaccg | 1560 |
| agccgagggct | cgtcgccgat | gccgagccgg | ggctcatcac | ccgtgcacct | gcttcacaag | 1620 |
| ggcatggggc | ggtcggacga | ccccagagc | gcgcccacct | cgccaaggac | ccagcaggag | 1680 |

```
gctagggaca tgtacccggt tgtggtggcg cacccggtgc acagactaaa tcctaacgac    1740
aggaggaggt ccgcctcgtc gtcggccctc gaagccgaca tccccagtgc agattttccc    1800
ttcagccagg gatgagacaa gtttctgtat tcatgttagt ccaatgtata gccaacatag    1860
gatgtgatga ttcgtacaat aagaaataca attttttaaa aaaaaa                  1906
```

<210> SEQ ID NO 30
<211> LENGTH: 593
<212> TYPE: PRT
<213> ORGANISM: Cucumis sativus
<220> FEATURE:
<223> OTHER INFORMATION: Sequence listing for 58633.

<400> SEQUENCE: 30

```
Met Ala Gly Gly Gly Ala Gly Arg Ser Leu Glu Glu Thr Pro Thr Trp
1               5                   10                  15

Ala Val Ala Ala Val Cys Phe Val Leu Val Leu Ile Ser Ile Ile Ile
            20                  25                  30

Glu His Ile Leu His Leu Ile Gly Lys Trp Leu Lys Lys His Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Thr Val Gly Gln Ser Leu Ile Thr
65                  70                  75                  80

Asn Val Cys Ile Pro Pro Asp Val Ala Ala Thr Trp His Pro Cys Ser
                85                  90                  95

Pro Gln Arg Glu Glu Leu Thr Lys Glu Ala Asp Leu Val Asp Ser
            100                 105                 110

Asp Gln Asn Arg Arg Lys Leu Leu Ala Leu Ser His His Val Asn Ala
        115                 120                 125

Thr Phe Arg Arg Ser Leu Ala Ala Ala Gly Gly Thr Asp Lys Cys Ala
    130                 135                 140

Ala Lys Gly Lys Val Pro Phe Val Ser Glu Gly Gly Ile His Gln Leu
145                 150                 155                 160

His Ile Phe Ile Phe Val Leu Ala Val Phe His Val Leu Tyr Cys Val
                165                 170                 175

Leu Thr Leu Ala Leu Gly Asn Ala Lys Met Arg Ser Trp Lys Ser Trp
            180                 185                 190

Glu Lys Glu Thr Arg Thr Val Glu Tyr Gln Phe Ser His Asp Pro Glu
        195                 200                 205

Arg Phe Arg Phe Ala Arg Asp Thr Ser Phe Gly Arg Arg His Leu Ser
    210                 215                 220

Phe Trp Thr Lys Ser Pro Phe Leu Ile Trp Ile Val Cys Phe Arg
225                 230                 235                 240

Gln Phe Val Arg Ser Val Pro Lys Val Asp Tyr Leu Thr Leu Arg His
                245                 250                 255

Gly Phe Val Met Ala His Leu Ala Pro His Ser Asp Gln Lys Phe Asp
            260                 265                 270

Phe Gln Lys Tyr Ile Lys Arg Ser Leu Glu Glu Asp Phe Lys Val Val
        275                 280                 285

Val Ser Ile Ser Pro Pro Ile Trp Phe Phe Ala Val Leu Phe Leu Leu
    290                 295                 300

Phe Asn Thr His Gly Trp Arg Ala Tyr Leu Trp Leu Pro Phe Val Pro
305                 310                 315                 320
```

Leu Ile Ile Val Leu Leu Val Gly Thr Lys Leu Gln Val Ile Ile Thr
                325                 330                 335

Lys Met Ala Leu Arg Ile Gln Glu Arg Gly Glu Val Val Lys Gly Val
            340                 345                 350

Pro Val Val Glu Pro Gly Asp Asp Leu Phe Trp Phe Asn Arg Pro Arg
        355                 360                 365

Leu Ile Leu Tyr Leu Ile Asn Phe Val Leu Phe Gln Asn Ala Phe Gln
    370                 375                 380

Leu Ala Phe Phe Ala Trp Thr Trp Lys Glu Phe Gly Met Lys Ser Cys
385                 390                 395                 400

Phe His Glu His Thr Glu Asp Leu Val Ile Arg Ile Thr Met Gly Val
                405                 410                 415

Leu Val Gln Ile Leu Cys Ser Tyr Val Thr Leu Pro Leu Tyr Ala Leu
            420                 425                 430

Val Thr Gln Met Gly Ser Thr Met Lys Pro Thr Ile Phe Asn Glu Arg
        435                 440                 445

Val Ala Thr Ala Leu Arg Asn Trp His His Thr Ala Arg Lys His Ile
    450                 455                 460

Lys Gln Asn Arg Gly Ser Met Thr Pro Met Ser Ser Arg Pro Ala Thr
465                 470                 475                 480

Pro Ser His His Leu Ser Pro Val His Leu Leu Arg His Tyr Arg Ser
                485                 490                 495

Glu Leu Asp Ser Val His Thr Ser Pro Arg Arg Ser Asn Phe Asp Thr
            500                 505                 510

Asp Gln Trp Asp Pro Asp Ser Pro Ser Pro Ser Pro Ser His His Phe
        515                 520                 525

His Arg Arg Pro His Pro Gly Asp Gly Ser Ile Ser Asn His His Arg
    530                 535                 540

Asp Val Glu Ala Gly Asp Leu Asp Val Asp Val Glu Ser Pro Gln Pro
545                 550                 555                 560

Asp Arg Thr Thr Gln Ser Ile Asn Pro Thr Asn Ile Glu His His Glu
                565                 570                 575

Ile Asp Val Gly Ser Asn Glu Phe Ser Phe Asp Arg Arg Val Asp Arg
            580                 585                 590

Val

<210> SEQ ID NO 31
<211> LENGTH: 1782
<212> TYPE: DNA
<213> ORGANISM: Cucumis sativus
<220> FEATURE:
<223> OTHER INFORMATION: Sequence listing for 58633.

<400> SEQUENCE: 31
atggccggag gtggcgccgg aaggtccttg gaagagacgc cgacatgggc cgtcgccgcc      60
gtgtgctttg ttttggttct gatttctatt atcatcgaac acattctcca tctcatcgga     120
aagtggctaa agaagaaaca caaacgagct ctctacgaag ctctggagaa gattaaatca     180
gaactgatgc tgttgggatt catatcgctg ctgctgacgg tgggacaaag cctaatcaca     240
aatgtttgta taccacctga cgtggcagcc acgtggcatc catgtagtcc tcaaagagaa     300
gaagaattaa ctaaagaagc tgacctcgtc gattccgacc aaaatcgtcg aaaacttctc     360
gccctctccc atcacgtcaa cgccaccttc cgccgttccc tcgccgctgc cggtggtacc     420
gacaaatgtg ctgccaaggg taaagttcca tttgtatcgg aagggggtat tcatcagcta     480

-continued

```
catatattca tcttcgtact ggcagttttc catgttttgt attgtgtttt aactttagct    540
ttgggcaatg ccaagatgag aagttggaag tcatgggaaa aagagacaag aactgtggag    600
tatcaattct cacacgatcc ggaacggttt cgatttgcaa gagacacgtc atttgggaga    660
agacatttaa gcttttggac aaaatcccct tcctcatat ggattgtttg tttcttcaga     720
caattcgtta ggtcggttcc aaaggttgat tacttgacct taagacatgg tttcgtcatg    780
gcacatctgg caccgcacag cgatcagaaa tttgactttc aaaaatacat aaaacgatct    840
cttgaagaag atttcaaggt ggtggtcagt atcagccctc cgatatggtt ctttgctgtc    900
ctcttcctac ttttcaacac ccacgggtgg agggcttatc tatggctacc ctttgttccg    960
ttaattatag tgttattggt ggggacaaag ttgcaagtga ataacgaa atggcgctg      1020 aggatacaag aaagaggaga agtggtgaaa ggagtgccgg tggtagagcc aggggatgac   1080
cttttttggt tcaatcgccc tcgtcttatt ctttacctta tcaattttgt cctcttccag   1140
aatgcctttc agcttgcctt ttttgcttgg acttggaaag aatttgggat gaaatcttgt   1200
ttccatgagc acacagagga tttggtcatc agaataacaa tggggttct cgttcaaatc    1260 ctttgcagtt atgtcacatt gccactttac gctctagtca cacagatggg ttcgacgatg   1320
aagcccacga ttttcaacga aagagtagcg acggcgttga gaaattggca ccacaccgct   1380
cgtaaacaca taaaacaaaa tcgtggctca atgacgccga tgtcgagccg ccctgcaacc   1440
ccctcccacc acttgtcacc cgtccacctc cttcgccact atcgaagcga attagatagc   1500
gttcatacgt ctcctagaag atccaatttc gacaccgatc agtgggaccc tgattcccct   1560
tccccttccc cttctcacca ctttcatcgt cgtccccatc ccggcgacgg ctccatttcc   1620
aaccatcacc gtgatgtgga ggccggggat cttgatgtcg atgttgaatc gcctcaaccc   1680
gaccgaacga cccagtcaat aaacccaaca aatattgagc accatgaaat tgacgtgggg   1740
tctaacgaat tctcattcga tagaagagtt gatagagtat aa                      1782
```

<210> SEQ ID NO 32
<211> LENGTH: 582
<212> TYPE: PRT
<213> ORGANISM: Cucumis sativus
<220> FEATURE:
<223> OTHER INFORMATION: Sequence listing for 58633.

<400> SEQUENCE: 32

```
Met Ala Gly Ala Ala Gly Gly Lys Ser Leu Glu Gln Thr Pro Thr Trp
1               5                   10                  15

Ala Val Ala Val Val Cys Phe Val Leu Leu Val Ile Ser Ile Phe Ile
            20                  25                  30

Glu Tyr Ser Leu His Leu Ile Gly His Trp Leu Lys Lys Arg His Lys
        35                  40                  45

Arg Ala Leu Phe Glu Ala Leu Glu Lys Ile Lys Ser Glu Leu Met Leu
    50                  55                  60

Leu Gly Phe Ile Ser Leu Leu Thr Val Gly Gln Gly Pro Ile Thr
65                  70                  75                  80

Glu Ile Cys Ile Pro Gln His Val Ala Ala Thr Trp His Pro Cys Thr
                85                  90                  95

Lys Glu Arg Glu Asp Glu Met Asn Lys Glu Val Glu Lys Ser Val Glu
            100                 105                 110

His Leu Gly Leu Asn Arg Arg Leu Leu His Leu Leu Gly Asn Gly
        115                 120                 125

Glu Ser Phe Arg Arg Ser Leu Ala Ala Ala Gly Gly Glu Asp Lys Cys
```

```
                130               135               140
Ala Ala Lys Gly Lys Ala Ser Phe Ile Ser Ala Asp Gly Ile His Gln
145               150               155               160

Leu His Ile Phe Ile Phe Val Leu Ala Val Phe His Val Leu Tyr Cys
                165               170               175

Val Leu Thr Tyr Ala Leu Ala Arg Ala Lys Met Arg Ser Trp Lys Thr
            180               185               190

Trp Glu Lys Glu Thr Lys Thr Ala Glu Tyr Gln Phe Ser His Asp Pro
        195               200               205

Glu Arg Phe Arg Phe Ala Arg Asp Thr Ser Phe Gly Arg Arg His Leu
    210               215               220

Ser Phe Trp Thr Lys Asn Pro Ala Leu Met Trp Ile Val Cys Phe Phe
225               230               235               240

Arg Gln Phe Val Arg Ser Val Pro Lys Val Asp Tyr Leu Thr Leu Arg
                245               250               255

His Gly Phe Ile Met Ala His Leu Ala Pro Gln Ser His Thr Gln Phe
            260               265               270

Asp Phe Gln Lys Tyr Ile Asn Arg Ser Leu Glu Glu Asp Phe Lys Val
        275               280               285

Val Val Gly Ile Ser Pro Pro Ile Trp Phe Phe Ala Val Leu Phe Leu
    290               295               300

Leu Ser Asn Thr His Gly Trp Arg Ala Tyr Leu Trp Leu Pro Phe Ile
305               310               315               320

Pro Leu Ile Ile Leu Leu Leu Ile Gly Thr Lys Leu Gln Val Ile Ile
                325               330               335

Thr Lys Met Ala Leu Arg Ile Gln Glu Arg Gly Val Val Lys Gly
            340               345               350

Val Pro Val Glu Pro Gly Asp Asp Leu Phe Trp Phe Asn Arg Pro
        355               360               365

Arg Leu Ile Leu Tyr Leu Ile Asn Phe Val Leu Phe Gln Asn Ala Phe
    370               375               380

Gln Val Ala Phe Phe Ala Trp Thr Trp Tyr Glu Phe Gly Leu Asn Ser
385               390               395               400

Cys Phe His Glu His Ile Glu Asp Val Val Ile Arg Ile Ser Met Gly
                405               410               415

Val Leu Val Gln Ile Leu Cys Ser Tyr Val Thr Leu Pro Leu Tyr Ala
            420               425               430

Leu Val Thr Gln Met Gly Ser Thr Met Lys Pro Thr Ile Phe Asn Glu
        435               440               445

Arg Val Ala Glu Ala Leu Arg Asn Trp Tyr His Ser Ala Arg Lys His
    450               455               460

Ile Lys His Asn Arg Gly Ser Val Thr Pro Met Ser Ser Arg Pro Ala
465               470               475               480

Thr Pro Thr His Ser Met Ser Pro Val His Leu Leu Arg His Tyr Lys
                485               490               495

Ser Glu Val Asp Ser Phe His Thr Ser Pro Arg Arg Ser Pro Phe Asp
            500               505               510

Thr Asp Arg Trp Asp Asn Asp Ser Pro Ser Pro Ser Arg His Val Asp
        515               520               525

Gly Ser Ser Ser Gln Pro His Val Glu Met Gly Gly Tyr Glu Lys
    530               535               540

Asp Pro Val Glu Ser Ser Ser Ser Gln Val Asp Pro Val Gln Pro Ser
545               550               555               560
```

Arg Asn Arg Asn Gln His Glu Ile His Ile Gly Gly Pro Lys Asp Phe
            565                 570                 575

Ser Phe Asp Arg Val Glu
            580

<210> SEQ ID NO 33
<211> LENGTH: 1749
<212> TYPE: DNA
<213> ORGANISM: Cucumis sativus
<220> FEATURE:
<223> OTHER INFORMATION: Sequence listing for 58633.

<400> SEQUENCE: 33

| | | | | | |
|---|---|---|---|---|---|
| atggcggggg | cagccggtgg | caagtcgctg | gagcaaacac | cgacatgggc | cgttgccgtt | 60 |
| gtttgctttg | ttttgctcgt | catctctatt | ttcatcgaat | atagtctcca | tcttatcgga | 120 |
| cattggctaa | agaagagaca | caaacgggcg | ttgtttgaag | cattagagaa | gatcaaatca | 180 |
| gagcttatgt | tattggggtt | tatatcattg | ctactaacgg | tggggcaagg | accaataacg | 240 |
| gagatatgta | ttccacaaca | tgtagctgca | acgtggcatc | catgtacaaa | ggaaagagaa | 300 |
| gatgagatga | acaaagaggt | ggagaaatct | gtggaacatt | tgggtcttaa | tcgccggaga | 360 |
| ctccttcatc | tcctcggaaa | tggtgaaagt | ttccggcgga | gtttggccgc | tgcgggagga | 420 |
| gaggataaat | gtgccgccaa | gggtaaagct | tcctttattt | cagcagatgg | aattcatcaa | 480 |
| cttcatatct | tcattttgt | gttggctgtt | tttcatgttt | tgtattgtgt | tctaacttat | 540 |
| gcgttggcta | gagctaagat | gaggagttgg | aaaacatggg | aaaaagagac | caaaactgct | 600 |
| gaataccaat | tctcacatga | tccagagagg | tttaggtttg | caagagacac | ctcatttggg | 660 |
| agaagacatt | tgagcttttg | gaccaaaaat | cctgccttga | tgtggatcgt | ttgtttcttc | 720 |
| agacaatttg | taagatctgt | tccaaaagtt | gattacttga | cattaagaca | tgggtttata | 780 |
| atggcacatt | tagcacctca | aagtcataca | caatttgatt | tcaaaaata | cattaataga | 840 |
| tcccttgaag | aagacttcaa | agttgttgtg | ggaatcagcc | caccaatttg | gttctttgct | 900 |
| gttctatttc | tcctctcaaa | cactcacggt | tggaggcgt | atctatggct | gccattcatc | 960 |
| ccactaatca | ttttgctgtt | gattggaaca | aaattgcaag | tgatcataac | gaaaatggca | 1020 |
| ctaagaatac | aagaaagagg | tgaagtagta | aagggcgtgc | cggtggtgga | gcctggcgat | 1080 |
| gacctctttt | ggtttaatcg | acctcgcctt | attctttatc | tcatcaactt | tgttctcttc | 1140 |
| caaaatgcct | tccaagttgc | cttctttgct | tggacttggt | atgagtttgg | gttgaattct | 1200 |
| tgcttccatg | agcatataga | agatgtggta | atcagaattt | ctatggggt | gcttgtacaa | 1260 |
| atcctttgca | gttatgttac | tcttcctctt | tatgcactag | tcactcagat | gggttcaaca | 1320 |
| atgaagccaa | ctatattcaa | tgagagagtg | gcagaggccc | ttcgcaattg | gtaccactcg | 1380 |
| gctcgaaagc | acatcaaaca | caaccgcggt | tcggtcactc | caatgtcgag | ccgacccgcc | 1440 |
| acccgactc | acagcatgtc | acctgtccac | cttctccgac | actacaagag | tgaagtcgat | 1500 |
| agcttccaca | cctcaccgag | aaggtcaccg | ttcgacaccg | atcgttggga | caacgattcg | 1560 |
| ccctctccat | ctcgccatgt | tgatggttcg | tcttcgtcac | aaccccacgt | tgagatggga | 1620 |
| ggttatgaaa | aagatcccgt | tgaatcaagt | tcgtctcaag | ttgatccggt | tcaaccatct | 1680 |
| cgaaaccgca | atcaacatga | gattcatatt | ggaggcccca | aagacttttc | atttgataga | 1740 |
| gttgaatga | | | | | | 1749 |

<210> SEQ ID NO 34

<211> LENGTH: 539
<212> TYPE: PRT
<213> ORGANISM: Cucumis sativus
<220> FEATURE:
<223> OTHER INFORMATION: Sequence listing for 58633.

<400> SEQUENCE: 34

Met Ala Ser Leu Glu Arg Thr Pro Thr Trp Ala Val Ala Thr Val Cys
1               5                   10                  15

Phe Leu Leu Ile Leu Ile Ser Ile Ser Thr Glu Tyr Leu Leu His Phe
            20                  25                  30

Leu Val Lys Arg Phe Phe Ser Ile Lys Arg Arg Lys Ser Leu Arg Gln
        35                  40                  45

Ala Leu Asp Asn Ile Lys Ser Glu Leu Met Leu Leu Gly Phe Val Ser
    50                  55                  60

Leu Leu Leu Thr Val Ser Glu Lys Gly Ile Ala Asn Ile Cys Ile Pro
65                  70                  75                  80

Lys Ser Leu Asn His Lys Phe Leu Pro Cys His Thr Ile Asn Phe Asn
                85                  90                  95

Ser Thr Tyr Phe Leu Glu Glu Pro Lys Cys Asp Ser Gln Gly Lys Ala
            100                 105                 110

Ser Leu Leu Ser Arg Asp Gly Ala Lys Gln Val Lys Tyr Leu Ile Ile
        115                 120                 125

Cys Leu Ala Phe Val His Ile Phe Ser Ser Leu Leu Ser Tyr Ser Leu
    130                 135                 140

Gly Ile Ala Lys Met Arg Arg Trp Gln Ser Trp Glu Ala Lys Thr Arg
145                 150                 155                 160

Thr Leu Glu Tyr Gln Phe Thr Thr Asp Pro Arg Arg Phe Gln Phe Ala
                165                 170                 175

Arg Gln Thr Ser Phe Gly Lys Arg His Leu Lys Phe Trp Ser Asp His
            180                 185                 190

His Ile Leu Arg Trp Pro Ala Cys Phe Val Arg Gln Phe Tyr Glu Ser
        195                 200                 205

Val Ser Ala Ala Asp Tyr Leu Thr Leu Arg His Gly Phe Ile Thr Ala
    210                 215                 220

His Leu Gly Glu Gly Thr Asn Phe Asp Phe Gln Lys Tyr Ile Thr Arg
225                 230                 235                 240

Ala Leu Asp Asn Asp Phe Ser Val Val Gly Ile Ser Trp Trp Val
                245                 250                 255

Trp Val Phe Ser Val Ile Phe Ile Phe Phe Ser Ala His Gly Phe His
            260                 265                 270

Ser Tyr Leu Trp Leu Pro Phe Ile Pro Leu Leu Met Leu Leu Leu Val
        275                 280                 285

Gly Thr Lys Leu Gln Gly Ile Met Thr Glu Met Cys Leu Asp Ser His
    290                 295                 300

Glu Lys Ser His Val Val Arg Gly Thr Leu Leu Val Arg Pro Ser Asp
305                 310                 315                 320

His Tyr Phe Trp Leu Gly Arg Pro Lys Leu Leu Leu Tyr Phe Ile His
                325                 330                 335

Phe Ile Phe Phe Gln Asn Ser Phe Gln Leu Ala Phe Phe Ala Trp Ala
            340                 345                 350

Trp Leu Lys Phe Gly Leu Arg Ser Cys Phe Gln Arg Glu Ile Ala Asp
        355                 360                 365

Leu Val Ile Gly Val Ser Val Gly Val Leu Val Gln Phe Ile Cys Gly
    370                 375                 380

```
Tyr Val Thr Leu Pro Leu Tyr Ala Leu Val Ala Gln Met Gly Ser Ser
385                 390                 395                 400

Met Lys Lys Thr Val Phe Thr Glu Gly Val Val Glu Gly Leu Arg Lys
                405                 410                 415

Trp Lys Gly Arg Ala Lys Lys Val Ala Arg Arg Gln Arg Gly Gln
            420                 425                 430

His Gly Cys Asp His Asn Phe Ser Gln Ser Pro Asp Asn Ala Ser Val
            435                 440                 445

Asp Ala Gly Val Asp Ser Pro Pro Ser Phe Arg Leu Glu Ala Thr Pro
            450                 455                 460

Met Ala Ser Val Asp Tyr Tyr Gly Arg Leu Gln Leu Ala Gly Ala Asn
465                 470                 475                 480

Asn Asn Lys Gln Tyr Asn Asn Asn Asn Ser Cys Ser Ala Ala Val
                485                 490                 495

Ser Val Asn Gly Asp Glu Asp Lys Leu Lys Gly Lys Lys Pro Ile Glu
                500                 505                 510

Glu Ala Asp Gln Lys Ser Ile Ser Leu Asp Ala Phe Asp Trp Ala Asn
            515                 520                 525

Lys Ile His Arg Asn Phe Ser Arg His Ala Met
        530                 535

<210> SEQ ID NO 35
<211> LENGTH: 1620
<212> TYPE: DNA
<213> ORGANISM: Cucumis sativus
<220> FEATURE:
<223> OTHER INFORMATION: Sequence listing for 58633.

<400> SEQUENCE: 35
atggcgagtt tggaacgaac ccccacatgg gcagtggcca ctgtctgctt tttgttgatt      60
ctcatttcca tttccacaga atatttgctt cattttcttg tcaaacggtt tttcagcatc     120
aaaagaagga aatccctcag gcaagctctc gacaatatca aatccgaatt gatgcttttg     180
ggatttgtat cgctgttatt gacggtgagc gagaaaggaa ttgctaacat ttgcattcct     240
aagagtttga atcacaaatt tctgccctgt cacactatca acttcaattc cacttacttc     300
ttggaagaac ccaagtgtga ttcacagggg aaagcttcat tgctgtctag agatggtgca     360
aagcaagtta gtatttgat catttgttta gcctttgttc atatcttctc cagtctactc     420
agctatagtc ttggaatcgc caagatgaga agatggcagt cttgggaagc aaaaaccaga     480
actttggaat atcaatttac aactgatcca agaagatttc aatttgctcg tcaaacatcc     540
tttggcaaga ggcatcttaa attctggagt gaccaccaca ttcttcgatg ccggcctgt      600 tttgttagac aattttatga atctgtgtct gcagctgatt atctcactct tagacatggt     660
ttcattacgg cccatcttgg agaaggaacc aactttgact ccaaaagta taacaaga      720 gctctagata tgatttcag tgtcgttgtg ggaatcagtt ggtgggtttg ggtgttttct     780
gtaatcttca tattcttcag tgcacatggg tttcacagct atctatggct tccctttatt     840
ccattattaa tgcttttgtt ggttgggaca aaattacaag ggattatgac ggagatgtgt     900
ttggatagcc atgagaagtc tcatgtcgtt cgaggaactc tgcttgttag gcccagtgac     960
cattattttt ggttgggccg ccccaaattg cttctctatt tcatacactt cattttcttc    1020
cagaattcat tccaattagc attttttgca tgggcatggc tgaaatttgg gctgagatcg    1080
tgctttcaaa gagagatagc agatttggta ataggagttt ctgttggggt gttggtgcag    1140
```

-continued

```
ttcatttgtg ttatgttac tctgcctctc tatgcacttg tggctcagat ggggagttcg   1200
atgaagaaaa cggtattcac ggaggggtg gttgagggcc tgaggaaatg gaaagggaga   1260
gcgaagaaaa aggttgctcg aaggcaaaga ggccaacatg gctgcgacca caacttctca   1320
cagtcgccgc cgcggacatc agttgacgcc ggcgttgact cgccgccatc tttcagactg   1380
gaggcgacgc ccatggcatc agtggattat tatggtcgtt tacaactggc gggtgccaat   1440
aataataaac aatacaacaa caacaacaac agttgttcgg ctgcggtttc agttaatggc   1500
gatgaggata aactaaaagg caaaaaacca atcgaagagg cggatcagaa gtccatctca   1560
ttggatgcct ttgattgggc taacaaaata caccgtaatt tttcaagaca tgcaatgtag   1620
```

```
<210> SEQ ID NO 36
<211> LENGTH: 416
<212> TYPE: PRT
<213> ORGANISM: Cucumis sativus
<220> FEATURE:
<223> OTHER INFORMATION: Sequence listing for 58633.

<400> SEQUENCE: 36

Met Ala Gly Ala Ala Gly Gly Lys Ser Leu Glu Gln Thr Pro Thr Trp
1               5                   10                  15

Ala Val Ala Val Val Cys Phe Val Leu Val Ile Ser Ile Phe Ile
            20                  25                  30

Glu Tyr Ser Leu His Leu Ile Gly His Trp Leu Lys Lys Arg His Lys
        35                  40                  45

Arg Ala Leu Phe Glu Ala Leu Glu Lys Ile Lys Ser Glu Leu Met Leu
    50                  55                  60

Leu Gly Phe Ile Ser Leu Leu Thr Val Gly Gln Gly Pro Ile Thr
65                  70                  75                  80

Glu Ile Cys Ile Pro Gln His Val Ala Ala Thr Trp His Pro Cys Thr
                85                  90                  95

Lys Glu Arg Glu Asp Glu Met Asn Lys Glu Val Glu Lys Ser Val Glu
            100                 105                 110

His Leu Gly Leu Asn Arg Arg Leu Leu His Leu Leu Gly Asn Gly
        115                 120                 125

Glu Ser Phe Arg Arg Ser Leu Ala Ala Ala Gly Gly Glu Asp Lys Cys
    130                 135                 140

Ala Ala Lys Gly Lys Ala Ser Phe Ile Ser Ala Asp Gly Ile His Gln
145                 150                 155                 160

Leu His Ile Phe Ile Phe Val Leu Ala Val Phe His Val Leu Tyr Cys
                165                 170                 175

Val Leu Thr Tyr Ala Leu Ala Arg Ala Lys Met Arg Ser Trp Lys Thr
            180                 185                 190

Trp Glu Lys Glu Thr Lys Thr Ala Glu Tyr Gln Phe Ser His Asp Pro
        195                 200                 205

Glu Arg Phe Arg Phe Ala Arg Asp Thr Ser Phe Gly Arg Arg His Leu
    210                 215                 220

Ser Phe Trp Thr Lys Asn Pro Ala Leu Met Trp Ile Val Cys Phe Phe
225                 230                 235                 240

Arg Gln Phe Val Arg Ser Val Pro Lys Val Asp Tyr Leu Thr Leu Arg
                245                 250                 255

His Gly Phe Ile Met Ala His Leu Ala Pro Gln Ser His Thr Gln Phe
            260                 265                 270

Asp Phe Gln Lys Tyr Ile Asn Arg Ser Leu Glu Glu Asp Phe Lys Val
        275                 280                 285
```

```
Val Val Gly Ile Ser Pro Pro Ile Trp Phe Phe Ala Val Leu Phe Leu
    290                 295                 300

Leu Ser Asn Thr His Gly Trp Arg Ala Tyr Leu Trp Leu Pro Phe Ile
305                 310                 315                 320

Pro Leu Ile Ile Leu Leu Ile Gly Thr Lys Leu Gln Val Ile Ile
                325                 330                 335

Thr Lys Met Ala Leu Arg Ile Gln Glu Arg Gly Glu Val Val Lys Gly
            340                 345                 350

Val Pro Val Val Glu Pro Gly Asp Asp Leu Phe Trp Phe Asn Arg Pro
        355                 360                 365

Arg Leu Ile Leu Tyr Leu Ile Asn Phe Val Leu Phe Gln Asn Ala Phe
    370                 375                 380

Gln Val Ala Phe Phe Ala Trp Thr Trp Tyr Glu Phe Gly Leu Asn Ser
385                 390                 395                 400

Cys Phe His Glu His Ile Glu Asp Val Val Ile Arg Ile Ser Met Gly
                405                 410                 415
```

<210> SEQ ID NO 37
<211> LENGTH: 1251
<212> TYPE: DNA
<213> ORGANISM: Cucumis sativus
<220> FEATURE:
<223> OTHER INFORMATION: Sequence listing for 58633.

<400> SEQUENCE: 37

```
atggcggggg cagccggtgg caagtcgctg gagcaaacac cgacatgggc cgttgccgtt        60
gtttgctttg ttttgctcgt catctctatt ttcatcgaat atagtctcca tcttatcgga       120
cattggctaa agaagagaca caaacgggcg ttgtttgaag cattagagaa gatcaaatca       180
gagcttatgt tattggggtt tatatcattg ctactaacgg tggggcaagg accaataacg       240
gagatatgta ttccacaaca tgtagctgca acgtggcatc catgtacaaa ggaaagagaa       300
gatgagatga acaaagaggt ggagaaatct gtggaacatt gggtcttaa tcgccggaga       360
ctccttcatc tcctcggaaa tggtgaaagt ttccggcgga gtttggccgc tgcgggagga       420
gaggataaat gtgccgccaa gggtaaagct tcctttattt cagcagatgg aattcatcaa       480
cttcatatct tcattttgt gttggctgtt tttcatgttt tgtattgtgt tctaacttat       540
gcgttggcta gagctaagat gaggagttgg aaaacatggg aaaagagac caaaactgct       600
gaataccaat tctcacatga tccagagagg tttaggtttg caagagacac ctcatttggg       660
agaagacatt tgagcttttg gaccaaaaat cctgccttga tgtggatcgt ttgtttcttc       720
agacaatttg taagatctgt tccaaaagtt gattacttga cattaagaca tgggtttata       780
atggcacatt tagcacctca aagtcataca caatttgatt ttcaaaaata cattaataga       840
tcccttgaag aagacttcaa agttgttgtg ggaatcagcc caccaatttg gttctttgct       900
gttctatttc tcctctcaaa cactcacggt tggagggcgt atctatggct gccattcatc       960
ccactaatca ttttgctgtt gattggaaca aaattgcaag tgatcataac gaaaatggca      1020
ctaagaatac aagaaagagg tgaagtagtg aagggcgtgc cggtggtgga gcctggcgat      1080
gacctctttt ggtttaatcg acctcgcctt attctttatc tcatcaactt tgttctcttc      1140
caaaatgcct tccaagttgc cttctttgct tggacttggt atgagtttgg gttgaattct      1200
tgcttccatg agcatataga agatgtggtg atcagaattt ctatggggta a              1251
```

<210> SEQ ID NO 38

<211> LENGTH: 582
<212> TYPE: PRT
<213> ORGANISM: lactuca sativa
<220> FEATURE:
<223> OTHER INFORMATION: Sequence listing for 58633.

<400> SEQUENCE: 38

```
Met Ala Gly Gly Thr Asp Gly Arg Ser Leu Glu Gln Thr Pro Thr Trp
1               5                   10                  15

Ala Val Ala Thr Val Cys Phe Val Leu Ile Leu Ile Ser Ile Phe Ile
            20                  25                  30

Glu Gln Ile Ile His Met Ile Gly His Trp Phe Lys Lys Arg Lys
        35                  40                  45

Lys Ala Leu Tyr Glu Ser Leu Glu Lys Ile Lys Ala Glu Leu Met Leu
    50                  55                  60

Leu Gly Phe Ile Ser Leu Leu Thr Ala Gly Thr Thr Pro Ile Thr
65                  70                  75                  80

Lys Ile Cys Ile Ser Glu Gly Ala Ala Asn Ser Trp His Pro Cys Ser
                85                  90                  95

Arg Glu Glu Glu Ser Ala Gly Asp Ser Gly Glu Ser Arg Arg Arg
            100                 105                 110

Leu Leu Thr Trp Ser Lys Met Gly Asp Ser Thr Arg Arg Ile Leu Ala
        115                 120                 125

Gly Ser Gly Gly Asp Asp Lys Cys Ala Glu Gly Lys Val Ser Phe Met
130                 135                 140

Ser Tyr Asp Gly Val His Gln Leu His Ile Phe Ile Phe Ala Leu Ala
145                 150                 155                 160

Leu Phe His Val Ile Tyr Cys Ile Leu Thr Met Ala Leu Gly Gln Ala
                165                 170                 175

Lys Met Arg Arg Trp Lys His Trp Glu Lys Gly Thr Lys Thr Val Glu
            180                 185                 190

Tyr Gln Phe Ser His Asp Pro Glu Arg Phe Arg Phe Ala Arg Asp Thr
        195                 200                 205

Ser Phe Gly Arg Arg His Leu Asn Phe Trp Ser Lys Ser Pro Ile Leu
210                 215                 220

Leu Trp Ile Val Cys Phe Arg Gln Phe Phe Arg Ser Val Pro Lys
225                 230                 235                 240

Val Asp Tyr Leu Thr Leu Arg His Gly Phe Ile Met Ala His Leu Ala
                245                 250                 255

Pro Gln Ser Gln Ser Gly Phe Asp Phe Gln Lys Tyr Ile Asn Arg Ser
            260                 265                 270

Leu Glu Glu Asp Phe Lys Val Val Gly Ile Ser Pro Pro Ile Trp
        275                 280                 285

Leu Phe Ala Ile Val Phe Leu Phe Asn Thr His Gly Leu Tyr Ser
290                 295                 300

Tyr Leu Trp Leu Pro Phe Ile Pro Leu Val Ile Ile Leu Leu Val Gly
305                 310                 315                 320

Thr Lys Leu Gln Val Ile Ile Thr Lys Met Gly Leu Ser Ile Gln Glu
                325                 330                 335

Arg Gly Glu Val Val Gln Gly Val Pro Val Val Gln Pro Gly Asp Asp
            340                 345                 350

Leu Phe Trp Phe Asn Arg Pro Arg Leu Ile Leu Tyr Leu Ile Asn Phe
        355                 360                 365

Val Leu Phe Gln Asn Ala Phe Gln Ile Ala Phe Phe Ala Trp Thr Trp
370                 375                 380
```

```
Tyr Glu Phe Gly Leu Lys Ser Cys Phe His Glu His Thr Glu Asp Ile
385                 390                 395                 400

Val Ile Arg Ile Ser Met Gly Ile Leu Val Gln Ile Leu Cys Ser Tyr
            405                 410                 415

Val Thr Leu Pro Leu Tyr Ala Leu Val Thr Gln Met Gly Ser Thr Met
            420                 425                 430

Lys Pro Thr Ile Phe Asn Glu Arg Val Ala Thr Ala Leu Lys Thr Trp
            435                 440                 445

His Gln Ser Ala Arg Lys Gln Ile Lys Arg Asn Lys Lys Ser Gly Gln
            450                 455                 460

Val Thr Pro Met Ser Ser Arg Pro Gly Thr Pro Thr His Gly Met Ser
465                 470                 475                 480

Pro Val His Leu Leu Gln Asn Tyr Arg Thr Asp Ile Asp Ser Phe Pro
            485                 490                 495

Pro Ser Asp Asn Ala Ala Asn Phe Asp Ser Asp Asn Trp Asp Thr Asp
            500                 505                 510

Gly Ser Pro Ser Pro Ser Tyr His Gln Arg Arg Val Asn Glu Met Ser
            515                 520                 525

Ile Val Pro His Glu Val Glu Leu Gly Asn Arg Glu Gln Gly Asn Glu
530                 535                 540

Ile His Asp Ala Ser Ser Ser Gln Leu Ala Ile Val Val Asp Thr Gly
545                 550                 555                 560

Ala Ser Glu Gln His Glu Val Thr Ile Gly Val Pro Lys Glu Phe Ser
            565                 570                 575

Phe Asp Lys Arg Asn Ile
            580

<210> SEQ ID NO 39
<211> LENGTH: 1854
<212> TYPE: DNA
<213> ORGANISM: lactuca sativa
<220> FEATURE:
<223> OTHER INFORMATION: Sequence listing for 58633.

<400> SEQUENCE: 39
aaaacccatc cctctacttc actttaaatt ctcccagtaa tttcgtacga ataaagtcga    60
aaatacaaca actccatggc cggaggaact gacggcagat cttagagca aacgccgaca   120 tgggcggttg ccaccgtttg ctttgtgctc attctcatct ccatttttat cgaacaaatc   180
atccatatga tcggacattg gttcaagaag aaacgaaaga aagctctata tgaatccttg   240
gaaaagatta agcagagct tatgttgttg ggattcatat cgctgttgtt aacggcgggg   300
acgacaccaa ttacaaagat tgtatatcg gaggagctg ccaattcttg gcatccgtgc    360
agccgagaag aagaggaatc cgccggcgac agcggagaga gccgccggag gctgctcact   420
tggtcaaaaa tgggcgacag cacacggcga atcttagctg gtagtggcgg cgatgacaag   480
tgtgcagagg gaaaagtttc ttttatgtcg tatgatgggg ttcatcaact tcatatattc   540
atcttcgctc tcgccttatt tcatgttatt tactgtatcc ttaccatggc tttaggacaa   600
gcaaagatga agatggaa gcattgggag aaggagacaa aaaccgtaga gtatcaattt   660
tctcatgatc cagagaggtt tagatttgca agagacacat cgttcggaag aagacatcta   720
aatttctgga gcaagtctcc gattctacta tggattgttt gtttctttag acaatttttt   780
cgatcggtcc ctaagttga ttatctcact ttgagcatg gattcatcat ggcacatcta    840
gccccacaaa gccaatcagg attcgacttt cagaaataca tcaatagatc tcttgaagaa   900
```

```
gatttcaagg tcgttgtggg tataagtcca ccgatctggt tattcgccat tgtcttcttg    960
ctctttaata cccatggttt gtattcctat ttgtggctac cattcatacc attggttatt   1020
attctactag ttggaacaaa actacaagtg ataattacga aaatgggatt aagtattcaa   1080
gaaagaggag aggtcgtaca aggtgtacct gtggttcaac ctggtgatga cctcttttgg   1140
ttcaatcgcc ctcgtctcat tctctatctc atcaactttg tcctctttca gaatgctttt   1200
cagatagctt tctttgcatg gacttggtat gaatttgggc taaaatcttg ctttcatgaa   1260
catacagaag acattgtcat caggatctcc atggggatac ttgttcagat cctatgcagt   1320
tacgttactc ttcctctata tgctcttgtc acacagatgg gatcgactat gaagccaaca   1380
atattcaatg aaagagtagc aaccgcatta aaaacatggc accaatctgc aagaaaacaa   1440
attaaaagaa ataaaaagtc gggccaagtg actccgatgt caagtaggcc tggaacacca   1500
acccatggca tgtcgcctgt tcatctctta caaaactacc gaactgatat tgatagcttt   1560
ccaccatctc cgagaactgc aaactttgat agtgataatt gggacactga tggttcgccc   1620
tcaccctcct atcaccaacg aagggttaat gaaatgtcga tagtgccaca tgaggtggaa   1680
ttggggaata gagagcaagg taatgagatc catgatgcaa gttcgtcaca attggcaata   1740
gttgttgaca cgggtgctag tgaacaacat gaggtgacga taggagttcc taaagaattt   1800
tcgtttgata aagaaatat atgatataga aatgtaagta aaaggaaaga tgtt           1854
```

<210> SEQ ID NO 40
<211> LENGTH: 574
<212> TYPE: PRT
<213> ORGANISM: Pisum sativum
<220> FEATURE:
<223> OTHER INFORMATION: Sequence listing for 58633.

<400> SEQUENCE: 40

```
Met Ala Glu Glu Gly Val Lys Glu Arg Thr Leu Glu Glu Thr Pro Thr
1               5                   10                  15

Trp Ala Val Ala Val Val Cys Leu Val Leu Leu Ala Val Ser Ile Leu
            20                  25                  30

Ile Glu His Ile Ile His Val Ile Gly Lys Trp Leu Lys Lys Arg Asn
        35                  40                  45

Lys Asn Ala Leu Tyr Glu Ala Leu Glu Lys Ile Lys Gly Glu Leu Met
    50                  55                  60

Leu Leu Gly Phe Ile Ser Leu Leu Leu Thr Val Phe Gln Asp Asn Ile
65                  70                  75                  80

Ser Lys Ile Cys Val Ser Gln Lys Ile Gly Ser Thr Trp His Pro Cys
                85                  90                  95

Ser Thr Ser Asn Thr Lys Ala Lys Ala Lys Ser Asp Glu Ser Leu Asp
            100                 105                 110

Tyr Lys Thr Asn Asn Asp Arg Lys Leu Leu Glu Tyr Phe Asp Pro Ile
        115                 120                 125

Pro Arg Arg Ile Leu Ala Thr Lys Gly Tyr Asp Lys Cys Phe Asp Lys
    130                 135                 140

Gly Gln Val Ala Leu Val Ser Ala Tyr Gly Ile His Gln Leu His Ile
145                 150                 155                 160

Phe Ile Phe Val Leu Ala Leu Phe His Ile Leu Gln Cys Ile Ile Thr
                165                 170                 175

Leu Thr Leu Gly Arg Ile Lys Met Arg Lys Trp Lys Thr Trp Glu Asp
            180                 185                 190
```

-continued

Glu Thr Arg Thr Val Glu Tyr Gln Phe Tyr Asn Asp Pro Glu Arg Phe
            195                 200                 205

Arg Phe Ala Arg Asp Thr Thr Phe Gly Arg Arg His Leu Ser Met Trp
210                 215                 220

Ala Gln Ser Pro Ile Leu Leu Trp Ile Val Ser Phe Phe Arg Gln Phe
225                 230                 235                 240

Phe Gly Ser Ile Ser Arg Val Asp Tyr Met Ala Leu Arg His Gly Phe
            245                 250                 255

Ile Met Ala His Leu Pro Pro Gly His Asp Ala Gln Phe Asp Phe Gln
            260                 265                 270

Lys Tyr Ile Ser Arg Ser Ile Glu Glu Asp Phe Lys Val Val Val Gly
            275                 280                 285

Ile Ser Pro Thr Ile Trp Leu Phe Thr Val Leu Phe Leu Leu Thr Asn
290                 295                 300

Thr His Gly Trp Tyr Ser Tyr Tyr Trp Leu Pro Phe Leu Pro Leu Ile
305                 310                 315                 320

Val Ile Leu Leu Val Gly Ala Lys Leu Gln Met Ile Ile Thr Lys Met
            325                 330                 335

Gly Leu Arg Ile Gln Asp Arg Gly Glu Val Ile Lys Gly Ala Pro Val
            340                 345                 350

Val Glu Pro Gly Asp His Leu Phe Trp Phe Asn Arg Pro His Leu Leu
            355                 360                 365

Leu Phe Thr Ile His Leu Val Leu Phe Gln Asn Ala Phe Gln Leu Ala
            370                 375                 380

Phe Phe Ala Trp Ser Thr Tyr Glu Phe Ser Ile Thr Ser Cys Phe His
385                 390                 395                 400

Lys Thr Thr Ala Asp Ser Val Ile Arg Ile Thr Val Gly Val Val Ile
            405                 410                 415

Gln Thr Leu Cys Ser Tyr Val Thr Leu Pro Leu Tyr Ala Leu Val Thr
            420                 425                 430

Gln Met Gly Ser Thr Met Lys Pro Thr Ile Phe Asn Glu Arg Val Ala
            435                 440                 445

Thr Ala Leu Lys Asn Trp His His Thr Ala Lys Lys Gln Val Lys Gln
450                 455                 460

Ser Asn His Ser Asn Asn Thr Thr Pro Tyr Ser Ser Arg Pro Ser Thr
465                 470                 475                 480

Pro Thr His Ala Met Ser Pro Val His Leu Leu His Arg His Thr Ala
            485                 490                 495

Gly Asn Ser Asp Ser Leu Gln Thr Ser Pro Glu Lys Ser Asp Tyr Lys
            500                 505                 510

Asn Glu Gln Trp Asp Ile Glu Gly Glu Pro Thr Ser Leu Arg Asn
            515                 520                 525

Asp Gln Thr Gly Gln His Glu Ile Gln Ile Ala Gly Val Glu Ser Phe
530                 535                 540

Ser Ser Thr Glu Leu Pro Val Arg Ile Arg His Glu Ser Thr Ser Gly
545                 550                 555                 560

Ser Lys Asp Phe Ser Phe Glu Lys Arg His Leu Gly Ser Asn
            565                 570

<210> SEQ ID NO 41
<211> LENGTH: 1928
<212> TYPE: DNA
<213> ORGANISM: Pisum sativum
<220> FEATURE:
<223> OTHER INFORMATION: Sequence listing for 58633.

<400> SEQUENCE: 41

| | | | | | |
|---|---|---|---|---|---|
| aaaacaacaa | gtcaaaaaag | aaagaaaaaa | tggctgaaga | gggagttaag | gaacgaactt | 60 |
| tggaagaaac | accaacttgg | gctgttgcag | ttgtgtgtct | tgtgttgcta | gctgtttcaa | 120 |
| tcttaattga | acatattatt | catgttattg | gaaagtggtt | gaagaagaga | aacaaaaatg | 180 |
| ctctttatga | agctttggaa | aagatcaaag | gagagcttat | gctactagga | ttcatatcct | 240 |
| tgcttctaac | tgtcttccaa | gataatattt | ctaaaatatg | cgtatcacaa | aaaattggat | 300 |
| caacttggca | tccttgttcc | acttcaaaca | caaaggccaa | ggctaaatct | gatgaatcat | 360 |
| tagactataa | aaccaacaat | gatagaaaac | tcttggagta | ttttgatcct | attcctcgga | 420 |
| gaattcttgc | tacaaaagga | tatgataaat | gttttgataa | gggtcaagtt | gcattagttt | 480 |
| ctgcatatgg | aattcaccaa | ctccatatat | tcattttgt | gctggcacta | tttcatatcc | 540 |
| ttcaatgtat | aataacatta | actttgggaa | gaatcaagat | gaggaagtgg | aagacttggg | 600 |
| aagatgagac | aagaacagtt | gaatatcaat | tttataatga | tcctgagagg | tttaggtttg | 660 |
| caagggacac | aacatttgga | agaaggcact | tgagcatgtg | ggctcagtca | cctattttgt | 720 |
| tatggattgt | tagcttcttc | agacaattct | ttggatctat | cagtagagtt | gattatatgg | 780 |
| ctcttaggca | tggatttatc | atggctcatc | ttcctccagg | acatgatgca | caatttgatt | 840 |
| tccaaaagta | tataagtaga | tcaattgaag | aggattttaa | agttgttgta | ggaataagtc | 900 |
| caactatctg | gctcttcaca | gtgctttcc | ttcttacaaa | tactcatggg | tggtattctt | 960 |
| attattggct | tccatttctt | ccactaattg | taatcttatt | agttggtgct | aagttacaaa | 1020 |
| tgatcataac | aaaaatggga | ttaaggattc | aagacagagg | agaagtaatc | aagggtgcac | 1080 |
| ctgtggttga | gcctggagat | cacctttct | ggttcaatcg | tcctcacctt | cttctcttca | 1140 |
| cgattcatct | tgttctcttt | cagaatgcct | ttcaacttgc | atttttgct | tggagtacat | 1200 |
| atgagttttc | cataacctct | tgcttccaca | aaacaactgc | agatagtgtc | attagaatca | 1260 |
| ctgtaggggt | tgtaatacaa | actctatgta | gctatgtgac | tttgcctctt | tatgctctag | 1320 |
| tcacacagat | gggatcaacc | atgaaaccaa | ccatttcaa | cgaaagagtg | gcaacagcgc | 1380 |
| ttaagaactg | gcaccacaca | gccaaaaagc | aggtaaaaca | gagcaaccac | tcaaacaaca | 1440 |
| cgacaccgta | ttcaagcagg | ccatcaaccc | caacacatgc | catgtctcct | gttcacctgc | 1500 |
| tccatagaca | cactgctgga | aacagcgaca | gtctacaaac | ttctccggaa | aagtctgatt | 1560 |
| ataaaaatga | acagtgggat | attgaaggag | aaggaccaac | ttccctaaga | aacgatcaaa | 1620 |
| cagggcaaca | tgagattcaa | atagcgggtg | tcgagtcatt | ttcgtcaacc | gaattgccgg | 1680 |
| ttagaattag | acatgaaagc | acctctggtt | caaaagattt | ttctttcgag | aagcgccact | 1740 |
| tagggagcaa | ttagaattgt | aggtattgat | aaccagttca | atgtatacca | attaggtaca | 1800 |
| ttcttgcaga | taaagataga | ggaactcctt | ctaagaatgg | agtgtaaatt | tgttgaggta | 1860 |
| gcagcttgat | ttgtggatat | aatcataggg | tatgaaaatg | caagactata | ttttgtaaaa | 1920 |
| aaaaaaaa | | | | | | 1928 |

<210> SEQ ID NO 42
<211> LENGTH: 593
<212> TYPE: PRT
<213> ORGANISM: Medicago truncatula
<220> FEATURE:
<223> OTHER INFORMATION: Sequence listing for 58633.

<400> SEQUENCE: 42

```
Met Ala Gly Gly Ser Val Gly Arg Ser Leu Thr Glu Thr Pro Thr Trp
 1               5                  10                  15
Ala Val Ala Val Val Cys Phe Val Ile Leu Ser Ile Ser Ile Phe Ile
             20                  25                  30
Glu His Ile Phe His Ile Ile Glu Lys Trp Leu Lys Lys His Lys
         35                  40                  45
Ser Ala Leu Tyr Glu Ser Leu Glu Lys Ile Lys Ser Glu Leu Met Leu
 50                  55                  60
Leu Gly Phe Ile Ser Leu Leu Thr Val Gly Glu Gly Leu Ile Ser
 65                  70                  75                  80
Arg Ile Cys Ile Ser Glu Lys Val Ala Ala Thr Trp His Pro Cys Ser
                 85                  90                  95
Asn Asn Ala Asn Ile Glu Ser Asp Asp Glu Glu Leu Ile Asp His Glu
             100                 105                 110
Thr Gly Gly Ser Arg Arg Leu Leu Ala Ala Leu Leu Ala Ser Gln Gly
             115                 120                 125
Asp Asn His His Arg Ile Leu Ala Gly Gly Gly Asp Lys Cys Ala
         130                 135                 140
Glu Glu Gly Lys Val Ala Phe Val Ser Ala Gly Ala Ile His Gln Leu
145                 150                 155                 160
His Ile Phe Ile Phe Val Leu Ala Val Phe His Ile Leu Tyr Cys Ile
                 165                 170                 175
Leu Thr Leu Ala Leu Gly Arg Ala Lys Met Arg Arg Trp Lys Arg Trp
                 180                 185                 190
Glu Glu Ala Thr Lys Thr Pro Glu Tyr Gln Phe Ser His Asp Pro Glu
             195                 200                 205
Arg Phe Arg Phe Ala Asn Glu Thr Ser Phe Gly Arg Arg His Leu Ser
         210                 215                 220
Phe Trp Thr Lys Asn Pro Val Leu Ile Trp Ile Val Cys Phe Phe Arg
225                 230                 235                 240
Gln Phe Val Arg Ser Val Pro Glu Val Asp Tyr Leu Thr Leu Arg His
                 245                 250                 255
Gly Phe Met Met Ala His Leu Ala Pro Gln Ser His Leu Lys Phe Asp
             260                 265                 270
Phe Arg Gln Tyr Ile Lys Arg Cys Leu Glu Glu Asp Phe Lys Val Val
         275                 280                 285
Val Gly Ile Ser Pro Pro Ile Trp Phe Ile Thr Val Phe Phe Leu Leu
         290                 295                 300
Phe His Thr His Gly Trp His Ser Tyr Leu Trp Leu Pro Phe Leu Pro
305                 310                 315                 320
Leu Ile Ile Val Leu Leu Val Gly Thr Lys Leu Gln Val Ile Ile Thr
                 325                 330                 335
Gln Met Gly Leu Arg Ile Gln Lys Gln Gly Met Val Val Lys Gly Glu
             340                 345                 350
Pro Val Val Gln Pro Arg Asp Asp Leu Phe Trp Phe Asn Lys Pro Arg
             355                 360                 365
Leu Ile Leu Phe Leu Ile Asn Phe Val Leu Phe Gln Asn Ala Phe Gln
370                 375                 380
Leu Ala Phe Phe Ser Trp Thr Ala Leu Gln Phe Gly Val Thr Ser Cys
385                 390                 395                 400
Tyr Asn Ser Arg Lys Asp Gly Val Val Ile Arg Ile Cys Met Gly Val
                 405                 410                 415
Phe Val Gln Ile Leu Cys Ser Tyr Val Thr Leu Pro Leu Tyr Ala Leu
```

```
                420           425           430
Val Thr Gln Met Gly Ser Thr Met Lys Pro Thr Ile Phe Asn Glu Arg
                    435               440               445
Val Ala Thr Ala Leu Arg Asn Trp His His Thr Ala Arg Lys Asn Ile
            450               455               460
Lys His Asn Arg Gly Ser Gly Ser Gln Thr Pro Phe Ser Ser Arg Ser
465               470               475               480
Ile Thr Pro Ala Arg Ser Met Ser Pro Ala Gln Ile Leu Arg His Tyr
                    485               490               495
Arg Asn Gln Met Asp Thr Pro Thr Arg Leu Asn Phe Glu Thr Ser His
                500               505               510
His Tyr Glu Ser Tyr Ser Pro Ser Pro Ser Asn Ser His His His Lys
            515               520               525
Val Glu Ile Asn Val Ala Ser Ser Ser Ser Thr His Leu His Glu Met
            530               535               540
Glu Met Gly His Leu Ala His Val Gln Gln Glu Val Ile Lys Pro
545               550               555               560
Asn Ser Ile Ser Val Gly Ser Gly Arg Pro Gln Phe Glu Ile Asp Ile
                    565               570               575
Gln Gln Ser Asp Glu Leu Ser Phe Ser Thr Met Pro Thr Asn Gln Leu
                580               585               590
Glu

<210> SEQ ID NO 43
<211> LENGTH: 1782
<212> TYPE: DNA
<213> ORGANISM: Medicago truncatula
<220> FEATURE:
<223> OTHER INFORMATION: Sequence listing for 58633.

<400> SEQUENCE: 43
atggcaggag gaagcgttgg aagaagctta actgaaacac ctacttgggc cgttgcagtt      60
gtttgctttg ttatactttc tatttctatc ttcattgaac acattttcca catcatagaa     120
aagtggttga agaagaagca taaaagtgcc ttgtatgagt cacttgaaaa gatcaaatca     180
gagctaatgt tactagggtt catatcattg ctcctaacag taggagaagg tttaatatca     240
agaatatgta tatcagaaaa agttgcagcc acatggcatc catgtagcaa caatgcaaat     300
attgaatcag atgatgaaga gttaatagac catgaaaccg gtggcagccg agattacta      360 gccgcgttgc ttgcttctca aggcgacaat caccaccgta ttttggctgg tggaggaggt     420
gacaaatgtg cagaagaggg aaaagtagca tttgtatcag caggggccat tcatcaactc     480
catatattta tatttgtgct tgctgttttt catatcctct actgcatact tactctggct     540
ctaggtagag caaagatgag aaggtggaaa agatgggaag aggcaaccaa gacacctgag     600 taccaattttt cacacgatcc tgaaagattc agattcgcta acgagacttc gtttggaaga     660
agacacttaa gtttctggac caaaaatcct gtcctcattt ggattgtatg tttttttagg     720
caatttgtaa ggtcagttcc tgaagtggat tacttgacct taaggcatgg atttatgatg     780
gcacatttgg ctcctcaaag tcacctgaag tttgactta gacaatacat caaaagatgt     840
ttggaagaag acttcaaagt tgttgttgga atcagtcctc caatttggtt catcacagtg     900
ttcttcctcc tgttccatac tcatgggtgg cactcttatc tatggctacc atttcttcct     960
ttgattattg tccattagt tggaacaaag ctgcaagtga tcataactca aatgggtctt    1020
agaattcaaa acaaggaat ggtggtaaag ggtgagccag tggtgcaacc tagggatgac    1080
```

```
ctcttttggt taacaaaacc tagacttatt ctcttcctta ttaatttgt actctttcag    1140 aatgccttcc agcttgcttt cttttcatgg actgctcttc aatttggggt gacatcctgt    1200
tacaattcac gtaaagatgg tgttgtcatt agaatttgca tgggagtctt cgttcaaatc    1260 cttttgcagct acgtcactct ccctctctat gctctcgtga cgcagatggg ttcgaccatg    1320
aaaccaacca tattcaacga aagagtagct acagctctac ggaattggca ccacaccgca    1380
aggaagaaca taaagcacaa ccgtggatcg ggctctcaaa ccccatttc aagtcggtcc      1440 ataactccgg cacgttcaat gtctccggcc caaatccttc gtcattaccg caaccaaatg    1500
gacactccaa caagactcaa tttgagacc agtcaccact atgaatctta ttcaccctca     1560
ccttccaact cacaccacca caaggttgag atcaatgttg cttcttccag ctcaactcat    1620
cttcatgaaa tggaaatggg tcacctagcc atgttgaac aacaagaagt cattaagccc      1680
aatagtattt ctgtgggctc aggccggcct caatttgaaa ttgatatcca acagagtgat    1740
gaactctcat tttcaacaat gcccacaaat caattagaat ga                       1782
```

<210> SEQ ID NO 44
<211> LENGTH: 563
<212> TYPE: PRT
<213> ORGANISM: Glycine Max
<220> FEATURE:
<223> OTHER INFORMATION: Sequence listing for 58633.

<400> SEQUENCE: 44

```
Met Ser Lys Val Leu Gln Ala Lys Leu Glu Ala Thr Pro Thr Trp Ala
1               5                   10                  15

Val Ala Val Val Cys Phe Val Met Leu Ala Ile Ser Ile Leu Ile Glu
                20                  25                  30

His Ile Leu Glu Glu Leu Gly Lys Trp Leu Lys Lys Lys His Lys Lys
            35                  40                  45

Ala Leu His Glu Ala Leu Glu Lys Val Lys Gly Glu Leu Met Leu Leu
        50                  55                  60

Gly Phe Ile Ser Leu Leu Leu Val Met Phe Gln Asp His Ile Ser Asn
65                  70                  75                  80

Ile Cys Ile Pro Lys Ser Val Ala Ser Thr Trp His Pro Cys Asp Pro
                85                  90                  95

Gly Asp Glu Arg Lys Lys Pro Asp Gly Tyr Tyr Asp Lys Cys Ala Asp
            100                 105                 110

Lys Gly Lys Asp Gln Val Ala Phe Met Ser Glu Tyr Ser Ile His Gln
        115                 120                 125

Leu His Ile Phe Val Phe Val Leu Ala Ile Phe His Ile Leu Gln Cys
    130                 135                 140

Ile Met Thr Leu Thr Leu Gly Arg Thr Lys Met Ser Ile Trp Arg Lys
145                 150                 155                 160

Trp Glu Asp Glu Thr Lys Ser Leu Gly His Gln Phe His His Asp Pro
                165                 170                 175

Glu Arg Phe Arg Phe Ala Arg Asp Thr Thr Phe Gly Arg Arg His Leu
            180                 185                 190

Ser Ser Trp Ser Arg Ser Pro Gly Ser Leu Trp Ile Val Ser Phe Phe
        195                 200                 205

Arg Gln Phe Tyr Gly Ser Leu Asn Lys Val Asp Tyr Met Ala Leu Arg
    210                 215                 220

His Gly Phe Leu Val Ala His Leu Thr Pro Ala Asn Glu Ala Lys Phe
225                 230                 235                 240
```

-continued

Asp Phe Gln Asn Tyr Ile Lys Arg Thr Leu Asp Glu Asp Phe Ala Ala
                245                 250                 255

Val Val Gly Ile Thr Pro Thr Ile Trp Phe Ala Val Leu Ile Leu
            260                 265                 270

Leu Thr Asn Thr His Gly Trp Tyr Ser Tyr Trp Ile Pro Phe Ile
        275                 280                 285

Pro Val Ile Ile Ile Leu Leu Val Gly Thr Lys Leu Gln Met Ile Ile
    290                 295                 300

Thr Glu Met Ala Leu Lys Ile Gln Asp Arg Gly Glu Val Val Lys Gly
305                 310                 315                 320

Ala Pro Leu Val Glu Pro Gly Asp Glu Leu Phe Trp Phe Asn Arg Pro
                325                 330                 335

Arg Leu Ile Leu Phe Leu Ile His Leu Val Leu Phe Gln Asn Ala Phe
            340                 345                 350

Gln Leu Ala Phe Phe Ala Trp Ser Thr Tyr Asp Asn Gly Phe Lys Ile
        355                 360                 365

Asn Ser Cys Phe His Lys Thr Thr Ala Asp Ile Val Ile Arg Leu Thr
    370                 375                 380

Met Gly Val Leu Thr Gln Val Leu Cys Ser Tyr Val Thr Leu Pro Leu
385                 390                 395                 400

Tyr Ala Leu Val Thr Gln Met Gly Ser Thr Met Lys Pro Thr Ile Phe
                405                 410                 415

Asn Glu Asn Val Ala Val Ala Leu Lys Asn Trp His His Thr Ala Lys
            420                 425                 430

Lys His Ile Lys His Asn Lys Asp Ser Thr Ser Asn Thr Pro Phe Ser
        435                 440                 445

Ser Arg Pro Gly Thr Pro Thr His Gly Met Ser Pro Val His Leu Leu
    450                 455                 460

His Lys His Pro Arg His Ser Asp Ser Pro Val Val Ser Pro Arg Ala
465                 470                 475                 480

Tyr Asn Tyr Glu Asn Glu Gln Trp Gly Val Glu Gly Ile His Ser Pro
                485                 490                 495

Ser His His Ala Arg Asp His Asp Pro Asp His Glu Lys Thr Met Gln
            500                 505                 510

Met Gln Met Gln Met Gln Gln Arg Pro Ala Pro Thr Ala Glu Leu
        515                 520                 525

Pro Pro Ser Gly Leu Asn Pro Ile Arg Thr Gln His Glu Ile Asn Ile
    530                 535                 540

Ala Leu Ser Glu Phe Ser Phe Gly Arg Gly His His Thr Gly Ser Asn
545                 550                 555                 560

Thr Asn Asn

<210> SEQ ID NO 45
<211> LENGTH: 2105
<212> TYPE: DNA
<213> ORGANISM: Glycine Max
<220> FEATURE:
<223> OTHER INFORMATION: Sequence listing for 58633.

<400> SEQUENCE: 45
ggattataca atatcatcag caagagtctc caaaaagatt ggtgttgtat accatcgtcc      60
ttaatttata ttatacacgt ctctagctag ctacataata ttctcttctt ccacacacac     120 aaagaaaaa agaaaattgt ttagagtgtg gagggtaaaa aatgagcaaa gttcttcagg      180

| | |
|---|---|
| cgaagttgga ggcaactcca acatgggctg ttgcagttgt gtgctttgtg atgcttgcta | 240 |
| tttcaatcct cattgaacat attcttgaag aacttggaaa gtggttaaaa aagaaacaca | 300 |
| aaaaggctct tcatgaagcg ctggaaaagg ttaaaggaga gcttatgctg ctgggattca | 360 |
| tatcgttgct cctagtgatg tttcaagatc acatttctaa tatatgcatc ccaaaaagcg | 420 |
| ttgcatccac ttggcatcct tgtgatcccg gtgatgagcg taaaaaacca gacggatatt | 480 |
| atgacaaatg cgcagataaa ggtaaagacc aagtagcttt tatgtctgaa tatagtattc | 540 |
| accagctcca tatattcgtc tttgtgcttg ctattttca catcctacag tgcatcatga | 600 |
| cactgacttt gggtagaacc aagatgtcta tatggaggaa gtgggaagac gaaacaaaga | 660 |
| gtcttggcca tcagttccac catgatcctg agaggttcag gtttgctagg gatacaacgt | 720 |
| ttggacgaag gcacttgagc tcatggagtc gatcaccagg ttccttatgg atagttagct | 780 |
| tcttccgaca attctacggg tcacttaata aagtagacta catggcattg cggcatggat | 840 |
| tcctcgtggc acatttgact ccagcaaatg aggcaaaatt tgatttccag aactatatca | 900 |
| agagaacact tgatgaggat tttgcagctg tggtgggcat aactccaacc atatggttct | 960 |
| ttgctgtgct aattctgctc acaaatactc atgggtggta ttcttatttt tggattccat | 1020 |
| ttatcccagt aattataatc ttgttggtgg aacaaaagc acaaatgatc ataacagaga | 1080 |
| tggcactaaa gattcaagat agggggggaag tggtcaaggg tgcacctttg gttgagccag | 1140 |
| gagatgaatt gttctggttc aatcgacccc gcctcatcct cttttgatt catcttgttc | 1200 |
| tctttcagaa tgcatttcaa ctagcgtttt ttgcttggag cacatatgac aatgggttca | 1260 |
| aaataaactc ttgtttccac aaaactactg cagatattgt cattagactt acaatggggg | 1320 |
| ttctcacaca agttctatgc agttatgtga ctttgcctct ttatgctcta gtcacccaga | 1380 |
| tgggttctac catgaaacct actatttca atgaaaatgt tgcagtagcc ctgaagaact | 1440 |
| ggcatcacac tgctaaaaag cacatcaaac acaacaagga ttctacttca aatacaccat | 1500 |
| tctcaagcag gccaggaacc ccgacacatg gcatgtctcc agttcacttg cttcacaagc | 1560 |
| accctagaca cagtgacagt ccagtagttt ctccaagggc atacaattac gaaaatgaac | 1620 |
| agtggggtgt tgaagggata cattccccaa gccaccacgc aagagatcat gatcctgatc | 1680 |
| atgaaaagac catgcagatg cagatgcaga tgcagcagca gcggccagct ccaacagcag | 1740 |
| aattgcctcc tagtggactc aatcctattc gaactcaaca tgaaatcaac attgctttat | 1800 |
| ctgaattttc atttgggagg ggacaccaca ctggtagtaa tactaataac taaatatgag | 1860 |
| tattagaaac atttccttgt tttgttttgt tttttttttt tttttttat cttttagct | 1920 |
| tcaattcata tcgagcacat ctacgttgta agtaaaagac gggcagtgct tttgaagatt | 1980 |
| tttattatct gtatatgtta agatagtaac ttttcctctt ttatttttt aatcatccga | 2040 |
| tcaaccttat atttgttagt ttttaaagat tgaaatgaaa gttaagtaat atatttttac | 2100 |
| aaaaa | 2105 |

<210> SEQ ID NO 46
<211> LENGTH: 563
<212> TYPE: PRT
<213> ORGANISM: Glycine Max
<220> FEATURE:
<223> OTHER INFORMATION: Sequence listing for 58633.

<400> SEQUENCE: 46

Met Ser Lys Val Leu Gln Ala Lys Leu Glu Ala Thr Pro Thr Trp Ala
1               5                   10                  15

```
Val Ala Val Val Cys Phe Val Met Leu Ala Ile Ser Ile Leu Ile Glu
             20                  25                  30

His Ile Leu Glu Glu Leu Gly Lys Trp Leu Lys Lys His Lys Lys
         35                  40                  45

Ala Leu His Glu Ala Leu Glu Lys Val Lys Gly Glu Leu Met Leu Leu
 50                  55                  60

Gly Phe Ile Ser Leu Leu Leu Val Met Phe Gln Asp His Ile Ser Asn
 65                  70                  75                  80

Ile Cys Ile Pro Lys Ser Val Ala Ser Thr Trp His Pro Cys Asp Pro
                 85                  90                  95

Gly Asp Glu Arg Lys Lys Pro Asp Gly Tyr Tyr Asp Lys Cys Ala Asp
            100                 105                 110

Lys Gly Lys Asp Gln Val Ala Phe Met Ser Glu Tyr Ser Ile His Gln
        115                 120                 125

Leu His Ile Phe Val Phe Val Leu Ala Ile Phe His Ile Leu Gln Cys
    130                 135                 140

Ile Met Thr Leu Thr Leu Gly Arg Thr Lys Met Ser Ile Trp Arg Lys
145                 150                 155                 160

Trp Glu Asp Glu Thr Lys Ser Leu Gly His Gln Phe His His Asp Pro
                165                 170                 175

Glu Arg Phe Arg Phe Ala Arg Asp Thr Thr Phe Gly Arg Arg His Leu
            180                 185                 190

Ser Ser Trp Ser Arg Ser Pro Gly Ser Leu Trp Ile Val Ser Phe Phe
        195                 200                 205

Arg Gln Phe Tyr Gly Ser Leu Asn Lys Val Asp Tyr Met Ala Leu Arg
    210                 215                 220

His Gly Phe Leu Val Ala His Leu Thr Pro Ala Asn Glu Ala Lys Phe
225                 230                 235                 240

Asp Phe Gln Asn Tyr Ile Lys Arg Thr Leu Asp Glu Asp Phe Ala Ala
                245                 250                 255

Val Val Gly Ile Thr Pro Thr Ile Trp Phe Phe Ala Val Leu Ile Leu
            260                 265                 270

Leu Thr Asn Thr His Gly Trp Tyr Ser Tyr Phe Trp Ile Pro Phe Ile
        275                 280                 285

Pro Val Ile Ile Ile Leu Leu Val Gly Thr Lys Leu Gln Met Ile Ile
    290                 295                 300

Thr Glu Met Ala Leu Asn Ser Ala Arg Gly Gly Glu Val Val Lys Gly
305                 310                 315                 320

Ala Pro Leu Val Glu Pro Gly Asp Glu Leu Phe Trp Phe Asn Arg Pro
                325                 330                 335

Arg Leu Ile Leu Phe Leu Ile His Leu Val Leu Phe Gln Asn Ala Phe
            340                 345                 350

Gln Leu Ala Phe Phe Ala Trp Ser Thr Tyr Asp Asn Gly Phe Lys Ile
        355                 360                 365

Asn Ser Cys Phe His Lys Thr Thr Ala Asp Ile Val Ile Arg Leu Thr
370                 375                 380

Met Gly Val Leu Thr Gln Val Leu Cys Ser Tyr Val Thr Leu Pro Leu
385                 390                 395                 400

Tyr Ala Leu Val Thr Gln Met Gly Ser Thr Met Lys Pro Thr Ile Phe
                405                 410                 415

Asn Glu Asn Val Ala Val Ala Leu Lys Asn Trp His His Thr Ala Lys
            420                 425                 430

Lys His Ile Lys His Asn Lys Asp Ser Thr Ser Asn Thr Pro Phe Ser
```

|  |  | 435 |  |  | 440 |  |  | 445 |  |  |  |
|---|---|---|---|---|---|---|---|---|---|---|---|
| Ser | Arg | Pro | Gly | Thr | Pro | Thr | His | Gly | Met | Ser | Pro | Val | His | Leu | Leu |
|  |  |  | 450 |  |  |  | 455 |  |  |  | 460 |

His Lys His Pro Arg His Ser Asp Ser Pro Val Val Ser Pro Arg Ala
465                 470                475                480

Tyr Asn Tyr Glu Asn Glu Gln Trp Gly Val Glu Gly Ile His Ser Pro
                485                 490                 495

Ser His His Ala Arg Asp His Asp Pro Asp His Glu Lys Thr Met Gln
            500                 505                 510

Met Gln Met Gln Met Gln Gln Arg Pro Ala Pro Thr Ala Glu Leu
        515                 520                 525

Pro Pro Ser Gly Leu Asn Pro Ile Arg Thr Gln His Glu Ile Asn Ile
        530                 535                 540

Ala Leu Ser Glu Phe Ser Phe Gly Arg Gly His His Thr Gly Ser Asn
545                 550                 555                 560

Thr Asn Asn

```
<210> SEQ ID NO 47
<211> LENGTH: 2059
<212> TYPE: DNA
<213> ORGANISM: Glycine Max
<220> FEATURE:
<223> OTHER INFORMATION: Sequence listing for 58633.

<400> SEQUENCE: 47
ggatttcgtc ctccttaatt tatattatac acgtctctag ctagctacat aatattctct      60
tcttccacac acacaaaaga aaaagaaaaa ttgtttagag tgtggagggt aaaaaatgag     120
caaagttctt caggcgaagt tggaggcaac tccaacatgg gctgttgcag ttgtgtgctt     180
tgtgatgctt gctatttcaa tcctcattga acatattctt gaagaacttg gaaagtggtt     240 aaaaagaaa cacaaaaagg ctcttcatga agcgctggaa aaggttaaag gagagcttat      300
gctgctggga ttcatatcgt tgctcctagt gatgtttcaa gatcacattt ctaatatatg     360
catcccaaaa agcgttgcat ccacttggca tccttgtgat cccggtgatg agcgtaaaaa     420
accagacgga tattatgaca aatgcgcaga taaaggtaaa gaccaagtag cttttatgtc     480
tgaatatagt attcaccagc tccatatatt cgtctttgtg cttgctattt ttcacatcct     540
acagtgcatc atgacactga ctttgggtag aaccaagatg tctatatgga ggaagtggga     600
agacgaaaca aagagtcttg gccatcagtt ccaccatgat cctgagaggt tcaggtttgc     660
tagggataca acgtttggac gaaggcactt gagctcatgg agtcgatcac caggttcctt     720
atggatagtt agcttcttcc gacaattcta cgggtcactt aataaagtag actacatggc     780
attgcggcat ggattcctcg tggcacattt gactccagca aatgaggcaa atttgattt      840 ccagaactat atcaagagaa cacttgatga ggattttgca gctgtggtgg cataactcc      900 aaccatatgg ttctttgctg tgctaattct gctcacaaat actcatgggt ggtattctta     960
tttttggatt ccatttatcc cagtaattat aatcttgttg gtgggaacaa agctacaaat    1020
gatcataaca gagatggcac taaattcggc tcgaggggg gaagtggtca agggtgcacc    1080
tttggttgag ccaggagatg aattgttctg gttcaatcga ccccgcctca tcctcttttt    1140
gattcatctt gttctctttc agaatgcatt tcaactagcg ttttttgctt ggagcacata    1200
tgacaatggg ttcaaaataa actcttgttt ccacaaaact actgcagata ttgtcattag    1260
acttacaatg ggggttctca cacaagttct atgcagttat gtgactttgc ctctttatgc    1320
```

```
tctagtcacc cagatgggtt ctaccatgaa acctactatt ttcaatgaaa atgttgcagt    1380
agccctgaag aactggcatc acactgctaa aaagcacatc aaacacaaca aggattctac    1440
ttcaaataca ccattctcaa gcaggccagg aaccccgaca catggcatgt ctccagttca    1500
cttgcttcac aagcacccta gacacagtga cagtccagta gtttctccaa gggcatacaa    1560
ttacgaaaat gaacagtggg gtgttgaagg gatacattcc ccaagccacc acgcaagaga    1620
tcatgatcct gatcatgaaa agaccatgca gatgcagatg cagatgcagc agcagcggcc    1680
agctccaaca gcagaattgc ctcctagtgg actcaatcct attcgaactc aacatgaaat    1740
caacattgct ttatctgaat ttcatttgg gaggggacac cacactggta gtaatactaa    1800
taactaaata tgagtattag aaacatttcc ttgttttgtt ttgtttttttt tttttttttt    1860 ttatcttttt agcttcaatt catatcgagc acatctacgt tgtaagtaaa agacgggcag    1920
tgcttttgaa gatttttatt atctgtatat gttaagatag taacttttcc tcttttattt    1980
ttttaatcat ccgatcaacc ttatatttgt tagtttttaa agattgaaat gaaagttaag    2040
taatatattt ttacaaaaa                                                 2059
```

<210> SEQ ID NO 48
<211> LENGTH: 587
<212> TYPE: PRT
<213> ORGANISM: Capsicum annuum
<220> FEATURE:
<223> OTHER INFORMATION: Sequence listing for 58633.

<400> SEQUENCE: 48

```
Met Ala Gly Gly Gly Gly Arg Ser Leu Glu Gln Thr Pro Thr Trp
 1               5                  10                  15

Ala Val Ala Val Val Cys Phe Ala Leu Val Ala Ile Ser Val Ile
                20                  25                  30

Glu Phe Ile Ile His Leu Ile Gly Lys Trp Leu Lys Ser Lys Gln Lys
            35                  40                  45

Arg Ala Leu Tyr Glu Ala Leu Glu Lys Ile Lys Ser Glu Leu Met Leu
        50                  55                  60

Leu Gly Phe Ile Ser Leu Leu Thr Val Gly Gln Asp Pro Ile Ser
65                  70                  75                  80

Asn Ile Cys Val Ser Glu Lys Ile Ala Ser Thr Trp His Pro Cys Thr
                85                  90                  95

Lys Gln Lys Glu Asn Glu Ile Asn Lys Glu Lys Ser Asp Asp Leu Glu
            100                 105                 110

Gly His Arg Arg Arg Leu Leu Thr Ala Ser Asp Gly Gly Val Arg Arg
        115                 120                 125

Val Leu Ala Ala Val Gly Thr Asp Lys Cys Ala Asp Lys Gly Lys Val
    130                 135                 140

Ala Phe Val Ser Ala Asp Gly Ile His Gln Leu His Ile Phe Ile Phe
145                 150                 155                 160

Val Leu Ala Leu Phe His Ile Phe Tyr Cys Ile Thr Thr Leu Ala Leu
                165                 170                 175

Gly Arg Ala Lys Met Ser Ser Trp Lys Ala Trp Glu Asn Glu Thr Arg
            180                 185                 190

Thr Ala Glu Tyr Gln Phe Thr Asn Asp Pro Glu Arg Phe Arg Phe Ala
        195                 200                 205

Arg Asp Thr Ser Phe Gly Arg Arg His Leu Ser Phe Trp Thr Lys Asn
    210                 215                 220

Ser Val Leu Leu Trp Ile Val Cys Phe Phe Arg Gln Phe Val Arg Ser
```

```
               225                 230                 235                 240
Val Pro Lys Val Asp Tyr Leu Thr Leu Arg His Gly Phe Ile Met Ala
                245                 250                 255

His Leu Ala Pro Gln Ser Gln Ile Asn Phe Asp Phe Gln Lys Tyr Ile
                260                 265                 270

Lys Arg Ser Leu Glu Glu Asp Phe Lys Val Val Ser Ile Ser Pro
            275                 280                 285

Pro Ile Trp Phe Leu Ala Val Leu Phe Leu Leu Phe Asn Thr His Gly
            290                 295                 300

Trp Tyr Ser Tyr Leu Trp Leu Pro Phe Ile Pro Leu Phe Val Ile Leu
305                 310                 315                 320

Leu Val Gly Thr Lys Leu Gln Val Ile Ile Thr Lys Met Gly Leu Arg
                325                 330                 335

Ile Gln Glu Arg Gly Glu Val Val Lys Gly Val Pro Val Gln Pro
            340                 345                 350

Gly Asp Asp Leu Phe Trp Phe Asn Arg Pro Arg Leu Leu Leu Tyr Leu
            355                 360                 365

Ile Asn Phe Val Leu Phe Gln Asn Ala Phe Gln Leu Ala Phe Phe Ala
        370                 375                 380

Trp Thr Trp Tyr Glu Phe Gly Leu Lys Ser Cys Phe His Asp Lys Thr
385                 390                 395                 400

Glu Asp Ile Val Ile Arg Met Thr Met Gly Val Leu Ile Gln Ile Leu
                405                 410                 415

Cys Ser Tyr Val Thr Leu Pro Leu Tyr Ala Leu Val Thr Gln Met Gly
                420                 425                 430

Ser Ser Met Lys Pro Thr Ile Phe Asn Glu Arg Val Ala Thr Ala Leu
            435                 440                 445

Arg Lys Trp His His Gly Ala Lys Lys His Ile Lys Glu Ile Asn Lys
            450                 455                 460

His His Ser Asn Pro Ala Thr Pro Met Ser Ser Arg Pro Thr Thr Pro
465                 470                 475                 480

Thr His Gly Met Ser Pro Val His Leu Leu Arg Gly Ile Arg Thr Ser
                485                 490                 495

Asp Met Asp Val Ser Pro Gln Arg Ser Asn Tyr Asn Val Asp His Trp
                500                 505                 510

Asp Ile Glu Gly Ser Ser Ser Pro Thr Arg Phe Tyr Gln Gly Gly Gly
            515                 520                 525

Gly Asp Gly Ser Ser Ser Pro Ser His Met His Gln Ile Ile Gln Ser
            530                 535                 540

Gly His Asp Leu Arg His Asp Asp Ser Glu Gly His Glu Pro Ser Leu
545                 550                 555                 560

Pro Gln Thr Ala Arg Asp Gln His Glu Val Asn Ile Ala Arg Pro Arg
                565                 570                 575

Glu Phe Ser Phe Asp Lys Arg Thr Thr Ser Val
                580                 585

<210> SEQ ID NO 49
<211> LENGTH: 1973
<212> TYPE: DNA
<213> ORGANISM: Capsicum annuum
<220> FEATURE:
<223> OTHER INFORMATION: Sequence listing for 58633.

<400> SEQUENCE: 49
tcaattcgag attttcatt tattaagagt gaaaaagtc tcatttctct tgatcacatg      60
```

```
atcttttaat cacacgaact tttgaacgaa ttaaggtttc aagatggcgg gaggaggggg       120
aggaagatcg ttggagcaaa cgccgacgtg ggcggttgcc gtagtttgtt ttgcgttggt       180
tgctatttct gtcgtaatag agttcatcat ccatcttatt ggcaagtggt tgaagtccaa       240 acaaaaaga gcattatatg aagcacttga aagataaaa tcagaattaa tgttgttggg        300
atttatatcc ctactactaa cagtagggca agatccaatt tcaaatattt gtgtatctga       360
aaaaattgct agtacatggc atccatgtac taagcaaaaa gaaaatgaaa taataaaga       420 aaagtccgat gacttagagg gtcatcgccg gcgactactt acggcttctg atggcggagt       480
ccggcgagtt ttggcggctg ttggaaccga caaatgtgcg gataagggaa aagtagcatt       540
tgtgtctgca gatggaattc atcaattaca tattttatt tttgtgctgg ctcttttca        600 tatattttat tgtattacta cattggcttt gggaagagct aagatgagta gttggaaggc      660
atgggaaaac gaaacaagaa cagctgagta ccaatttaca aatgatccag agagatttcg      720
atttgctaga gacacatcat ttggaagaag acatttgagc ttttggacaa aaaattcagt      780
gcttctatgg attgtttgtt ttttcagaca atttgtaaga tctgttccaa agttgatta       840 tttgacccta cgtcatggtt ttatcatggc acatttggca cctcagagcc aaataaattt      900
tgatttccaa aaatatatta agaggtcatt agaagaagat ttcaaagtag tagttagcat      960
aagtcctcca atttggttcc ttgctgtatt attcctactc ttcaatactc atggctggta     1020
ttcttatctg tggctaccat tcattccact atttgtgata ttgttagtag ggaccaaatt     1080
acaagtgatt ataacaaaaa tgggattaag aattcaagaa aggggagaag tagtgaaagg     1140
tgtacctgtg gttcagcctg agatgatttt attttggttt aatcgtcctc gtcttcttct    1200
ttatctaatt aattttgtgc ttttttcagaa tgcttttcaa ttggctttct ttgcttggac    1260
ttggtatgaa tttgggctga aatcttgttt ccatgacaaa actgaggata tcgtcattag     1320
aatgacaatg ggggttctta ttcaaattct ttgcagctat gtaactcttc cattatatgc     1380
ccttgtgaca cagatgggat catcaatgaa accaacaatt ttcaatgaaa gagtagcaac     1440
agcattgagg aagtggcatc atggtgccaa gaagcacatc aaagagatca acaaacatca     1500
ttcaaatcca gcaacaccaa tgtcaagtag gccaacaacg cccactcatg gcatgtcacc     1560
tgtccatctc ctacgcggga tccggacgag tgacatggat gtgagtccac aaagatcgaa     1620
ttataatgtg gaccattggg acatcgaggg gtcgtcatct cccacccgat tctaccaagg     1680
tggtggtgga gatggctcgt cttcgccgtc ccatatgcat caaattattc aaagtggtca     1740
tgacttacgt catgacgact cagaaggtca cgagcctagt ctgccacaaa cggctcgtga     1800
ccaacacgaa gtcaacattg cccgtccaag ggaattctct tttgataaaa gaacaactag     1860
tgtataaatt ttaagagttc atgttagtgg caaagtcacc tttgttgaaa gttgaaacaa     1920
atctttatca aaaaattata ctacattgat aggtcaaaaa aaaaaaaaaa aaa           1973
```

<210> SEQ ID NO 50
<211> LENGTH: 513
<212> TYPE: PRT
<213> ORGANISM: Solanum lycopersicum
<220> FEATURE:
<223> OTHER INFORMATION: Sequence listing for 58633.

<400> SEQUENCE: 50

Met Ala Lys Glu Arg Ser Met Glu Ala Thr Pro Thr Trp Ala Ile Ala
1               5                   10                  15

Val Val Cys Phe Ile Leu Leu Ala Ile Ser Ile Phe Ile Glu Gln Ile

-continued

```
                20                  25                  30
Ile His His Ile Gly Glu Trp Leu Leu Glu Lys Arg Lys Lys Ser Leu
        35                  40                  45

Tyr Glu Ala Leu Glu Lys Ile Lys Ala Glu Leu Met Leu Leu Gly Phe
    50                  55                  60

Leu Ser Leu Leu Leu Thr Val Leu Gln Asp Pro Val Ser Asn Leu Cys
65                  70                  75                  80

Val Pro Lys Ser Val Gly Tyr Ser Trp His Pro Cys Met Ala Lys Glu
                85                  90                  95

Asp Ala Lys Ser Glu Tyr Asp Asp Pro Cys Leu Pro Lys Gly Lys Val
            100                 105                 110

Gln Phe Ala Ser Ser Tyr Ala Ile His Gln Leu His Ile Phe Ile Phe
        115                 120                 125

Val Leu Ala Val Ala His Val Leu Tyr Cys Ile Ala Thr Phe Ala Leu
    130                 135                 140

Gly Arg Leu Lys Met Arg Lys Trp Arg Ala Trp Glu Asp Glu Thr Lys
145                 150                 155                 160

Thr Met Glu Tyr Gln Phe Tyr Asn Asp Pro Glu Arg Phe Arg Phe Ala
                165                 170                 175

Arg Glu Thr Ser Phe Gly Arg Arg His Leu His Phe Trp Ser Lys Ser
            180                 185                 190

Pro Val Leu Leu Ser Ile Val Cys Phe Phe Arg Gln Phe Phe Ser Ser
        195                 200                 205

Val Ala Lys Val Asp Tyr Leu Thr Leu Arg His Gly Phe Met Met Ala
    210                 215                 220

His Leu Thr Pro Gln Asn Gln Asn Asn Phe Asp Phe Gln Leu Tyr Ile
225                 230                 235                 240

Asn Arg Ala Val Asp Lys Asp Phe Lys Val Val Val Gly Ile Ser Pro
                245                 250                 255

Ala Leu Trp Leu Phe Thr Val Leu Tyr Phe Leu Thr Thr Thr Asp Arg
            260                 265                 270

Leu Tyr Ser Tyr Leu Trp Val Pro Phe Ile Pro Leu Val Ile Ile Leu
        275                 280                 285

Leu Val Gly Thr Lys Leu Gln Met Ile Ile Thr Glu Met Gly Val Arg
    290                 295                 300

Ile Ser Glu Arg Gly Asp Ile Val Lys Gly Val Pro Val Val Glu Thr
305                 310                 315                 320

Gly Asp His Leu Phe Trp Phe Asn Arg Pro Ala Leu Val Leu Phe Leu
                325                 330                 335

Ile Asn Phe Val Leu Phe Gln Asn Ala Phe Gln Val Ala Phe Phe Phe
            340                 345                 350

Trp Ser Trp Trp Lys Phe Gly Phe Pro Ser Cys Phe His Lys Asn Ala
        355                 360                 365

Ala Asp Leu Ala Ile Arg Leu Thr Met Gly Val Ile Ile Gln Val His
    370                 375                 380

Cys Ser Tyr Val Thr Leu Pro Leu Tyr Ala Leu Val Thr Gln Met Gly
385                 390                 395                 400

Ser Ser Met Lys Pro Ile Ile Phe Gly Asp Asn Val Ala Thr Ala Leu
                405                 410                 415

Arg Ser Trp His His Thr Ala Lys Lys Arg Val Lys His Gly Leu Ser
            420                 425                 430

Gly His Thr Thr Pro Ala Asn Ser Arg Pro Thr Thr Pro Leu Arg Gly
        435                 440                 445
```

```
Thr Ser Pro Val His Leu Leu Arg Gly Tyr Pro Gln Tyr Asn Glu Asp
        450                 455                 460

Ser Val Gln Ala Ser Asp Asn Ala Ser Asn Val Glu Asn Glu Gly Trp
465                 470                 475                 480

Ala Asn Glu Asn Gln Glu Gly Glu Ile Leu Gln His Ala Ser Thr Asp
                485                 490                 495

His Asn Lys Gln Ile Glu Ile Thr Met Ser Asp Phe Thr Phe Gly Asn
            500                 505                 510

Lys

<210> SEQ ID NO 51
<211> LENGTH: 1847
<212> TYPE: DNA
<213> ORGANISM: Solanum lycopersicum
<220> FEATURE:
<223> OTHER INFORMATION: Sequence listing for 58633.

<400> SEQUENCE: 51
```

| | | | | | |
|---|---|---|---|---|---|
| gacttattgt | ttgaaacttg | caactacaat | tcttctttat | catcatttga | catttcccct | 60 |
| tcttcttatt | cctattttta | tttaaatata | ggaatatttc | tttcaaagga | agaaaatata | 120 |
| tatttccttc | aacaccacta | tatatagact | taattccata | atcctgttaa | tttaattgat | 180 |
| ggctaaagaa | cggtctatgg | aggcaacccc | tacgtgggca | attgctgtgg | tttgcttcat | 240 |
| cttgctcgct | atttctattt | ttattgaaca | aattattcat | cacattggag | agtggttact | 300 |
| ggaaaagcgg | aaaaagtctc | tatatgaagc | acttgaaaag | atcaaagctg | aacttatgct | 360 |
| gttgggattc | ttatcactgt | tgttgacagt | gttgcaagat | ccagtttcta | acttatgtgt | 420 |
| ccccaagagt | gttggttatt | catggcatcc | ttgtatggca | aaggaagatg | ccaagtctga | 480 |
| gtatgatgac | ccttgtctac | caaagggaaa | agtgcaattt | gcatcttcat | atgcaataca | 540 |
| ccagctccat | atcttcatct | ttgtattggc | agttgctcat | gtattgtact | gtatagcaac | 600 |
| ttttgctttg | ggcaggctaa | agatgagaaa | atggagggca | tgggaggatg | aaacaaaaac | 660 |
| aatggagtac | caattctaca | acgaccctga | gagattcaga | tttgcaaggg | agacctcgtt | 720 |
| tggacgtagg | catttgcatt | tctggagcaa | gtccccgtg | ttgctctcga | tagtttgttt | 780 |
| ctttcggcaa | ttcttctcat | cagttgcaaa | agttgactat | ttaaccctta | gacatgggtt | 840 |
| catgatggca | catttaactc | cacaaaatca | aaataatttt | gatttcaat | tatacattaa | 900 |
| cagagcagtt | gacaaagact | tcaaagttgt | tgttggaata | agtcctgcat | tatggctctt | 960 |
| cacggtgcta | tattttctga | ctactaccga | tcgattgtac | tcgtatcttt | gggtgccatt | 1020 |
| tatcccactt | gtaataatat | tgctagttgg | cacaaaactt | caaatgatca | taacagaaat | 1080 |
| gggagtaagg | atttcagaaa | ggggagacat | agtaaaaggt | gtacctgtgg | tggagactgg | 1140 |
| tgaccatctt | ttctggttta | atcgccctgc | ccttgtccta | ttcttgatta | actttgtact | 1200 |
| ctttcagaat | gcgtttcaag | ttgctttctt | tttttggagt | tggtggaaat | ttggttttcc | 1260 |
| atcttgcttt | cataagaatg | ctgcagacct | agccataagg | ctaaccatgg | gggtgatcat | 1320 |
| acaggtccat | tgcagctatg | tgactctccc | tctttatgcc | ttagttacac | agatgggttc | 1380 |
| atcaatgaag | cctatcatct | ttggtgataa | tgtggcaaca | gctcttagaa | gctggcacca | 1440 |
| tacagcgaaa | aaacgggtga | aacatgggct | atcaggacat | accacccctg | caaacagcag | 1500 |
| accaaccaca | ccattgcgtg | gtacctcccc | tgttcactta | ttacgcggtt | atccacaata | 1560 |
| taatgaggac | agtgttcaag | catctcctcg | gacatccaat | gtcgaaaatg | aagggtgggc | 1620 |

| | | |
|---|---|---|
| taatgaaaat caggagggag agatcctgca gcatgcctcc actgatcata acaagcaaat | | 1680 |
| tgagattaca atgtcagatt ttacttttgg aaacaaataa atgtaaaaac gaattttctt | | 1740 |
| cttcattgtt ttaagttcat tactgtagtt caaatggcaa tgattttgta aaattttata | | 1800 |
| cagaggtact catgcatggt gctcttcatt tcaaggtaaa aaaaaaa | | 1847 |

```
<210> SEQ ID NO 52
<211> LENGTH: 517
<212> TYPE: PRT
<213> ORGANISM: Solanum lycopersicum
<220> FEATURE:
<223> OTHER INFORMATION: Sequence listing for 58633.

<400> SEQUENCE: 52
```

Met Ala Ser Thr Gly Cys Ile Arg Thr Cys Asp Glu Arg Pro Leu Asp
1               5                   10                  15

Glu Thr Pro Thr Trp Ala Val Ala Met Val Cys Phe Val Leu Val Val
                20                  25                  30

Ile Ser Leu Phe Ile Glu Gln Leu Ile His His Leu Gly Glu Trp Leu
            35                  40                  45

Trp Lys Lys Gln Lys Arg Pro Leu Tyr Glu Ala Leu Glu Lys Ile Lys
        50                  55                  60

Ser Glu Leu Met Leu Leu Gly Phe Ile Ser Leu Phe Leu Thr Val Val
65                  70                  75                  80

Gln Asp Pro Met Ser Lys Ile Cys Ile Pro Arg Ser Val Gly Arg Ser
                85                  90                  95

Trp His Pro Cys Asp Ile Asn Lys His Ile Asp Asp Gln Tyr Leu Asp
            100                 105                 110

Pro Cys Arg Ile Lys Gly Lys Leu Gln Phe Ala Ser Lys Tyr Ala Ile
        115                 120                 125

His Gln Leu His Ile Phe Ile Phe Val Leu Ala Val Ala His Val Leu
    130                 135                 140

Tyr Cys Ile Thr Thr Leu Gly Ile Gly Lys Leu Arg Met Arg Thr Trp
145                 150                 155                 160

Arg Ala Trp Glu Asp Glu Ser Lys Thr Ile Glu Tyr Gln Phe Tyr Asn
                165                 170                 175

Asp Pro Glu Arg Phe Arg Phe Ala Arg Glu Thr Ser Phe Gly Arg Lys
            180                 185                 190

His Leu His Phe Trp Ser Asn Ser Pro Ile Leu Leu Trp Ile Val Cys
        195                 200                 205

Phe Phe Arg Gln Phe Tyr Ala Ser Val Glu Lys Val Asp Tyr Leu Thr
    210                 215                 220

Leu Arg His Gly Phe Ala Met Ala His Leu Ala Pro Gln Gln Glu Lys
225                 230                 235                 240

Asn Phe Asp Phe Gln Leu Tyr Ile Asn Arg Ala Leu Glu Glu Asp Phe
                245                 250                 255

Lys Asp Val Val Gly Ile Ser Pro Leu Leu Trp Met Phe Ala Val Leu
            260                 265                 270

Tyr Phe Leu Thr Thr Thr Asn Gly Trp Tyr Ser Tyr Trp Leu Pro
        275                 280                 285

Phe Ile Pro Leu Ile Ile Leu Leu Val Gly Thr Lys Leu Gln Val
    290                 295                 300

Ile Ile Thr Lys Met Gly Leu Arg Ile Lys Glu Arg Gly Asp Ile Val
305                 310                 315                 320

Lys Gly Thr Pro Leu Val Glu Pro Gly Asp Asp Leu Phe Trp Phe Asn

```
              325                 330                 335
Arg Pro Asp Leu Leu His Phe Phe Ile His Phe Val Leu Phe Gln Asn
            340                 345                 350

Ala Tyr Gln Leu Ala Phe Phe Ala Trp Ser Trp Lys Phe Asn Leu
            355                 360                 365

Pro Ser Cys Phe His Lys Asn Val Thr Asp Ile Ala Ile Thr Leu Ser
            370                 375                 380

Met Gly Ala Leu Ile Gln Val Leu Cys Ser Tyr Val Thr Leu Pro Leu
385                 390                 395                 400

Tyr Ala Leu Val Thr Gln Met Gly Ser Thr Met Lys Pro Val Ile Phe
                405                 410                 415

Gly Asp Asn Val Ala Tyr Ala Ile Arg Thr Trp His Gln Thr Ala Lys
                420                 425                 430

Gln Arg Ala Lys Asp Gly Arg Pro Ser Lys Asn Ala Ser Pro Val Arg
                435                 440                 445

Ser Arg Ala Val Ser Pro Leu Arg Gly Gly Ser Ser Pro Val Gln Gln
450                 455                 460

Lys His Gly Gln Leu Tyr Pro Pro Ser Pro Asn Pro Ser Arg Arg Arg
465                 470                 475                 480

Ser Gly Gly Asn Pro Glu Ser Ser Ser Arg Gln Ile Phe Asp Asp Gly
                485                 490                 495

Ser His Glu Gln Ser Glu Ile Glu Ile Thr Leu Asn Asp Leu Ser Leu
                500                 505                 510

Glu Asn Lys Leu Ser
        515

<210> SEQ ID NO 53
<211> LENGTH: 1852
<212> TYPE: DNA
<213> ORGANISM: Solanum lycopersicum
<220> FEATURE:
<223> OTHER INFORMATION: Sequence listing for 58633.

<400> SEQUENCE: 53
atgtatattt aaaatataaa gtctttgttt tttctcaaag aagtctctca caaatttccc     60
ttatcattaa aaacaaaaaa aaagttgtat agtactgaag cttaatggct agcacaggct    120
gtattagaac gtgtgatgaa cgtcctctag atgagacacc aacatgggct gtagccatgg    180
tttgctttgt attagttgta atctcccttt tcattgaaca acttattcat catcttggag    240
agtggttatg gaagaaacaa aagagaccat tgtatgaagc acttgagaag atcaagtcag    300
aactcatgtt attagggttt atatccttat tcttgacggt tgtacaggat cctatgtcta    360
agatatgtat tcctaggagt gttggacgct cttggcatcc atgtgacata aacaaacata    420
ttgatgacca atatctcgat ccatgtagaa ttaaggggaa actccaattt gcttcaaaat    480
atgcaattca ccaactccac attttatct ttgtgttagc cgttgcacat gtgttgtatt     540
gtattaccac tttgggaatt ggcaaactaa ggatgaggac atggagagct tgggaggatg    600
aatctaaaac aattgaatac caattctata cgatcctga gagatttaga tttgcaagag     660
aaacatcatt tggacgtaaa catttgcatt tctggagcaa ctctccaatt cttctctgga    720
tagtttgttt cttcagacag ttctatgcat cagttgaaaa agtagactat cttaccctta    780
gacatggctt tgctatggca catttagcac ctcagcaaga aaagaatttt gattttcaat    840
tgtatataaa tagagcactt gaagaagatt ttaaagatgt tgtgggaata agtccactgt    900
tatggatgtt tgcagtcctc tactttctca ctactaccaa tggttggtat tcatactatt    960
```

```
ggctgccgtt cattcctttt aattataatat tactggtggg cacaaaatta caagtgatta    1020
taacaaaaat gggattaagg attaaagaaa gaggagacat tgttaaagga acaccattag    1080
ttgaaccagg ggatgatctt ttctggttta atcgtcctga tcttttgcac ttcttcattc    1140
actttgttct ctttcagaat gcatatcaac ttgctttctt tgcttggagc tggtggaaat    1200
ttaatttacc atcttgcttc cacaaaaatg taacagacat agccataaca ctttccatgg    1260
gggctctcat tcaagttctt tgcagctacg tgacactccc cctatatgcc ttagttactc    1320
agatgggatc aacaatgaaa ccagttatct ttggtgacaa cgtggcatac gcgatacgga    1380
catggcatca gacagcaaag caacgggcaa agacgggcg tccgtcgaaa aatgcgagtc    1440
cagtgagaag cagggcagtg tcaccattgc gtggaggttc ctctccggtt caacaaaaac    1500
acgggcaatt atatcctcca tcacctaatc cttcgcgtag gaggagtgga ggtaatccag    1560
aatcgagttc taggcaaatc tttgatgatg gaagtcatga gcaatctgaa attgaaatta    1620
ccttgaatga tttatcactt gaaaacaaat taagttgaac ttgttagggt ctgatccatg    1680
tacgtatata gttaagtagt gcatcttgta cgtgtttacc tttgaaatct ttttgtataa    1740
ttgtatgtgg gaactgagct atgaagcgcc aagtgtgtga atgtattttt ggtacattta    1800
tggacttgca agttgcacat atattatgtt ggttcttatg ttaaaaaaaa aa    1852
```

<210> SEQ ID NO 54
<211> LENGTH: 534
<212> TYPE: PRT
<213> ORGANISM: Triticum aestivum
<220> FEATURE:
<223> OTHER INFORMATION: Sequence listing for 58633.

<400> SEQUENCE: 54

```
Met Ala Lys Asp Asp Gly Tyr Pro Pro Ala Arg Thr Leu Pro Glu Thr
1               5                   10                  15

Pro Ser Trp Ala Val Ala Leu Val Phe Ala Val Met Ile Ile Val Ser
                20                  25                  30

Val Leu Leu Glu His Ala Leu His Lys Leu Gly His Trp Phe His Lys
            35                  40                  45

Arg His Lys Asn Ala Leu Ala Glu Ala Leu Glu Lys Met Lys Ala Glu
        50                  55                  60

Leu Met Leu Val Gly Phe Ile Ser Leu Leu Ala Val Thr Gln Asp
65                  70                  75                  80

Pro Ile Ser Gly Ile Cys Ile Ser Gln Lys Ala Ser Ile Met Arg
                85                  90                  95

Pro Cys Lys Val Glu Pro Gly Ser Val Lys Ser Lys Tyr Lys Asp Tyr
                100                 105                 110

Tyr Cys Ala Lys Glu Gly Lys Val Ala Leu Met Ser Thr Gly Ser Leu
            115                 120                 125

His Gln Leu His Ile Phe Ile Phe Val Leu Ala Val Phe His Val Thr
        130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
            180                 185                 190

His Leu Gly Leu Ser Ser Thr Pro Gly Val Arg Trp Val Val Ala Phe
        195                 200                 205
```

Phe Arg Gln Phe Phe Arg Ser Val Thr Lys Val Asp Tyr Leu Ile Leu
        210                 215                 220

Arg Ala Gly Phe Ile Asn Ala His Leu Ser Gln Asn Ser Lys Phe Asp
225                 230                 235                 240

Phe His Lys Tyr Ile Lys Arg Ser Met Glu Asp Phe Lys Val Val
                245                 250                 255

Val Gly Ile Ser Leu Pro Leu Trp Ala Val Ala Ile Leu Thr Leu Phe
                260                 265                 270

Leu Asp Ile Asp Gly Ile Gly Thr Leu Thr Trp Val Ser Phe Ile Pro
                275                 280                 285

Leu Ile Ile Leu Leu Cys Val Gly Thr Lys Leu Glu Met Ile Ile Met
            290                 295                 300

Glu Met Ala Leu Glu Ile Gln Asp Arg Ser Ser Val Ile Lys Gly Ala
305                 310                 315                 320

Pro Val Val Glu Pro Ser Asn Lys Phe Phe Trp Phe His Arg Pro Asp
                325                 330                 335

Trp Val Leu Phe Phe Ile His Leu Thr Leu Phe Gln Asn Ala Phe Gln
                340                 345                 350

Met Ala His Phe Val Trp Thr Val Ala Thr Pro Gly Leu Lys Asp Cys
                355                 360                 365

Phe His Met Asn Ile Gly Leu Ser Ile Met Lys Val Val Leu Gly Leu
370                 375                 380

Ala Leu Gln Phe Leu Cys Ser Tyr Ile Thr Phe Pro Leu Tyr Ala Leu
385                 390                 395                 400

Val Thr Gln Met Gly Ser Asn Met Lys Arg Ser Ile Phe Asp Glu Gln
                405                 410                 415

Thr Ala Lys Ala Leu Thr Asn Trp Arg Asn Thr Ala Lys Glu Lys Lys
                420                 425                 430

Lys Val Arg Asp Thr Asp Met Leu Met Ala Gln Met Ile Gly Asp Ala
                435                 440                 445

Thr Pro Ser Arg Gly Thr Ser Pro Met Pro Ser Arg Gly Ser Ser Pro
            450                 455                 460

Val His Leu Leu Gln Lys Gly Met Gly Arg Ser Asp Asp Pro Gln Ser
465                 470                 475                 480

Ala Pro Thr Ser Asp Asn Ala Met Glu Glu Ala Arg Asp Met Tyr Pro
                485                 490                 495

Val Val Val Ala His Pro Val His Arg Leu Asn Pro Ala Asp Arg Arg
                500                 505                 510

Arg Ser Val Ser Ser Ser Ala Leu Asp Ala Asp Ile Pro Ser Ala Asp
            515                 520                 525

Phe Ser Phe Ser Gln Gly
    530

<210> SEQ ID NO 55
<211> LENGTH: 1819
<212> TYPE: DNA
<213> ORGANISM: Triticum aestivum
<220> FEATURE:
<223> OTHER INFORMATION: Sequence listing for 58633.

<400> SEQUENCE: 55
ggccgcggga attcgattgt gcatctgcgt gtgcgtacgt acgttttcgt tttcctttct      60
tgctccggcc ggccggccgg ccacgtagaa tagatacctg cccaggtacg tacctcgttg    120
gctcagacga tcggcggttg gacttgggtg cgcgccctgc cctgctccgg ccaaggaaag    180

```
aggttgcgct aaagacgggc ggatggcaaa ggacgacggg tacccccgg cgcggacgct    240 gccggagacg ccgtcctggg cggtggcgct ggtcttcgcc gtcatgatca tcgtctccgt    300
cctcctggag cacgcgctcc acaagctcgg ccattggttc cacaagcggc acaagaacgc    360
gctggcggag cgctggagaa agatgaaggc ggagctgatg ctggtgggat tcatctcgct    420
gctgctcgcc gtcacgcagg acccaatctc cgggatatgc atctcccaga aggccgccag    480
catcatgcgc ccctgcaagg tggaacccgg ttccgtcaag agcaagtaca aggactacta    540
ctgcgccaaa gagggcaagg tggcgctcat gtccacgggc agcctgcacc agctccacat    600
attcatcttc gtgctagccg tcttccatgt cacctacagc gtcatcatca tggctctaag    660
ccgtctcaag atgagaacat ggaagaaatg ggagacagag accgcctcct ggaatacca     720 gttcgcaaat gatcctgcgc ggttccgctt cacgcaccag acgtcgttcg tgaagcggca    780
cctgggcctg tccagcaccc ccggcgtcag atgggtggtg gccttcttca ggcagttctt    840
caggtcggtc accaaggtgg actacctcat cttgagggca ggcttcatca acgcgcactt    900
gtcgcagaac agcaagttcg acttccacaa gtacatcaag aggtccatgg aggacgactt    960
caaagtcgtc gttggcatca gcctcccgct gtgggctgtg cgatcctca ccctcttcct    1020 tgatatcgac gggatcggca cactcacctg gtttctttc atccctctca tcatcctctt    1080
gtgtgttgga accaagctag agatgatcat catggagatg gccctggaga tccaggaccg    1140
gtcgagcgtc atcaaggggg cacccgtggt cgagcccagc aacaagttct ctgttcca     1200 ccgcccccgac tgggtcctct tcttcataca cctgacgctg ttccagaacg cgtttcagat   1260
ggcacatttc gtgtggacag tggccacgcc cggcttgaag gactgcttcc atatgaacat   1320
cgggctgagc atcatgaagg tcgtgctggg gctggctctc cagttcctgt gcagctacat   1380
caccttcccc ctctacgcgc tagtcacaca gatgggatca acatgaaga ggtccatctt    1440 tgacgagcag acagccaagg cgctgaccaa ctggcggaac acggccaagg agaagaagaa   1500
ggtccgagac acggacatgc tgatggcgca gatgatcggc gacgcaacac ccagccgagg   1560
cacgtccccg atgcctagcc ggggctcatc gccggtgcac ctgcttcaga agggcatggg   1620
acggtctgac gatccccaga gcgcaccgac ctcgccaagg accatggagg aggctaggga   1680
catgtacccg gttgtggtgg cgcatcctgt acacagacta atcctgctg acaggcggag    1740 gtcggtctct tcatcagccc tcgatgccga catccccagc gcagattttt ccttcagcca   1800
gggatgagac aagtttctg                                                1819
```

<210> SEQ ID NO 56
<211> LENGTH: 534
<212> TYPE: PRT
<213> ORGANISM: Triticum aestivum
<220> FEATURE:
<223> OTHER INFORMATION: Sequence listing for 58633.

<400> SEQUENCE: 56

```
Met Ala Asp Asp Asp Glu Tyr Pro Pro Ala Arg Thr Leu Pro Glu Thr
1               5                  10                  15

Pro Ser Trp Ala Val Ala Leu Val Phe Ala Val Met Ile Ile Val Ser
            20                  25                  30

Val Leu Leu Glu His Ala Leu His Lys Leu Gly His Trp Phe His Lys
        35                  40                  45

Arg His Lys Asn Ala Leu Ala Glu Ala Leu Glu Lys Ile Lys Ala Glu
    50                  55                  60
```

-continued

```
Leu Met Leu Val Gly Phe Ile Ser Leu Leu Ala Val Thr Gln Asp
 65                  70                  75                  80

Pro Ile Ser Gly Ile Cys Ile Pro Glu Lys Ala Ala Ser Ile Met Arg
                 85                  90                  95

Pro Cys Lys Leu Pro Pro Gly Ser Val Lys Ser Lys Tyr Lys Asp Tyr
                100                 105                 110

Tyr Cys Ala Lys Gln Gly Lys Val Ser Leu Met Ser Thr Gly Ser Leu
                115                 120                 125

His Gln Leu His Ile Phe Ile Phe Val Leu Ala Val Phe His Val Thr
                130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
                180                 185                 190

His Leu Gly Leu Ser Ser Thr Pro Gly Val Arg Trp Val Ala Ser
                195                 200                 205

Phe Arg Gln Phe Phe Arg Ser Val Thr Lys Val Asp Tyr Leu Thr Leu
210                 215                 220

Arg Ala Gly Phe Ile Asn Ala His Leu Ser His Asn Ser Lys Phe Asp
225                 230                 235                 240

Phe His Lys Tyr Ile Lys Arg Ser Met Glu Asp Phe Lys Val Val
                245                 250                 255

Val Gly Ile Ser Leu Pro Leu Trp Cys Val Ala Ile Leu Thr Leu Phe
                260                 265                 270

Leu Asp Ile Asp Gly Ile Gly Thr Leu Thr Trp Ile Ser Phe Ile Pro
                275                 280                 285

Leu Val Ile Leu Leu Cys Val Gly Thr Lys Leu Glu Met Ile Ile Met
                290                 295                 300

Glu Met Ala Leu Glu Ile Gln Asp Arg Ala Ser Val Ile Lys Gly Ala
305                 310                 315                 320

Pro Val Val Glu Pro Ser Asn Lys Phe Phe Trp Phe His Arg Pro Asp
                325                 330                 335

Trp Val Leu Phe Phe Ile His Leu Thr Leu Phe Gln Asn Ala Phe Gln
                340                 345                 350

Met Ala His Phe Val Trp Thr Val Ala Thr Arg Gly Leu Lys Lys Cys
                355                 360                 365

Phe His Met His Ile Gly Leu Ser Ile Met Lys Val Val Leu Gly Leu
370                 375                 380

Ala Leu Gln Phe Leu Cys Ser Tyr Ile Thr Phe Pro Leu Tyr Ala Leu
385                 390                 395                 400

Val Thr Gln Met Gly Ser Asn Met Lys Arg Ser Ile Phe Asp Glu Gln
                405                 410                 415

Thr Ala Lys Ala Leu Thr Asn Trp Arg Asn Thr Ala Lys Glu Lys Lys
                420                 425                 430

Lys Val Arg Asp Thr Asp Met Leu Met Ala Gln Met Ile Gly Asp Ala
                435                 440                 445

Thr Pro Ser Arg Gly Ala Ser Pro Met Pro Ser Arg Gly Ser Ser Pro
                450                 455                 460

Val His Leu Leu His Lys Gly Met Gly Arg Ser Asp Asp Pro Gln Ser
465                 470                 475                 480

Thr Pro Thr Ser Pro Arg Ala Met Glu Glu Ala Arg Asp Met Tyr Pro
```

```
            485                 490                 495
Val Val Val Ala His Pro Val His Arg Leu Asn Pro Ala Asp Arg Arg
            500                 505                 510

Arg Ser Val Ser Ser Ala Leu Asp Val Asp Ile Pro Ser Ala Asp
            515                 520                 525

Phe Ser Phe Ser Gln Gly
    530

<210> SEQ ID NO 57
<211> LENGTH: 1721
<212> TYPE: DNA
<213> ORGANISM: Triticum aestivum
<220> FEATURE:
<223> OTHER INFORMATION: Sequence listing for 58633.

<400> SEQUENCE: 57
ggccgcggga attcgatttt gctccgggca aggaaggagg ttgcgctcgg ggaccgatgg     60
cggacgacga cgagtacccc ccagcgagga cgctgccgga cgccgtcc tgggcggtgg     120
ccctcgtctt cgccgtcatg atcatcgtgt ccgtcctcct ggagcacgcg ctccataagc    180
tcggccattg gttccacaag cggcacaaga acgcgctggc ggaggcgctg agaagatca     240
aggcggagct catgctggtg ggcttcatct cgctgctgct cgccgtgacg caggacccca    300
tctccgggat atgcatcccc gagaaggccg ccagcatcat cgggccctgc aagctgcccc    360
ctggctccgt caagagcaag tacaaagact actactcgc caaacagggc aaggtgtcgc    420
tcatgtccac gggcagcttg caccagctgc acatattcat cttcgtgctc gccgtcttcc    480
atgtcaccta cagcgtcatc atcatggctc taagccgtct caaaatgaga acctggaaga    540
aatgggagac agagaccgcc tccctggaat accagttcgc aaatgatcct gcgcggttcc    600
gcttcacgca ccagacgtcg ttcgtgaagc ggcacctggg cctctccagc accccgggcg    660
tcagatgggt ggtggcctcc ttcaggcagt tcttcaggtc ggtcaccaag gtggactacc    720
tcaccttgag ggcaggcttc atcaacgcgc atttgtcgca taacagcaag ttcgacttcc    780
acaagtacat caagaggtcc atggaggacg acttcaaagt cgtcgttggc atcagcctcc    840
cgctgtggtg tgtggcgatc ctcacccctct tccttgacat tgacgggatc ggcacgctca    900
cctggatttc tttcatccct ctcgtcatcc tcttgtgtgt tggaaccaag ctggagatga    960
tcatcatgga gatggccctg agatccagg accgggcgag cgtcatcaag ggggcgcccg    1020
tggttgagcc cagcaacaag ttcttctggt tccaccgccc cgactgggtc ctcttcttca    1080
tacacctgac gctattccag aacgcgtttc agatggcaca tttcgtgtgg acagtggcca    1140
cgcgcggctt gaagaaatgc ttccatatgc acatcgggct gagcatcatg aaggtcgtgc    1200
tggggctggc tcttcagttc ctctgcagct atatcacctt cccgctctac cgctcgtca    1260
cacagatggg atcaaacatg aagaggtcca tcttcgacga gcagacggcc aaggcgctga    1320
caaactggcg gaacacggcc aaggagaaga agaaggtccg agacacggac atgctgatgg    1380
cgcagatgat cggcgacgcg acgcccagcc gagggcgtc gcccatgcct agccggggct    1440
cgtcgccagt gcacctgctt cacaagggca tgggacggtc cgacgatccc cagagcacgc    1500
caacctcgcc aagggccatg gaggaggcta gggacatgta cccggttgtg gtggcgcatc    1560
cagtccacag actaaatcct gctgacagga gaaggtcggt ctcgtcgtcg gcactcgatg    1620
tcgacattcc cagcgcagat ttttccttca gccaaggatg agacaagttt ctgtattgat    1680
gttagtccaa tgtatagcca acataggatg tgatgattcg t                       1721
```

```
<210> SEQ ID NO 58
<211> LENGTH: 534
<212> TYPE: PRT
<213> ORGANISM: Triticum aestivum
<220> FEATURE:
<223> OTHER INFORMATION: Sequence listing for 58633.

<400> SEQUENCE: 58
```

Met Ala Asp Asp Glu Tyr Pro Pro Ala Arg Thr Leu Pro Glu Thr
1               5                  10                  15

Pro Ser Trp Ala Val Ala Leu Val Phe Ala Val Met Ile Ile Val Ser
            20                  25                  30

Val Leu Leu Glu His Ala Leu His Lys Leu Gly His Trp Phe His Lys
        35                  40                  45

Arg His Lys Asn Ala Leu Ala Glu Ala Leu Glu Lys Ile Lys Ala Glu
    50                  55                  60

Leu Met Leu Val Gly Phe Ile Ser Leu Leu Ala Val Thr Gln Asp
65                  70                  75                  80

Pro Ile Ser Gly Ile Cys Ile Ser Glu Lys Ala Ala Ser Ile Met Arg
                85                  90                  95

Pro Cys Lys Leu Pro Pro Gly Ser Val Lys Ser Lys Tyr Lys Asp Tyr
            100                 105                 110

Tyr Cys Ala Lys Gln Gly Lys Val Ser Leu Met Ser Thr Gly Ser Leu
        115                 120                 125

His Gln Leu His Ile Phe Ile Phe Val Leu Ala Val Phe His Val Thr
    130                 135                 140

Tyr Ser Val Ile Ile Met Ala Leu Ser Arg Leu Lys Met Arg Thr Trp
145                 150                 155                 160

Lys Lys Trp Glu Thr Glu Thr Ala Ser Leu Glu Tyr Gln Phe Ala Asn
                165                 170                 175

Asp Pro Ala Arg Phe Arg Phe Thr His Gln Thr Ser Phe Val Lys Arg
            180                 185                 190

His Leu Gly Leu Ser Ser Thr Pro Gly Val Arg Trp Val Val Ala Phe
        195                 200                 205

Phe Arg Gln Phe Phe Arg Ser Val Thr Lys Val Asp Tyr Phe Thr Leu
    210                 215                 220

Arg Ala Gly Phe Ile Asn Ala His Leu Ser His Asn Ser Lys Phe Asp
225                 230                 235                 240

Phe His Lys Tyr Ile Lys Arg Ser Met Glu Asp Asp Phe Lys Val Val
                245                 250                 255

Val Gly Ile Ser Leu Pro Leu Trp Cys Val Ala Ile Leu Thr Leu Phe
            260                 265                 270

Leu Asp Ile Asp Gly Ile Gly Thr Leu Thr Trp Ile Ser Phe Ile Pro
        275                 280                 285

Leu Val Ile Leu Leu Cys Val Gly Thr Lys Leu Glu Met Ile Ile Met
    290                 295                 300

Glu Met Ala Leu Glu Ile Gln Asp Arg Ala Ser Val Ile Lys Gly Ala
305                 310                 315                 320

Pro Val Val Glu Pro Ser Asn Lys Phe Phe Trp Phe His Arg Pro Asp
                325                 330                 335

Trp Val Leu Phe Phe Ile His Leu Thr Leu Phe Gln Asn Ala Phe Gln
            340                 345                 350

Met Ala His Phe Val Trp Thr Val Ala Thr Pro Gly Leu Lys Lys Cys
        355                 360                 365

```
Phe His Met His Ile Gly Leu Ser Ile Met Lys Val Val Leu Gly Leu
    370                 375                 380

Ala Leu Gln Phe Leu Cys Ser Tyr Ile Thr Phe Pro Leu Tyr Ala Leu
385                 390                 395                 400

Val Thr Gln Met Gly Ser Asn Met Lys Arg Ser Ile Phe Asp Glu Gln
                405                 410                 415

Thr Ala Lys Ala Leu Thr Asn Trp Arg Asn Thr Ala Lys Glu Lys Lys
            420                 425                 430

Lys Val Arg Asp Thr Asp Met Leu Met Ala Gln Met Ile Gly Asp Ala
        435                 440                 445

Thr Pro Ser Arg Gly Ala Ser Pro Met Pro Ser Arg Gly Ser Ser Pro
450                 455                 460

Val His Leu Leu His Lys Gly Met Gly Arg Ser Asp Asp Pro Gln Ser
465                 470                 475                 480

Thr Pro Thr Ser Pro Arg Ala Met Glu Glu Ala Arg Asp Met Tyr Pro
                485                 490                 495

Val Val Val Ala His Pro Val His Arg Leu Asn Pro Ala Asp Arg Arg
                500                 505                 510

Arg Ser Val Ser Ser Ser Ala Leu Asp Val Asp Ile Pro Ser Ala Asp
            515                 520                 525

Phe Ser Phe Ser Gln Gly
    530

<210> SEQ ID NO 59
<211> LENGTH: 1730
<212> TYPE: DNA
<213> ORGANISM: Triticum aestivum
<220> FEATURE:
<223> OTHER INFORMATION: Sequence listing for 58633.

<400> SEQUENCE: 59
aaagaggttg cgctcgggga ccgatggcgg acgacgacga gtaccccca gcgaggacgc      60 tgccggagac gccgtcctgg gcggtggccc tcgtcttcgc cgtcatgatc atcgtgtccg     120
tcctcctgga gcacgcgctc cataagctcg gccattggtt ccacaagcgg cacaagaacg     180
cgctggcgga ggcgctggag aagatcaagg cggagctcat gctggtgggc ttcatctcgc     240
tgctgctcgc cgtgacgcag gaccccatct ccgggatatg catctccgag aaggccgcca     300
gcatcatgcg gccctgcaag ctgccccctg gctccgtcaa gagcaagtac aaagactact     360
actgcgccaa acagggcaag gtgtcgctca tgtccacggg cagcttgcac cagctgcaca     420
tattcatctt cgtgctcgcc gtcttccatg tcacctacag cgtcatcatc atggctctaa     480
gccgtctcaa aatgagaacc tggaagaaat gggagacaga gaccgcctcc ctggaatacc     540
agttcgcaaa tgatcctgcg cggttccgct cacgcacca gacgtcgttc gtgaagcggc     600
acctgggcct ctccagcacc cccggcgtca gatgggtggt ggccttcttc aggcagttct     660
tcaggtcggt caccaaggtg gactacttca ccttgagggc aggcttcatc aacgcgcatt     720
tgtcgcataa cagcaagttc gacttccaca agtacatcaa gaggtccatg gaggacgact     780
tcaaagtcgt cgttggcatc agcctcccgc tgtggtgtgt ggcgatcctc accctcttcc     840
ttgacattga cggatcggc acgctcacct ggatttcttt catccctctc gtcatcctct     900
tgtgtgttgg aaccaagctg gagatgatca tcatggagat ggccctggag atccaggacc     960
gggcgagcgt catcaagggg cgcccgtgg ttgagcccag caacaagttc ttctggttcc    1020
accgccccga ctgggtcctc ttcttcatac acctgacgct attccagaac gcgtttcaga    1080
```

-continued

| | |
|---|---|
| tggcacattt cgtgtggaca gtggccacgc ccggcttgaa gaaatgcttc catatgcaca | 1140 |
| tcgggctgag catcatgaag gtcgtgctgg ggctggctct tcagttcctc tgcagctata | 1200 |
| tcaccttccc gctctacgcg ctcgtcacac agatgggatc aaacatgaag aggtccatct | 1260 |
| tcgacgagca gacggccaag gcgctaacaa actggcggaa cacggccaag agaagaaga | 1320 |
| aggtccgaga cacggacatg ctgatggcgc agatgatcgg cgacgcgacg cccagccgag | 1380 |
| gggcgtcgcc catgcctagc cggggctcgt cgccagtgca cctgcttcac aagggcatgg | 1440 |
| gacggtccga cgatccccag agcacgccaa cctcgccaag gccatggag gaggctaggg | 1500 |
| acatgtaccc ggttgtggtg gcgcatccag tgcacagact aaatcctgct gacaggagaa | 1560 |
| ggtcggtctc gtcgtcggca ctcgatgtcg acattcccag cgcagatttt tccttcagcc | 1620 |
| agggatgaga caagtttctg tattgatgtt agtccaatgt atagccaaca taggatgtca | 1680 |
| tgattcgtac aataagaaat acaaattttt actgagtcaa aaaaaaaaa | 1730 |

<210> SEQ ID NO 60
<211> LENGTH: 539
<212> TYPE: PRT
<213> ORGANISM: Vitis vinifera
<220> FEATURE:
<223> OTHER INFORMATION: Sequence listing for 58633.

<400> SEQUENCE: 60

Met Ala Asp Glu Leu Glu Glu Arg Ser Leu Glu Glu Thr Pro Thr Trp
1               5                   10                  15

Ala Val Ala Val Val Cys Phe Val Leu Leu Ala Val Ser Ile Phe Ile
            20                  25                  30

Glu His Ile Phe His Leu Ile Gly Ser Arg Leu Lys Gly Arg His Arg
        35                  40                  45

Arg Ala Leu Tyr Glu Ser Leu Glu Lys Ile Lys Ala Glu Leu Met Leu
    50                  55                  60

Leu Gly Phe Ile Ser Leu Leu Thr Ile Leu Gln Asp Tyr Ile Ser
65                  70                  75                  80

Lys Ile Cys Ile Ser Lys Ser Val Gly Ser Thr Trp His Pro Cys Lys
                85                  90                  95

Lys Glu Ser Lys Asp Phe Lys Asn Thr Cys Ser Glu Gly Lys Val Pro
            100                 105                 110

Leu Val Ser Ser Tyr Gly Ile His Gln Leu His Ile Phe Ile Phe Val
        115                 120                 125

Leu Ala Leu Phe His Val Ile Tyr Cys Val Ala Thr Leu Ala Leu Gly
    130                 135                 140

Arg Thr Lys Met Arg Arg Trp Lys Ala Trp Glu Asp Gln Thr Lys Thr
145                 150                 155                 160

Ile Glu Tyr Gln Tyr Ser His Asp Pro Glu Arg Phe Arg Phe Ala Arg
                165                 170                 175

Asp Thr Ser Phe Gly Arg Arg His Leu Asn Phe Trp Ser Arg Ser Pro
            180                 185                 190

Val Leu Leu Trp Ile Val Cys Phe Phe Arg Gln Phe Phe Arg Ser Val
        195                 200                 205

Asn Asn Val Asp Tyr Leu Thr Leu Arg His Gly Phe Ile Met Ala His
    210                 215                 220

Leu Ser Pro Gly Ser Glu Thr Lys Phe Asp Phe Arg Asn Tyr Ile Lys
225                 230                 235                 240

Arg Ser Leu Glu Glu Asp Phe Lys Val Val Val Ser Ile Ser Pro Val
                245                 250                 255

Ile Trp Phe Cys Ala Val Leu Phe Leu Leu Thr Asn Thr His Gly Trp
                260                 265                 270

Tyr Ser Tyr Leu Trp Leu Pro Phe Ile Pro Leu Val Ile Ile Leu Leu
            275                 280                 285

Val Gly Thr Lys Leu Gln Val Ile Ile Thr Lys Leu Gly Leu Arg Ile
        290                 295                 300

Ala Glu Arg Gly Asp Val Val Lys Gly Thr Pro Val Val Glu Pro Ala
305                 310                 315                 320

Asn Asp Leu Phe Trp Phe Asn Arg Pro His Leu Ile Leu Phe Leu Ile
                325                 330                 335

Asn Phe Val Leu Phe Leu Asn Ala Phe Gln Leu Ala Phe Phe Ala Trp
                340                 345                 350

Ser Thr Tyr Glu Phe Gly Leu Gln Ser Cys Tyr His Gln Lys Thr Glu
            355                 360                 365

Asp Ile Ala Ile Arg Ile Ser Met Gly Val Ile Thr Gln Val Leu Cys
        370                 375                 380

Ser Tyr Val Thr Leu Pro Leu Tyr Ala Leu Val Thr Gln Met Gly Ser
385                 390                 395                 400

Thr Met Arg Pro Thr Ile Phe Asn Glu Arg Val Ala Thr Ala Leu Arg
                405                 410                 415

Ser Trp His Gln Ala Ala Arg Lys His Thr Lys His Gly Arg His Ser
                420                 425                 430

Asn Gly Val Ser Pro Gln Ser Ser Arg Pro Ala Thr Pro Ser Tyr Gly
            435                 440                 445

Met Ser Pro Val His Leu Leu Gln Gly Tyr His Asn His Thr Pro Asp
        450                 455                 460

Met Ser Pro Arg Arg Ser Asn Leu Asp Asn Glu Trp Tyr Gly Glu Gly
465                 470                 475                 480

Ala Gly Ser Pro Gly Lys Lys Asp Asp Glu His Glu Lys Glu Lys
                485                 490                 495

Phe Glu Ser Arg Glu Gln Gly Gln Gly Ile Glu Asp Ser Ser Ser Thr
                500                 505                 510

Gln Leu Pro Leu Gly Pro Arg Pro Ile Arg Thr Gln His Glu Ile Asn
            515                 520                 525

Ile Thr Leu Ser Asp Phe Ser Phe Ala Lys Arg
        530                 535

<210> SEQ ID NO 61
<211> LENGTH: 1762
<212> TYPE: DNA
<213> ORGANISM: Vitis vinifera
<220> FEATURE:
<223> OTHER INFORMATION: Sequence listing for 58633.

<400> SEQUENCE: 61
catggctgat gaacttgaag agcgtagttt ggaggaaacg cctacttggg ctgttgcagt    60
ggtctgcttt tgtgttgcttg ctgtttcgat cttcatcgaa catatttttc atcttattgg   120
atcgaggtta aaaggcagac acaggcgagc cctttatgaa tctctggaaa agatcaaagc   180
ggagcttatg ctgttgggat tcatatcctt gctgcttaca atattacaag attacatttc   240
aaagatatgc atttctaaga gtgttgggtc cacttggcac ccttgtaaaa aggaaagcaa   300
agattttaag aacacatgct ctgagggaaa agtcccatta gtgtcttcct atgggatcca   360
tcaactccat atattcatct ttgtgttagc tctctttcat gtgatctact gtgtggccac   420

```
cttggctttg ggaagaacca agatgagaag atggaaggct tgggaggatc aaactaagac    480
gattgaatat caatactctc atgatccaga gaggtttagg tttgcaaggg atacatcctt    540
tgggcgcagg catttgaatt tctggagccg ctctcctgtt ctcctctgga ttgtctgctt    600
cttcagacaa ttcttcagat cggttaacaa cgttgactat cttacattaa gacatggatt    660
tatcatggca catttgtcac ctggaagtga aacaaaattt gatttccgaa attacatcaa    720
aagatcgctt gaagaggact tcaaagttgt agtgagcatc agcccagtaa tatggttctg    780
tgcagtattg ttcctactca ccaacacaca tgggtggtat tcttacttgt ggcttccatt    840
catcccctta gttataatac tcttggtggg aacaaagctt caagtgatca taaccaaact    900
gggattgagg attgcagaga gaggtgatgt ggtgaagggt acaccagtag ttgagccagc    960
caacgacctc ttctggttca atcgccctca cctcatcctc tttctgatca actttgttct   1020
cttcctgaat gcatttcagc tggctttctt cgcatggagc acgtatgagt ttgggctgca   1080
atcttgctat caccaaaaga cagaagacat tgccatcaga atctcaatgg gggtcatcac   1140
acaggtacta tgcagttatg tgacactccc actctatgcc ttggtgacac agatgggctc   1200
caccatgaga ccgacaattt taacgagag agtggccacg gctctaagaa gctggcacca   1260
ggcggccagg aagcacacaa acatgggcg ccactcgaat ggtgtgtccc cacagtcgag   1320
taggccagcg actccatcat atgggatgtc ccctgttcat ctattgcaag gctaccacaa   1380
ccacactcct gatatgtctc caagacgatc aaacttggac aacgaatggt atggggaagg   1440
agcagggtct ccagggaaga aggatgatga tgagcatgaa aggagaaat ttgaatccag   1500
agagcaggga caagggattg aagactcgag ctcaacccaa ctgccccttg accccgccc   1560
aatccgaacc aacatgaga tcaacattac tttatcggat ttctcatttg caaagcgctg   1620
aaggacatga ttgatcagga caaaactagg catattgatt tggttttttg tttttcctt   1680
ctgcggcttg tattttgcat gtatatttgt tacacttgtg atttcaatat acttttcttt   1740
aattcaaaaa aaaaaaaaaa aa                                           1762
```

<210> SEQ ID NO 62
<211> LENGTH: 545
<212> TYPE: PRT
<213> ORGANISM: Vitis vinifera
<220> FEATURE:
<223> OTHER INFORMATION: Sequence listing for 58633.

<400> SEQUENCE: 62

```
Met Ala Asp Glu Leu Glu Asp Arg Ser Leu Thr Glu Thr Pro Thr Trp
1               5                   10                  15

Ala Val Ala Val Val Cys Phe Val Leu Ala Val Ser Ile Phe Ile
            20                  25                  30

Glu His Ile Ile His His Ile Gly Ser Trp Leu Ala Arg Arg Asn Lys
        35                  40                  45

Arg Ala Leu Tyr Glu Ala Leu Glu Lys Ile Lys Ala Glu Leu Met Leu
    50                  55                  60

Leu Gly Phe Met Ser Leu Leu Leu Thr Val Leu Gln Thr Pro Ile Ser
65                  70                  75                  80

Lys Ile Cys Ile Ser Lys Ser Val Gly Ser Thr Trp Tyr Pro Cys Asp
                85                  90                  95

Val Asp Glu Lys Glu Phe Lys Asn Thr Cys Gly Thr Glu Ser Gly Lys
            100                 105                 110

Val Pro Phe Val Ser Tyr Tyr Gly Ile His Gln Leu His Ile Phe Ile
        115                 120                 125
```

-continued

Phe Val Leu Ala Leu Phe His Val Ile Tyr Cys Val Ala Thr Leu Ala
        130                 135                 140

Leu Gly Thr Tyr Lys Met Arg Arg Trp Lys Thr Trp Glu Asp Glu Thr
145                 150                 155                 160

Arg Thr Ala Glu Tyr Gln Tyr Ser His Asp Pro Glu Arg Phe Arg Tyr
                165                 170                 175

Ala Arg Glu Thr Ser Phe Gly Arg Arg His Leu Asn Phe Trp Ser Ser
            180                 185                 190

Ser Pro Val Leu Leu Trp Ile Val Cys Phe Phe Arg Gln Phe Tyr Gly
        195                 200                 205

Ser Val His Arg Asp Asp Tyr Leu Ala Leu Arg His Gly Phe Ile Val
        210                 215                 220

Ala His Leu Ala Pro Glu Ser Glu Arg Lys Phe Asp Phe Arg Lys Tyr
225                 230                 235                 240

Ile His Arg Ser Leu Glu Glu Asp Phe Lys Ala Val Val Gly Ile Ser
                245                 250                 255

Pro Val Ile Trp Phe Cys Ala Ile Leu Phe Leu Leu Thr Asn Thr His
            260                 265                 270

Gly Trp Tyr Ser Tyr Phe Trp Leu Pro Phe Ile Pro Leu Ile Ile Leu
        275                 280                 285

Leu Leu Val Gly Thr Lys Leu Gln Val Ile Ile Thr Glu Leu Gly Leu
290                 295                 300

Arg Ile Ala Glu Arg Gly Val Val Lys Gly Thr Pro Ile Val Glu
305                 310                 315                 320

Pro Gly Asp His Leu Phe Trp Phe Asn Arg Pro Ser Leu Met Leu Phe
                325                 330                 335

Leu Ile Asn Phe Val Leu Phe Leu Asn Ala Phe Gln Leu Ala Phe Phe
            340                 345                 350

Ala Trp Ser Thr Tyr Gly Leu Lys Ser Cys Tyr His Asp Thr Thr Glu
        355                 360                 365

Asp Tyr Val Ile Arg Ile Thr Met Gly Val Met Thr Gln Val Leu Cys
        370                 375                 380

Ser Tyr Val Thr Leu Pro Leu Tyr Ala Leu Val Thr Gln Met Gly Thr
385                 390                 395                 400

Thr Met Arg Ser Thr Val Phe Asn Asp Lys Val Ala Val Ala Leu Arg
                405                 410                 415

Asp Trp His Glu Thr Ala Arg Lys His Thr Arg His Gly His Ser Asp
            420                 425                 430

Gly Val Ser Pro Gln Ser Ser Arg Pro Ser Thr Pro Ser Tyr Gly Met
        435                 440                 445

Ser Pro Val His Leu Leu Gln Ser Tyr Asp Asn Thr Pro Asp Met
450                 455                 460

Ser Pro Val Ala Ser Asn Tyr Asp Asn Glu Arg Trp Tyr Gly Glu Gly
465                 470                 475                 480

Ser Gly Ser Leu Gly Lys Lys Asp Asp Glu Gln Arg Pro Glu Asn
                485                 490                 495

Phe Glu Ser Arg Glu Pro Gly Arg Gly Thr Gln Asp Ser Ser Ser Ala
            500                 505                 510

Gln Leu Ala Leu Gly Pro Leu Pro Ile Gln Thr Gln His Glu Val Asn
        515                 520                 525

Ile Thr Ser Ser Glu Phe Ser Phe Arg Arg Ser Pro Arg Ser Pro Arg
530                 535                 540

Pro
545

<210> SEQ ID NO 63
<211> LENGTH: 1792
<212> TYPE: DNA
<213> ORGANISM: Vitis vinifera
<220> FEATURE:
<223> OTHER INFORMATION: Sequence listing for 58633.

<400> SEQUENCE: 63

| | | | | | |
|---|---|---|---|---|---|
| ccatggctga | tgaacttgaa | gatcgtagtt | tgacggaaac | gcctacttgg | gctgttgcag | 60 |
| tggtctgttt | tgtgttgctt | gctgtttcga | tcttcatcga | acatattatt | catcatattg | 120 |
| gatcgtggtt | agcaagaaga | aacaagcgag | cccctttatga | agctctggaa | aagatcaaag | 180 |
| cagagcttat | gctgttggga | ttcatgtcct | tgctgcttac | agtattacaa | actcccattt | 240 |
| caaagatatg | catttctaag | agtgttggat | ccacttggta | cccttgtgat | gttgatgaga | 300 |
| aagaatttaa | aaacacatgc | ggcactgaat | caggaaaagt | cccatttgtg | tcttactatg | 360 |
| ggatccatca | gctccatata | tttatctttg | tgctagctct | ctttcatgtg | atctactgcg | 420 |
| tggccacctt | ggctttggga | acatacaaga | tgagaagatg | gaagacttgg | gaggatgaaa | 480 |
| ctaggacagc | tgaatatcaa | tactctcatg | atccagagag | gtttaggtat | gcaagggaaa | 540 |
| catcctttgg | gcgcaggcat | ttgaatttct | ggagcagctc | tcctgttctc | ctatggattg | 600 |
| tgtgcttctt | tagacaattc | tacggatcgg | ttcacagaga | tgactatctt | gctttaagac | 660 |
| atggattat | cgtggcacat | ttggcacccg | aaagcgaaag | aaaatttgat | ttccggaagt | 720 |
| acatccacag | atcacttgaa | gaggacttca | agctgtagt | gggcatcagc | ccagtaatat | 780 |
| ggttctgtgc | aatattgttc | ctactcacca | acacacatgg | gtggtattct | tacttttggc | 840 |
| ttccattcat | cccccttaatt | atactgctct | tggtgggaac | aaagctacaa | gtgataataa | 900 |
| ccgaattggg | attgaggatt | gcagagagag | gtgttgtggt | gaagggtaca | ccaatagttg | 960 |
| aaccaggcga | ccacctcttt | tggttcaatc | gccccagcct | catgctcttt | ctgatcaact | 1020 |
| tcgttctctt | tctgaatgca | tttcagctgg | ctttctttgc | atggagcacg | tatgggttga | 1080 |
| aatcttgcta | tcatgacact | actgaagatt | atgtcatcag | aatcacaatg | ggggtcatga | 1140 |
| cacaggtact | gtgcagttat | gtgacactcc | cactctatgc | cttagtgaca | cagatgggca | 1200 |
| ccaccatgag | atcgactgtt | tttaatgaca | agtagccgt | ggctctaaga | gactggcacg | 1260 |
| agacggccag | aaagcacact | agacacgggc | actcggatgg | tgtgtcccca | cagtcaagta | 1320 |
| ggccatcgac | cccatcatat | gggatgtccc | cagttcatct | gttgcaaagc | tacgacaaca | 1380 |
| acactcctga | tatgtctcca | gtggcatcaa | actacgacaa | cgaacggtgg | tatggagaag | 1440 |
| gatcagggtc | tctagggaag | aaggatgatg | atgagcaaag | gccagagaat | tttgaatcga | 1500 |
| gagagccggg | acgagggact | caagactcaa | gctcagccca | attggccctg | gaccccctcc | 1560 |
| ccattcaaac | tcaacatgag | gtcaacatca | cttcatcaga | gttctcattt | cgtaggagcc | 1620 |
| caaggagccc | aaggccatga | cttcgatgat | gcgaaggatg | attaattgag | gacaaaactc | 1680 |
| cgcgtattga | tttggtattt | tgttttttcgt | ttctgcagtt | tgtattttgc | atgtacattt | 1740 |
| gttaccttg | taattcgatc | aatttatgtt | tcttcaaaaa | aaaaaaaaa | aa | 1792 |

<210> SEQ ID NO 64
<211> LENGTH: 510
<212> TYPE: PRT
<213> ORGANISM: Vitis vinifera
<220> FEATURE:

-continued

<223> OTHER INFORMATION: Sequence listing for 58633.

<400> SEQUENCE: 64

```
Met Ala Gly Asp Glu Thr Thr Thr Thr Thr Ala Ala Thr Leu
1               5                   10                  15

Glu Thr Thr Ser Thr Trp Ala Val Ala Ser Val Cys Phe Ile Leu Ile
            20                  25                  30

Ala Leu Ser Ile Leu Ile Glu His Ala Leu His Leu Leu Ala Lys Tyr
        35                  40                  45

Phe Asn Lys Lys Arg Arg Ser Leu Ile His Ala Leu Asn Asn Val
    50                  55                  60

Lys Ser Glu Leu Met Leu Leu Gly Phe Val Ser Leu Leu Leu Thr Val
65                  70                  75                  80

Cys Gln Lys Tyr Ile Ala Lys Ile Cys Ile Pro Arg Ser Val Gly Glu
                85                  90                  95

Thr Phe Leu Pro Cys Lys Thr Leu Thr Glu Ser Asp Ser Glu Glu Glu
            100                 105                 110

Thr Lys Cys Glu Glu Gln Gly Lys Met Ser Leu Leu Ser Thr Gln Gly
        115                 120                 125

Val Glu Glu Leu Gln Tyr Leu Ile Phe Val Leu Ala Phe Phe His Ser
130                 135                 140

Leu Tyr Cys Val Leu Thr Phe Gly Leu Gly Met Ala Lys Met Lys Lys
145                 150                 155                 160

Trp Glu Ser Trp Glu Ala Glu Thr Arg Thr Leu Glu Tyr Gln Phe Thr
                165                 170                 175

Asn Asp Pro Arg Arg Phe Thr Leu Ile His Gln Thr Ser Phe Gly Lys
            180                 185                 190

Gln His Leu Arg Tyr Trp Ser Glu His Arg Ile Leu Arg Trp Pro Val
        195                 200                 205

Cys Phe Ile Gln Gln Phe Tyr Pro Ser Val Ser Lys Val Asp Tyr Leu
210                 215                 220

Thr Leu Arg His Gly Phe Ile Met Ala His Phe Ala Glu Gly Ser Asn
225                 230                 235                 240

Tyr Asp Phe Gln Lys Tyr Ile Lys Arg Ala Leu Glu Lys Asp Phe Gly
                245                 250                 255

Val Val Val Gly Gly Ser Phe Trp Val Trp Ser Phe Ser Met Leu Phe
            260                 265                 270

Val Phe Phe Asn Ala Gln Val Phe Tyr Asn Tyr Leu Trp Leu Pro Phe
        275                 280                 285

Ile Pro Leu Val Met Leu Leu Val Gly Thr Lys Leu Gln Gly Ile
290                 295                 300

Ile Thr Lys Met Cys Leu Asp Ser His Asp Lys Ala Leu Val Val Arg
305                 310                 315                 320

Gly Thr Leu Leu Val Arg Pro Ser Asp His Phe Phe Trp Phe Gly Lys
                325                 330                 335

Pro Glu Leu Leu Leu His Leu Met His Phe Ile Leu Phe Gln Asn Ser
            340                 345                 350

Phe Gln Leu Ala Phe Phe Thr Trp Thr Trp Tyr Lys Phe Gly Phe Arg
        355                 360                 365

Ser Cys Phe His Asp Thr Thr Glu Asp Ile Val Ile Arg Leu Val Met
370                 375                 380

Gly Val Leu Val Gln Leu Leu Cys Gly Tyr Val Thr Leu Pro Leu Tyr
385                 390                 395                 400
```

Ala Leu Val Thr Gln Met Gly Thr Ser Met Arg Thr Ile Val Phe Thr
            405                 410                 415

Glu Gly Val Val Glu Gly Leu Asn Arg Trp Arg Arg Lys Ala Lys Lys
        420                 425                 430

Asn Ile Ala Arg Arg Asn Asn His Ser Ala Arg Pro Ser Leu Asp Ala
    435                 440                 445

Ser Leu Asp Asn Ser Pro Ser Phe Asn Thr Leu Asp Thr Ser Phe Ser
450                 455                 460

Val Asp Leu Asp Gln Pro Ser Ser Asp Ala Gly Tyr Leu Thr Val Glu
465                 470                 475                 480

Ile Ser Asp Glu Glu Thr Val Ala Thr Lys Gln Pro Glu Pro Arg Gln
                485                 490                 495

Lys Leu Gly Cys Phe Glu Gly Phe Asp Leu Arg Lys Thr Ser
            500                 505                 510

<210> SEQ ID NO 65
<211> LENGTH: 1950
<212> TYPE: DNA
<213> ORGANISM: Vitis vinifera
<220> FEATURE:
<223> OTHER INFORMATION: Sequence listing for 58633.

<400> SEQUENCE: 65

```
atcacagtat tgctttctag aatttgtggc aacagaccca ggttgccaag taaggggaag     60
agaggatatg gctggcgacg aggagacgac gacgacgacg acggcagcaa cacttgaaac    120
aacgtccact tgggctgttg cctctgtttg cttcattttg attgcactct ccatacttat    180
tgagcatgct ctccatctct tagccaagta cttcaacaag aagcggagga ggtctctcat    240
tcatgctctt aacaacgtca aatcggagtt gatgctcttg gggttcgtat ctttgttgct    300
gactgtgtgc caaaagtata ttgcgaagat ttgtatccca aggagcgtag gtgaaacttt    360
tcttccctgc aagaccttga cagaaagtga ttcagaagaa gaaaccaaat gcgaagagca    420
gggaaagatg tctttgttgt ctacacaagg cgtggaggaa ctacagtact aattttcgt     480
gctggccttc ttccattcgc tctactgcgt cctcacattc ggtcttggga tggccaagat    540
gaagaaatgg gagtcctggg aggcagaaac aagaacactg aatatcagt ttacaaatga     600
tccacggagg ttcacgctca tccatcagac atcatttgga aagcaacatc tgagatattg    660
gagtgagcat cggatacttc gttggccggt ttgttttatt cagcagttct atccatccgt    720
ctccaaagtg gattacttga ctcttagaca tgggttcatt atggcccatt ttgcagaagg    780
aagcaactat gacttccaaa agtatataaa aagagctttg gaaaaagact tggagtggt     840
ggtgggagga agtttctggg tttggagttt ctccatgctt tttgtgttct tcaatgctca    900
agtattttac aactatttat ggctacccct tattccattg gtgatgctgt tgttggttgg    960
aacaaagcta cagggcatta taactaagat gtgcctagat agccatgata aagctctcgt   1020
tgttagagga acttttgcttg tcaggcccag tgatcacttc ttctggtttg gaaaaccgga   1080
attgctccta catcttatgc actttatatt gtttcagaac tcttttcaac tggcgttctt   1140
tacatggact tggtacaaat ttggattcag atcatgcttc catgatacaa ctgaggatat   1200
cgtcataagg cttgtcatgg gtgtgttagt acaactcctt tgtggctacg tgacactgcc   1260
tctgtatgcc ctggtcacgc agatggggac atcaatgagg acaattgtct ttactgaggg   1320
agtcgttgaa ggtctgaaca gatggagaag gaaagccaag aaaaacatag cacgcaggaa   1380
caaccactca gctcgtccct ccctggatgc ttcactggac aattcacctt cttttaacac   1440
```

| | | |
|---|---|---|
| tctggatact tctttctctg tagacctcga tcagccatca tcagatgctg gctatttgac | 1500 | |
| tgttgaaata tcagatgaag agacggtcgc aactaaacag ccagaaccgc gtcagaagtt | 1560 | |
| gggatgtttt gagggtttcg acttgcgcaa acatcataa tatctgatta tgagaggatt | 1620 | |
| cgattaaaag ctattcttga caagccatat gcaatgccca catcgcttgt cagtgatcaa | 1680 | |
| tgatgaggtt gttgattcaa ttcgaagctt aaacagtact aagctcaaca caaatcaaat | 1740 | |
| ggcatggtga tcatagttca gtggtggctg aaagagaggt tgtacagtca tttctgctat | 1800 | |
| tttttcatct ctctatatat tagaagcagt gtacgtatat attgatagat gatattcatt | 1860 | |
| tacagaagaa cacaaaaaca atgatgcctt ctatgttaat taaacataca tgatgtgatt | 1920 | |
| ttgttttcca aaaaaaaaaa aaaaaaaaaa | 1950 | |

<210> SEQ ID NO 66
<211> LENGTH: 583
<212> TYPE: PRT
<213> ORGANISM: Vitis vinifera
<220> FEATURE:
<223> OTHER INFORMATION: Sequence listing for 58633.

<400> SEQUENCE: 66

Met Ala Lys Gly Ser Lys Asp Arg Ser Leu Glu Gln Thr Pro Thr Trp
1               5                   10                  15

Ala Val Ala Val Val Cys Phe Val Leu Val Leu Ile Ser Ile Ile Ile
            20                  25                  30

Glu Tyr Ile Leu His Leu Ile Gly Lys Trp Leu Thr Lys Arg Asn Lys
        35                  40                  45

Arg Ala Leu Tyr Glu Ala Leu Glu Lys Ile Lys Ser Glu Leu Met Leu
    50                  55                  60

Leu Gly Phe Ile Ser Leu Leu Thr Val Gly Gln Gly Thr Ile Ala
65                  70                  75                  80

Gly Ile Cys Ile Ser Glu Lys Ile Ala Ala Thr Trp His Pro Cys Gly
                85                  90                  95

Lys Lys Gln Glu Ile Lys Tyr Val Ser Asn Glu Glu Asp Tyr Gly Lys
            100                 105                 110

Arg Arg Leu Leu Glu Ile Ser Asp Ser Asp Gly Ser Asn Arg Arg Val
        115                 120                 125

Leu Ala Ala Gly Asp Asp Lys Cys Gly Glu Gly Lys Val Pro Phe
    130                 135                 140

Val Ser Asn Tyr Gly Ile His Gln Leu His Ile Phe Ile Phe Val Leu
145                 150                 155                 160

Ala Val Phe His Val Leu Tyr Cys Ile Ile Thr Leu Ala Leu Gly Arg
                165                 170                 175

Ala Lys Met Arg Lys Trp Lys Ala Trp Glu Met Glu Thr Arg Thr Ala
            180                 185                 190

Glu Tyr Arg Phe Ala Asn Asp Pro Glu Arg Phe Arg Phe Ala Arg Asp
        195                 200                 205

Thr Ser Phe Gly Arg Arg His Leu His Ser Trp Ser Thr Ser Pro Val
    210                 215                 220

Leu Leu Trp Ile Val Cys Phe Phe Arg Gln Phe Val Arg Ser Val Pro
225                 230                 235                 240

Lys Val Asp Tyr Leu Thr Leu Arg His Gly Phe Ile Ile Ala His Leu
                245                 250                 255

Ala Pro Glu Ser His Thr Arg Phe Asp Phe Gln Lys Tyr Ile Lys Arg
            260                 265                 270

| | | | | | | | | | | | | | | |
|---|---|---|---|---|---|---|---|---|---|---|---|---|---|---|
|Ser|Leu|Glu|Glu|Asp|Phe|Lys|Val|Val|Gly|Ile|Ser|Pro|Ile|Ile|
| | |275| | | | |280| | | |285| | | |
|Trp|Phe|Cys|Ala|Val|Leu|Phe|Leu|Leu|Phe|Asn|Thr|His|Gly|Trp|His|
| |290| | | | |295| | | | |300| | | | |
|Ser|Tyr|Leu|Trp|Leu|Pro|Phe|Ile|Pro|Leu|Ile|Ile|Ile|Leu|Met|Val|
|305| | | | |310| | | | |315| | | | |320|
|Gly|Thr|Lys|Leu|Gln|Val|Ile|Ile|Thr|Lys|Met|Gly|Leu|Arg|Ile|Gln|
| | | | |325| | | | |330| | | | |335| |
|Glu|Arg|Gly|Glu|Val|Val|Lys|Gly|Thr|Pro|Val|Val|Glu|Pro|Gly|Asp|
| | | |340| | | | |345| | | | |350| | |
|Asp|Leu|Phe|Trp|Phe|Asn|Gln|Pro|Arg|Leu|Ile|Leu|Tyr|Leu|Ile|Asn|
| | |355| | | | |360| | | | |365| | | |
|Phe|Val|Leu|Phe|Gln|Asn|Ala|Phe|Gln|Val|Ala|Phe|Phe|Ala|Trp|Thr|
| |370| | | | |375| | | | |380| | | | |
|Trp|Tyr|Glu|Phe|Gly|Leu|Lys|Ser|Cys|Phe|His|Glu|Arg|Ile|Glu|Asp|
|385| | | | |390| | | | |395| | | | |400|
|Val|Val|Ile|Arg|Ile|Ser|Met|Gly|Val|Ile|Val|Gln|Ile|Leu|Cys|Ser|
| | | |405| | | | |410| | | | |415| | |
|Tyr|Val|Thr|Leu|Pro|Leu|Tyr|Ala|Leu|Val|Thr|Gln|Met|Gly|Ser|Thr|
| | | |420| | | | |425| | | | |430| | |
|Met|Lys|Pro|Thr|Ile|Phe|Asn|Asp|Arg|Val|Ala|Lys|Ala|Leu|Arg|Asn|
| | |435| | | | |440| | | | |445| | | |
|Trp|His|His|Ala|Ala|Arg|Lys|His|Ile|Lys|Gln|Ser|Lys|Gln|Ser|Ser|
| |450| | | | |455| | | | |460| | | | |
|Ala|Val|Thr|Pro|Val|Ser|Ser|Arg|Ala|Gly|Thr|Pro|Phe|Ser|Ser|Arg|
|465| | | | |470| | | | |475| | | | |480|
|Pro|Gly|Thr|Pro|Leu|His|Gly|Met|Ser|Pro|Val|His|Leu|Leu|Arg|His|
| | | | |485| | | | |490| | | | |495| |
|His|Arg|Ser|Glu|Leu|Asp|Ser|Val|Gln|Thr|Ser|Pro|Arg|Met|Ser|Asn|
| | | |500| | | | |505| | | | |510| | |
|Phe|Asp|Asn|Glu|Gly|Pro|Glu|Thr|Asp|Glu|Tyr|Arg|His|Arg|Glu|Asp|
| | |515| | | | |520| | | | |525| | | |
|Ile|Ser|Trp|Ser|Glu|His|His|Arg|Asn|Pro|Gly|Pro|Glu|Glu|Glu|Gly|
| |530| | | | |535| | | | |540| | | | |
|Arg|Asp|Thr|Asn|His|Arg|Ile|Leu|Thr|Arg|Thr|Met|Pro|Ala|Pro|Gln|
|545| | | | |550| | | | |555| | | | |560|
|Ala|Asp|Asn|Ala|Gln|His|Glu|Ile|Asp|Ile|Gln|Pro|Met|Asp|Phe|Ser|
| | | | |565| | | | |570| | | | |575| |
|Phe|Asp|Lys|Arg|Ala|Arg|Thr| | | | | | | | | |
| | | | |580| | | | | | | | | | | |

<210> SEQ ID NO 67
<211> LENGTH: 2136
<212> TYPE: DNA
<213> ORGANISM: Vitis vinifera
<220> FEATURE:
<223> OTHER INFORMATION: Sequence listing for 58633.

<400> SEQUENCE: 67

```
atattgcaca atcatttcga gtgacacaac tgcaaattac tacttttag gaagcaggcc      60
atatagaaag gatatggcta agggatcaaa ggatcgatct ttggagcaaa caccgacttg     120
ggcggttgca gtggtctgtt ttgtgctggt tttgatatca attatcatcg aatacatcct     180
tcacttaatt ggaaagtggc taacaaagag aaacaaacga gctctttatg aagcacttga     240
aaagattaag tcagaactta tgctactggg gttcatatcg ctgctcctaa cggtaggaca     300
```

```
aggaactatt gcgggaatat gcatatcaga gaagattgca gcaacctggc acccatgtgg    360
gaagaaacaa gaaatcaagt atgtttctaa tgaagaagat tatggcaaga gaaggcttct    420
tgaaatttca gattccgatg gaagtaatcg acgtgtgtta gcggccgcgg gagatgacaa    480
atgtggagag ggtaaagtcc cgtttgtctc caattatggg atccaccaac ttcacatatt    540
catcttcgtt cttgctgttt tccacgtact ttattgtata atcacattgg ctttgggcag    600
agctaagatg aggaagtgga aggcgtggga aatggaaaca agaacagccg agtaccggtt    660
cgcaaacgat ccagagagat ttaggtttgc aagagacacc tcatttggga gaaggcattt    720
gcactcctgg agcacctccc cagttctcct ttggattgtg tgtttcttca gacaatttgt    780
cagatcagtt cccaaagttg attacttgac cttgcgccat gggtttatca ttgcacattt    840
ggcacccgag agtcatacta gatttgattt ccagaaatac atcaagagat cactcgagga    900
ggatttcaaa gttgtagtcg gtatcagtcc aataatctgg ttctgtgctg tactcttcct    960
actattcaac acccatggtt ggcattctta tctatggtta ccctttatcc cactaattat   1020
catcctgatg gtggggacaa aactacaagt tatcataaca aagatggggc tgagaataca   1080
ggagagagga gaggtggtaa aaggaacccc agtggtggag cctggtgatg atcttttctg   1140
gttcaaccag ccacgtctca ttctctacct gattaacttt gttctctttc agaacgcatt   1200
ccaggttgcc ttctttgcat ggacctggta tgagtttggc ttgaaatctt gtttccacga   1260
aaggatagaa gatgtggtca tccgcatatc aatgggagtc atagtacaaa tactctgcag   1320
ctatgtgact cttcctctgt atgccttggt tacacagatg ggatctacca tgaagcccac   1380
catcttcaat gacagagtgg cgaaagctct gagaaactgg caccacgctg caaggaagca   1440
cataaaacag agcaagcaat caagcgctgt gacccctgta tcaagtaggg caggcactcc   1500
cttttcaagt aggccaggca ccccttaca tggcatgtcc cctgttcatc tactccgcca   1560
ccaccgcagt gagctcgaca gtgttcaaac atctcctaga atgtccaatt ttgacaatga   1620
aggtccggag acagacgagt atcgccaccg tgaggatata tcatggtcag aacatcatag   1680
aaatcctggt ccagaagaag aggggaggga cacaaatcat aggatcttga cccgtaccat   1740
gccagctcct caagctgaca atgctcagca cgaaattgac attcagccca tggactttc    1800 attcgataaa agagcaagaa cttgaataga gtgatgaaga ttggattgag gaagcaagaa   1860
tgacaacaaa acccatccct ggttgtatag tggatacaat gttgaacttg caccttggcc   1920 ttgtatttt ttttttttg aggatcactc gtatagctgt gggcaacgaa tttttctgaa      1980
aagtaactct tgtagttctg taagttttaa atttcgttgt accgtatatc ataaattgtg   2040
agcagtcaaa ttcttacatg agttctcgtg taagaatcaa ctaaatgccc aaaatcaagc   2100
caatgctttc cccaaaaaaa aaaaaaaaaa aaaaaa                             2136
```

<210> SEQ ID NO 68  
<211> LENGTH: 563  
<212> TYPE: PRT  
<213> ORGANISM: Zea mays  
<220> FEATURE:  
<223> OTHER INFORMATION: Sequence listing for 58633.

<400> SEQUENCE: 68

Met Ala Gly Gly Gly Gly Gly Arg Asp Leu Pro Ser Thr Pro Thr Trp
1               5                   10                  15

Ala Val Ala Leu Val Cys Ala Val Ile Val Leu Val Ser Val Ala Met
            20                  25                  30

```
Glu His Gly Leu His Lys Leu Gly His Trp Phe His Thr Arg Gln Lys
             35                  40                  45

Lys Ala Met Arg Glu Ala Leu Glu Lys Ile Lys Ala Glu Leu Met Leu
 50                  55                  60

Met Gly Phe Ile Ser Leu Leu Ala Val Gly Gln Thr Pro Ile Ser
 65                  70                  75                  80

Lys Ile Cys Ile Pro Ala Lys Ala Gly Ser Ile Met Leu Pro Cys Lys
                 85                  90                  95

Pro Pro Lys Gly Ala Ala Ala Ala Asp Asp Lys Ser Asp Gly
                100                 105                 110

Arg Arg Arg Leu Leu Trp Tyr Pro Pro Tyr Pro Gly Tyr Asp Glu Pro
                115                 120                 125

Gly His His Arg Arg Phe Leu Ala Gly Ala Ala Pro Asp Asp Asn Tyr
                130                 135                 140

Cys Ser Asp Gln Gly Lys Val Ser Leu Ile Ser Ser Ala Gly Val His
145                 150                 155                 160

Gln Leu His Ile Phe Ile Phe Val Leu Ala Val Phe His Ile Val Tyr
                165                 170                 175

Ser Val Ala Thr Met Ala Leu Gly Arg Leu Lys Met Arg Lys Trp Lys
                180                 185                 190

Lys Trp Glu Ser Glu Thr Asn Ser Leu Glu Tyr Gln Tyr Ala Asn Asp
                195                 200                 205

Pro Ser Arg Phe Arg Phe Thr His Gln Thr Ser Phe Val Lys Arg His
                210                 215                 220

Leu Gly Leu Ser Ser Thr Pro Gly Val Arg Trp Val Ala Phe Phe
225                 230                 235                 240

Arg Gln Phe Phe Ala Ser Val Thr Lys Val Asp Tyr Leu Thr Met Arg
                245                 250                 255

Gln Gly Phe Ile Asn Tyr His Leu Ser Pro Ser Thr Lys Phe Asn Phe
                260                 265                 270

Gln Gln Tyr Ile Lys Arg Ser Leu Glu Asp Asp Phe Lys Val Val Val
                275                 280                 285

Gly Ile Ser Leu Pro Leu Trp Phe Val Ala Ile Phe Thr Leu Leu Ile
                290                 295                 300

Asp Ile Lys Gly Phe Gly Thr Leu Val Trp Ile Ser Phe Val Pro Leu
305                 310                 315                 320

Val Ile Leu Leu Leu Val Gly Ala Lys Leu Glu Val Val Ile Met Glu
                325                 330                 335

Met Ala Lys Glu Ile Gln Asp Lys Ala Thr Val Ile Lys Gly Ala Pro
                340                 345                 350

Val Val Glu Pro Ser Asp Arg Phe Phe Trp Phe Asn Arg Pro Gly Trp
                355                 360                 365

Val Leu Phe Leu Ile His Leu Thr Leu Phe Gln Asn Ala Phe Gln Met
                370                 375                 380

Ala His Phe Val Trp Thr Leu Thr Pro Asp Leu Lys Lys Cys Tyr
385                 390                 395                 400

His Glu Arg Leu Gly Leu Ser Ile Met Lys Val Ala Val Gly Leu Val
                405                 410                 415

Leu Gln Val Leu Cys Ser Tyr Ile Thr Phe Pro Leu Tyr Ala Leu Val
                420                 425                 430

Thr Gln Met Gly Ser His Met Lys Lys Thr Ile Phe Glu Glu Gln Thr
                435                 440                 445

Ala Lys Ala Val Met Lys Trp Arg Lys Thr Ala Lys Asp Lys Val Arg
```

```
                   450                 455                 460
Gln Arg Glu Ala Ala Gly Phe Leu Asp Val Leu Thr Ser Ala Asp Thr
465                 470                 475                 480

Thr Pro Ser His Ser Arg Ala Thr Ser Pro Ser Arg Gly Asn Ser Pro
                485                 490                 495

Val His Leu Leu His Lys Tyr Arg Gly Arg Ser Glu Glu Pro Gln Ser
            500                 505                 510

Gly Pro Ala Ser Pro Gly Arg Glu Leu Gly Asp Met Tyr Pro Val Ala
        515                 520                 525

Asp Gln His Arg Leu His Arg Leu Asp Pro Glu Arg Met Arg Pro Ala
    530                 535                 540

Ser Ser Thr Ala Val Asn Ile Asp Ile Ala Asp Ala Asp Phe Ser Phe
545                 550                 555                 560

Ser Met Arg

<210> SEQ ID NO 69
<211> LENGTH: 1872
<212> TYPE: DNA
<213> ORGANISM: Zea mays
<220> FEATURE:
<223> OTHER INFORMATION: Sequence listing for 58633.

<400> SEQUENCE: 69
```

| | | | | | |
|---|---|---|---|---|---|
| tggcaaagga | cggcacatgg | cggggggcgg | gggcggccgg | gacctgccgt | cgacgccgac | 60 |
| gtgggcggtg | gccctggtgt | gcgccgtcat | cgtgctcgtc | tccgtcgcca | tggagcatgg | 120 |
| cctccacaag | ctcggccact | ggttccatac | gcggcagaag | aaggccatgc | gggaggccct | 180 |
| ggagaagatc | aaagcagagt | tgatgctgat | gggcttcatc | tcgctgctcc | tcgccgtggg | 240 |
| gcagacgccc | atctccaaga | tatgcatccc | ggccaaggct | ggcagcatca | tgctgccgtg | 300 |
| caagccgccg | aaaggcgccg | ccgccgccgc | cgacgacgac | aagagcgacg | gccgccggag | 360 |
| actcctctgg | tacccgccgt | accctggata | cgatgagccc | gggcaccacc | gccgtttcct | 420 |
| cgccggcgcg | gctccggacg | acaactactg | cagtgaccaa | ggcaaggtgt | ccctcatctc | 480 |
| ctcggccggc | gtccaccagc | tgcacatctt | catcttcgtg | ctcgcggtgt | tccatatcgt | 540 |
| ctacagcgtc | gccaccatgg | cgctggggcg | tctcaaaatg | aggaaatgga | agaaatggga | 600 |
| atcggagacc | aactccctgg | aataccagta | cgcaaacgac | ccttcacggt | tccggttcac | 660 |
| gcaccagacg | tcgttcgtga | agcggcacct | gggcctctcg | agcaccctg | gagtgagatg | 720 |
| ggtcgtggcg | ttcttcaggc | agttcttcgc | gtccgtgacc | aagtggatt | acctgaccat | 780 |
| gcggcagggg | ttcatcaact | accatctgtc | gcccagcacc | aagttcaact | tccagcagta | 840 |
| catcaagcgg | tccttggagg | acgacttcaa | agtcgtcgtt | ggcatcagtc | tcccgctgtg | 900 |
| gttcgtcgcc | atcttcactc | tcttgatcga | tatcaaggga | ttcggcacgc | ttgtctggat | 960 |
| ctcttttgtc | ccgctcgtta | tactcctgct | agttggggcc | aagctggagg | ttgtcatcat | 1020 |
| ggagatggcc | aaggagatac | aggacaaggc | gacggtcatc | aaggggcgc | ctgtggtgga | 1080 |
| gccaagtgac | aggttcttct | ggtttaaccg | ccctggctgg | gtcctcttcc | tcatccacct | 1140 |
| cacgctcttc | cagaacgcct | tccagatggc | gcatttcgtt | tggacactgc | tcaccccaga | 1200 |
| cctgaagaaa | tgctaccacg | agaggctggg | cctgagcatc | atgaaagttg | cggtggggct | 1260 |
| ggttctccag | gtcctctgca | gttacatcac | cttcccgctc | tacgcgctcg | tcacgcagat | 1320 |
| ggggtcgcac | atgaagaaga | ccatcttcga | ggagcagacg | gccaaggcgg | tgatgaagtg | 1380 |
| gcgcaagacg | gccaaggata | aggtgcggca | gcgggaggcg | gcaggcttcc | tcgacgtgct | 1440 |

-continued

```
gacgagcgcc gacaccacgc cgagccacag ccgcgcgacg tcgccgagcc ggggcaactc    1500
gccggtgcac ctgctccaca agtacagggg caggtcggag gaaccgcaga gcgggccggc    1560
gtcgccgggg cgggagctcg gggacatgta cccggtggct gaccagcatc gcctgcacag    1620
gctggacccc gagaggatga ggcccgcctc gtccaccgcc gtcaacattg acatcgctga    1680
tgccgatttt tcttttagca tgcggtgacc tgaccttgaa cgaattctgt gtccttactc    1740
ttgtataggg aagcaaaagc atagacggag aacataatga cacgttacgt tagggaaagt    1800
ttcgtttatt catcataaaa tagaatacgt aataaactag tatctccctc ttcaaaaaaa    1860
aaaaaaaaaa aa                                                        1872
```

<210> SEQ ID NO 70
<211> LENGTH: 563
<212> TYPE: PRT
<213> ORGANISM: Sorghum bicolor
<220> FEATURE:
<223> OTHER INFORMATION: Sequence listing for 58633.

<400> SEQUENCE: 70

```
Met Ala Gly Gly Gly Gly Arg Asp Leu Pro Ser Thr Pro Thr Trp
1               5                   10                  15

Ala Val Ala Val Val Cys Ala Val Ile Val Leu Val Ser Val Ala Met
                20                  25                  30

Glu His Gly Leu His Lys Leu Gly His Trp Phe His Thr Arg Gln Lys
            35                  40                  45

Lys Ala Met Arg Glu Ala Leu Glu Lys Ile Lys Ala Glu Leu Met Leu
        50                  55                  60

Met Gly Phe Ile Ser Leu Leu Ala Val Gly Gln Thr Pro Ile Ser
65                  70                  75                  80

Lys Ile Cys Ile Pro Thr Lys Ala Gly Asn Ile Met Leu Pro Cys Lys
                85                  90                  95

Ala Gln Lys Asp Asp Ser Glu Ser Gly Gly Asp Ala Arg Arg Arg
            100                 105                 110

Leu Leu Trp Tyr Ser Pro Tyr Ser Gly Glu Glu Tyr Gly His His Arg
        115                 120                 125

Arg Phe Leu Ala Gly Ala Ala Ala Thr Asp Asp Tyr Cys Asp Lys Gln
    130                 135                 140

Gly Lys Val Ser Leu Ile Ser Thr Asn Gly Val His Gln Leu His Ile
145                 150                 155                 160

Phe Ile Phe Val Leu Ala Val Phe His Ile Ser Tyr Ser Val Ala Thr
                165                 170                 175

Met Ala Leu Gly Arg Leu Lys Met Arg Lys Trp Lys Lys Trp Glu Leu
            180                 185                 190

Glu Thr Asn Ser Val Glu Tyr Gln Phe Ala Asn Asp Pro Ser Arg Phe
        195                 200                 205

Arg Phe Thr His Gln Thr Ser Phe Val Lys Arg His Leu Gly Leu Ser
    210                 215                 220

Ser Thr Pro Gly Val Arg Trp Ile Val Gly Phe Phe Arg Gln Phe Phe
225                 230                 235                 240

Ala Ser Val Thr Lys Val Asp Tyr Leu Thr Met Arg Gln Gly Phe Ile
                245                 250                 255

Asn Tyr His Leu Ser Pro Asn Ala Lys Phe Asn Phe Gln Gln Tyr Ile
            260                 265                 270

Lys Arg Ser Leu Glu Asp Asp Phe Lys Val Val Val Gly Ile Ser Leu
```

```
                275                 280                 285
    Pro Leu Trp Phe Val Ala Ile Phe Ile Leu Leu Asp Ile Glu Gly
    290                 295                 300

Leu Gly Thr Leu Ile Trp Ile Ser Phe Val Pro Leu Val Ile Leu Leu
    305                 310                 315                 320

Leu Val Gly Thr Lys Leu Glu Val Val Ile Met Glu Met Ala Asn Glu
                    325                 330                 335

Ile Gln Asp Lys Ala Thr Val Ile Lys Gly Ala Pro Ala Val Glu Pro
                340                 345                 350

Ser Asp Arg Phe Phe Trp Phe Asn Arg Pro Arg Trp Val Leu Phe Leu
                355                 360                 365

Ile His Leu Thr Leu Phe Gln Asn Ala Phe Gln Met Ala His Phe Val
                370                 375                 380

Trp Thr Leu Leu Thr Pro Asp Leu Lys Lys Cys Tyr His Glu Gln Met
    385                 390                 395                 400

Gly Leu Thr Ile Met Lys Val Val Gly Val Ala Leu Gln Val Leu
                    405                 410                 415

Cys Ser Tyr Ile Thr Phe Pro Leu Tyr Ala Leu Val Thr Gln Met Gly
                    420                 425                 430

Ser His Met Lys Lys Thr Ile Phe Glu Glu Gln Thr Ala Lys Ala Val
                    435                 440                 445

Met Lys Trp Arg Lys Thr Ala Lys Asp Asn Val Lys Gln Arg Glu Ala
    450                 455                 460

Lys Gly Tyr Leu Asp Gly Leu Met Ser Ala Thr Thr Pro Ser His
    465                 470                 475                 480

Ser Arg Ala Thr Ser Pro Ser Arg Gly Asn Ser Pro Val His Leu Leu
                    485                 490                 495

His Lys Tyr Lys Gly Arg Ser Glu Glu Pro Gln Ser Ala Pro Thr Ser
                    500                 505                 510

Pro Gly Arg Gly Arg Gly Gln Glu Leu Gly Asp Met Tyr Pro Val Ala
                    515                 520                 525

Asp His Gln Arg Leu His Arg Leu Asp Pro Glu Arg Lys Arg Ala Ala
                530                 535                 540

Ser Ser Thr Ala Ile Asp Ile Asp Ile Ala Asp Ala Asp Phe Ser Phe
    545                 550                 555                 560

Ser Thr Arg

<210> SEQ ID NO 71
<211> LENGTH: 2099
<212> TYPE: DNA
<213> ORGANISM: Sorghum bicolor
<220> FEATURE:
<223> OTHER INFORMATION: Sequence listing for 58633.

<400> SEQUENCE: 71
actcggttgc tccgctcgat cgctcgagag gcaagagacg tgcgtgcgtt gtgcgtgcgt      60
gcctggcgcg agagagcgcg caccacagca gccagcaggc agctactacc cccgagctcc     120
gccgcggcct gcttgtcggt tcgcttcgct ttgctccagg tctccaggag aagctactag     180
ctagcgacgg catggcgggg ggcggggggcg gccgggacct gccgtcgacg ccgacgtggg     240
cggtagcggt cgtgtgcgcc gtcatcgtgc tcgtctccgt cgccatggag cacggcctcc     300
acaagctcgg ccactggttc catacgaggc agaagaaggc catgcgggag gcgctggaga     360
agatcaaagc agagttgatg ctgatgggct tcatctcgct gctcctcgcc gtggggcaga     420
```

-continued

```
cgcccatctc caagatatgt atccccacca aggccggcaa catcatgctg ccgtgcaagg     480
cgcagaaaga cgacgacagc gagagcggcg gcgatgcccg ccggaggctc ctctggtact     540
cgccgtactc tggagaagaa tacggccacc accgtcggtt cttggccggc gcggctgcga     600
cagacgacta ctgcgataaa caaggcaagg tgtccctcat ctccacgaac ggtgtccacc     660
agctgcacat cttcatcttt gtgcttgcgg tgttccatat ctcttacagc gtcgccacca     720
tggcgttagg gcgtctgaaa atgagaaaat ggaagaaatg ggaattggag accaactcgg     780
tggaatatca attcgcaaac gatccttcac gattccgatt cacgcaccaa acatcgttcg     840
tgaagcggca cctgggcctc tcgagcactc ctggagtcag atggattgtg ggattcttca     900
ggcagttctt cgcgtcggtg accaaggtgg attacctgac catgcggcaa ggattcatca     960
attatcatct gtcgcccaac gctaagttca atttccaaca gtacatcaag cggtccttgg    1020
aggacgactt caaagtcgtc gttggcataa gtctcccgct gtggttcgtc gccatcttca    1080
tcctcctcct cgatatcgaa ggactcggca cgcttatctg gatctctttt gtcccgctcg    1140
ttatactctt gttggttggg accaagctgg aggttgtcat catggagatg ccaacgaga     1200
tacaggacaa ggcgacggtg atcaagggggg cgcctgcggt ggagccaagt gacaggttct    1260
tctggttcaa ccgccctcgc tgggtcctct tcctcatcca cctcacgctc ttccagaacg    1320
ccttccagat ggcgcatttc gtgtggacac tgctcacccc agacttgaag aaatgctacc    1380
atgagcagat gggcctgacc atcatgaaag ttgtagtggg tgtggctctt caggtcctct    1440
gcagctacat caccttcccg ctctacgcgc tcgtcacaca gatggggtct cacatgaaga    1500
agaccatctt cgaggagcag acggccaagg cggtgatgaa gtggcgcaag acggccaagg    1560
acaatgtgaa gcagcgggag gcgaaaggtt acctcgacgg gctgatgagc gccgacacga    1620
cgccgagcca cagccgcgcc acgtcgccga gccggggcaa ctcgccggtg cacctgctcc    1680
acaagtacaa gggccggtcg gaggagccgc agagcgcccc gacgtctccg ggaagggatc    1740
gggggcagga gctcggggac atgtacccgg tggccgacca ccagcggctg cacaggcttg    1800
acccagagag gaagagggcg gcctcgtcca ccgccatcga cattgacatc gctgatgccg    1860
attttcgtt tagcacgcgg tgattttgaa cgaattttgt gcagcatgtt ttgtatttat    1920
ttacttttgt atagggaaaa acatagatga aaaatacaac gacacgttag ggaagtttcg    1980
tttattcatc ataaaataga atatgcaata gagtgggtag ctttgtgcaa catacccctct   2040
ctgaacaaac gtgcaaacaa gcattttaaa gtaataataa acctcccaac tctctatgg    2099
```

<210> SEQ ID NO 72
<211> LENGTH: 555
<212> TYPE: PRT
<213> ORGANISM: Oryza sativa
<220> FEATURE:
<223> OTHER INFORMATION: Sequence listing for 58633.

<400> SEQUENCE: 72

| Met | Ala | Gly | Gly | Gly | Gly | Arg | Ala | Leu | Pro | Glu | Thr | Pro | Thr | Trp |
|---|---|---|---|---|---|---|---|---|---|---|---|---|---|---|
| 1 | | | | 5 | | | | | 10 | | | | | 15 |

| Ala | Val | Ala | Val | Val | Cys | Ala | Val | Ile | Val | Leu | Val | Ser | Val | Ala | Met |
|---|---|---|---|---|---|---|---|---|---|---|---|---|---|---|---|
| | | | 20 | | | | | 25 | | | | | 30 | | |

| Glu | His | Gly | Leu | His | Lys | Leu | Gly | His | Trp | Phe | His | Lys | Arg | Glu | Lys |
|---|---|---|---|---|---|---|---|---|---|---|---|---|---|---|---|
| | | 35 | | | | | 40 | | | | | 45 | | | |

| Lys | Ala | Met | Gly | Glu | Ala | Leu | Glu | Lys | Ile | Lys | Ala | Glu | Leu | Met | Leu |
|---|---|---|---|---|---|---|---|---|---|---|---|---|---|---|---|
| | 50 | | | | | 55 | | | | | 60 | | | | |

Leu Gly Phe Ile Ser Leu Leu Leu Thr Val Ala Gln Thr Pro Ile Ser

```
                65                  70                  75                  80
Lys Ile Cys Ile Pro Glu Ser Ala Ala Asn Ile Met Leu Pro Cys Lys
                    85                  90                  95
Ala Gly Gln Asp Ile Val Lys Gly Leu Lys Gly Lys Lys Asp His Arg
                    100                 105                 110
Arg Arg Leu Leu Trp Tyr Thr Gly Glu Glu Ser His Arg Arg Ser
                    115                 120                 125
Leu Ala Gly Ala Ala Gly Glu Asp Tyr Cys Ala Gln Ser Gly Lys Val
                    130                 135                 140
Ala Leu Met Ser Ser Gly Gly Met His Gln Leu His Ile Phe Ile Phe
145                     150                 155                 160
Val Leu Ala Val Phe His Val Thr Tyr Cys Val Ile Thr Met Ala Leu
                    165                 170                 175
Gly Arg Leu Lys Met Lys Lys Trp Lys Lys Trp Glu Leu Glu Thr Asn
                    180                 185                 190
Ser Leu Glu Tyr Gln Phe Ala Asn Asp Pro Ser Arg Phe Arg Phe Thr
                    195                 200                 205
His Gln Thr Ser Phe Val Lys Arg His Leu Gly Leu Ser Ser Thr Pro
                    210                 215                 220
Gly Leu Arg Trp Ile Val Ala Phe Phe Arg Gln Phe Phe Gly Ser Val
225                     230                 235                 240
Thr Lys Val Asp Tyr Leu Thr Met Arg Gln Gly Phe Ile Asn Ala His
                    245                 250                 255
Leu Ser Gln Asn Ser Lys Phe Asp Phe His Lys Tyr Ile Lys Arg Ser
                    260                 265                 270
Leu Glu Asp Asp Phe Lys Val Val Gly Ile Ser Leu Pro Leu Trp
                    275                 280                 285
Phe Val Ala Ile Leu Val Leu Phe Leu Asp Ile Gln Gly Phe Gly Thr
                    290                 295                 300
Leu Ile Trp Ile Ser Phe Val Pro Leu Val Ile Leu Met Leu Val Gly
305                     310                 315                 320
Thr Lys Leu Glu Met Val Ile Met Glu Met Ala Gln Glu Ile Gln Asp
                    325                 330                 335
Arg Ala Thr Val Ile Lys Gly Ala Pro Val Val Glu Pro Ser Asn Lys
                    340                 345                 350
Tyr Phe Trp Phe Asn Arg Pro Asp Trp Val Leu Phe Phe Ile His Leu
                    355                 360                 365
Ile Leu Phe Gln Asn Ala Phe Gln Met Ala His Phe Val Trp Thr Leu
                    370                 375                 380
Ala Thr Pro Gly Leu Lys Lys Cys Phe His Glu Asn Met Gly Leu Ser
385                     390                 395                 400
Ile Met Lys Val Val Val Gly Ile Phe Ile Gln Phe Leu Cys Ser Tyr
                    405                 410                 415
Ser Thr Phe Pro Leu Tyr Ala Leu Val Thr Gln Met Gly Ser Asn Met
                    420                 425                 430
Lys Lys Thr Ile Phe Glu Glu Gln Thr Met Lys Ala Leu Met Asn Trp
                    435                 440                 445
Arg Lys Thr Ala Arg Glu Lys Lys Leu Arg Asp Ala Asp Glu Phe
                    450                 455                 460
Leu Ala Gln Met Ser Gly Asp Thr Thr Pro Ser Arg Gly Ser Ser Pro
465                     470                 475                 480
Val His Leu Leu His Lys Gln Arg Val Arg Ser Glu Asp Pro Pro Ser
                    485                 490                 495
```

Ala Pro Ala Ser Pro Gly Phe Ala Gly Glu Ala Arg Asp Met Tyr Pro
            500                 505                 510

Val Pro Val Ala Pro Val Val Arg Pro His Gly Phe Asn Arg Met Asp
        515                 520                 525

Pro Asp Lys Arg Arg Ala Ala Ser Ser Ser Ala Ile Gln Val Asp Ile
    530                 535                 540

Ala Asp Ser Asp Phe Ser Phe Ser Val Gln Arg
545                 550                 555

<210> SEQ ID NO 73
<211> LENGTH: 2004
<212> TYPE: DNA
<213> ORGANISM: Oryza sativa
<220> FEATURE:
<223> OTHER INFORMATION: Sequence listing for 58633.

<400> SEQUENCE: 73

| | | | | | |
|---|---|---|---|---|---|
| tggcgaaaaa | ccggatcaac | gcgagcaagc | gctcacctca | ccacctcacc | ctgcagcgac | 60 |
| agaaagagtc | tgtagtagcg | tacgatcgcg | gctagctatc | gagctccagc | gagaggcgta | 120 |
| cgtgagtgcg | tgcgtacgtg | cgggaggagg | aggaggggga | gatggcaggg | ggaggagggg | 180 |
| ggagggcgtt | gccggagacg | ccgacgtggg | cggtggccgt | ggtctgcgcc | gtcatcgtgc | 240 |
| tcgtctccgt | cgccatggag | cacggcctcc | acaagctcgg | ccattggttc | cataagcggg | 300 |
| agaagaaggc | catgggcgaa | gcgctcgaga | agatcaaagc | agagttgatg | ctgctgggct | 360 |
| tcatatcgct | gctcctcact | gtggcacaaa | cgcccatctc | caagatatgc | atcccggagt | 420 |
| cagctgccaa | catcatgctg | ccgtgcaagg | cagggcaaga | tatcgtcaag | ggcctgaagg | 480 |
| gaaaaaagga | ccatcgccgg | aggcttctct | ggtacaccgg | agaagaagag | agccatcgcc | 540 |
| ggtcactggc | cggcgccgcc | ggcgaggatt | actgcgcgca | atcgggcaag | gtggcgctga | 600 |
| tgtcatcggg | cggcatgcac | cagctgcaca | tattcatttt | cgtgctcgcg | gtgttccacg | 660 |
| tcacctactg | cgtcatcacc | atggctctag | gcgtctcaa | aatgaagaaa | tggaagaaat | 720 |
| gggaattaga | gaccaactcg | ttggagtatc | agttcgcaaa | cgatccttca | cgattccggt | 780 |
| tcacgcatca | gacatcgttc | gtgaaacggc | atctgggact | gtcaagcaca | cctgggctca | 840 |
| gatggattgt | ggcgttcttc | aggcagttct | tcgggtctgt | caccaaggtg | gactacctga | 900 |
| ccatgcggca | aggcttcatc | aatgcgcatt | tgtcgcagaa | tagcaagttc | gacttccaca | 960 |
| aatacatcaa | gaggtcatta | gaggacgatt | tcaaagttgt | cgttggcatc | agcctcccat | 1020 |
| tgtggttttgt | cgccgatcctt | tgtgctcttcc | ttgatatcca | agggttcggc | acgcttatct | 1080 |
| ggatctcttt | tgttccactc | gtcatcctca | tgttggttgg | gacaaagctg | gagatggtta | 1140 |
| tcatggagat | ggcacaggag | atacaggaca | gggcaactgt | gatcaaggga | gcaccggtcg | 1200 |
| ttgaaccaag | caacaagtac | ttctggttta | accggcctga | ttgggtcttg | ttcttcatac | 1260 |
| acttgatact | gttccagaac | gcatttcaga | tggcacattt | cgtgtggact | ctggcaaccc | 1320 |
| ctggcctgaa | gaaatgcttc | catgaaaaca | tgggcttgag | tatcatgaaa | gttgtagtgg | 1380 |
| ggatattcat | tcagttccta | tgcagctaca | gcaccttccc | tctctacgca | ctcgtcacac | 1440 |
| agatgggatc | aaacatgaag | aagaccatct | tcgaggagca | gacgatgaag | gccctgatga | 1500 |
| actggaggaa | gacggcgagg | gagaagaaga | agctccggga | cgccgacgag | ttcctagcac | 1560 |
| agatgagcgg | cgacacgacg | ccgagccgcg | gctcgtcgcc | ggtgcacctg | ctgcacaagc | 1620 |
| aaagggtgag | gtcggaagat | ccgccgagcg | caccggcatc | gccggggttc | gccggagagg | 1680 |

-continued

```
ccagggacat gtacccggtg cccgtggcgc cggtggtgcg gccgcatggg tttaaccgga    1740
tggacccgga taagaggagg gcggcgtcct cgtcggccat ccaagttgac atcgccgatt    1800
ctgatttctc cttcagtgta caacggtgat ggccgaaagg tttctctgta cttaagttgt    1860
atagcagcaa atataggagt acaatgtata gttggtacac tacatataga gattagaaaa    1920
gtacagtcga ttttttttaag aaacaataaa agcataactt tgtataacat attctttcgg    1980
aagaaagatg cggcagcatt gggg                                           2004
```

```
<210> SEQ ID NO 74
<211> LENGTH: 528
<212> TYPE: PRT
<213> ORGANISM: Oryza sativa
<220> FEATURE:
<223> OTHER INFORMATION: Sequence listing for 58633.

<400> SEQUENCE: 74

Met Ala Gly Gly Arg Ser Gly Ser Arg Glu Leu Pro Glu Thr Pro Thr
1               5                   10                  15

Trp Ala Val Ala Val Cys Ala Val Leu Val Leu Val Ser Val Ala
            20                  25                  30

Met Glu His Gly Leu His Asn Leu Ser His Trp Phe Arg Arg Arg Gln
        35                  40                  45

Lys Lys Ala Met Gly Asp Ala Leu Asp Lys Ile Lys Ala Glu Leu Met
    50                  55                  60

Leu Leu Gly Phe Ile Ser Leu Leu Thr Val Ala Gln Ala Pro Ile
65                  70                  75                  80

Ser Lys Ile Cys Ile Pro Lys Ser Ala Ala Asn Ile Leu Leu Pro Cys
                85                  90                  95

Lys Ala Gly Gln Asp Ala Ile Glu Glu Glu Ala Ala Ser Asp Arg Arg
            100                 105                 110

Ser Leu Ala Gly Ala Gly Gly Asp Tyr Cys Ser Lys Phe Asp Gly
        115                 120                 125

Lys Val Ala Leu Met Ser Ala Lys Ser Met His Gln Leu His Ile Phe
    130                 135                 140

Ile Phe Val Leu Ala Val Phe His Val Thr Tyr Cys Val Ile Thr Met
145                 150                 155                 160

Gly Leu Gly Arg Leu Lys Met Lys Lys Trp Lys Lys Trp Glu Ser Gln
                165                 170                 175

Thr Asn Ser Leu Glu Tyr Gln Phe Ala Ile Asp Pro Ser Arg Phe Arg
            180                 185                 190

Phe Thr His Gln Thr Ser Phe Val Lys Arg His Leu Gly Ser Phe Ser
        195                 200                 205

Ser Thr Pro Gly Leu Arg Trp Ile Val Ala Phe Phe Arg Gln Phe Phe
    210                 215                 220

Gly Ser Val Thr Lys Val Asp Tyr Leu Thr Met Arg Gln Gly Phe Ile
225                 230                 235                 240

Asn Ala His Leu Ser Gln Asn Ser Lys Phe Asp Phe His Lys Tyr Ile
                245                 250                 255

Lys Arg Ser Leu Glu Asp Asp Phe Lys Val Val Gly Ile Ser Leu
            260                 265                 270

Pro Leu Trp Phe Val Gly Ile Leu Val Leu Phe Leu Asp Ile His Gly
        275                 280                 285

Leu Gly Thr Leu Ile Trp Ile Ser Phe Val Pro Leu Ile Ile Val Leu
    290                 295                 300
```

```
Leu Val Gly Thr Lys Leu Glu Met Val Ile Met Gln Met Ala Gln Glu
305                 310                 315                 320

Ile Gln Asp Arg Ala Thr Val Ile Gln Gly Ala Pro Val Val Glu Pro
            325                 330                 335

Ser Asn Lys Tyr Phe Trp Phe Asn Arg Pro Asp Trp Val Leu Phe Phe
        340                 345                 350

Ile His Leu Thr Leu Phe His Ala Thr Pro Gly Leu Lys Lys Cys Phe
            355                 360                 365

His Glu Asn Ile Trp Leu Ser Ile Val Glu Val Ile Val Gly Ile Ser
        370                 375                 380

Leu Gln Val Leu Cys Ser Tyr Ile Thr Phe Pro Leu Tyr Ala Leu Val
385                 390                 395                 400

Thr Gln Met Gly Ser Asn Met Lys Lys Thr Ile Phe Glu Glu Gln Thr
            405                 410                 415

Met Lys Ala Leu Met Asn Trp Arg Lys Lys Ala Met Glu Lys Lys Lys
        420                 425                 430

Val Arg Asp Ala Asp Ala Phe Leu Ala Gln Met Ser Val Asp Phe Ala
            435                 440                 445

Thr Pro Ala Ser Ser Arg Ser Ala Ser Pro Val His Leu Leu Gln Asp
450                 455                 460

His Arg Ala Arg Ser Asp Asp Pro Pro Ser Pro Ile Thr Val Ala Ser
465                 470                 475                 480

Pro Pro Ala Pro Glu Glu Asp Ile Tyr Pro Val Pro Ala Ala Ala Ala
            485                 490                 495

Ser Arg Gln Leu Leu Asp Asp Pro Pro Asp Arg Arg Trp Met Ala Ser
        500                 505                 510

Ser Ser Ala Asp Ile Ala Asp Ser Asp Phe Ser Phe Ser Ala Gln Arg
        515                 520                 525

<210> SEQ ID NO 75
<211> LENGTH: 1587
<212> TYPE: DNA
<213> ORGANISM: Oryza sativa
<220> FEATURE:
<223> OTHER INFORMATION: Sequence listing for 58633.

<400> SEQUENCE: 75
atggcaggtg ggagatcggg atcgcgggag ttgccggaga cgccgacgtg ggcggtggcc      60
gtcgtctgcg ccgtcctcgt gctcgtctcc gtcgccatgg agcacggcct ccacaacctc     120
agccattggt tccgtaggcg gcagaagaag gccatgggcg acgccctcga caagatcaaa     180
gcagagctga tgctgctggg cttcatatcc ctgcttctca ccgtggcaca ggcgcccatc     240
tccaagatct gcatccccaa gtcggctgcc aacatcttgt tgccgtgcaa ggcaggccaa     300
gatgccatcg aagaagaagc agcaagtgat cgccggtcct tggccggcgc cggcggcggg     360
gactactgct cgaaattcga tggcaaggtg gcgctgatgt cggcaaagag catgcaccag     420
ctgcacattt tcatcttcgt gctcgccgtg ttccatgtta cctactgcgt catcaccatg     480
ggtttagggc gcctcaaaat gaagaaatgg aagaagtggg agtcacagac caactcattg     540
gagtatcagt tcgcaatcga tccttcacga ttcaggttca cgcatcagac gtcgttcgtg     600
aagcggcatc tgggatcatt ctcaagcacc cctgggctca gatggatcgt agcattcttc     660
aggcagttct ttgggtccgt caccaaggtg gactacctga ccatgcggca aggcttcatc     720
aatgcgcatt gtcgcagaa tagcaagttc gacttccaca atacatcaa gaggtctttg     780 gaggacgact tcaaagttgt cgttggcatc agcctccctc tgtggttcgt cggaatcctt     840
```

```
gtactcttcc tcgatatcca cggtcttggc acacttattt ggatctcttt tgttcctctc    900
atcatcgtct tgttagttgg gaccaagcta gagatggtga tcatgcagat ggcccaagag    960
atacaggaca gggccactgt gatccaggga gcacctgtgg ttgaaccaag caacaagtac   1020
ttctggttca accgccctga ctgggtcttg ttcttcatac acctgacact cttccatgca   1080
acacctggtc tgaagaaatg cttccatgaa atatttggc tgagcatcgt ggaagtcatt    1140
gtggggatct ctcttcaggt gctatgcagc tacatcacct tcccgctcta cgcgctcgtc   1200
acacagatgg gatcgaacat gaagaagaca atcttcgagg agcaaacgat gaaggcgctg   1260
atgaactgga ggaagaaggc gatggagaag aagaaggtcc gggacgcgga cgcgttcctg   1320
gcgcagatga gcgtcgactt cgcgacgccg gcgtcgagcc ggtccgcgtc gccggtgcac   1380
ctgctgcagg atcacagggc gaggtcggac gacccgccga gcccaatcac ggtggcctca   1440
ccaccggcac cggaggagga catatacccg gtgccggcgg cggctgcgtc tcgccagctg   1500
ctagacgacc cgccggacag gaggtggatg gcatcctcgt cggccgacat cgccgattct   1560
gattttttcct tcagcgcaca acggtga                                      1587
```

<210> SEQ ID NO 76
<211> LENGTH: 536
<212> TYPE: PRT
<213> ORGANISM: Oryza sativa
<220> FEATURE:
<223> OTHER INFORMATION: Sequence listing for 58633.

<400> SEQUENCE: 76

Met Ala Gly Gly Arg Ser Gly Ser Arg Glu Leu Pro Glu Thr Pro Thr
1               5                   10                  15
Trp Ala Val Ala Val Val Cys Ala Val Leu Val Leu Ser Val Ala
            20                  25                  30
Met Glu His Gly Leu His Asn Leu Ser His Gly Ser Val Gly Gly Arg
        35                  40                  45
Arg Arg Pro Trp Ala Thr Pro Ser Thr Arg Ser Lys Gln Gly Phe Ile
    50                  55                  60
Ser Leu Leu Leu Thr Val Ala Gln Ala Pro Ile Ser Lys Ile Cys Ile
65                  70                  75                  80
Pro Lys Ser Ala Ala Asn Ile Leu Leu Pro Cys Lys Ala Gly Gln Asp
                85                  90                  95
Ala Ile Glu Glu Glu Ala Ala Ser Asp Arg Arg Ser Leu Ala Gly Ala
            100                 105                 110
Gly Gly Gly Asp Tyr Cys Ser Lys Phe Asp Gly Lys Val Ala Leu Met
        115                 120                 125
Ser Ala Lys Ser Met His Gln Leu His Ile Phe Ile Phe Val Leu Ala
    130                 135                 140
Val Phe His Val Thr Tyr Cys Val Ile Thr Met Gly Leu Gly Arg Leu
145                 150                 155                 160
Lys Met Lys Lys Trp Lys Lys Trp Glu Ser Gln Thr Asn Ser Leu Glu
                165                 170                 175
Tyr Gln Phe Ala Ile Asp Pro Ser Arg Phe Arg Phe Thr His Gln Thr
            180                 185                 190
Ser Phe Val Lys Arg His Leu Gly Ser Phe Ser Thr Pro Gly Leu
        195                 200                 205
Arg Trp Ile Val Ala Phe Phe Arg Gln Phe Phe Gly Val Thr Lys
    210                 215                 220

Val Asp Tyr Leu Thr Met Arg Gln Gly Phe Ile Asn Val Tyr Thr Asn
225                 230                 235                 240

Gln Asn Ser Lys Phe Asp Phe His Lys Tyr Ile Lys Arg Ser Leu Glu
            245                 250                 255

Asp Asp Phe Lys Val Val Gly Ile Arg Ser Leu Pro Leu Trp Phe
                260                 265                 270

Val Gly Ile Leu Val Leu Phe Leu Asp Ile His Gly Leu Gly Thr Leu
        275                 280                 285

Ile Trp Ile Ser Phe Val Pro Leu Ile Ile Val Leu Leu Val Gly Thr
    290                 295                 300

Lys Leu Glu Met Val Ile Met Gln Met Ala Gln Glu Ile Gln Asp Arg
305                 310                 315                 320

Ala Thr Val Ile Gln Gly Ala Pro Val Val Glu Pro Ser Asn Lys Tyr
                325                 330                 335

Phe Trp Phe Asn Arg Pro Asp Trp Val Leu Phe Ile His Leu Thr
                340                 345                 350

Leu Phe His Asn Ala Phe Gln Met Ala His Phe Val Trp Thr Met Ala
        355                 360                 365

Thr Pro Gly Leu Lys Lys Cys Phe His Glu Asn Ile Trp Leu Ser Ile
370                 375                 380

Val Glu Val Ile Val Gly Ile Ser Leu Gln Val Leu Cys Ser Tyr Ile
385                 390                 395                 400

Thr Phe Pro Leu Tyr Ala Leu Val Thr Gln Met Gly Ser Asn Met Lys
                405                 410                 415

Lys Thr Ile Phe Glu Glu Gln Thr Met Lys Ala Leu Met Asn Trp Arg
        420                 425                 430

Lys Lys Ala Met Glu Lys Lys Val Arg Asp Ala Asp Ala Phe Leu
435                 440                 445

Ala Gln Met Ser Val Asp Phe Ala Thr Pro Ala Ser Ser Arg Ser Ala
    450                 455                 460

Ser Pro Val His Leu Leu Gln Asp His Arg Ala Arg Ser Asp Asp Pro
465                 470                 475                 480

Pro Ser Pro Ile Thr Val Ala Ser Pro Pro Ala Pro Glu Glu Asp Ile
                485                 490                 495

Tyr Pro Val Pro Ala Ala Ala Ser Arg Gln Leu Leu Asp Asp Pro
            500                 505                 510

Pro Asp Arg Arg Trp Met Ala Ser Ser Ser Ala Asp Ile Ala Asp Ser
        515                 520                 525

Asp Phe Ser Phe Ser Ala Gln Arg
530                 535

<210> SEQ ID NO 77
<211> LENGTH: 1611
<212> TYPE: DNA
<213> ORGANISM: Oryza sativa
<220> FEATURE:
<223> OTHER INFORMATION: Sequence listing for 58633.

<400> SEQUENCE: 77
atggcaggtg ggagatcggg atcgcgggag ttgccggaga cgccgacgtg ggcggtggcc      60
gtcgtctgcg ccgtcctcgt gctcgtctcc gtcgccatgg agcacggcct ccacaacctc     120
agccatggtt ccgtaggcgg cagaagaagg ccatgggcga cgccctcgac aagatcaaag     180
cagggcttca tatccctgct tctcaccgtg gcacaggcgc ccatctccaa gatctgcatc     240
cccaagtcgg ctgccaacat cttgttgccg tgcaaggcag gccaagatgc catcgaagaa     300

```
gaagcagcaa gtgatcgccg gtccttggcc ggcgccggcg gcggggacta ctgctcgaaa      360
ttcgatggca aggtggcgct gatgtcggca aagagcatgc accagctgca cattttcatc      420
ttcgtgctcg ccgtgttcca tgttacctac tgcgtcatca ccatgggttt agggcgcctc      480
aaaatgaaga aatggaagaa gtgggagtca cagaccaact cattggagta tcagttcgca      540
atcgatcctt cacgattcag gttcacgcat cagacgtcgt tcgtgaagcg gcatctggga      600
tcattctcaa gcacccctgg gctcagatgg atcgtagcat tcttcaggca gttctttggg      660
tccgtcacca aggtggacta cctgaccatg cggcaaggct tcatcaatgt atatactaat      720
caaaatagca agttcgactt ccacaaatac atcaagaggt cttttggagga cgacttcaaa      780 gttgtcgttg catcaggtc cctccctctg tggttcgtcg gaatccttgt actcttcctc      840
gatatccacg gtcttggcac acttatttgg atctcttttg ttcctctcat catcgtcttg      900
ttagttggga ccaagctaga gatggtgatc atgcagatgg cccaagagat acaggacagg      960
gccactgtga tccagggagc acctgtggtt gaaccaagca acaagtactt ctggttcaac      1020
cgccctgact gggtcttgtt cttcatacac ctgacactct tccataacgc atttcagatg      1080
gcgcatttcg tatggactat ggcaacacct ggtctgaaga atgcttcca tgaaaatatt      1140 tggctgagca tcgtggaagt cattgtgggg atctctcttc aggtgctatg cagctacatc      1200
accttcccgc tctacgcgct cgtcacacag atgggatcga acatgaagaa gacaatcttc      1260
gaggagcaaa cgatgaaggc gctgatgaac tggaggaaga aggcgatgga gaagaagaag      1320
gtccgggacg cggacgcgtt cctggcgcag atgagcgtcg acttcgcgac gccggcgtcg      1380
agccggtccg cgtcgccggt gcacctgctg caggatcaca gggcgaggtc ggacgacccg      1440
ccgagcccaa tcacggtggc ctcaccaccg gcaccggagg aggacatata cccggtgccg      1500
gcggcggctg cgtctcgcca gctgctagac gacccgccgg acaggaggtg gatggcatcc      1560
tcgtcggccg acatcgccga ttctgatttt tccttcagcg cacaacggtg a              1611
```

<210> SEQ ID NO 78
<211> LENGTH: 554
<212> TYPE: PRT
<213> ORGANISM: Oryza sativa
<220> FEATURE:
<223> OTHER INFORMATION: Sequence listing for 58633.

<400> SEQUENCE: 78

```
Met Ala Gly Gly Gly Gly Arg Ala Leu Pro Glu Thr Pro Thr Trp
1               5                   10                  15

Ala Val Ala Val Val Cys Ala Val Ile Val Leu Val Ser Val Ala Met
                20                  25                  30

Glu His Gly Leu His Lys Leu Gly His Trp Phe His Lys Arg Glu Lys
            35                  40                  45

Lys Ala Met Gly Glu Ala Leu Gly Lys Ile Lys Ala Glu Leu Met Leu
        50                  55                  60

Leu Gly Phe Ile Ser Leu Leu Leu Thr Val Ala Gln Thr Pro Ile Ser
65                  70                  75                  80

Lys Ile Cys Ile Pro Glu Ser Ala Ala Asn Ile Met Leu Pro Cys Lys
                85                  90                  95

Ala Gly Gln Asp Ile Val Lys Gly Leu Lys Gly Lys Lys Asp His Arg
            100                 105                 110

Arg Arg Leu Leu Trp Tyr Thr Gly Glu Glu Ser His Arg Arg Ser
        115                 120                 125
```

```
Leu Ala Gly Ala Ala Gly Glu Asp Tyr Cys Ala Gln Ser Gly Lys Val
130                 135                 140

Ala Leu Met Ser Ser Gly Gly Met His Gln Leu His Ile Phe Ile Phe
145                 150                 155                 160

Val Leu Ala Val Phe His Val Thr Tyr Cys Val Ile Thr Met Gly Leu
                165                 170                 175

Gly Arg Leu Lys Met Lys Lys Trp Lys Lys Trp Glu Ser Gln Thr Asn
                180                 185                 190

Ser Leu Glu Tyr Gln Phe Ala Ile Asp Pro Ser Arg Phe Arg Phe Thr
                195                 200                 205

His Gln Thr Ser Phe Val Lys Arg His Leu Gly Ser Phe Ser Ser Thr
210                 215                 220

Pro Gly Leu Arg Trp Ile Val Ala Phe Phe Arg Gln Phe Phe Gly Ser
225                 230                 235                 240

Val Thr Lys Val Asp Tyr Leu Thr Met Arg Gln Gly Phe Ile Asn Ala
                245                 250                 255

His Leu Ser Gln Asn Ser Lys Phe Asp Phe His Lys Tyr Ile Lys Arg
                260                 265                 270

Ser Leu Glu Asp Asp Phe Lys Val Val Val Gly Ile Ser Leu Pro Leu
                275                 280                 285

Trp Phe Val Gly Ile Leu Val Leu Phe Leu Asp Ile His Gly Leu Gly
                290                 295                 300

Thr Leu Ile Trp Ile Ser Phe Val Pro Leu Ile Ile Val Leu Leu Val
305                 310                 315                 320

Gly Thr Lys Leu Glu Met Val Ile Met Gln Met Ala Gln Glu Ile Gln
                325                 330                 335

Asp Arg Ala Thr Val Ile Gln Gly Ala Pro Val Val Glu Pro Ser Asn
                340                 345                 350

Lys Tyr Phe Trp Phe Asn Arg Pro Asp Trp Val Leu Phe Phe Ile His
                355                 360                 365

Leu Thr Leu Phe His Asn Ala Phe Gln Met Ala His Phe Val Trp Thr
370                 375                 380

Met Ala Thr Pro Gly Leu Lys Lys Cys Phe His Glu Asn Ile Trp Leu
385                 390                 395                 400

Ser Ile Val Glu Val Ile Val Gly Ile Ser Leu Gln Val Leu Cys Ser
                405                 410                 415

Tyr Ile Thr Phe Pro Leu Tyr Ala Leu Val Thr Gln Met Gly Ser Asn
                420                 425                 430

Met Lys Lys Thr Ile Phe Glu Glu Gln Thr Met Lys Ala Leu Met Asn
                435                 440                 445

Trp Arg Lys Lys Ala Met Glu Lys Lys Val Arg Asp Ala Asp Ala
450                 455                 460

Phe Leu Ala Gln Met Ser Val Asp Phe Ala Thr Pro Ala Ser Ser Arg
465                 470                 475                 480

Ser Ala Ser Pro Val His Leu Leu Gln Asp His Arg Ala Arg Leu Asp
                485                 490                 495

Asp Pro Pro Ser Pro Ile Thr Val Ala Ser Pro Ala Pro Glu Glu
                500                 505                 510

Asp Ile Tyr Pro Val Pro Ala Ala Ala Phe Cys Gln Leu Leu Asp
                515                 520                 525

Asp Pro Pro Asp Arg Arg Trp Met Ala Ser Leu Ser Ala Asp Ile Pro
530                 535                 540

Asp Phe Asp Phe Ser Phe Ser Ala Gln Arg
```

545         550

<210> SEQ ID NO 79
<211> LENGTH: 1894
<212> TYPE: DNA
<213> ORGANISM: Oryza sativa
<220> FEATURE:
<223> OTHER INFORMATION: Sequence listing for 58633.

<400> SEQUENCE: 79

```
gcgagcaagc gttcacctca ccacctcacc ctgcagcgac agaaagagtc tgtagtagcg    60
tacgatcgcg gctagctatc gagctccagc gagaggcgta cgtgagtgcg tgcgtacgtg   120
cgggagggag gaggagggga gatggcaggg ggaggagggg ggagggcgtt gccggagacg   180
ccgacgtggg cggtggccgt ggtctgcgcc gtcatcgtgc tcgtctccgt cgccatggag   240
cacggcctcc acaagctcgg ccattggttc cataagcggg agaagaaggc catgggcgaa   300
gcgctcggga agatcaaagc agagttgatg ctgctgggct tcatatcgct gctcctcact   360
gtggcacaaa cgcccatctc caagatatgc atcccggagt cagctgccaa catcatgctg   420
ccgtgcaagg cagggcaaga tatcgtcaag ggcctgaagg gaaaaaagga ccatcgccgg   480
aggcttctct ggtacaccgg agaagaagag agccatcgcc ggtcactggc cggcgccgcc   540
ggcgaggatt actgcgcgca atcgggcaag gtggcgctga tgtcatcggg cggcatgcac   600
cagctgcaca tattcatttt cgtgctcgcg gtgttccacg tcacctactg cgtcatcacc   660
atgggtttag gcgcctcaa aatgaagaaa tggaagaagt gggagtcaca gaccaactca   720
ttggagtatc agttcgcaat cgatccttca cgattcaggt tcacgcatca gacgtcgttc   780
gtgaagcggc atctgggatc attctcaagc acccctgggc tcagatggat cgtagcattc   840
ttcaggcagt tctttgggtc cgtcaccaag gtggactacc tgaccatgcg gcaaggcttc   900
atcaatgcgc atttgtcgca gaatagcaag ttcgacttcc acaaatacat caagaggtct   960
ttggaggacg acttcaaagt tgtcgttggc atcagcctcc ctctgtggtt cgtcggaatc  1020
cttgtactct tcctcgatat ccacggtctt ggcacactta tttggatctc ttttgttcct  1080
ctcatcatcg tcttgttagt tgggaccaag ctagagatgg tgatcatgca gatggcccaa  1140
gagatacagg acagggccac tgtgatccag ggagcacctg tggttgaacc aagcaacaag  1200
tacttctggt tcaaccgccc tgactgggtc ttgttcttca tacacctgac actcttccat  1260
aacgcatttc agatggcgca tttcgtatgg actatggcaa cacctggtct gaagaaatgc  1320
ttccatgaaa atatttggct gagcatcgtg gaagtcattg tggggatctc tcttcaggtg  1380
ctatgcagct acatcacctt cccgctctac gcgctcgtca cacagatggg atcgaacatg  1440
aagaagacaa tcttcgagga gcaaacgatg aaggcgctga tgaactggag gaagaaggcg  1500
atggagaaga agaaggtccg ggacgcggac gcgttcctgg cgcagatgag cgtcgacttc  1560
gcgacgccgg cgtcgagccg gtccgcgtcg ccggtgcacc tgctgcagga tcacagggcg  1620
aggttggacg acccgccgag cccaatcacg gtggcctcac caccggcacc ggaggaggac  1680
atatacccgg tgccggcggc ggctgcgttt tgccagctgc tagacgaccc gccggacagg  1740
aggtggatgg catccttgtc ggccgacatt cccgattttg attttttcct cagcgcacaa  1800
cggtgacggg ggcgatcggt ttctgtattg atgctgtacc aaacatagga gtttaatata  1860
tatataattg ttacggtaaa aaaaaaaaaa aaaa                              1894
```

<210> SEQ ID NO 80
<211> LENGTH: 200

<212> TYPE: DNA
<213> ORGANISM: Hordeum vulgare
<220> FEATURE:
<223> OTHER INFORMATION: Sequence listing for 58633.

<400> SEQUENCE: 80

| atgtcggaca aaaaggggt gccggcgcgg gagctgccgg agacgccgtc gtgggcggtg | 60 |
| gcggtggtct tcgccgccat ggtgctcgtg tccgtcctca tggagcacgg cctccacaag | 120 |
| ctcggccatt ggttccagca ccggcacaag aaggccctgt gggaggcgct ggagaagatg | 180 |
| aaggcggagc tcatgctggt | 200 |

<210> SEQ ID NO 81
<211> LENGTH: 200
<212> TYPE: DNA
<213> ORGANISM: Hordeum vulgare
<220> FEATURE:
<223> OTHER INFORMATION: Sequence listing for 58633.

<400> SEQUENCE: 81

| accagcatga gctccgcctt catcttctcc agcgcctccc acagggcctt cttgtgccgg | 60 |
| tgctggaacc aatggccgag cttgtggagg ccgtgctcca tgaggacgga cacgagcacc | 120 |
| atggcggcga agaccaccgc caccgcccac gacggcgtct ccggcagctc ccgcgccggc | 180 |
| accccttttt tgtccgacat | 200 |

<210> SEQ ID NO 82
<211> LENGTH: 200
<212> TYPE: DNA
<213> ORGANISM: Hordeum vulgare
<220> FEATURE:
<223> OTHER INFORMATION: Sequence listing for 58633.

<400> SEQUENCE: 82

| acaagggcat ggggcggtcg gacgaccccc agagcgcgcc cacctcgcca aggacccagc | 60 |
| aggaggctag ggacatgtac ccggttgtgg tggcgcaccc ggtgcacaga ctaaatccta | 120 |
| acgacaggag gaggtccgcc tcgtcgtcgg ccctcgaagc cgacatcccc agtgcagatt | 180 |
| tttccttcag ccagggatga | 200 |

<210> SEQ ID NO 83
<211> LENGTH: 200
<212> TYPE: DNA
<213> ORGANISM: Hordeum vulgare
<220> FEATURE:
<223> OTHER INFORMATION: Sequence listing for 58633.

<400> SEQUENCE: 83

| tcatccctgg ctgaaggaaa aatctgcact ggggatgtcg gcttcgaggg ccgacgacga | 60 |
| ggcggacctc ctcctgtcgt taggatttag tctgtgcacc gggtgcgcca ccacaaccgg | 120 |
| gtacatgtcc ctagcctcct gctgggtcct tggcgaggtg ggcgcgctct gggggtcgtc | 180 |
| cgaccgcccc atgcccttgt | 200 |

<210> SEQ ID NO 84
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 84

```
atggccggag gtggcgccgg aaggtccttg gaagagacgc cgacatgggc cgtcgccgcc      60
gtgtgctttg ttttggttct gatttctatt atcatcgaac acattctcca tctcatcgga     120
aagtggctaa agaagaaaca caaacgagct ctctacgaag ctctggagaa gattaaatca     180
gaactgatgc tgttgggatt                                                  200
```

<210> SEQ ID NO 85
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 85

```
aatcccaaca gcatcagttc tgatttaatc ttctccagag cttcgtagag agctcgtttg      60
tgtttcttct ttagccactt tccgatgaga tggagaatgt gttcgatgat aatagaaatc     120
agaaccaaaa caaagcacac ggcggcgacg gcccatgtcg gcgtctcttc caaggacctt     180
ccggcgccac ctccggccat                                                  200
```

<210> SEQ ID NO 86
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 86

```
ttcatcgtcg tccccatccc ggcgacggct ccatttccaa ccatcaccgt gatgtggagg      60
ccggggatct tgatgtcgat gttgaatcgc ctcaacccga ccgaacgacc cagtcaataa     120
acccaacaaa tattgagcac catgaaattg acgtggggtc taacgaattc tcattcgata     180
gaagagttga tagagtataa                                                  200
```

<210> SEQ ID NO 87
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 87

```
ttatactcta tcaactcttc tatcgaatga gaattcgtta gaccccacgt caatttcatg      60
gtgctcaata tttgttgggt ttattgactg ggtcgttcgg tcgggttgag gcgattcaac     120
atcgacatca agatccccgg cctccacatc acggtgatgg ttggaaatgg agccgtcgcc     180
gggatgggga cgacgatgaa                                                  200
```

<210> SEQ ID NO 88
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 88

```
atggcgagtt tggaacgaac ccccacatgg gcagtggcca ctgtctgctt tttgttgatt      60
ctcatttcca tttccacaga atatttgctt cattttcttg tcaaacggtt tttcagcatc     120
aaaagaagga aatccctcag gcaagctctc gacaatatca aatccgaatt gatgcttttg     180
ggatttgtat cgctgttatt                                                  200
```

<210> SEQ ID NO 89
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 89

```
aataacagcg atacaaatcc caaaagcatc aattcggatt tgatattgtc gagagcttgc    60
ctgagggatt tccttctttt gatgctgaaa accgtttga caagaaaatg aagcaaatat   120
tctgtggaaa tggaaatgag aatcaacaaa agcagacag tggccactgc ccatgtgggg   180
gttcgttcca aactcgccat                                              200
```

<210> SEQ ID NO 90
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 90

```
tacaactggc gggtgccaat aataataaac aatacaacaa caacaacaac agttgttcgg    60
ctgcggtttc agttaatggc gatgaggata aactaaaagg caaaaaacca atcgaagagg   120
cggatcagaa gtccatctca ttggatgcct tgattgggc taacaaaata caccgtaatt   180
tttcaagaca tgcaatgtag                                              200
```

<210> SEQ ID NO 91
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 91

```
ctacattgca tgtcttgaaa aattacggtg tattttgtta gcccaatcaa aggcatccaa    60
tgagatggac ttctgatccg cctcttcgat tggttttttg cctttttagtt tatcctcatc   120 gccattaact gaaaccgcag ccgaacaact gttgttgttg ttgttgtatt gtttattatt   180
attggcaccc gccagttgta                                              200
```

<210> SEQ ID NO 92
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 92

```
atggcgagtt tggaacgaac ccccacatgg gcagtggcca ctgtctgctt tttgttgatt    60
ctcatttcca tttccacaga atatttgctt cattttcttg tcaaacggtt tttcagcatc   120
aaaagaagga aatccctcag gcaagctctc gacaatatca aatccgaatt gatgcttttg   180
ggatttgtat cgctgttatt                                              200
```

<210> SEQ ID NO 93
<211> LENGTH: 200
<212> TYPE: DNA
<213> ORGANISM: Cucumis sativus
<220> FEATURE:

<223> OTHER INFORMATION: Sequence listing for 58633.

<400> SEQUENCE: 93

```
aataacagcg atacaaatcc caaaagcatc aattcggatt tgatattgtc gagagcttgc    60
ctgagggatt tccttctttt gatgctgaaa aaccgtttga caagaaaatg aagcaaatat   120
tctgtggaaa tggaaatgag aatcaacaaa aagcagacag tggccactgc ccatgtgggg   180
gttcgttcca aactcgccat                                               200
```

<210> SEQ ID NO 94
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 94

```
tacaactggc gggtgccaat aataataaac aatacaacaa caacaacaac agttgttcgg    60
ctgcggtttc agttaatggc gatgaggata aactaaaagg caaaaaacca atcgaagagg   120
cggatcagaa gtccatctca ttggatgcct ttgattgggc taacaaaata caccgtaatt   180
tttcaagaca tgcaatgtag                                               200
```

<210> SEQ ID NO 95
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 95

```
ctacattgca tgtcttgaaa aattacggtg tattttgtta gcccaatcaa aggcatccaa    60
tgagatggac ttctgatccg cctcttcgat tggttttttg ccttttagtt tatcctcatc   120
gccattaact gaaaccgcag ccgaacaact gttgttgttg ttgttgtatt gtttattatt   180
attggcaccc gccagttgta                                               200
```

<210> SEQ ID NO 96
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 96

```
atggcggggg cagccggtgg caagtcgctg gagcaaacac cgacatgggc cgttgccgtt    60
gtttgctttg ttttgctcgt catctctatt ttcatcgaat atagtctcca tcttatcgga   120
cattggctaa agaagagaca caaacggccg ttgtttgaag cattagagaa gatcaaatca   180
gagcttatgt tattggggtt                                               200
```

<210> SEQ ID NO 97
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 97

```
aaccccaata acataagctc tgatttgatc ttctctaatg cttcaaacaa cgcccgtttg    60
tgtctcttct ttagccaatg tccgataaga tggagactat attcgatgaa aatagagatg   120
```

```
acgagcaaaa caaagcaaac aacggcaacg gcccatgtcg gtgtttgctc cagcgacttg    180
ccaccggctg cccccgccat                                                 200

<210> SEQ ID NO 98
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 98
agggcgtgcc ggtggtggag cctggcgatg acctcttttg gtttaatcga cctcgcctta    60
ttctttatct catcaacttt gttctctttc aaaatgcctt ccaagttgcc ttctttgctt    120
ggacttggta tgagtttggg ttgaattctt gcttccatga gcatatagaa gatgtggtga    180
tcagaatttc tatggggtaa                                                 200

<210> SEQ ID NO 99
<211> LENGTH: 200
<212> TYPE: DNA
<213> ORGANISM: Cucumis sativus
<220> FEATURE:
<223> OTHER INFORMATION: Sequence listing for 58633.

<400> SEQUENCE: 99
ttaccccata gaaattctga tcaccacatc ttctatatgc tcatggaagc aagaattcaa    60
cccaaactca taccaagtcc aagcaaagaa ggcaacttgg aaggcatttt gaaagagaac    120
aaagttgatg agataaagaa taaggcgagg tcgattaaac caaagaggt catcgccagg     180 ctccaccacc ggcacgccct                                                 200

<210> SEQ ID NO 100
<211> LENGTH: 200
<212> TYPE: DNA
<213> ORGANISM: Lactuca sativa
<220> FEATURE:
<223> OTHER INFORMATION: Sequence listing for 58633.

<400> SEQUENCE: 100
atggccggag gaactgacgg cagatctttta gagcaaacgc cgacatgggc ggttgccacc    60
gtttgctttg tgctcattct catctccatt tttatcgaac aaatcatcca tatgatcgga    120
cattggttca agaagaaacg aaagaaagct ctatatgaat ccttggaaaa gattaaagca    180
gagcttatgt tgttgggatt                                                 200

<210> SEQ ID NO 101
<211> LENGTH: 200
<212> TYPE: DNA
<213> ORGANISM: Lactuca sativa
<220> FEATURE:
<223> OTHER INFORMATION: Sequence listing for 58633.

<400> SEQUENCE: 101
aatcccaaca acataagctc tgctttaatc ttttccaagg attcatatag agctttcttt    60
cgtttcttct tgaaccaatg tccgatcata tggatgattt gttcgataaa aatggagatg    120
agaatgagca caaagcaaac ggtggcaacc gcccatgtcg gcgtttgctc taaagatctg    180
ccgtcagttc ctccggccat                                                 200

<210> SEQ ID NO 102
```

```
<211> LENGTH: 200
<212> TYPE: DNA
<213> ORGANISM: Lactuca sativa
<220> FEATURE:
<223> OTHER INFORMATION: Sequence listing for 58633.

<400> SEQUENCE: 102
cctcctatca ccaacgaagg gttaatgaaa tgtcgatagt gccacatgag gtggaattgg      60
ggaatagaga gcaaggtaat gagatccatg atgcaagttc gtcacaattg caatagttg     120 ttgacacggg tgctagtgaa caacatgagg tgacgatagg agttcctaaa gaattttcgt    180
ttgataaaag aaatatatga                                                200

<210> SEQ ID NO 103
<211> LENGTH: 200
<212> TYPE: DNA
<213> ORGANISM: Lactuca sativa
<220> FEATURE:
<223> OTHER INFORMATION: Sequence listing for 58633.

<400> SEQUENCE: 103
tcatatattt cttttatcaa acgaaaattc tttaggaact cctatcgtca cctcatgttg      60
ttcactagca cccgtgtcaa caactattgc caattgtgac gaacttgcat catggatctc    120
attaccttgc tctctattcc ccaattccac ctcatgtggc actatcgaca tttcattaac    180
ccttcgttgg tgataggagg                                                200

<210> SEQ ID NO 104
<211> LENGTH: 200
<212> TYPE: DNA
<213> ORGANISM: Pisum sativum
<220> FEATURE:
<223> OTHER INFORMATION: Sequence listing for 58633.

<400> SEQUENCE: 104
atggctgaag agggagttaa ggaacgaact ttggaagaaa caccaacttg ggctgttgca      60
gttgtgtgtc ttgtgttgct agctgtttca atcttaattg aacatattat tcatgttatt    120
ggaaagtggt tgaagaagag aaacaaaaat gctctttatg aagctttgga aaagatcaaa    180
ggagagctta tgctactagg                                                200

<210> SEQ ID NO 105
<211> LENGTH: 200
<212> TYPE: DNA
<213> ORGANISM: Pisum sativum
<220> FEATURE:
<223> OTHER INFORMATION: Sequence listing for 58633.

<400> SEQUENCE: 105
cctagtagca taagctctcc tttgatcttt tccaaagctt cataaagagc atttttgttt      60
ctcttcttca accactttcc aataacatga ataatatgtt caattaagat tgaaacagct    120
agcaacacaa gacacacaac tgcaacagcc caagttggtg tttcttccaa agttcgttcc    180
ttaactccct cttcagccat                                                200

<210> SEQ ID NO 106
<211> LENGTH: 200
<212> TYPE: DNA
<213> ORGANISM: Pisum sativum
<220> FEATURE:
<223> OTHER INFORMATION: Sequence listing for 58633.

<400> SEQUENCE: 106
```

```
ctgattataa aaatgaacag tgggatattg aaggagaagg accaacttcc ctaagaaacg      60
atcaaacagg gcaacatgag attcaaatag cgggtgtcga gtcattttcg tcaaccgaat     120
tgccggttag aattagacat gaaagcacct ctggttcaaa agattttct ttcgagaagc      180 gccacttagg gagcaattag                                                  200
```

```
<210> SEQ ID NO 107
<211> LENGTH: 200
<212> TYPE: DNA
<213> ORGANISM: Pisum sativum
<220> FEATURE:
<223> OTHER INFORMATION: Sequence listing for 58633.

<400> SEQUENCE: 107
ctaattgctc cctaagtggc gcttctcgaa agaaaaatct tttgaaccag aggtgctttc      60
atgtctaatt ctaaccggca attcggttga cgaaaatgac tcgacacccg ctatttgaat    120
ctcatgttgc cctgtttgat cgtttcttag ggaagttggt ccttctcctt caatatccca    180
ctgttcattt ttataatcag                                                  200
```

```
<210> SEQ ID NO 108
<211> LENGTH: 200
<212> TYPE: DNA
<213> ORGANISM: Medicago truncatula
<220> FEATURE:
<223> OTHER INFORMATION: Sequence listing for 58633.

<400> SEQUENCE: 108
atggcaggag gaagcgttgg aagaagctta actgaaacac ctacttgggc cgttgcagtt      60
gtttgctttg ttatactttc tatttctatc ttcattgaac acattttcca catcatagaa    120
aagtggttga agaagaagca taaagtgcc ttgtatgagt cacttgaaaa gatcaaatca     180
gagctaatgt tactagggtt                                                  200
```

```
<210> SEQ ID NO 109
<211> LENGTH: 200
<212> TYPE: DNA
<213> ORGANISM: Medicago truncatula
<220> FEATURE:
<223> OTHER INFORMATION: Sequence listing for 58633.

<400> SEQUENCE: 109
aaccctagta acattagctc tgatttgatc ttttcaagtg actcatacaa ggcacttta       60 tgcttcttct tcaaccactt ttctatgatg tggaaaatgt gttcaatgaa gatagaaata    120
gaaagtataa caaagcaaac aactgcaacg cccaagtag gtgtttcagt taagcttctt    180
ccaacgcttc ctcctgccat                                                  200
```

```
<210> SEQ ID NO 110
<211> LENGTH: 200
<212> TYPE: DNA
<213> ORGANISM: Medicago truncatula
<220> FEATURE:
<223> OTHER INFORMATION: Sequence listing for 58633.

<400> SEQUENCE: 110
aggttgagat caatgttgct tcttccagct caactcatct tcatgaaatg gaaatgggtc      60
acctagccca tgttgaacaa caagaagtca ttaagcccaa tagtatttct gtgggctcag    120
gccggcctca atttgaaatt gatatccaac agagtgatga actctcattt tcaacaatgc    180
```

```
ccacaaatca attagaatga                                                  200
```

<210> SEQ ID NO 111
<211> LENGTH: 200
<212> TYPE: DNA
<213> ORGANISM: Medicago truncatula
<220> FEATURE:
<223> OTHER INFORMATION: Sequence listing for 58633.

<400> SEQUENCE: 111

```
tcattctaat tgatttgtgg gcattgttga aaatgagagt tcatcactct gttggatatc       60
aatttcaaat tgaggccggc ctgagcccac agaaatacta tgggcttaa tgacttcttg      120
ttgttcaaca tgggctaggt gacccatttc catttcatga agatgagttg agctggaaga     180
agcaacattg atctcaacct                                                  200
```

<210> SEQ ID NO 112
<211> LENGTH: 200
<212> TYPE: DNA
<213> ORGANISM: Glycine max
<220> FEATURE:
<223> OTHER INFORMATION: Sequence listing for 58633.

<400> SEQUENCE: 112

```
atgagcaaag ttcttcaggc gaagttggag gcaactccaa catgggctgt tgcagttgtg       60
tgctttgtga tgcttgctat ttcaatcctc attgaacata ttcttgaaga acttggaaag     120
tggttaaaaa agaaacacaa aaaggctctt catgaagcgc tggaaaaggt taaggagag      180
cttatgctgc tgggattcat                                                  200
```

<210> SEQ ID NO 113
<211> LENGTH: 200
<212> TYPE: DNA
<213> ORGANISM: Glycine max
<220> FEATURE:
<223> OTHER INFORMATION: Sequence listing for 58633.

<400> SEQUENCE: 113

```
atgaatccca gcagcataag ctctcctta acctttcca gcgcttcatg aagagccttt        60
ttgtgtttct tttttaacca ctttccaagt tcttcaagaa tatgttcaat gaggattgaa     120
atagcaagca tcacaaagca cacaactgca acagcccatg ttggagttgc ctccaacttc     180
gcctgaagaa ctttgctcat                                                  200
```

<210> SEQ ID NO 114
<211> LENGTH: 200
<212> TYPE: DNA
<213> ORGANISM: Glycine max
<220> FEATURE:
<223> OTHER INFORMATION: Sequence listing for 58633.

<400> SEQUENCE: 114

```
accacgcaag agatcatgat cctgatcatg aaaagaccat gcagatgcag atgcagatgc       60
agcagcagcg gccagctcca acagcagaat tgcctcctag tggactcaat cctattcgaa    120
ctcaacatga aatcaacatt gctttatctg aattttcatt tgggaggga caccacactg     180
gtagtaatac taataactaa                                                  200
```

<210> SEQ ID NO 115
<211> LENGTH: 200
<212> TYPE: DNA
<213> ORGANISM: Glycine max
<220> FEATURE:
<223> OTHER INFORMATION: Sequence listing for 58633.

<400> SEQUENCE: 115

```
ttagttatta gtattactac cagtgtggtg tccctccca aatgaaaatt cagataaagc      60
aatgttgatt tcatgttgag ttcgaatagg attgagtcca ctaggaggca attctgctgt    120
tggagctggc cgctgctgct gcatctgcat ctgcatctgc atggtctttt catgatcagg    180
atcatgatct cttgcgtggt                                                 200
```

<210> SEQ ID NO 116
<211> LENGTH: 200
<212> TYPE: DNA
<213> ORGANISM: Glycine max
<220> FEATURE:
<223> OTHER INFORMATION: Sequence listing for 58633.

<400> SEQUENCE: 116

```
atgagcaaag ttcttcaggc gaagttggag gcaactccaa catgggctgt tgcagttgtg      60
tgctttgtga tgcttgctat ttcaatcctc attgaacata ttcttgaaga acttggaaag    120
tggttaaaaa agaaacacaa aaaggctctt catgaagcgc tggaaaaggt taaaggagag    180
cttatgctgc tgggattcat                                                 200
```

<210> SEQ ID NO 117
<211> LENGTH: 200
<212> TYPE: DNA
<213> ORGANISM: Glycine max
<220> FEATURE:
<223> OTHER INFORMATION: Sequence listing for 58633.

<400> SEQUENCE: 117

```
atgaatccca gcagcataag ctctcctttta acctttttcca gcgcttcatg aagagccttt      60
ttgtgtttct tttttaacca ctttccaagt tcttcaagaa tatgttcaat gaggattgaa    120
atagcaagca tcacaaagca cacaactgca acagcccatg ttggagttgc ctccaacttc    180
gcctgaagaa ctttgctcat                                                 200
```

<210> SEQ ID NO 118
<211> LENGTH: 200
<212> TYPE: DNA
<213> ORGANISM: Glycine max
<220> FEATURE:
<223> OTHER INFORMATION: Sequence listing for 58633.

<400> SEQUENCE: 118

```
accacgcaag agatcatgat cctgatcatg aaaagaccat gcagatgcag atgcagatgc      60
agcagcagcg gccagctcca acagcagaat gcctcctag tggactcaat cctattcgaa    120
ctcaacatga aatcaacatt gctttatctg aattttcatt tgggagggga caccacactg    180
gtagtaatac taataactaa                                                 200
```

<210> SEQ ID NO 119
<211> LENGTH: 200
<212> TYPE: DNA
<213> ORGANISM: Glycine max
<220> FEATURE:
<223> OTHER INFORMATION: Sequence listing for 58633.

<400> SEQUENCE: 119

```
ttagttatta gtattactac cagtgtggtg tccctccca aatgaaaatt cagataaagc      60
```

-continued

```
aatgttgatt tcatgttgag ttcgaatagg attgagtcca ctaggaggca attctgctgt    120
tggagctggc cgctgctgct gcatctgcat ctgcatctgc atggtctttt catgatcagg    180
atcatgatct cttgcgtggt                                                200
```

<210> SEQ ID NO 120
<211> LENGTH: 200
<212> TYPE: DNA
<213> ORGANISM: Capsicum annuum
<220> FEATURE:
<223> OTHER INFORMATION: Sequence listing for 58633.

<400> SEQUENCE: 120

```
atggcgggag gaggggagg aagatcgttg gagcaaacgc cgacgtgggc ggttgccgta     60
gtttgttttg cgttggttgc tatttctgtc gtaatagagt tcatcatcca tcttattggc    120
aagtggttga agtccaaaca aaaagagca ttatatgaag cacttgagaa gataaaatca     180
gaattaatgt tgttgggatt                                                200
```

<210> SEQ ID NO 121
<211> LENGTH: 200
<212> TYPE: DNA
<213> ORGANISM: Capsicum annuum
<220> FEATURE:
<223> OTHER INFORMATION: Sequence listing for 58633.

<400> SEQUENCE: 121

```
aatcccaaca acattaattc tgattttatc ttctcaagtg cttcatataa tgctcttttt    60
tgtttggact tcaaccactt gccaataaga tggatgatga actctattac gacagaaata   120
gcaaccaacg caaaacaaac tacggcaacc gcccacgtcg gcgtttgctc caacgatctt   180
cctccccctc ctcccgccat                                               200
```

<210> SEQ ID NO 122
<211> LENGTH: 200
<212> TYPE: DNA
<213> ORGANISM: Capsicum annuum
<220> FEATURE:
<223> OTHER INFORMATION: Sequence listing for 58633.

<400> SEQUENCE: 122

```
gattctacca aggtggtggt ggagatggct cgtcttcgcc gtcccatatg catcaaatta    60
ttcaaagtgg tcatgactta cgtcatgacg actcagaagg tcacgagcct agtctgccac   120
aaacggctcg tgaccaacac gaagtcaaca ttgcccgtcc aagggaattc tcttttgata   180
aaagaacaac tagtgtataa                                               200
```

<210> SEQ ID NO 123
<211> LENGTH: 200
<212> TYPE: DNA
<213> ORGANISM: Capsicum annuum
<220> FEATURE:
<223> OTHER INFORMATION: Sequence listing for 58633.

<400> SEQUENCE: 123

```
ttatacacta gttgttcttt tatcaaaaga gaattcccctt ggacgggcaa tgttgacttc    60
gtgttggtca cgagccgttt gtggcagact aggctcgtga ccttctgagt cgtcatgacg   120
taagtcatga ccactttgaa taatttgatg catatgggac ggcgaagacg agccatctcc   180
accaccacct tggtagaatc                                               200
```

<210> SEQ ID NO 124
<211> LENGTH: 200
<212> TYPE: DNA
<213> ORGANISM: Solanum lycopersicum
<220> FEATURE:
<223> OTHER INFORMATION: Sequence listing for 58633.

<400> SEQUENCE: 124

```
atggctaaag aacggtctat ggaggcaacc cctacgtggg caattgctgt ggtttgcttc    60
atcttgctcg ctatttctat ttttattgaa caaattattc atcacattgg agagtggtta   120
ctggaaaagc ggaaaaagtc tctatatgaa gcacttgaaa agatcaaagc tgaacttatg   180
ctgttgggat tcttatcact                                                200
```

<210> SEQ ID NO 125
<211> LENGTH: 200
<212> TYPE: DNA
<213> ORGANISM: Solanum lycopersicum
<220> FEATURE:
<223> OTHER INFORMATION: Sequence listing for 58633.

<400> SEQUENCE: 125

```
agtgataaga atcccaacag cataagttca gctttgatct tttcaagtgc ttcatataga    60
gacttttttcc gctttttccag taaccactct ccaatgtgat gaataatttg ttcaataaaa   120
atagaaatag cgagcaagat gaagcaaacc acagcaattg cccacgtagg ggttgcctcc   180
atagaccgtt ctttagccat                                                200
```

<210> SEQ ID NO 126
<211> LENGTH: 200
<212> TYPE: DNA
<213> ORGANISM: Solanum lycopersicum
<220> FEATURE:
<223> OTHER INFORMATION: Sequence listing for 58633.

<400> SEQUENCE: 126

```
ggctatcagg acataccacc cctgcaaaca gcagaccaac cacaccattg cgtggtacct    60
cccctgttca cttattacgc ggttatccac aatataatga ggacagtgtt caagcatctc   120
ctcggacatc caatgtcgaa aatgaagggt gggctaatga aaatcaggag ggagagatcc   180
tgcagcatgc ctccactgat                                                200
```

<210> SEQ ID NO 127
<211> LENGTH: 200
<212> TYPE: DNA
<213> ORGANISM: Solanum lycopersicum
<220> FEATURE:
<223> OTHER INFORMATION: Sequence listing for 58633.

<400> SEQUENCE: 127

```
atcagtggag gcatgctgca ggatctctcc ctcctgattt tcattagccc acccttcatt    60
ttcgacattg gatgtccgag gagatgcttg aacactgtcc tcattatatt gtggataacc   120
gcgtaataag tgaacagggg aggtaccacg caatggtgtg gttggtctgc tgtttgcagg   180
ggtggtatgt cctgatagcc                                                200
```

<210> SEQ ID NO 128
<211> LENGTH: 200
<212> TYPE: DNA
<213> ORGANISM: Solanum lycopersicum
<220> FEATURE:
<223> OTHER INFORMATION: Sequence listing for 58633.

```
<400> SEQUENCE: 128
atggctagca caggctgtat tagaacgtgt gatgaacgtc ctctagatga gacaccaaca    60
tgggctgtag ccatggtttg ctttgtatta gttgtaatct ccctttttcat tgaacaactt   120 attcatcatc ttggagagtg gttatggaag aaacaaaaga gaccattgta tgaagcactt   180
gagaagatca agtcagaact                                                200

<210> SEQ ID NO 129
<211> LENGTH: 200
<212> TYPE: DNA
<213> ORGANISM: Solanum lycopersicum
<220> FEATURE:
<223> OTHER INFORMATION: Sequence listing for 58633.

<400> SEQUENCE: 129
agttctgact tgatcttctc aagtgcttca tacaatggtc tcttttgttt cttccataac    60
cactctccaa gatgatgaat aagttgttca atgaaaaggg agattacaac taatacaaag   120
caaaccatgg ctacagccca tgttggtgtc tcatctagag acgttcatc acacgttcta    180 atacagcctg tgctagccat                                                200

<210> SEQ ID NO 130
<211> LENGTH: 200
<212> TYPE: DNA
<213> ORGANISM: Solanum lycopersicum
<220> FEATURE:
<223> OTHER INFORMATION: Sequence listing for 58633.

<400> SEQUENCE: 130
tgtcaccatt gcgtggaggt tcctctccgg ttcaacaaaa acacgggcaa ttatatcctc    60
catcacctaa tccttcgcgt aggaggagtg gaggtaatcc agaatcgagt tctaggcaaa   120
tctttgatga tggaagtcat gagcaatctg aaattgaaat taccttgaat gatttatcac   180
ttgaaaacaa attaagttga                                                200

<210> SEQ ID NO 131
<211> LENGTH: 200
<212> TYPE: DNA
<213> ORGANISM: Solanum lycopersicum
<220> FEATURE:
<223> OTHER INFORMATION: Sequence listing for 58633.

<400> SEQUENCE: 131
tcaacttaat ttgttttcaa gtgataaatc attcaaggta atttcaattt cagattgctc    60
atgacttcca tcatcaaaga tttgcctaga actcgattct ggattaccctc cactcctcct   120 acgcgaagga ttaggtgatg gaggatataa ttgcccgtgt ttttgttgaa ccggagagga   180
acctccacgc aatggtgaca                                                200

<210> SEQ ID NO 132
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 132
atggcaaagg acgacgggta ccccccggcg cggacgctgc cggagacgcc gtcctgggcg    60
gtggcgctgg tcttcgccgt catgatcatc gtctccgtcc tctgagca cgcgctccac    120 aagctcggcc attggttcca caagcggcac aagaacgcgc tggcggaggc gctggagaag   180
```

```
atgaaggcgg agctgatgct                                                  200

<210> SEQ ID NO 133
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 133
agcatcagct ccgccttcat cttctccagc gcctccgcca gcgcgttctt gtgccgcttg       60
tggaaccaat ggccgagctt gtggagcgcg tgctccagga ggacggagac gatgatcatg      120
acggcgaaga ccagcgccac cgcccaggac ggcgtctccg gcagcgtccg cgccgggggg      180
tacccgtcgt cctttgccat                                                  200

<210> SEQ ID NO 134
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 134
agaagggcat gggacggtct gacgatcccc agagcgcacc gacctcgcca aggaccatgg       60
aggaggctag ggacatgtac ccggttgtgg tggcgcatcc tgtacacaga ctaaatcctg      120
ctgacaggcg gaggtcggtc tcttcatcag ccctcgatgc cgacatcccc agcgcagatt      180
tttccttcag ccagggatga                                                  200

<210> SEQ ID NO 135
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 135
tcatccctgg ctgaaggaaa aatctgcgct ggggatgtcg gcatcgaggg ctgatgaaga       60
gaccgacctc cgcctgtcag caggatttag tctgtgtaca ggatgcgcca ccacaaccgg      120
gtacatgtcc ctagcctcct ccatggtcct tggcgaggtc ggtgcgctct ggggatcgtc      180
agaccgtccc atgcccttct                                                  200

<210> SEQ ID NO 136
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 136
atggcggacg acgacgagta cccccccagcg aggacgctgc cggagacgcc gtcctgggcg      60
gtggccctcg tcttcgccgt catgatcatc gtgtccgtcc tcctggagca cgcgctccat      120
aagctcggcc attggttcca caagcggcac aagaacgcgc tggcggaggc gctggagaag      180
atcaaggcgg agctcatgct                                                  200

<210> SEQ ID NO 137
<211> LENGTH: 200
<212> TYPE: DNA
```

<213> ORGANISM: Triticum aestivum
<220> FEATURE:
<223> OTHER INFORMATION: Sequence listing for 58633.

<400> SEQUENCE: 137

```
agcatgagct ccgccttgat cttctccagc gcctccgcca gcgcgttctt gtgccgcttg    60
tggaaccaat ggccgagctt atggagcgcg tgctccagga ggacggacac gatgatcatg   120
acggcgaaga cgagggccac cgcccaggac ggcgtctccg gcagcgtcct cgctgggggg   180
tactcgtcgt cgtccgccat                                               200
```

<210> SEQ ID NO 138
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 138

```
acaagggcat gggacggtcc gacgatcccc agagcacgcc aacctcgcca agggccatgg    60
aggaggctag gacatgtac ccggttgtgg tggcgcatcc agtccacaga ctaaatcctg    120
ctgacaggag aaggtcggtc tcgtcgtcgg cactcgatgt cgacattccc agcgcagatt   180
tttccttcag ccaaggatga                                               200
```

<210> SEQ ID NO 139
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 139

```
tcatccttgg ctgaaggaaa aatctgcgct gggaatgtcg acatcgagtg ccgacgacga    60
gaccgacctt ctcctgtcag caggatttag tctgtggact ggatgcgcca ccacaaccgg   120
gtacatgtcc ctagcctcct ccatggccct tggcgaggtt ggcgtgctct ggggatcgtc   180
ggaccgtccc atgcccttgt                                               200
```

<210> SEQ ID NO 140
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 140

```
atggcggacg acgacgagta ccccccagcg aggacgctgc cggagacgcc gtcctgggcg    60
gtggccctcg tcttcgccgt catgatcatc gtgtccgtcc tcctggagca cgcgctccat   120
aagctcggcc attggttcca caagcggcac aagaacgcgc tggcggaggc gctggagaag   180
atcaaggcgg agctcatgct                                               200
```

<210> SEQ ID NO 141
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 141

```
agcatgagct ccgccttgat cttctccagc gcctccgcca gcgcgttctt gtgccgcttg    60
```

```
tggaaccaat ggccgagctt atggagcgcg tgctccagga ggacggacac gatgatcatg    120
acggcgaaga cgagggccac cgcccaggac ggcgtctccg gcagcgtcct cgctgggggg    180
tactcgtcgt cgtccgccat                                                200
```

<210> SEQ ID NO 142
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 142

```
acaagggcat gggacggtcc gacgatcccc agagcacgcc aacctcgcca agggccatgg    60
aggaggctag ggacatgtac ccggttgtgg tggcgcatcc agtgcacaga ctaaatcctg    120
ctgacaggag aaggtcggtc tcgtcgtcgg cactcgatgt cgacattccc agcgcagatt    180
tttccttcag ccagggatga                                                200
```

<210> SEQ ID NO 143
<211> LENGTH: 200
<212> TYPE: DNA
<213> ORGANISM: Triticum aestivum
<220> FEATURE:
<223> OTHER INFORMATION: Sequence listing for 58633.

<400> SEQUENCE: 143

```
tcatccctgg ctgaaggaaa aatctgcgct gggaatgtcg acatcgagtg ccgacgacga    60
gaccgacctt ctcctgtcag caggatttag tctgtgcact ggatgcgcca ccacaaccgg    120
gtacatgtcc ctagcctcct ccatggccct tggcgaggtt ggcgtgctct ggggatcgtc    180
ggaccgtccc atgcccttgt                                                200
```

<210> SEQ ID NO 144
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 144

```
atggctgatg aacttgaaga gcgtagtttg gaggaaacgc ctacttgggc tgttgcagtg    60
gtctgctttg tgttgcttgc tgtttcgatc ttcatcgaac atattttca tcttattgga     120 tcgaggttaa aaggcagaca caggcgagcc ctttatgaat ctctggaaaa gatcaaagcg    180
gagcttatgc tgttgggatt                                                200
```

<210> SEQ ID NO 145
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 145

```
aatcccaaca gcataagctc cgctttgatc ttttccagag attcataaag ggctcgcctg    60
tgtctgcctt ttaacctcga tccaataaga tgaaaaatat gttcgatgaa gatcgaaaca    120
gcaagcaaca caaagcagac cactgcaaca gcccaagtag gcgtttcctc caaactacgc    180
tcttcaagtt catcagccat                                                200
```

-continued

<210> SEQ ID NO 146
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 146

```
acgaatggta tggggaagga gcagggtctc cagggaagaa ggatgatgat gagcatgaaa        60
aggagaaatt tgaatccaga gagcagggac aagggattga agactcgagc tcaacccaac       120
tgccccttgg accccgccca atccgaaccc aacatgagat caacattact ttatcggatt       180
tctcatttgc aaagcgctga                                                    200
```

<210> SEQ ID NO 147
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 147

```
tcagcgcttt gcaaatgaga aatccgataa agtaatgttg atctcatgtt gggttcggat        60
tgggcggggt ccaaggggca gttgggttga gctcgagtct tcaatccctt gtccctgctc       120
tctggattca aatttctcct tttcatgctc atcatcatcc ttcttccctg agaccctgc        180 tccttcccca taccattcgt                                                    200
```

<210> SEQ ID NO 148
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 148

```
atggctgatg aacttgaaga tcgtagtttg acggaaacgc ctacttgggc tgttgcagtg        60
gtctgttttg tgttgcttgc tgtttcgatc ttcatcgaac atattattca tcatattgga       120
tcgtggttag caagaagaaa caagcgagcc ctttatgaag ctctggaaaa gatcaaagca       180
gagcttatgc tgttgggatt                                                    200
```

<210> SEQ ID NO 149
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 149

```
aatcccaaca gcataagctc tgctttgatc ttttccagag cttcataaag ggctcgcttg        60
tttcttcttg ctaaccacga tccaatatga tgaataatat gttcgatgaa gatcgaaaca       120
gcaagcaaca caaaacagac cactgcaaca gcccaagtag gcgtttccgt caaactacga       180
tcttcaagtt catcagccat                                                    200
```

<210> SEQ ID NO 150
<211> LENGTH: 200
<212> TYPE: DNA
<213> ORGANISM: Vitis vinifera
<220> FEATURE:
<223> OTHER INFORMATION: Sequence listing for 58633.

```
<400> SEQUENCE: 150
gatcagggtc tctagggaag aaggatgatg atgagcaaag gccagagaat tttgaatcga    60
gagagccggg acgagggact caagactcaa gctcagccca attggccctg ggacccctcc   120
ccattcaaac tcaacatgag gtcaacatca cttcatcaga gttctcattt cgtaggagcc   180
caaggagccc aaggccatga                                                200

<210> SEQ ID NO 151
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 151
tcatggcctt gggctccttg ggctcctacg aaatgagaac tctgatgaag tgatgttgac    60
ctcatgttga gttgaatgg ggaggggtcc cagggcaat tgggctgagc ttgagtcttg    120
agtccctcgt cccggctctc tcgattcaaa attctctggc ctttgctcat catcatcctt   180
cttccctaga gaccctgatc                                                200

<210> SEQ ID NO 152
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 152
atggctggcg acgaggagac gacgacgacg acgacggcag caacacttga aacaacgtcc    60
acttgggctg ttgcctctgt ttgcttcatt ttgattgcac tctccatact tattgagcat   120
gctctccatc tcttagccaa gtacttcaac aagaagcgga ggaggtctct cattcatgct   180
cttaacaacg tcaaatcgga                                                200

<210> SEQ ID NO 153
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 153
tccgatttga cgttgttaag agcatgaatg agagacctcc tccgcttctt gttgaagtac    60
ttggctaaga gatggagagc atgctcaata agtatggaga gtgcaatcaa aatgaagcaa   120
acagaggcaa cagcccaagt ggacgttgtt tcaagtgttg ctgccgtcgt cgtcgtcgtc   180
gtctcctcgt cgccagccat                                                200

<210> SEQ ID NO 154
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 154
ccctggatgc ttcactggac aattcacctt cttttaacac tctggatact tctttctctg    60
tagacctcga tcagccatca tcagatgctg gctatttgac tgttgaaata tcagatgaag   120
```

```
agacggtcgc aactaaacag ccagaaccgc gtcagaagtt gggatgtttt gagggtttcg    180
acttgcgcaa aacatcataa                                                200

<210> SEQ ID NO 155
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 155
ttatgatgtt ttgcgcaagt cgaaaccctc aaaacatccc aacttctgac gcggttctgg    60
ctgtttagtt gcgaccgtct cttcatctga tatttcaaca gtcaaatagc cagcatctga   120
tgatggctga tcgaggtcta cagagaaaga agtatccaga gtgttaaaag aaggtgaatt   180
gtccagtgaa gcatccaggg                                               200

<210> SEQ ID NO 156
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 156
atggctaagg gatcaaagga tcgatctttg gagcaaacac cgacttgggc ggttgcagtg    60
gtctgttttg tgctggtttt gatatcaatt atcatcgaat acatccttca cttaattgga   120
aagtggctaa caaagagaaa caaacgagct ctttatgaag cacttgaaaa gattaagtca   180
gaacttatgc tactggggtt                                               200

<210> SEQ ID NO 157
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 157
aaccccagta gcataagttc tgacttaatc ttttcaagtg cttcataaag agctcgtttg    60
tttctctttg ttagccactt tccaattaag tgaaggatgt attcgatgat aattgatatc   120
aaaaccagca caaacagac cactgcaacc gcccaagtcg gtgtttgctc caaagatcga   180
tcctttgatc ccttagccat                                               200

<210> SEQ ID NO 158
<211> LENGTH: 200
<212> TYPE: DNA
<213> ORGANISM: Vitis vinifera
<220> FEATURE:
<223> OTHER INFORMATION: Sequence listing for 58633.

<400> SEQUENCE: 158
cggagacaga cgagtatcgc caccgtgagg atatatcatg gtcagaacat catagaaatc    60
ctggtccaga agaagagggg agggacacaa atcataggat cttgacccgt accatgccag   120
ctcctcaagc tgacaatgct cagcacgaaa ttgacattca gcccatggac ttttcattcg   180
ataaaagagc aagaacttga                                               200

<210> SEQ ID NO 159
<211> LENGTH: 200
```

```
<212> TYPE: DNA
<213> ORGANISM: Vitis vinifera
<220> FEATURE:
<223> OTHER INFORMATION: Sequence listing for 58633.

<400> SEQUENCE: 159
tcaagttctt gctctttat cgaatgaaaa gtccatgggc tgaatgtcaa tttcgtgctg    60
agcattgtca gcttgaggag ctggcatggt acgggtcaag atcctatgat ttgtgtccct   120
cccctcttct tctggaccag gatttctatg atgttctgac catgatatat cctcacggtg   180
gcgatactcg tctgtctccg                                               200

<210> SEQ ID NO 160
<211> LENGTH: 200
<212> TYPE: DNA
<213> ORGANISM: Zea mays
<220> FEATURE:
<223> OTHER INFORMATION: Sequence listing for 58633.

<400> SEQUENCE: 160
atggcggggg gcgggggcgg ccgggacctg ccgtcgacgc cgacgtgggc ggtggccctg    60
gtgtgcgccg tcatcgtgct cgtctccgtc gccatggagc atggcctcca caagctcggc   120
cactggttcc atacgcggca aagaaggcc atgcgggagg ccctggagaa gatcaaagca   180
gagttgatgc tgatgggctt                                               200

<210> SEQ ID NO 161
<211> LENGTH: 200
<212> TYPE: DNA
<213> ORGANISM: Zea mays
<220> FEATURE:
<223> OTHER INFORMATION: Sequence listing for 58633.

<400> SEQUENCE: 161
aagcccatca gcatcaactc tgctttgatc ttctccaggg cctcccgcat ggccttcttc    60
tgccgcgtat ggaaccagtg gccgagcttg tggaggccat gctccatggc gacggagacg   120
agcacgatga cggcgcacac cagggccacc gcccacgtcg cgtcgacgg caggtcccgg   180 ccgcccccgc cccccgccat                                               200

<210> SEQ ID NO 162
<211> LENGTH: 200
<212> TYPE: DNA
<213> ORGANISM: Zea mays
<220> FEATURE:
<223> OTHER INFORMATION: Sequence listing for 58633.

<400> SEQUENCE: 162
acctgctcca caagtacagg ggcaggtcgg aggaaccgca gagcgggccg gcgtcgccgg    60
ggcgggagct cggggacatg tacccggtgg ctgaccagca tcgcctgcac aggctggacc   120
ccgagaggat gaggcccgcc tcgtccaccg ccgtcaacat tgacatcgct gatgccgatt   180
tttcttttag catgcggtga                                               200

<210> SEQ ID NO 163
<211> LENGTH: 200
<212> TYPE: DNA
<213> ORGANISM: Zea mays
<220> FEATURE:
<223> OTHER INFORMATION: Sequence listing for 58633.

<400> SEQUENCE: 163
```

```
tcaccgcatg ctaaaagaaa aatcggcatc agcgatgtca atgttgacgg cggtggacga    60
ggcgggcctc atcctctcgg ggtccagcct gtgcaggcga tgctggtcag ccaccgggta   120
catgtccccg agctcccgcc ccggcgacgc cggcccgctc tgcggttcct ccgacctgcc   180
cctgtacttg tggagcaggt                                               200
```

```
<210> SEQ ID NO 164
<211> LENGTH: 200
<212> TYPE: DNA
<213> ORGANISM: Sorghum bicolor
<220> FEATURE:
<223> OTHER INFORMATION: Sequence listing for 58633.

<400> SEQUENCE: 164
atggcggggg gcggggggcgg ccgggacctg ccgtcgacgc cgacgtgggc ggtagcggtc    60
gtgtgcgccg tcatcgtgct cgtctccgtc gccatggagc acggcctcca caagctcggc   120
cactggttcc atacgaggca gaagaaggcc atgcgggagg cgctggagaa gatcaaagca   180
gagttgatgc tgatgggctt                                               200
```

```
<210> SEQ ID NO 165
<211> LENGTH: 200
<212> TYPE: DNA
<213> ORGANISM: Sorghum bicolor
<220> FEATURE:
<223> OTHER INFORMATION: Sequence listing for 58633.

<400> SEQUENCE: 165
aagcccatca gcatcaactc tgctttgatc ttctccagcg cctcccgcat ggccttcttc    60
tgcctcgtat ggaaccagtg gccgagcttg tggaggccgt gctccatggc gacggagacg   120
agcacgatga cggcgcacac gaccgctacc gcccacgtcg gcgtcgacgg caggtcccgg   180
ccgcccccgc ccccgccat                                                200
```

```
<210> SEQ ID NO 166
<211> LENGTH: 200
<212> TYPE: DNA
<213> ORGANISM: Sorghum bicolor
<220> FEATURE:
<223> OTHER INFORMATION: Sequence listing for 58633.

<400> SEQUENCE: 166
agtacaaggg ccggtcggag gagccgcaga gcgccccgac gtctccggga aggggtcggg    60
ggcaggagct cggggacatg tacccggtgg ccgaccacca gcggctgcac aggcttgacc   120
cagagaggaa gagggcggcc tcgtccaccg ccatcgacat tgacatcgct gatgccgatt   180
tttcgtttag cacgcggtga                                               200
```

```
<210> SEQ ID NO 167
<211> LENGTH: 200
<212> TYPE: DNA
<213> ORGANISM: Sorghum bicolor
<220> FEATURE:
<223> OTHER INFORMATION: Sequence listing for 58633.

<400> SEQUENCE: 167
tcaccgcgtg ctaaacgaaa aatcggcatc agcgatgtca atgtcgatgg cggtggacga    60
ggccgccctc ttcctctctg ggtcaagcct gtgcagccgc tggtggtcgg ccaccgggta   120
catgtccccg agctcctgcc cccgacccct tcccggagac gtcggggcgc tctgcggctc   180
ctccgaccgg cccttgtact                                               200
```

<210> SEQ ID NO 168
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 168

```
atggcagggg gaggaggggg gagggcgttg ccggagacgc cgacgtgggc ggtggccgtg      60
gtctgcgccg tcatcgtgct cgtctccgtc gccatggagc acggcctcca caagctcggc     120
cattggttcc ataagcggga gaagaaggcc atgggcgaag cgctcgagaa gatcaaagca     180
gagttgatgc tgctgggctt                                                 200
```

<210> SEQ ID NO 169
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 169

```
aagcccagca gcatcaactc tgctttgatc ttctcgagcg cttcgcccat ggccttcttc      60
tcccgcttat ggaaccaatg gccgagcttg tggaggccgt gctccatggc gacggagacg     120
agcacgatga cggcgcagac cacggccacc gcccacgtcg gcgtctccgg caacgccctc     180
cccccctcctc ccctgccat                                                200
```

<210> SEQ ID NO 170
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 170

```
ggtcggaaga tccgccgagc gcaccggcat cgccggggtt cgccggagag gccagggaca      60
tgtacccggt gcccgtggcg ccggtggtgc ggccgcatgg gtttaaccgg atggacccgg     120
ataagaggag ggcggcgtcc tcgtcggcca tccaagttga catcgccgat tctgatttct     180
ccttcagtgt acaacggtga                                                200
```

<210> SEQ ID NO 171
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 171

```
tcaccgttgt acactgaagg agaaatcaga atcggcgatg tcaacttgga tggccgacga      60
ggacgccgcc ctcctcttat ccgggtccat ccggttaaac ccatgcggcc gcaccaccgg     120
cgccacgggc accgggtaca tgtccctggc ctctccggcg aaccccggcg atgccggtgc     180
gctcggcgga tcttccgacc                                                200
```

<210> SEQ ID NO 172
<211> LENGTH: 200
<212> TYPE: DNA
<213> ORGANISM: Oryza sativa japonica
<220> FEATURE:

<223> OTHER INFORMATION: Sequence listing for 58633.

<400> SEQUENCE: 172

| atggcaggtg ggagatcggg atcgcgggag ttgccggaga cgccgacgtg ggcggtggcc | 60 |
| gtcgtctgcg ccgtcctcgt gctcgtctcc gtcgccatgg agcacggcct ccacaacctc | 120 |
| agccattggt tccgtaggcg gcagaagaag gccatgggcg acgccctcga caagatcaaa | 180 |
| gcagagctga tgctgctggg | 200 |

<210> SEQ ID NO 173
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 173

| cccagcagca tcagctctgc tttgatcttg tcgagggcgt cgcccatggc cttcttctgc | 60 |
| cgcctacgga accaatggct gaggttgtgg aggccgtgct ccatggcgac ggagacgagc | 120 |
| acgaggacgg cgcagacgac ggccaccgcc cacgtcggcg tctccggcaa ctcccgcgat | 180 |
| cccgatctcc cacctgccat | 200 |

<210> SEQ ID NO 174
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 174

| aggatcacag ggcgaggtcg gacgacccgc cgagcccaat cacggtggcc tcaccaccgg | 60 |
| caccggagga ggacatatac ccggtgccgg cggcggctgc gtctcgccag ctgctagacg | 120 |
| acccgccgga caggaggtgg atggcatcct cgtcggccga catcgccgat tctgattttt | 180 |
| ccttcagcgc acaacggtga | 200 |

<210> SEQ ID NO 175
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 175

| tcaccgttgt gcgctgaagg aaaaatcaga atcggcgatg tcggccgacg aggatgccat | 60 |
| ccacctcctg tccggcgggt cgtctagcag ctggcgagac gcagccgccg ccggcaccgg | 120 |
| gtatatgtcc tcctccggtg ccggtggtga ggccaccgtg attgggctcg gcgggtcgtc | 180 |
| cgacctcgcc ctgtgatcct | 200 |

<210> SEQ ID NO 176
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 176

| atggcaggtg ggagatcggg atcgcgggag ttgccggaga cgccgacgtg ggcggtggcc | 60 |
| gtcgtctgcg ccgtcctcgt gctcgtctcc gtcgccatgg agcacggcct ccacaacctc | 120 |

```
agccatggtt ccgtaggcgg cagaagaagg ccatgggcga cgccctcgac aagatcaaag    180
cagggcttca tatccctgct                                                200

<210> SEQ ID NO 177
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 177
agcagggata tgaagccctg ctttgatctt gtcgagggcg tcgcccatgg ccttcttctg    60
ccgcctacgg aaccatggct gaggttgtgg aggccgtgct ccatggcgac ggagacgagc    120
acgaggacgg cgcagacgac ggccaccgcc cacgtcggcg tctccggcaa ctcccgcgat    180
cccgatctcc cacctgccat                                                200

<210> SEQ ID NO 178
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 178
aggatcacag ggcgaggtcg gacgacccgc cgagcccaat cacggtggcc tcaccaccgg    60
caccggagga ggacatatac ccggtgccgg cggcggctgc gtctcgccag ctgctagacg    120
acccgccgga caggaggtgg atggcatcct cgtcggccga catcgccgat tctgattttt    180
ccttcagcgc acaacggtga                                                200

<210> SEQ ID NO 179
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 179
tcaccgttgt gcgctgaagg aaaaatcaga atcggcgatg tcggccgacg aggatgccat    60
ccacctcctg tccggcgggt cgtctagcag ctggcgagac gcagccgccg ccggcaccgg    120
gtatatgtcc tcctccggtg ccggtggtga ggccaccgtg attgggctcg gcgggtcgtc    180
cgacctcgcc ctgtgatcct                                                200

<210> SEQ ID NO 180
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 180
atggcagggg gaggaggggg gagggcgttg ccggagacgc cgacgtgggc ggtggccgtg    60
gtctgcgccg tcatcgtgct cgtctccgtc gccatggagc acggcctcca caagctcggc    120
cattggttcc ataagcggga gaagaaggcc atgggcgaag cgctcgggaa gatcaaagca    180
gagttgatgc tgctgggctt                                                200

<210> SEQ ID NO 181
```

```
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 181
aagcccagca gcatcaactc tgctttgatc ttcccgagcg cttcgcccat ggccttcttc      60
tcccgcttat ggaaccaatg gccgagcttg tggaggccgt gctccatggc gacgagacg     120 agcacgatga cggcgcagac cacgccacc gcccacgtcg gcgtctccgg caacgccctc     180 cccctcctc cccctgccat                                                  200

<210> SEQ ID NO 182
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 182
aggatcacag ggcgaggttg gacgacccgc cgagcccaat cacggtggcc tcaccaccgg      60
caccggagga ggacatatac ccggtgccgga cggcggctgc gttttgccag ctgctagacg    120
acccgccgga caggaggtgg atggcatcct tgtcggccga cattcccgat tttgattttt    180
ccttcagcgc acaacggtga                                                  200

<210> SEQ ID NO 183
<211> LENGTH: 200
<212> TYPE: DNA
<213> ORGANISM: Oryza sativa japonica
<220> FEATURE:
<223> OTHER INFORMATION: Sequence listing for 58633.

<400> SEQUENCE: 183
tcaccgttgt gcgctgaagg aaaaatcaaa atcgggaatg tcggccgaca aggatgccat      60
ccacctcctg tccggcgggt cgtctagcag ctggcaaaac gcagccgccg ccggcaccgg    120
gtatatgtcc tcctccggtg ccggtggtga ggccaccgtg attgggctcg gcgggtcgtc    180
caacctcgcc ctgtgatcct                                                  200

<210> SEQ ID NO 184
<211> LENGTH: 24
<212> TYPE: DNA
<213> ORGANISM: Hordeum sp.

<400> SEQUENCE: 184
ggggtgctgg agaggcccag gtgg                                             24

<210> SEQ ID NO 185
<211> LENGTH: 23
<212> TYPE: DNA
<213> ORGANISM: Hordeum sp.

<400> SEQUENCE: 185
cgacgtctgg tgcgtgaacc gga                                              23

<210> SEQ ID NO 186
<211> LENGTH: 23
<212> TYPE: DNA
<213> ORGANISM: Hordeum sp.

<400> SEQUENCE: 186
```
ctggtattcc aaggaggtgg tct                                                   23

<210> SEQ ID NO 187
<211> LENGTH: 23
<212> TYPE: DNA
<213> ORGANISM: Hordeum sp.

<400> SEQUENCE: 187
gatgaggagc agggatatga agc                                                   23

<210> SEQ ID NO 188
<211> LENGTH: 23
<212> TYPE: DNA
<213> ORGANISM: Hordeum sp.

<400> SEQUENCE: 188
atgagctccg ccttcatctt ctc                                                   23

<210> SEQ ID NO 189
<211> LENGTH: 23
<212> TYPE: DNA
<213> ORGANISM: Hordeum sp.

<400> SEQUENCE: 189
ggccttcttg tgccggtgct gga                                                   23

<210> SEQ ID NO 190
<211> LENGTH: 23
<212> TYPE: DNA
<213> ORGANISM: Hordeum sp.

<400> SEQUENCE: 190
ctgtccacac aaaatgcgcc atc                                                   23

<210> SEQ ID NO 191
<211> LENGTH: 22
<212> TYPE: DNA
<213> ORGANISM: Hordeum sp.

<400> SEQUENCE: 191
gttctggaac aacgtcaggt gt                                                    22

<210> SEQ ID NO 192
<211> LENGTH: 22
<212> TYPE: DNA
<213> ORGANISM: Hordeum sp.

<400> SEQUENCE: 192
gtcggggcgg tggaaccaga ag                                                    22

<210> SEQ ID NO 193
<211> LENGTH: 21
<212> TYPE: DNA
<213> ORGANISM: Hordeum sp.

<400> SEQUENCE: 193
aaaaatctgc actgggatg t                                                      21

<210> SEQ ID NO 194
<211> LENGTH: 24
<212> TYPE: DNA
<213> ORGANISM: Hordeum sp.

```
<400> SEQUENCE: 194
gatttagtct gtgcaccggg tgcg                                              24

<210> SEQ ID NO 195
<211> LENGTH: 24
<212> TYPE: DNA
<213> ORGANISM: Hordeum sp.

<400> SEQUENCE: 195
aaccgggtac atgtccctag cctc                                              24

<210> SEQ ID NO 196
<211> LENGTH: 25
<212> TYPE: DNA
<213> ORGANISM: Aqueoria sp.

<400> SEQUENCE: 196
gttgtagttg tactccatct tattg                                             25

<210> SEQ ID NO 197
<211> LENGTH: 24
<212> TYPE: RNA
<213> ORGANISM: Barley

<400> SEQUENCE: 197
ggggugcugg agaggcccag gugg                                              24

<210> SEQ ID NO 198
<211> LENGTH: 23
<212> TYPE: RNA
<213> ORGANISM: Barley

<400> SEQUENCE: 198
gaugaggagc agggauauga agc                                               23

<210> SEQ ID NO 199
<211> LENGTH: 23
<212> TYPE: DNA
<213> ORGANISM: Barley

<400> SEQUENCE: 199
cuguccacac aaaaugcgcc auc                                               23

<210> SEQ ID NO 200
<211> LENGTH: 22
<212> TYPE: RNA
<213> ORGANISM: Barley

<400> SEQUENCE: 200
gucggggcgg uggaaccaga ag                                                22

<210> SEQ ID NO 201
<211> LENGTH: 21
<212> TYPE: RNA
<213> ORGANISM: Barley

<400> SEQUENCE: 201
aaaaaucugc acuggggaug u                                                 21

<210> SEQ ID NO 202
<211> LENGTH: 25
<212> TYPE: RNA
<213> ORGANISM: Barley
```

```
<400> SEQUENCE: 202
cgccuucauc uucuccagcg ccucc                                         25

<210> SEQ ID NO 203
<211> LENGTH: 25
<212> TYPE: RNA
<213> ORGANISM: Barley

<400> SEQUENCE: 203
gucguccucc aucgaccucu ugaug                                         25

<210> SEQ ID NO 204
<211> LENGTH: 25
<212> TYPE: RNA
<213> ORGANISM: Barley

<400> SEQUENCE: 204
ucagcccgau cugcgugugg uagca                                         25

<210> SEQ ID NO 205
<211> LENGTH: 25
<212> TYPE: RNA
<213> ORGANISM: A. victoria

<400> SEQUENCE: 205
guuguaguug uacuccaucu uauug                                         25

<210> SEQ ID NO 206
<211> LENGTH: 150
<212> TYPE: RNA
<213> ORGANISM: Barley

<400> SEQUENCE: 206
augucggaca aaaaggggu gccggcgcgg gagcugccgg agacgccguc gugggcggug     60
gcgguggucu ucgccgccau ggugcucgug uccguccuca uggaacacgg ccuccacaag   120
cucggccauu gguuccagca ccggcacaag                                   150

<210> SEQ ID NO 207
<211> LENGTH: 150
<212> TYPE: RNA
<213> ORGANISM: Barley

<400> SEQUENCE: 207
cgucgucggc ccucgaagcc gacauccca gugcagauuu uuccuucagc cagggaugag     60
acaaguuucu guauucaugu uagucccaau guauagccaa cauaggaugu gaugauucgu   120
acaauaagaa aucaauuuu uuacugaguc                                    150

<210> SEQ ID NO 208
<211> LENGTH: 150
<212> TYPE: RNA
<213> ORGANISM: Barley

<400> SEQUENCE: 208 ugguggugggg gcuagcucuc caguuccucu gcagcuauau gaccuuccc cucuacgcgc    60 ucgucacaca gaugggauca aacaugaaga gguccaucuu cgacgagcag acguccaagg   120
cgcucaccaa cuggcggaac acggccaagg                                   150

<210> SEQ ID NO 209
```

```
<211> LENGTH: 100
<212> TYPE: RNA
<213> ORGANISM: Barley

<400> SEQUENCE: 209
gugggcggug gcgguggucu ucgccgccau ggugcucgug uccguccuca uggaacacgg      60
ccuccacaag cucggccauu gguuccagca ccggcacaag                          100

<210> SEQ ID NO 210
<211> LENGTH: 100
<212> TYPE: RNA
<213> ORGANISM: Barley

<400> SEQUENCE: 210
cagggaugag acaaguuucu guauucaugu uagucccaau guauagccaa cauaggaugu      60
gaugauucgu acaauaagaa auacaauuuu uuacugaguc                          100

<210> SEQ ID NO 211
<211> LENGTH: 100
<212> TYPE: RNA
<213> ORGANISM: Barley

<400> SEQUENCE: 211
cucuacgcgc ucgucacaca gaugggauca aacaugaaga gguccaucuu cgacgagcag      60
acguccaagg cgcucaccaa cuggcggaac acggccaagg                          100

<210> SEQ ID NO 212
<211> LENGTH: 80
<212> TYPE: RNA
<213> ORGANISM: Barley

<400> SEQUENCE: 212
ucgccgccau ggugcucgug uccguccuca uggaacacgg ccuccacaag cucggccauu      60
gguuccagca ccggcacaag                                                 80

<210> SEQ ID NO 213
<211> LENGTH: 152
<212> TYPE: RNA
<213> ORGANISM: A. victoria

<400> SEQUENCE: 213
ucaaggagga uggcaacauc cugggcaaua agauggagua caacuacaac gcccacaaug      60
uguacaucau gaccgacaag gccaagaaug gcaucaaggu gaacuucaag auccgccaca     120
acaucgagga uggcagcgug cagcuggccg ac                                   152
```

METHODS AND COMPOSITIONS FOR PLANT PEST CONTROL

CROSS REFERENCE TO RELATED APPLICATIONS

This application is a Division of U.S. patent application Ser. No. 14/435,939, filed Apr. 15, 2015, which issued as U.S. Pat. No. 10,077,451, which claims priority to 35 U.S.C. § 371 National Phase of International Patent Application No. PCT/US2013/065561, filed Oct. 18, 2013 and incorporated herein by reference in its entirety, which claims the benefit of U.S. Provisional Patent Application No. 61/715,549, filed Oct. 18, 2012, all of which are incorporated herein by reference in their entireties.

INCORPORATION OF SEQUENCE LISTING

A sequence listing containing the file named "MTC58633_PCT_SeqListing.txt", which is 366,930 bytes (measured in MS-Windows®), contains 213 sequences, and was created on Oct. 14, 2013, is provided herewith and is incorporated herein by reference in its entirety.

BACKGROUND OF THE INVENTION

Powdery mildews are fungal diseases that affect a wide range of plants including cereals, grasses, vegetables, ornamentals, weeds, shrubs, fruit trees, broad-leaved shade and forest trees, that is caused by different species of fungi in the order Erysiphales. The disease is characterized by spots or patches of white to grayish, talcum-powder-like growth that produce tiny, pinhead-sized, spherical fruiting structures (the cleistothecia or overwintering bodies of the fungus), that are first white, later yellow-brown and finally black. The fungi that cause powdery mildews are host specific and cannot survive without the proper host plant. They produce mycelium (fungal threads) that grow only on the surface of the plant and feed by sending haustoria, or root-like structures, into the epidermal cells of the plant. The fungi overwinter on plant debris as cleistothecia or mycelia. In the spring, the cleistothecia produce spores that are moved to susceptible hosts by rain, wind or insects.

Powdery mildew disease is particularly prevalent in temperate and humid climates, where they frequently cause significant yield losses and quality reductions in various agricultural settings including greenhouse and field farming. This affects key cereals (e.g. barley and wheat), horticultural crops (e.g. grapevine, pea and tomato) and economically important ornamentals (e.g. roses). Limited access to natural sources of resistance to powdery mildews, rapid changes in pathogen virulence and the time consuming introgression of suitable resistance genes into elite varieties has led to the widespread use of fungicides to control the disease. This has, not surprisingly, led to the evolution and spread of fungicide resistance, which is especially dramatic amongst the most economically important powdery mildews.

Downy mildew diseases are caused by oomycete microbes from the family Peronosporaceae that are parasites of plants. Peronosporaceae are obligate biotrophic plant pathogens and parasitize their host plants as an intercellular mycelium using haustoria to penetrate the host cells. The downy mildews reproduce asexually by forming sporangia on distinctive white sporangiophores usually formed on the lower surface of infected leaves. These constitute the "downy mildew" and the initial symptoms appear on leaves as light green to yellow spots. The sporangia are wind-dispersed to the surface of other leaves. Depending on the genus, the sporangia may germinate by forming zoospores or by germ-tube. In the latter case, the sporangia behave like fungal conidia and are often referred to as such. Sexual reproduction is via oospores.

Most Peronosporaceae are pathogens of herbaceous dicots. Some downy mildew genera have relatively restricted host ranges, e.g. Basidiophora, Paraperonospora, Protobremia and *Bremia* on Asteraceae; Perofascia and Hyaloperonospora almost exclusively on Brassicaceae; Viennotia, Graminivora, Poakatesthia, Sclerospora and Peronosclerospora on Poaceae, Plasmoverna on Ranunculaceae. However, the largest genera, *Peronospora* and *Plasmopara*, have very wide host ranges.

In commercial agriculture, downy mildews are a particular problem for growers of crucifers, grapes and vegetables that grow on vines. Peronosporaceae of economic importance include *Plasmopara viticola* which infect grapevines, *Peronospora tabacina* which causes blue mold on tobacco, *Bremia lactucae*, a parasite on lettuce, and *Plasmopara halstedii* on sunflower.

Rusts (Pucciniales, formerly Uredinales) are obligate biotrophic parasites of vascular plants. Rusts affect a variety of plants; leaves, stems, fruits and seeds and is most commonly seen as coloured powder, composed of tiny aeciospores which land on vegetation producing pustules, or uredia, that form on the lower surfaces. During late spring or early summer, yellow orange or brown, hairlike or ligulate structures called telia grow on the leaves or emerge from bark of woody hosts. These telia produce teliospores which will germinate into aerial basidiospores, spreading and causing further infection.

In the monocot barley (*Hordeum vulgare*, Piffanelli et al. Nature. 2004 430 (7002):887-91) and the dicots *Arabidopsis thaliana* (Consonni et al. Nat Genet. 2006 38(6):716-20), tomato (*Solanum lycopersicum*, Bai et al. Mol Plant Microbe Interact. 2008 21(1):30-9) and pea (*Pisum sativum*, Humphry et al. Mol Plant Pathol. 2011 Apr. 21. EPUB), loss-of-function mutations in MLO (Mildew Resistance Locus O) genes confer highly effective broad-spectrum powdery mildew resistance. MLO resistance appears to act early and typically terminates fungal pathogenesis before invasion of the first host cell. The exceptional efficacy and longevity of MLO resistance, has resulted in elite barley lines carrying introgressed MLO alleles being successfully used in European agriculture for about three decades. However, MLO mutants have several undesirable agronomic qualities including environment-dependent necrotic leaf spotting and reduced yields (Molina-Cano et al. Theor Appl Genet. 2003 107(7):1278-87). In addition, barley MLO mutants also show enhanced susceptibility to the hemibiotroph *Magnaporthe grisea* and the necrotroph *Bipolaris sorokinianaare*. Lab studies with *Arabidopsis* powdery resistant MLO mutants suggest that these agronomic defects, including others such as spontaneous cell wall appositions, cell death, senescence-like chlorosis and enhanced susceptibility to *Alternaria alternata, A. brassicicola* and *Phytophthora infestans* (necrotrophic *Alternaria* spp. and hemibiotrophic *P. infestans*), respectively, are pleiotropic effects not simply linkage drag (Consonni et al. Nat Genet. 2006 38(6):716-20).

Recently a method to increase resistance to soybean rust via the transgenic knockdown of MLO genes has been disclosed (Markus et al. United States Patent Application 20100192254).

SUMMARY OF THE INVENTION

The present invention provides for compositions comprising polynucleotide molecules and methods for treating a plant to alter or regulate gene or gene transcript expression in the plant, for example, by providing RNA or DNA for inhibition of expression. Various aspects of the invention provide compositions comprising polynucleotide molecules and related methods for topically applying such compositions to plants to regulate endogenous Mildew Resistance Locus O (MLO) genes in a plant cell. The polynucleotides, compositions, and methods disclosed herein are useful in decreasing levels of MLO transcript and improving fungal disease and/or nematode resistance of a plant.

In an aspect of the invention, the polynucleotide molecules are provided in compositions that can permeate or be absorbed into living plant tissue to initiate localized, partially systemic, or systemic gene inhibition or regulation. In certain embodiments of the invention, the polynucleotide molecules ultimately provide to a plant, or allow the in planta production of, RNA that is capable of hybridizing under physiological conditions in a plant cell to RNA transcribed from a target endogenous gene or target transgene in the plant cell, thereby effecting regulation of the endogenous MLO target gene. In certain embodiments, regulation of the MLO target gene, such as by silencing or suppression of the target gene, leads to the upregulation of another gene that is itself affected or regulated by decreasing the MLO target gene's expression.

In certain aspects or embodiments of the invention, the topical application of a composition comprising an exogenous polynucleotide and a transfer agent to a plant or plant part according to the methods described herein does not necessarily result in nor require the exogenous polynucleotide's integration into a chromosome of the plant. In certain aspects or embodiments of the invention, the topical application of a composition comprising an exogenous polynucleotide and a transfer agent to a plant or plant part according to the methods described herein does not necessarily result in nor require transcription of the exogenous polynucleotide from DNA integrated into a chromosome of the plant. In certain embodiments, topical application of a composition comprising an exogenous polynucleotide and a transfer agent to a plant according to the methods described herein also does not necessarily require that the exogenous polynucleotide be physically bound to a particle, such as in biolistic mediated introduction of polynucleotides associated with a gold or tungsten particles into internal portions of a plant, plant part, or plant cell. An exogenous polynucleotide used in certain methods and compositions provided herein can optionally be associated with an operably linked promoter sequence in certain embodiments of the methods provided herein. However, in other embodiments, an exogenous polynucleotide used in certain methods and compositions provided herein is not associated with an operably linked promoter sequence. Also, in certain embodiments, an exogenous polynucleotide used in certain methods and compositions provided herein is not operably linked to a viral vector.

In certain embodiments, methods for improving fungal disease resistance and/or nematode resistance in a plant comprising topically applying compositions comprising a polynucleotide that suppresses the targeted MLO gene and a transfer agent are provided. In certain embodiments, methods for selectively suppressing the targeted MLO gene by topically applying the polynucleotide composition to a plant surface at one or more selected seed, vegetative, or reproductive stage(s) of plant growth are provided. Such methods can provide for gene suppression in a plant or plant part on an as needed or as desired basis. In certain embodiments, methods for selectively suppressing the target MLO gene by topically applying the polynucleotide composition to a plant surface at one or more pre-determined seed, vegetative, or reproductive stage(s) of plant growth are provided. Such methods can provide for MLO gene suppression in a plant or plant part that obviates any undesired or unnecessary effects of suppressing gene expression at certain seed, vegetative, or reproductive stage(s) of plant development.

In certain embodiments, methods for selectively improving fungal disease resistance and/or nematode resistance in a plant by topically applying the polynucleotide composition to the plant surface at one or more selected seed, vegetative, or reproductive stage(s) are provided. Such methods can provide for improved fungal disease resistance and/or nematode disease resistance in a plant or plant part on an as needed or as desired basis. In certain embodiments, methods for selectively improving fungal disease and/or nematode resistance in a plant by topically applying the polynucleotide composition to the plant surface at one or more predetermined seed, vegetative, or reproductive stage(s) are provided. Such methods can provide for improving fungal disease and/or nematode resistance in a plant or plant part that obviates any undesired or unnecessary effects of suppressing MLO gene expression at certain seed, vegetative, or reproductive stage(s) of plant development.

Polynucleotides that can be used to suppress a MLO include, but are not limited to, any of: i) polynucleotides comprising at least 18 contiguous nucleotides that are essentially identical or essentially complementary to a transcript of the gene(s) encoding a protein of Table 2 or 3 (SEQ ID NO:1-27, 28, 30, 32, 34, 36, 38, 40, 42, 44, 46, 48, 50, 52, 54, 56, 58, 60, 62, 64, 66, 68, 70, 72, 74, 76, or 78); ii) polynucleotides comprising at least 18 contiguous nucleotides that are essentially identical or essentially complementary to a MLO or MLO-like gene of Table 3 comprising a polynucleotide of SEQ ID NO: 29, 31, 33, 35, 37, 39, 41, 42, 43, 45, 47, 49, 51, 53, 55, 57, 59, 61, 63, 65, 67, 69, 71, 73, 75, 77, or 79; or, polynucleotides comprising at least 18 contiguous nucleotides that are essentially identical or essentially complementary to a polynucleotide of SEQ ID NO:80-195. In some embodiments, a polynucleotide that comprises a nucleotide sequence that is essentially identical or essentially complementary to at least 18 contiguous nucleotides of SEQ ID NO: 197-213 is provided. In some embodiments, the polynucleotide comprises a nucleotide sequence that is essentially identical or essentially complementary to SEQ ID NO: 197-213. Methods and compositions that provide for the topical application of certain polynucleotides in the presence of transfer agents can be used to suppress Mildew Resistance Locus O (MLO) gene expression in an optimal manner. In certain embodiments, the compositions provided herein can be applied on an "as needed" basis upon scouting for the occurrence of fungal disease or nematodes. In certain embodiments, the compositions provided herein can be applied as a prophylactic measure to prevent the occurrence of fungal disease or nematodes. In certain embodiments, the compositions can be applied in a manner that obviates any deleterious effects on yield or other characteristics that can be associated with suppression of MLO gene expression in a crop plant. The applied polynucleotides are complementary to the MLO target host gene in plants and their topical application leads to suppression of the MLO gene's activity.

Provided herein are compositions and methods for controlling plant fungal diseases. Plant fungal diseases that can be controlled with the methods and compositions provided herein include, but are not limited to, obligate biotrophic powdery mildew, downy mildew and rust fungal infestations. Certain embodiments relate to methods and compositions for reducing expression of one or more host plant MLO polynucleotide and/or protein molecules in one or more cells or tissues of the host plant such that the host plant is rendered less susceptible to fungal infections from the order Erysiphales, the family Peronosporaceae, or the order Pucciniales. In certain embodiments, nucleotide and amino acid sequences of plant Mildew Resistance Locus O (MLO) genes and gene products which can be downregulated by methods and compositions provided herein to increase plant resistance to powdery mildew, downy mildew or rust infection are disclosed.

Also provided herein are methods and compositions that provide for reductions in expression of targeted MLO polynucleotide and protein molecules in at least the cells of a plant root for improved resistance to nematodes. Nematodes that can be controlled by the methods and compositions provided herein include, but are not limited to, root knot nematodes (such as *Meloidogyne* sp.), cyst nematodes (such as *Globodera* sp. and *Heterodera* sp.), lesion nematodes (such as *Pratylenchus* sp.), and the like. In certain embodiments, MLO expression is reduced in plant root cells from which nematodes feed by providing topically to plant leaves, shoots, roots and/or seeds, compositions comprising polynucleotides that comprise at least 18 contiguous nucleotides that are essentially identical or essentially complementary to a Mildew Resistance Locus O (MLO) gene or to a transcript of a MLO gene; and a transfer agent.

Also provided are methods and compositions where topically induced reductions in MLO transcript or protein levels are used to achieve powdery mildew, downy mildew or rust control while minimizing deleterious pleotropic effects in the host plant. Such methods and compositions provide for optimized levels of MLO gene inhibition and/or optimized timing of MLO gene inhibition.

Certain embodiments of the invention are directed to methods for producing a plant exhibiting an improvement in fungal disease resistance and/or nematode resistance comprising topically applying to a plant surface a composition that comprises:

a. at least one polynucleotide that comprises at least 18 contiguous nucleotides that are essentially identical or essentially complementary to a Mildew Resistance Locus O (MLO) gene or to a transcript of the gene; and b. a transfer agent, wherein the plant exhibits an improvement in fungal disease resistance and/or nematode resistance that results from suppression of the Mildew Resistance Locus O (MLO) gene. In certain embodiments, the polynucleotide molecule comprises sense ssDNA, sense ssRNA, dsRNA, dsDNA, a double stranded DNA/RNA hybrid, anti-sense ssDNA, or anti-sense ssRNA. In certain embodiments, the polynucleotide is selected from the group consisting of SEQ ID NO: 80-195, or wherein the polynucleotide comprises at least 18 contiguous nucleotides that are essentially identical or essentially complementary to SEQ ID NO: 29, 31, 33, 35, 37, 39, 41, 43, 45, 47, 49, 51, 53, 55, 57, 59, 61, 63, 65, 67, 69, 71, 73, 75, 77, or 79. In some embodiments, a polynucleotide that comprises a nucleotide sequence that is essentially identical or essentially complementary to at least 18 contiguous nucleotides of SEQ ID NO: 197-213 is provided. In some embodiments, the polynucleotide comprises a nucleotide sequence that is essentially identical or essentially complementary to SEQ ID NO: 197-213. In certain embodiments: (a) the plant is a corn plant, the gene or the transcript is a corn Mildew Resistance Locus O (MLO) gene or transcript, and the polynucleotide molecule is selected from the group consisting of SEQ ID NO: 160-162, and SEQ ID NO: 163, or the polynucleotide comprises at least 18 contiguous nucleotides that are essentially identical or essentially complementary to SEQ ID NO:68-69; (b) the plant is a soybean plant, the gene or the transcript is a soybean Mildew Resistance Locus O (MLO) gene or transcript, and the polynucleotide molecule is selected from the group consisting of SEQ ID NO: 112-118, and SEQ ID NO: 119, or the polynucleotide comprises at least 18 contiguous nucleotides that are essentially identical or essentially complementary to SEQ ID NO:45 or 47, (c) the plant is a cotton plant, the gene or the transcript is a cotton Mildew Resistance Locus O (MLO) gene or transcript, and or the polynucleotide comprises at least 18 contiguous nucleotides that are essentially identical or essentially complementary to a cotton gene or transcript that encodes SEQ ID NO:4; (d) the plant is a barley plant, the gene or the transcript is a barley Mildew Resistance Locus O (MLO) gene or transcript, and the polynucleotide molecule is selected from the group consisting of SEQ ID NO:80-83, 184, 192, 194, and SEQ ID NO: 197-213, or the polynucleotide comprises at least 18 contiguous nucleotides that are essentially identical or essentially complementary to SEQ ID NO:29; (e) the plant is a cucumber plant, the gene or the transcript is a cucumber Mildew Resistance Locus O (MLO) gene or transcript, and the polynucleotide molecule is selected from the group consisting of SEQ ID NO:84-98, and SEQ ID NO:99, or the polynucleotide comprises at least 18 contiguous nucleotides that are essentially identical or essentially complementary to SEQ ID NO:31, 33, 35, or 37; (f) the plant is a lettuce plant, the gene or the transcript is a lettuce Mildew Resistance Locus O (MLO) gene or transcript, and the polynucleotide molecule is selected from the group consisting of SEQ ID NO:100-102, and SEQ ID NO:103, or the polynucleotide comprises at least 18 contiguous nucleotides that are essentially identical or essentially complementary to SEQ ID NO:39; (g) the plant is a pea plant, the gene or the transcript is a pea Mildew Resistance Locus O (MLO) gene or transcript, and the polynucleotide molecule is selected from the group consisting of SEQ ID NO:104-106, and SEQ ID NO:107, or the polynucleotide comprises at least 18 contiguous nucleotides that are essentially identical or essentially complementary to SEQ ID NO:41; (h) the plant is a *Medicago* plant, the gene or the transcript is a *Medicago* Mildew Resistance Locus O (MLO) gene or transcript, and the polynucleotide molecule is selected from the group consisting of SEQ ID NO:108-110, and SEQ ID NO:111, or the polynucleotide comprises at least 18 contiguous nucleotides that are essentially identical or essentially complementary to SEQ ID NO:43; (i) the plant is a pepper plant, the gene or the transcript is a pepper Mildew Resistance Locus O (MLO) gene or transcript, and the polynucleotide molecule is selected from the group consisting of SEQ ID NO:120-122, and SEQ ID NO:123, or the polynucleotide comprises at least 18 contiguous nucleotides that are essentially identical or essentially complementary to SEQ ID NO:49; (j) the plant is a tomato plant, the gene or the transcript is a tomato Mildew Resistance Locus O (MLO) gene or transcript, and the polynucleotide molecule is selected from the group consisting of SEQ ID NO:124-130, and SEQ ID NO:131, or the polynucleotide comprises at least 18 contiguous nucleotides that are essentially identical or essentially complementary to SEQ ID NO:51 or 53; (k) the plant is a wheat plant, the gene or the transcript is a wheat Mildew Resistance Locus O (MLO) gene or transcript, and the polynucleotide molecule is selected from the group consisting of SEQ ID NO:132-142, and SEQ ID NO:143, or the polynucleotide comprises at least 18 contiguous nucleotides that are essentially identical or essentially complementary to SEQ ID NO:55, 57 or 59; (1) the plant is a grape plant, the gene or the transcript is a grape Mildew Resistance Locus O (MLO) gene or transcript, and the polynucleotide molecule is selected from the group consisting of SEQ ID NO:144-158, and SEQ ID NO:159 or the polynucleotide comprises at least 18 contiguous nucleotides that are essentially identical or essentially complementary to SEQ ID NO:61, 63, 65, or 67; (m) the plant is a sorghum plant, the gene or the transcript is a sorghum Mildew Resistance Locus O (MLO) gene or transcript, and the polynucleotide molecule is selected from the group consisting of SEQ ID NO:164-166, and SEQ ID NO:167, or the polynucleotide comprises at least 18 contiguous nucleotides that are essentially identical or essentially complementary to SEQ ID NO:71; or, (n) the plant is a rice plant, the gene or the transcript is a rice Mildew Resistance Locus O (MLO) gene or transcript, and the polynucleotide molecule is selected from the group consisting of SEQ ID NO:168-182, and SEQ ID NO:183, or the polynucleotide comprises at least 18 contiguous nucleotides that are essentially identical or essentially complementary to SEQ ID NO:73, 75, 77, or 79. In certain embodiments, the composition comprises any combination of two or more polynucleotide molecules. In certain embodiments, the polynucleotide is at least 18 to about 24, about 25 to about 50, about 51 to about 100, about 101 to about 300, about 301 to about 500, or at least about 500 or more residues in length. In certain embodiments, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the composition further comprises a non-polynucleotide herbicidal molecule and the plant is resistant to the herbicidal molecule. In certain embodiments, the transfer agent comprises an organosilicone preparation. In certain embodiments, the polynucleotide is not operably linked to a viral vector. In certain embodiments, the polynucleotide is not integrated into the plant chromosome. Further embodiments of the invention are directed to: a plant made according to any of the above-described methods; progeny of plants that exhibit the improvements in fungal disease resistance and/or nematode resistance; seed of the plants, wherein seed from the plants exhibits the improvement in fungal disease resistance and/or nematode resistance; and a processed product of the plants, the progeny plants, or the seeds, wherein the processed products exhibit the improvement in fungal disease resistance and/or nematode resistance. In certain embodiments, the processed product of the plant or plant part exhibits an improved attribute relative to a processed product of an untreated control plant and the improved attribute results from the improved fungal disease resistance and/or nematode resistance. An improved attribute of a processed product can include, but is not limited to, decreased mycotoxin content, improved nutritional content, improved storage characteristics, improved flavor, improved consistency, and the like when compared to a processed product obtained from an untreated plant or plant part.

An additional embodiment of the invention is directed to a composition comprising a polynucleotide molecule that comprises at least 18 contiguous nucleotides that are essentially identical or essentially complementary to a Mildew Resistance Locus O (MLO) gene or transcript of the gene, wherein the polynucleotide is not operably linked to a promoter; and, b) a transfer agent. In certain embodiments, the polynucleotide is selected from the group consisting of SEQ ID NO: 80-195, or the polynucleotide comprises at least 18 contiguous nucleotides that are essentially identical or essentially complementary to SEQ ID NO: 29, 31, 33, 35, 37, 39, 41, 43, 45, 47, 49, 51, 53, 55, 57, 59, 61, 63, 65, 67, 69, 71, 73, 75, 77, or 79. In some embodiments, a polynucleotide that comprises a nucleotide sequence that is essentially identical or essentially complementary to at least 18 contiguous nucleotides of SEQ ID NO: 197-213 is provided. In some embodiments, the polynucleotide comprises a nucleotide sequence that is essentially identical or essentially complementary to SEQ ID NO: 197-213. In certain embodiments: (a) the gene or the transcript is a corn Mildew Resistance Locus O (MLO) Gene or transcript, and the polynucleotide molecule is selected from the group consisting of SEQ ID NO: 160-162, and SEQ ID NO: 163, or the polynucleotide comprises at least 18 contiguous nucleotides that are essentially identical or essentially complementary to SEQ ID NO:68-69; (b) the gene or the transcript is a soybean Mildew Resistance Locus O (MLO) gene or transcript, and the polynucleotide molecule is selected from the group consisting of SEQ ID NO: 112-118, and SEQ ID NO: 119, or the polynucleotide comprises at least 18 contiguous nucleotides that are essentially identical or essentially complementary to SEQ ID NO:45 or 47; (c) the gene or the transcript is a cotton Mildew Resistance Locus O (MLO) gene or transcript, and the polynucleotide comprises at least 18 contiguous nucleotides that are essentially identical or essentially complementary to a cotton gene or transcript that encodes SEQ ID NO:4; (d) the gene or the transcript is a barley Mildew Resistance Locus O (MLO) gene or transcript, and the polynucleotide molecule is selected from the group consisting of SEQ ID NO:80-83, 184, 192, 194, and SEQ ID NO:197-213, or the polynucleotide comprises at least 18 contiguous nucleotides that are essentially identical or essentially complementary to SEQ ID NO:29; (e) the gene or the transcript is a cucumber Mildew Resistance Locus O (MLO) gene or transcript, and the polynucleotide molecule is selected from the group consisting of SEQ ID NO:84-98, and SEQ ID NO:99, or the polynucleotide comprises at least 18 contiguous nucleotides that are essentially identical or essentially complementary to SEQ ID NO:31, 33, 35, or 37; (f) the gene or the transcript is a lettuce Mildew Resistance Locus O (MLO) gene or transcript, and the polynucleotide molecule is selected from the group consisting of SEQ ID NO:100-102, and SEQ ID NO:103, or the polynucleotide comprises at least 18 contiguous nucleotides that are essentially identical or essentially complementary to SEQ ID NO:39; (g) the gene or the transcript is a pea Mildew Resistance Locus O (MLO) gene or transcript, and the polynucleotide molecule is selected from the group consisting of SEQ ID NO:104-106, and SEQ ID NO:107, or the polynucleotide comprises at least 18 contiguous nucleotides that are essentially identical or essentially complementary to SEQ ID NO:41; (h) the gene or the transcript is a *Medicago* Mildew Resistance Locus O (MLO) gene or transcript, and the polynucleotide molecule is selected from the group consisting of SEQ ID NO:108-110, and SEQ ID NO:111, or the polynucleotide comprises at least 18 contiguous nucleotides that are essentially identical or essentially complementary to SEQ ID NO:43; (i) the gene or the transcript is a pepper Mildew Resistance Locus O (MLO) gene or transcript, and the polynucleotide molecule is selected from the group consisting of SEQ ID NO:120-122, and SEQ ID NO:123, or the polynucleotide comprises at least 18 contiguous nucleotides that are essentially identical or essentially complementary to SEQ ID NO:49; (j) the gene or the transcript is a tomato Mildew Resistance Locus O (MLO) gene or transcript, and the polynucleotide molecule is selected from the group consisting of SEQ ID NO:124-130, and SEQ ID NO:131, or the polynucleotide comprises at least 18 contiguous nucleotides that are essentially identical or essentially complementary to SEQ ID NO:51 or 53; (k) the gene or the transcript is a wheat Mildew Resistance Locus O (MLO) gene or transcript, and the polynucleotide molecule is selected from the group consisting of SEQ ID NO:132-142, and SEQ ID NO:143, or the polynucleotide comprises at least 18 contiguous nucleotides that are essentially identical or essentially complementary to SEQ ID NO:55, 57 or 59; (l) the gene or the transcript is a grape Mildew Resistance Locus O (MLO) gene or transcript, and the polynucleotide molecule is selected from the group consisting of SEQ ID NO:144-158, and SEQ ID NO:159 or the polynucleotide comprises at least 18 contiguous nucleotides that are essentially identical or essentially complementary to SEQ ID NO:61, 63, 65, or 67; (m) the gene or the transcript is a sorghum Mildew Resistance Locus O (MLO) gene or transcript, and the polynucleotide molecule is selected from the group consisting of SEQ ID NO:164-166, and SEQ ID NO:167, or the polynucleotide comprises at least 18 contiguous nucleotides that are essentially identical or essentially complementary to SEQ ID NO:71; or, (n) the gene or the transcript is a rice Mildew Resistance Locus O (MLO) gene or transcript, and the polynucleotide molecule is selected from the group consisting of SEQ ID NO:168-182, and SEQ ID NO:195, or the polynucleotide comprises at least 18 contiguous nucleotides that are essentially identical or essentially complementary to SEQ ID NO:73, 75, 77, or 79. In certain embodiments, the polynucleotide is at least 18 to about 24, about 25 to about 50, about 51 to about 100, about 101 to about 300, about 301 to about 500, or at least about 500 or more residues in length. In certain embodiments, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the transfer agent is an organosilicone preparation. In certain embodiments, the polynucleotide is not physically bound to a biolistic particle.

Another embodiment of the invention is directed to a method of making a composition comprising the step of combining at least: (a) a polynucleotide molecule comprising at least 18 contiguous nucleotides that are essentially identical or essentially complementary to a Mildew Resistance Locus O (MLO) gene or transcript of a plant, wherein the polynucleotide is not operably linked to a promoter or a viral vector; and, (b) a transfer agent. In certain embodiments, the polynucleotide is obtained by in vivo biosynthesis, in vitro enzymatic synthesis, or chemical synthesis. In certain embodiments, the method further comprises combining with the polynucleotide and the transfer agent at least one of a non-polynucleotide herbicidal molecule, a polynucleotide herbicidal molecule, an insecticide, a fungicide, and/or a nematocide. In certain embodiments, the transfer agent is an organosilicone preparation.

Yet another embodiment of the invention is directed to a method of identifying a polynucleotide for improving fungal disease resistance and/or nematode resistance in a plant comprising; (a) selecting a population of polynucleotides that are essentially identical or essentially complementary to a Mildew Resistance Locus O (MLO) gene or transcript of a plant; b) topically applying to a surface of at least one of the plants a composition comprising at least one polynucleotide from the population and an transfer agent to obtain a treated plant; and, c) identifying a treated plant that exhibits suppression of the Mildew Resistance Locus O (MLO) gene or exhibits an improvement in fungal disease resistance or exhibits an improvement in nematode resistance, thereby identifying a polynucleotide that improves fungal disease resistance and/or nematode resistance in the plant. In certain embodiments, the polynucleotide is selected from the group consisting of wherein the polynucleotide is selected from the group consisting of SEQ ID NO: 80-195, or wherein the polynucleotide comprises at least 18 contiguous nucleotides that are essentially identical or essentially complementary to SEQ ID NO: 29, 31, 33, 35, 37, 39, 41, 43, 45, 47, 49, 51, 53, 55, 57, 59, 61, 63, 65, 67, 69, 71, 73, 75, 77, or 79. In some embodiments, a polynucleotide that comprises a nucleotide sequence that is essentially identical or essentially complementary to at least 18 contiguous nucleotides of SEQ ID NO: 197-213 is provided. In some embodiments, the polynucleotide comprises a nucleotide sequence that is essentially identical or essentially complementary to SEQ ID NO: 197-213. In certain embodiments: (a) the plant is a corn plant, the gene or the transcript is a corn Mildew Resistance Locus O (MLO) gene or transcript, and the polynucleotide molecule is selected from the group consisting of SEQ ID NO: 160-162, and SEQ ID NO: 163, or the polynucleotide comprises at least 18 contiguous nucleotides that are essentially identical or essentially complementary to SEQ ID NO:68-69; (b) the plant is a soybean plant, the gene or the transcript is a soybean Mildew Resistance Locus O (MLO) gene or transcript, and the polynucleotide molecule is selected from the group consisting of SEQ ID NO: 112-118, and SEQ ID NO: 119, or the polynucleotide comprises at least 18 contiguous nucleotides that are essentially identical or essentially complementary to SEQ ID NO:45 or 47, (c) the plant is a cotton plant, the gene or the transcript is a cotton Mildew Resistance Locus O (MLO) gene or transcript, and or the polynucleotide comprises at least 18 contiguous nucleotides that are essentially identical or essentially complementary to a cotton gene or transcript that encodes SEQ ID NO:4; (d) the plant is a barley plant, the gene or the transcript is a barley Mildew Resistance Locus O (MLO) gene or transcript, and the polynucleotide molecule is selected from the group consisting of SEQ ID NO:80-83, 184, 192, 194, and SEQ ID NO: 197-213, or the polynucleotide comprises at least 18 contiguous nucleotides that are essentially identical or essentially complementary to SEQ ID NO:29; (e) the plant is a cucumber plant, the gene or the transcript is a cucumber Mildew Resistance Locus O (MLO) gene or transcript, and the polynucleotide molecule is selected from the group consisting of SEQ ID NO:84-98, and SEQ ID NO:99, or the polynucleotide comprises at least 18 contiguous nucleotides that are essentially identical or essentially complementary to SEQ ID NO:31, 33, 35, or 37; (f) the plant is a lettuce plant, the gene or the transcript is a lettuce Mildew Resistance Locus O (MLO) gene or transcript, and the polynucleotide molecule is selected from the group consisting of SEQ ID NO:100-102, and SEQ ID NO:103, or the polynucleotide comprises at least 18 contiguous nucleotides that are essentially identical or essentially complementary to SEQ ID NO:39; (g) the plant is a pea plant, the gene or the transcript is a pea Mildew Resistance Locus O (MLO) gene or transcript, and the polynucleotide molecule is selected from the group consisting of SEQ ID NO:104-106, and SEQ ID NO:107, or the polynucleotide comprises at least 18 contiguous nucleotides that are essentially identical or essentially complementary to SEQ ID NO:41; (h) the plant is a *Medicago* plant, the gene or the transcript is a *Medicago* Mildew Resistance Locus O (MLO) gene or transcript, and the polynucleotide molecule is selected from the group consisting of SEQ ID NO:108-110, and SEQ ID NO:111, or the polynucleotide comprises at least 18 contiguous nucleotides that are essentially identical or essentially complementary to SEQ ID NO:43; (i) the plant is a pepper plant, the gene or the transcript is a pepper Mildew Resistance Locus O (MLO) gene or transcript, and the polynucleotide molecule is selected from the group consisting of SEQ ID NO:120-122, and SEQ ID NO:123, or the polynucleotide comprises at least 18 contiguous nucleotides that are essentially identical or essentially complementary to SEQ ID NO:49; (j) the plant is a tomato plant, the gene or the transcript is a tomato Mildew Resistance Locus O (MLO) gene or transcript, and the polynucleotide molecule is selected from the group consisting of SEQ ID NO:124-130, and SEQ ID NO:131, or the polynucleotide comprises at least 18 contiguous nucleotides that are essentially identical or essentially complementary to SEQ ID NO:51 or 53; (k) the plant is a wheat plant, the gene or the transcript is a wheat Mildew Resistance Locus O (MLO) gene or transcript, and the polynucleotide molecule is selected from the group consisting of SEQ ID NO:132-142, and SEQ ID NO:143, or the polynucleotide comprises at least 18 contiguous nucleotides that are essentially identical or essentially complementary to SEQ ID NO:55, 57 or 59; (l) the plant is a grape plant, the gene or the transcript is a grape Mildew Resistance Locus O (MLO) gene or transcript, and the polynucleotide molecule is selected from the group consisting of SEQ ID NO:144-158, and SEQ ID NO:159 or the polynucleotide comprises at least 18 contiguous nucleotides that are essentially identical or essentially complementary to SEQ ID NO:61, 63, 65, or 67; (m) the plant is a sorghum plant, the gene or the transcript is a sorghum Mildew Resistance Locus O (MLO) gene or transcript, and the polynucleotide molecule is selected from the group consisting of SEQ ID NO:164-166, and SEQ ID NO:167, or the polynucleotide comprises at least 18 contiguous nucleotides that are essentially identical or essentially complementary to SEQ ID NO:71; or, (n) the plant is a rice plant, the gene or the transcript is a rice Mildew Resistance Locus O (MLO) gene or transcript, and the polynucleotide molecule is selected from the group consisting of SEQ ID NO:168-182, and SEQ ID NO:183, or the polynucleotide comprises at least 18 contiguous nucleotides that are essentially identical or essentially complementary to SEQ ID NO:73, 75, 77, or 79.

A further embodiment of the invention is directed to a plant comprising an exogenous polynucleotide that comprises at least 18 contiguous nucleotides that are essentially identical or essentially complementary to a Mildew Resistance Locus O (MLO) gene or transcript of the gene, wherein the exogenous polynucleotide is not operably linked to a promoter or to a viral vector, is not integrated into the chromosomal DNA of the plant, and is not found in a non-transgenic plant; and, wherein the plant exhibits an improvement in fungal disease resistance and/or nematode resistance that results from suppression of the Mildew Resistance Locus O (MLO) gene. In certain embodiments, plant further comprises an organosilicone compound or a component thereof. In certain embodiments, the polynucleotide is selected from the group consisting of SEQ ID NO: 80-195, or comprises at least 18 contiguous nucleotides that are essentially identical or essentially complementary to SEQ ID NO: 29, 31, 33, 35, 37, 39, 41, 43, 45, 47, 49, 51, 53, 55, 57, 59, 61, 63, 65, 67, 69, 71, 73, 75, 77, or 79. In some embodiments, a polynucleotide that comprises a nucleotide sequence that is essentially identical or essentially complementary to at least 18 contiguous nucleotides of SEQ ID NO: 197-213 is provided. In some embodiments, the polynucleotide comprises a nucleotide sequence that is essentially identical or essentially complementary to SEQ ID NO: 197-213. In certain embodiments: (a) the plant is a corn plant, the gene or the transcript is a corn Mildew Resistance Locus O (MLO) gene or transcript, and the polynucleotide molecule is selected from the group consisting of SEQ ID NO: 160-162, and SEQ ID NO: 163, or the polynucleotide comprises at least 18 contiguous nucleotides that are essentially identical or essentially complementary to SEQ ID NO:68-69; (b) the plant is a soybean plant, the gene or the transcript is a soybean Mildew Resistance Locus O (MLO) gene or transcript, and the polynucleotide molecule is selected from the group consisting of SEQ ID NO: 112-118, and SEQ ID NO: 119, or the polynucleotide comprises at least 18 contiguous nucleotides that are essentially identical or essentially complementary to SEQ ID NO:45 or 47, (c) the plant is a cotton plant, the gene or the transcript is a cotton Mildew Resistance Locus O (MLO) gene or transcript, and or the polynucleotide comprises at least 18 contiguous nucleotides that are essentially identical or essentially complementary to a cotton gene or transcript that encodes SEQ ID NO:4; (d) the plant is a barley plant, the gene or the transcript is a barley Mildew Resistance Locus O (MLO) gene or transcript, and the polynucleotide molecule is selected from the group consisting of SEQ ID NO:80-83, 184, 192, and SEQ ID NO: 197-213, or the polynucleotide comprises at least 18 contiguous nucleotides that are essentially identical or essentially complementary to SEQ ID NO:29; (e) the plant is a cucumber plant, the gene or the transcript is a cucumber Mildew Resistance Locus O (MLO) gene or transcript, and the polynucleotide molecule is selected from the group consisting of SEQ ID NO:84-98, and SEQ ID NO:99, or the polynucleotide comprises at least 18 contiguous nucleotides that are essentially identical or essentially complementary to SEQ ID NO:31, 33, 35, or 37; (f) the plant is a lettuce plant, the gene or the transcript is a lettuce Mildew Resistance Locus O (MLO) gene or transcript, and the polynucleotide molecule is selected from the group consisting of SEQ ID NO:100-102, and SEQ ID NO:103, or the polynucleotide comprises at least 18 contiguous nucleotides that are essentially identical or essentially complementary to SEQ ID NO:39; (g) the plant is a pea plant, the gene or the transcript is a pea Mildew Resistance Locus O (MLO) gene or transcript, and the polynucleotide molecule is selected from the group consisting of SEQ ID NO:104-106, and SEQ ID NO:107, or the polynucleotide comprises at least 18 contiguous nucleotides that are essentially identical or essentially complementary to SEQ ID NO:41; (h) the plant is a *Medicago* plant, the gene or the transcript is a *Medicago* Mildew Resistance Locus O (MLO) gene or transcript, and the polynucleotide molecule is selected from the group consisting of SEQ ID NO:108-110, and SEQ ID NO:111, or the polynucleotide comprises at least 18 contiguous nucleotides that are essentially identical or essentially complementary to SEQ ID NO:43; (i) the plant is a pepper plant, the gene or the transcript is a pepper Mildew Resistance Locus O (MLO) gene or transcript, and the polynucleotide molecule is selected from the group consisting of SEQ ID NO:120-122, and SEQ ID NO:123, or the polynucleotide comprises at least 18 contiguous nucleotides that are essentially identical or essentially complementary to SEQ ID NO:49; (j) the plant is a tomato plant, the gene or the transcript is a tomato Mildew Resistance Locus O (MLO) gene or transcript, and the polynucleotide molecule is selected from the group consisting of SEQ ID NO:124-130, and SEQ ID NO:131, or the polynucleotide comprises at least 18 contiguous nucleotides that are essentially identical or essentially complementary to SEQ ID NO:51 or 53; (k) the plant is a wheat plant, the gene or the transcript is a wheat Mildew Resistance Locus O (MLO) gene or transcript, and the polynucleotide molecule is selected from the group consisting of SEQ ID NO:132-142, and SEQ ID NO:143, or the polynucleotide comprises at least 18 contiguous nucleotides that are essentially identical or essentially complementary to SEQ ID NO:55, 57 or 59; (l) the plant is a grape plant, the gene or the transcript is a grape Mildew Resistance Locus O (MLO) gene or transcript, and the polynucleotide molecule is selected from the group consisting of SEQ ID NO:144-158, and SEQ ID NO:159 or the polynucleotide comprises at least 18 contiguous nucleotides that are essentially identical or essentially complementary to SEQ ID NO:61, 63, 65, or 67; (m) the plant is a sorghum plant, the gene or the transcript is a sorghum Mildew Resistance Locus O (MLO) gene or transcript, and the polynucleotide molecule is selected from the group consisting of SEQ ID NO:164-166, and SEQ ID NO:167, or the polynucleotide comprises at least 18 contiguous nucleotides that are essentially identical or essentially complementary to SEQ ID NO:71; or, (n) the plant is a rice plant, the gene or the transcript is a rice Mildew Resistance Locus O (MLO) gene or transcript, and the polynucleotide molecule is selected from the group consisting of SEQ ID NO:168-182, and SEQ ID NO:183, or the polynucleotide comprises at least 18 contiguous nucleotides that are essentially identical or essentially complementary to SEQ ID NO:73, 75, 77, or 79.

An additional embodiment of the invention is directed to a plant part comprising an exogenous polynucleotide that comprises at least 18 contiguous nucleotides that are essentially identical or essentially complementary to a Mildew Resistance Locus O (MLO) gene or transcript of the gene, wherein the exogenous polynucleotide is not operably linked to a promoter or to a viral vector and is not found in a non-transgenic plant; and, wherein the plant part exhibits an improvement in fungal disease resistance and/or nematode resistance that results from suppression of the Mildew Resistance Locus O (MLO) gene. In certain embodiments, the polynucleotide is selected from the group consisting of SEQ ID NO: 80-195, or wherein the polynucleotide comprises at least 18 contiguous nucleotides that are essentially identical or essentially complementary to SEQ ID NO: 29, 31, 33, 35, 37, 39, 41, 43, 45, 47, 49, 51, 53, 55, 57, 59, 61, 63, 65, 67, 69, 71, 73, 75, 77, or 79. In some embodiments, a polynucleotide that comprises a nucleotide sequence that is essentially identical or essentially complementary to at least 18 contiguous nucleotides of SEQ ID NO: 197-213 is provided. In some embodiments, the polynucleotide comprises a nucleotide sequence that is essentially identical or essentially complementary to SEQ ID NO: 197-213. In certain embodiments: (a) the plant part is a corn plant part, the gene or the transcript is a corn Mildew Resistance Locus O (MLO) gene or transcript, and the polynucleotide molecule is selected from the group consisting of SEQ ID NO: 160-162, and SEQ ID NO: 163, or the polynucleotide comprises at least 18 contiguous nucleotides that are essentially identical or essentially complementary to SEQ ID NO:68-69; (b) the plant part is a soybean plant part, the gene or the transcript is a soybean Mildew Resistance Locus O (MLO) gene or transcript, and the polynucleotide molecule is selected from the group consisting of SEQ ID NO: 112-118, and SEQ ID NO: 119, or the polynucleotide comprises at least 18 contiguous nucleotides that are essentially identical or essentially complementary to SEQ ID NO:45 or 47, (c) the plant part is a cotton plant part, the gene or the transcript is a cotton Mildew Resistance Locus O (MLO) gene or transcript, and or the polynucleotide comprises at least 18 contiguous nucleotides that are essentially identical or essentially complementary to a cotton gene or transcript that encodes SEQ ID NO:4; (d) the plant part is a barley plant part, the gene or the transcript is a barley Mildew Resistance Locus O (MLO) gene or transcript, and the polynucleotide molecule is selected from the group consisting of SEQ ID NO:80-83, 184, 192, 194, and SEQ ID NO: 197-213, or the polynucleotide comprises at least 18 contiguous nucleotides that are essentially identical or essentially complementary to SEQ ID NO:29; (e) the plant part is a cucumber plant part, the gene or the transcript is a cucumber Mildew Resistance Locus O (MLO) gene or transcript, and the polynucleotide molecule is selected from the group consisting of SEQ ID NO:84-98, and SEQ ID NO:99, or the polynucleotide comprises at least 18 contiguous nucleotides that are essentially identical or essentially complementary to SEQ ID NO:31, 33, 35, or 37; (f) the plant part is a lettuce plant part, the gene or the transcript is a lettuce Mildew Resistance Locus O (MLO) gene or transcript, and the polynucleotide molecule is selected from the group consisting of SEQ ID NO:100-102, and SEQ ID NO:103, or the polynucleotide comprises at least 18 contiguous nucleotides that are essentially identical or essentially complementary to SEQ ID NO:39; (g) the plant part is a pea plant part, the gene or the transcript is a pea Mildew Resistance Locus O (MLO) gene or transcript, and the polynucleotide molecule is selected from the group consisting of SEQ ID NO:104-106, and SEQ ID NO:107, or the polynucleotide comprises at least 18 contiguous nucleotides that are essentially identical or essentially complementary to SEQ ID NO:41; (h) the plant part is a *Medicago* plant part, the gene or the transcript is a *Medicago* Mildew Resistance Locus O (MLO) gene or transcript, and the polynucleotide molecule is selected from the group consisting of SEQ ID NO:108-110, and SEQ ID NO:111, or the polynucleotide comprises at least 18 contiguous nucleotides that are essentially identical or essentially complementary to SEQ ID NO:43; (i) the plant part is a pepper plant part, the gene or the transcript is a pepper Mildew Resistance Locus O (MLO) gene or transcript, and the polynucleotide molecule is selected from the group consisting of SEQ ID NO:120-122, and SEQ ID NO:123, or the polynucleotide comprises at least 18 contiguous nucleotides that are essentially identical or essentially complementary to SEQ ID NO:49; (j) the plant part is a tomato plant part, the gene or the transcript is a tomato Mildew Resistance Locus O (MLO) gene or transcript, and the polynucleotide molecule is selected from the group consisting of SEQ ID NO:124-130, and SEQ ID NO:131, or the polynucleotide comprises at least 18 contiguous nucleotides that are essentially identical or essentially complementary to SEQ ID NO:51 or 53; (k) the plant part is a wheat plant part, the gene or the transcript is a wheat Mildew Resistance Locus O (MLO) gene or transcript, and the polynucleotide molecule is selected from the group consisting of SEQ ID NO:132-142, and SEQ ID NO:143, or the polynucleotide comprises at least 18 contiguous nucleotides that are essentially identical or essentially complementary to SEQ ID NO:55, 57 or 59; (l) the plant part is a grape plant part, the gene or the transcript is a grape Mildew Resistance Locus O (MLO) gene or transcript, and the polynucleotide molecule is selected from the group consisting of SEQ ID NO:144-158, and SEQ ID NO:159 or the polynucleotide comprises at least 18 contiguous nucleotides that are essentially identical or essentially complementary to SEQ ID NO:61, 63, 65, or 67; (m) the plant part is a sorghum plant part, the gene or the transcript is a sorghum Mildew Resistance Locus O (MLO) gene or transcript, and the polynucleotide molecule is selected from the group consisting of SEQ ID NO:164-166, and SEQ ID NO:167, or the polynucleotide comprises at least 18 contiguous nucleotides that are essentially identical or essentially complementary to SEQ ID NO:71; or, (n) the plant part is a rice plant part, the gene or the transcript is a rice Mildew Resistance Locus O (MLO) gene or transcript, and the polynucleotide molecule is selected from the group consisting of SEQ ID NO:168-182, and SEQ ID NO:, or the polynucleotide comprises at least 18 contiguous nucleotides that are essentially identical or essentially complementary to SEQ ID NO:73, 75, 77, or 79. In certain embodiments, the plant part is a flower, meristem, ovule, stem, tuber, fruit, anther, pollen, leaf, root, or seed. In certain embodiments, the plant part is a seed. Also provided are processed plant products obtained from any of the aforementioned plant parts, wherein the processed plant products exhibit an improved attribute relative to a processed plant product of an untreated control plant and wherein the improved attribute results from the improved fungal disease resistance and/or nematode resistance. In certain embodiments, the processed product is a meal, a pulp, a feed, or a food product. Another embodiment of the invention is directed to a plant that exhibits an improvement in fungal disease resistance and/or nematode resistance, wherein the plant was topically treated with a composition that comprises: (a) at least one polynucleotide that comprises at least 18 contiguous nucleotides that are essentially identical or essentially complementary to a Mildew Resistance Locus O (MLO) gene or to a transcript of the gene; and (b) a transfer agent; and, wherein the plant exhibits an improvement in fungal disease resistance and/or nematode resistance that results from suppression of the Mildew Resistance Locus O (MLO) gene.

DETAILED DESCRIPTION

I. Definitions

Figure 1:
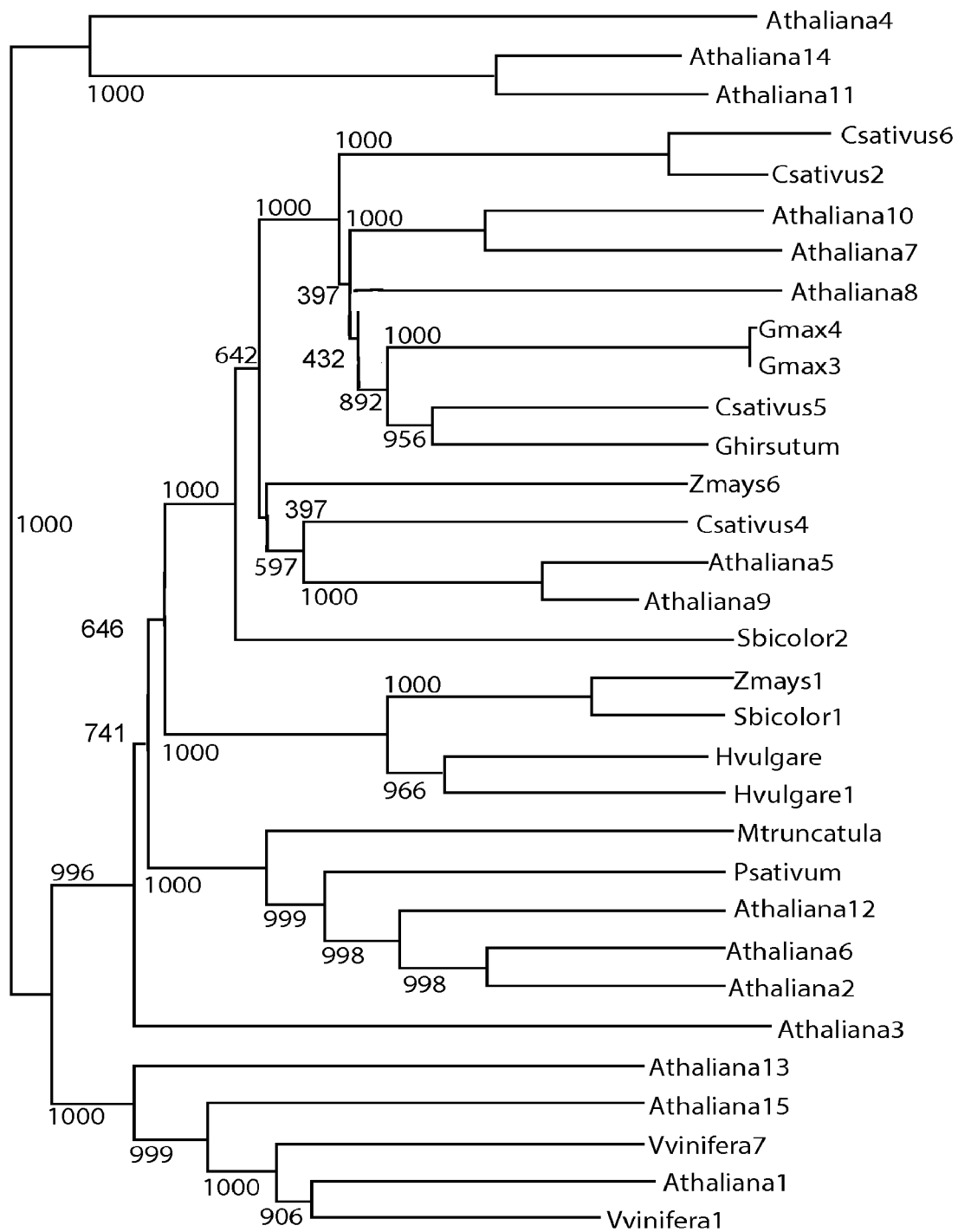
FIG. 1 presents a bootstrapped phylogenetic tree of MLO proteins

The following definitions and methods are provided to better define the present invention and to guide those of ordinary skill in the art in the practice of the present invention. Unless otherwise noted, terms are to be understood according to conventional usage by those of ordinary skill in the relevant art.

Where a term is provided in the singular, the inventors also contemplate aspects of the invention described by the plural of that term.

As used herein, the terms "DNA," "DNA molecule," and "DNA polynucleotide molecule" refer to a single-stranded DNA or double-stranded DNA molecule of genomic or synthetic origin, such as, a polymer of deoxyribonucleotide bases or a DNA polynucleotide molecule.

As used herein, the terms "DNA sequence," "DNA nucleotide sequence," and "DNA polynucleotide sequence" refer to the nucleotide sequence of a DNA molecule.

As used herein, the term "gene" refers to any portion of a nucleic acid that provides for expression of a transcript or encodes a transcript. A "gene" thus includes, but is not limited to, a promoter region, 5' untranslated regions, transcript encoding regions that can include intronic regions, and 3' untranslated regions.

As used herein, the terms "RNA," "RNA molecule," and "RNA polynucleotide molecule" refer to a single-stranded RNA or double-stranded RNA molecule of genomic or synthetic origin, such as, a polymer of ribonucleotide bases that comprise single or double stranded regions.

Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, a "plant surface" refers to any exterior portion of a plant. Plant surfaces thus include, but are not limited to, the surfaces of flowers, stems, tubers, fruit, anthers, pollen, leaves, roots, or seeds. A plant surface can be on a portion of a plant that is attached to other portions of a plant or on a portion of a plant that is detached from the plant.

As used herein, the phrase "polynucleotide is not operably linked to a promoter" refers to a polynucleotide that is not covalently linked to a polynucleotide promoter sequence that is specifically recognized by either a DNA dependent RNA polymerase II protein or by a viral RNA dependent RNA polymerase in such a manner that the polynucleotide will be transcribed by the DNA dependent RNA polymerase II protein or viral RNA dependent RNA polymerase. A polynucleotide that is not operably linked to a promoter can be transcribed by a plant RNA dependent RNA polymerase.

As used herein, any polynucleotide sequences of SEQ ID NO: 80-195, though displayed in the sequence listing in the form of ssDNA, encompass all other polynucleotide forms such as dsDNA equivalents, ssDNA equivalents, ssRNA equivalents, ssRNA complements, dsRNA, and ssDNA complements.

As used herein, any polynucleotide sequences of SEQ ID NO: 197-213, though displayed in the sequence listing in the form of one strand of a dsRNA molecule, encompass all other polynucleotide forms such as dsDNA equivalents, ssDNA equivalents, ssRNA equivalents, ssRNA complements, dsRNA, and ssDNA complements.

As used herein, a first nucleic-acid sequence is "operably" connected or "linked" with a second nucleic acid sequence when the first nucleic acid sequence is placed in a functional relationship with the second nucleic acid sequence. For instance, a promoter is operably linked to an RNA and/or protein-coding sequence if the promoter provides for transcription or expression of the RNA or coding sequence. Generally, operably linked DNA sequences are contiguous and, where necessary to join two protein-coding regions, are in the same reading frame.

As used herein, the phrase "organosilicone preparation" refers to a liquid comprising one or more organosilicone compounds, wherein the liquid or components contained therein, when combined with a polynucleotide in a composition that is topically applied to a target plant surface, enable the polynucleotide to enter a plant cell. Examples of organosilicone preparations include, but are not limited to, preparations marketed under the trade names "Silwet®" or "BREAK-THRU®" and preparations provided in Table 1. In certain embodiments, an organosilicone preparation can enable a polynucleotide to enter a plant cell in a manner permitting a polynucleotide suppression of target gene expression in the plant cell.

As used herein, the phrase "provides for an improvement in fungal disease resistance and/or nematode resistance" refers to any measurable increase in a plant's resistance to fungal- and/or nematode-induced damage. In certain embodiments, an improvement in fungal disease resistance and/or nematode resistance in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants.

As used herein, the phrase "provides for a reduction", when used in the context of a transcript or a protein in a plant or plant part, refers to any measurable decrease in the level of transcript or protein in a plant or plant part. In certain embodiments, a reduction of the level of a transcript or protein in a plant or plant part can be determined in comparison to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the phrase "wherein said plant does not comprise a transgene" refers to a plant that lacks either a DNA molecule comprising a promoter that is operably linked to an exogenous polynucleotide or a recombinant viral vector.

As used herein, the phrase "suppressing expression" or "suppression", when used in the context of a gene, refers any measurable decrease in the amount and/or activity of a product encoded by the gene. Thus, expression of a gene can be suppressed when there is a reduction in levels of a transcript from the gene, a reduction in levels of a protein encoded by the gene, a reduction in the activity of the transcript from the gene, a reduction in the activity of a protein encoded by the gene, any one of the preceding conditions, or any combination of the preceding conditions. In this context, the activity of a transcript includes, but is not limited to, its ability to be translated into a protein and/or to exert any RNA-mediated biologic or biochemical effect. In this context, the activity of a protein includes, but is not limited to, its ability to exert any protein-mediated biologic or biochemical effect. In certain embodiments, a suppression of gene expression in a plant or plant part can be determined in a comparison of gene product levels or activities in a treated plant to a control plant or plant part. When used in this context, a control plant or plant part is a plant or plant part that has not undergone treatment with a composition comprising a polynucleotide and a transfer agent. Such control plants or plant parts would include, but are not limited to, untreated or mock treated plants and plant parts.

As used herein, the term "transcript" corresponds to any RNA that is produced from a gene by the process of transcription. A transcript of a gene can thus comprise a primary transcription product which can contain introns or can comprise a mature RNA that lacks introns.

As used herein, the term "liquid" refers to both homogeneous mixtures such as solutions and non-homogeneous mixtures such as suspensions, colloids, micelles, and emulsions.

II. Overview

Provided herein are certain methods and polynucleotide compositions that can be applied to living plant cells/tissues to suppress expression of target genes and that provide improved fungal disease resistance and/or nematode resistance to a crop plant. Also provided herein are plants and plant parts exhibiting fungal disease resistance and/or nematode resistance as well as processed products of such plants or plant parts. The compositions may be topically applied to the surface of a plant, such as to the surface of a leaf, and include a transfer agent. Aspects of the method can be applied to various crops, for example, including but not limited to: i) row crop plants including, but are not limited to, corn, barley, sorghum, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e.g., an ornamental flowering plant or shrub or turf grass). The methods and compositions provided herein can also be applied to plants produced by a cutting, cloning, or grafting process (i.e., a plant not grown from a seed) that include fruit trees and plants. Fruit trees produced by such processes include, but are not limited to, citrus and apple trees. Plants produced by such processes include, but are not limited to, avocados, tomatoes, eggplant, cucumber, melons, watermelons, and grapes as well as various ornamental plants.

Without being bound by a particular theory, the compositions and methods of the present invention are believed to operate through one or more of the several natural cellular pathways involved in RNA-mediated gene suppression as generally described in Brodersen and Voinnet (2006), *Trends Genetics,* 22:268-280; Tomari and Zamore (2005) *Genes & Dev.,* 19:517-529; Vaucheret (2006) *Genes Dev.,* 20:759-771; Meins et al. (2005) *Annu. Rev. Cell Dev. Biol.,* 21:297-318; and Jones-Rhoades et al. (2006) *Annu. Rev. Plant Biol.,* 57:19-53. RNA-mediated gene suppression generally involves a double-stranded RNA (dsRNA) intermediate that is formed intra-molecularly within a single RNA molecule or inter-molecularly between two RNA molecules. This longer dsRNA intermediate is processed by a ribonuclease of the RNAase III family (Dicer or Dicer-like ribonuclease)

to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 to 24 base pairs (See, Hamilton et al. (2002) *EMBO J.*, 21:4671-4679).

Polynucleotides

As used herein, "polynucleotide" refers to a DNA or RNA molecule containing multiple nucleotides and generally refers both to "oligonucleotides" (a polynucleotide molecule of 18-25 nucleotides in length) and longer polynucleotides of 26 or more nucleotides. Embodiments of this invention include compositions including polynucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

Polynucleotide compositions used in the various embodiments of this invention include compositions including: RNA or DNA or RNA/DNA hybrids or chemically modified polynucleotides or a mixture thereof. In certain embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of a polynucleotide which can be partially or completely modified with phosphorothioate, phosphorodithioate, or methylphosphonate internucleotide linkage modifications, modified nucleoside bases or modified sugars can be used in polynucleotide synthesis, and polynucleotides can be labeled with a fluorescent moiety (e.g., fluorescein or rhodamine) or other label (e.g., biotin).

Polynucleotides can be single- or double-stranded RNA, single- or double-stranded DNA, double-stranded DNA/RNA hybrids, and modified analogues thereof. In certain embodiments of the invention, the polynucleotides that provide single-stranded RNA in the plant cell may be: (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, and (i) a double-stranded, hybridized RNA/DNA molecule, or combinations thereof. In certain embodiments, these polynucleotides can comprise both ribonucleic acid residues and deoxyribonucleic acid residues. In certain embodiments, these polynucleotides include chemically modified nucleotides or non-canonical nucleotides. In certain embodiments of the methods, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In certain embodiments where the polynucleotide is a dsRNA, the anti-sense strand will comprise at least 18 nucleotides that are essentially complementary to the target gene. In certain embodiments the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain embodiments, the polynucleotides can be operably linked to a promoter—generally a promoter functional in a plant, for example, a pol II promoter, a pol III promoter, a pol IV promoter, or a pol V promoter.

The polynucleotide molecules of the present invention are designed to modulate expression by inducing regulation or suppression of an endogenous gene in a plant and are designed to have a nucleotide sequence essentially identical or essentially complementary to the nucleotide sequence of an endogenous gene of a plant or to the sequence of RNA transcribed from an endogenous gene of a plant, which can be coding sequence or non-coding sequence. These effective polynucleotide molecules that modulate expression are referred to herein as "a trigger, or triggers". By "essentially identical" or "essentially complementary" it is meant that the trigger polynucleotides (or at least one strand of a double-stranded polynucleotide) have sufficient identity or complementarity to the endogenous gene or to the RNA transcribed from the endogenous gene (e.g. the transcript) to suppress expression of the endogenous gene (e.g., to effect a reduction in levels or activity of the gene transcript and/or encoded protein). Polynucleotides of the methods and compositions provided herein need not have 100 percent identity or complementarity to the endogenous gene or to the RNA transcribed from the endogenous gene (i.e. the transcript) to suppress expression of the endogenous gene (i.e. to effect a reduction in levels or activity of the gene transcript or encoded protein). Thus, in certain embodiments, the polynucleotide or a portion thereof is designed to be essentially identical to, or essentially complementary to, a sequence of at least 18 or 19 contiguous nucleotides in either the target gene or messenger RNA transcribed from the target gene (e.g. the transcript). In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene (e.g. the transcript). In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

In certain embodiments, polynucleotides used in the methods and compositions provided herein can be essentially identical or essentially complementary to any of: i) conserved regions of Mildew Resistance Locus O (MLO) genes of both monocot and dicot plants; ii) conserved regions of Mildew Resistance Locus O (MLO) genes of monocot plants; or iii) conserved regions of Mildew Resistance Locus O (MLO) genes of dicot plants. Such polynucleotides that are essentially identical or essentially complementary to such conserved regions can be used to improve fungal disease resistance and/or nematode disease resistance by suppressing expression of Mildew Resistance Locus O (MLO) genes in any of: i) both dicot and monocot plants, including, but not limited to, corn, barley, wheat, sorghum, rice, cucumber, pea, *Medicago* sp., soybean, pepper, tomato, and grape; ii) monocot plants, including, but not limited to, corn, barley, wheat, sorghum, and rice, and; or iii) dicot plants, including, but not limited to, cucumber, pea, *Medicago* sp., soybean, pepper, tomato, and grape.

Polynucleotides containing mismatches to the target gene or transcript can thus be used in certain embodiments of the compositions and methods provided herein. In certain embodiments, a polynucleotide can comprise at least 19 contiguous nucleotides that are essentially identical or essentially complementary to said gene or said transcript or comprises at least 19 contiguous nucleotides that are essentially identical or essentially complementary to the target gene or target gene transcript. In certain embodiments, a polynucleotide of 19 continuous nucleotides that is essentially identical or essentially complementary to the endogenous target gene or to RNA transcribed from the target gene (e.g. the transcript) can have 1 or 2 mismatches to the target gene or transcript. In certain embodiments, a polynucleotide of 20 or more nucleotides that contains a contiguous 19 nucleotide span of identity or complementarity to the endogenous target gene or to an RNA transcribed from the target gene can have 1 or 2 mismatches to the target gene or transcript. In certain embodiments, a polynucleotide of 21 continuous nucleotides that is essentially identical or essentially complementary to the endogenous target gene or to RNA transcribed from the target gene (e.g. the transcript) can have 1, 2, or 3 mismatches to the target gene or transcript. In certain embodiments, a polynucleotide of 22 or more nucleotides that contains a contiguous 21 nucleotide span of identity or complementarity to the endogenous target gene or to an RNA transcribed from the target gene can have 1, 2, or 3 mismatches to the target gene or transcript. In designing polynucleotides with mismatches to an endogenous target gene or to an RNA transcribed from the target gene, mismatches of certain types and at certain positions that are more likely to be tolerated can be used. In certain embodiments, mismatches formed between adenine and cytosine or guanosine and uracil residues are used as described by Du et al. Nucleic Acids Research, 2005, Vol. 33, No. 5 1671-1677. In certain embodiments, mismatches in 19 base pair overlap regions can be at the low tolerance positions 5, 7, 8 or 11 (from the 5' end of a 19 nucleotide target) with well tolerated nucleotide mismatch residues, at medium tolerance positions 3, 4, and 12-17, and/or at the high tolerance nucleotide positions at either end of the region of complementarity (i.e. positions 1, 2, 18, and 19) as described by Du et al. Nucleic Acids Research, 2005, Vol. 33, No. 5 1671-1677. It is further anticipated that tolerated mismatches can be empirically determined in assays where the polynucleotide is applied to the plants via the methods provided herein and the treated plants assayed for suppression of Mildew Resistance Locus O (MLO) expression or appearance of fungal disease resistance and/or nematode resistance.

In certain embodiments, polynucleotide molecules are designed to have 100 percent sequence identity with or complementarity to one allele or one family member of a given target gene coding or non-coding sequence of a MLO target gene. In other embodiments, the polynucleotide molecules are designed to have 100 percent sequence identity with or complementarity to multiple alleles or family members of a given Mildew Resistance Locus O (MLO) target gene. In certain embodiments, the polynucleotide can thus comprises at least 18 contiguous nucleotides that are identical or complementary to SEQ ID NO: 4, 29, 31, 33, 35, 37, 39, 41, 43, 45, 47, 49, 51, 53, 55, 57, 59, 61, 63, 65, 67, 69, 71, 73, 75, 77, or 79. In certain embodiments, the polynucleotide comprises at least 18 contiguous nucleotides that are essentially identical or essentially complementary to SEQ ID NO: 29, 31, 33, 35, 37, 39, 41, 43, 45, 47, 49, 51, 53, 55, 57, 59, 61, 63, 65, 67, 69, 71, 73, 75, 77, or 79.

In certain embodiments, polynucleotide compositions and methods provided herein typically effect regulation or modulation (e.g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue. In certain embodiments, methods of systemically suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or a transcript encoding a Mildew Resistance Locus O (MLO) gene of the plant are provided, whereby expression of the gene in said plant or progeny thereof is systemically suppressed in comparison to a control plant that has not been treated with the composition.

Compositions used to suppress a target gene can comprise one or more polynucleotides that are essentially identical or essentially complementary to multiple genes, or to multiple segments of one or more genes. In certain embodiments, compositions used to suppress a target gene can comprise one or more polynucleotides that are essentially identical or essentially complementary to multiple consecutive segments of a target gene, multiple non-consecutive segments of a target gene, multiple alleles of a target gene, or multiple target genes from one or more species.

In certain embodiments, the polynucleotide includes two or more copies of a nucleotide sequence (of 18 or more nucleotides) where the copies are arranged in tandem fashion. In another embodiment, the polynucleotide includes two or more copies of a nucleotide sequence (of 18 or more nucleotides) where the copies are arranged in inverted repeat fashion (forming an at least partially self-complementary strand). The polynucleotide can include both tandem and inverted-repeat copies. Whether arranged in tandem or inverted repeat fashion, each copy can be directly contiguous to the next, or pairs of copies can be separated by an optional spacer of one or more nucleotides. The optional spacer can be unrelated sequence (i.e., not essentially identical to or essentially complementary to the copies, nor essentially identical to, or essentially complementary to, a sequence of 18 or more contiguous nucleotides of the endogenous target gene or RNA transcribed from the endogenous target gene). Alternatively the optional spacer can include sequence that is complementary to a segment of the endogenous target gene adjacent to the segment that is targeted by the copies. In certain embodiments, the polynucleotide includes two copies of a nucleotide sequence of between about 20 to about 30 nucleotides, where the two copies are separated by a spacer no longer than the length of the nucleotide sequence.

Tiling

Polynucleotide trigger molecules can be identified by "tiling" gene targets in random length fragments, e.g., 200-300 polynucleotides in length, with partially overlapping regions, e.g., 25 or so nucleotide overlapping regions along the length of the target gene. Multiple gene target sequences can be aligned and polynucleotide sequence regions with homology in common are identified as potential trigger molecules for multiple targets. Multiple target sequences can be aligned and sequence regions with poor homology are identified as potential trigger molecules for selectively distinguishing targets. To selectively suppress a single gene, trigger sequences may be chosen from regions that are unique to the target gene either from the transcribed region or the non-coding regions, e.g., promoter regions, 3' untranslated regions, introns and the like.

Polynucleotides fragments are designed along the length of the full length coding and untranslated regions of a MLO gene or family member as contiguous overlapping fragments of 200-300 polynucleotides in length or fragment lengths representing a percentage of the target gene. These fragments are applied topically (as sense or anti-sense ssDNA or ssRNA, dsRNA, or dsDNA) to determine the relative effectiveness in providing the yield/quality phenotype. Fragments providing the desired activity may be further subdivided into 50-60 polynucleotide fragments which are evaluated for providing the yield/quality phenotype. The 50-60 base fragments with the desired activity may then be further subdivided into 19-30 base fragments which are evaluated for providing the yield/quality phenotype. Once relative effectiveness is determined, the fragments are utilized singly, or in combination in one or more pools to determine effective trigger composition or mixture of trigger polynucleotides for providing the yield/quality phenotype.

Coding and/or non-coding sequences of gene families in the crop of interest are aligned and 200-300 polynucleotide fragments from the least homologous regions amongst the aligned sequences are evaluated using topically applied polynucleotides (as sense or anti-sense ssDNA or ssRNA, dsRNA, or dsDNA) to determine their relative effectiveness in providing the yield/quality phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the yield/quality phenotype. Once relative effectiveness is determined, the fragments are utilized singly, or again evaluated in combination with one or more other fragments to determine the trigger composition or mixture of trigger polynucleotides for providing the yield/quality phenotype.

Coding and/or non-coding sequences of gene families in the crop of interest are aligned and 200-300 polynucleotide fragments from the most homologous regions amongst the aligned sequences are evaluated using topically applied polynucleotides (as sense or anti-sense ssDNA or ssRNA, dsRNA, or dsDNA) to determine their relative effectiveness in inducing the yield/quality phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the yield/quality phenotype. Once relative effectiveness is determined, the fragments may be utilized singly, or in combination with one or more other fragments to determine the trigger composition or mixture of trigger polynucleotides for providing the yield/quality phenotype.

Also, provided herein are methods for identifying a preferred polynucleotide for improving fungal disease and/or nematode resistance in a plant. Populations of candidate polynucleotides that are essentially identical or essentially complementary to a MLO gene or transcript of the gene can be generated by a variety of approaches, including but not limited to, any of the tiling, least homology, or most homology approaches provided herein. Such populations of polynucleotides can also be generated or obtained from any of the polynucleotides or genes provided herewith in SEQ ID NO: 29, 31, 33, 35, 37, 39, 41, 42, 43, 45, 47, 49, 51, 53, 55, 57, 59, 61, 63, 65, 67, 69, 71, 73, 75, 77, or 79. Such populations of polynucleotides can also be generated or obtained from any genes that are orthologous to the genes provided herewith in SEQ ID NO: 29, 31, 33, 35, 37, 39, 41, 42, 43, 45, 47, 49, 51, 53, 55, 57, 59, 61, 63, 65, 67, 69, 71, 73, 75, 77, or 79. Such populations of polynucleotides can also be generated or obtained from any genes that encode proteins that are orthologous to a protein of Table 2 or 3 (SEQ ID NO:1-27, 28, 30, 32, 34, 36, 38, 40, 42, 44, 46, 48, 50, 52, 54, 56, 58, 60, 62, 64, 66, 68, 70, 72, 74, 76, or 78). Such polynucleotides can be topically applied to a surface of plants in a composition comprising at least one polynucleotide from said population and a transfer agent to obtain treated plants. Treated plants that exhibit suppression of the MLO gene and/or exhibit an improvement fungal disease and/or nematode resistance are identified, thus identifying a preferred polynucleotide that improves improving fungal disease and/or nematode resistance in a plant. Suppression of the gene can be determined by any assay for the levels and/or activity of a gene product (i.e., transcript or protein). Suitable assays for transcripts include, but are not limited to, semi-quantitative or quantitative reverse transcriptase PCR® (qRT-PCR) assays. Suitable assays for proteins include, but are not limited to, semi-quantitative or quantitative immunoassays, biochemical activity assays, or biological activity assays. In certain embodiments, the polynucleotides can be applied alone. In other embodiments, the polynucleotides can be applied in pools of multiple polynucleotides. When a pool of polynucleotides provides for suppression of the MLO gene and/or an improvement in fungal disease resistance and/or nematode disease resistance are identified, the pool can be de-replicated and retested as necessary or desired to identify one or more preferred polynucleotide(s) that improves fungal disease resistance and/or nematode disease resistance in a plant.

Methods of making polynucleotides are well known in the art. Such methods of making polynucleotides can include in vivo biosynthesis, in vitro enzymatic synthesis, or chemical synthesis. In certain embodiments, RNA molecules can be made by either in vivo or in vitro synthesis from DNA templates where a suitable promoter is operably linked to the polynucleotide and a suitable DNA-dependent RNA polymerase is provided. DNA-dependent RNA polymerases include, but are not limited to, $E.\ coli$ or other bacterial RNA polymerases as well as the bacteriophage RNA polymerases such as the T7, T3, and SP6 RNA polymerases. Commercial preparation of polynucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end that encodes a bacteriophage T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score (Reynolds et al. Nature Biotechnology 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments, the sequence of a polynucleotide is screened against the genomic DNA of the intended plant to minimize unintentional silencing of other genes.

While there is no upper limit on the concentrations and dosages of polynucleotide molecules that can be useful in the methods and compositions provided herein, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotide molecules is about 1 nanomole (nmol) of polynucleotide molecules per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a ssDNA polynucleotide are applied. In certain embodiments, about 0.5 nmol to about 2 nmol of a dsRNA is applied. In certain embodiments, a composition containing about 0.5 to about 2.0 mg/mL, or about 0.14 mg/mL of dsRNA or ssDNA (21-mer) is applied. In certain embodiments, a composition of about 0.5 to about 1.5 mg/mL of a long dsRNA polynucleotide (i.e., about 50 to about 200 or more nucleotides) is applied. In certain embodiments, about 1 nmol to about 5 nmol of a dsRNA is applied to a plant. In certain embodiments, the polynucleotide composition as topically applied to the plant contains the at least one polynucleotide at a concentration of about 0.01 to about 10 milligrams per milliliter, or about 0.05 to about 2 milligrams per milliliter, or about 0.1 to about 2 milligrams per milliliter. In certain embodiments, a composition of about 0.5 to about 1.5 mg/mL of a long dsRNA polynucleotide (i.e. about 50 to about 200 or more nucleotides) is applied. Very large plants, trees, or vines may require correspondingly larger amounts of polynucleotides. When using long dsRNA molecules that can be processed into multiple polynucleotides, lower concentrations can be used. To illustrate embodiments of the invention, the factor 1×, when applied to polynucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The polynucleotide compositions of this invention are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e.g., seeds, leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the 9$^{th}$ Compendium of Herbicide Adjuvants, publicly available on the worldwide web (internet) at herbicide-.adjuvants.com can be used, e.g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL.REG.NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided. In certain embodiments of the methods and compositions provided herein, a composition that comprises a polynucleotide molecule and an organosilicone preparation comprising Silwet L-77 in the range of about 0.3 to about 1 percent by weight (wt percent) or about 0.5 to about 1%. by weight (wt percent) is used or provided.

In certain embodiments, any of the commercially available organosilicone preparations provided in the following Table 1 can be used as transfer agents in a polynucleotide composition. In certain embodiments where an organosilicone preparation of Table 1 is used as a pre-spray treatment of plant leaves or other surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation of Table 1 in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

TABLE 1

Examples of organosilicone preparations

| Name | CAS number | Manufacturer[1,2] |
|---|---|---|
| BREAK-THRU ® S 321 | na | Evonik Industries AG |
| BREAK-THRU ® S 200 | 67674-67-3 | Evonik Industries AG |
| BREAK-THRU ® OE 441 | 68937-55-3 | Evonik Industries AG |
| BREAK-THRU ® S 278 | 27306-78-1 | Evonik Goldschmidt |
| BREAK-THRU ® S 243 | na | Evonik Industries AG |
| Silwet ® L-77 | 27306-78-1 | Momentive Performance Materials |
| Silwet ® HS 429 | na | Momentive Performance Materials |
| Silwet ® HS 312 | na | Momentive Performance Materials |
| BREAK-THRU ® S 233 | 134180-76-0 | Evonik Industries AG |
| Silwet ® HS 508 | | Momentive Performance Materials |
| Silwet ® HS 604 | | Momentive Performance Materials |

[1]Evonik Industries AG, Essen, Germany
[2]Momentive Performance Materials, Albany, New York Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of a target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

(Compound I: polyalkyleneoxide heptamethyltrisiloxane, average n=7.5).

One organosilicone compound believed to be ineffective comprises the formula:

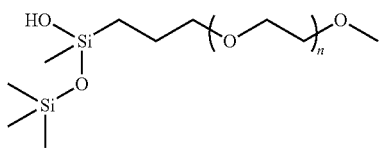

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, the polynucleotide compositions that comprise an organosilicone preparation can comprise a salt such as ammonium chloride, tetrabutylphosphonium bromide, and/or ammonium sulfate. Ammonium chloride, tetrabutylphosphonium bromide, and/or ammonium sulfate can be provided in the polynucleotide composition at a concentration of about 0.5% to about 5% (w/v). An ammonium chloride, tetrabutylphosphonium bromide, and/or ammonium sulfate concentration of about 1% to about 3%, or about 2% (w/v) can also be used in the polynucleotide compositions that comprise an organosilicone preparation. In certain embodiments, the polynucleotide compositions can comprise an ammonium salt at a concentration greater or equal to 300 millimolar. In certain embodiments, the polynucleotide compositions that comprise an organosilicone preparation can comprise ammonium sulfate at concentrations from about 80 to about 1200 mM or about 150 mM to about 600 mM.

In certain embodiments, the polynucleotide compositions can also comprise a phosphate salt. Phosphate salts used in the compositions include, but are not limited to, calcium, magnesium, potassium, or sodium phosphate salts. In certain embodiments, the polynucleotide compositions can comprise a phosphate salt at a concentration of at least about 5 millimolar, at least about 10 millimolar, or at least about 20 millimolar. In certain embodiments, the polynucleotide compositions will comprise a phosphate salt in a range of about 1 mM to about 25 mM or in a range of about 5 mM to about 25 mM. In certain embodiments, the polynucleotide compositions can comprise sodium phosphate at a concentration of at least about 5 millimolar, at least about 10 millimolar, or at least about 20 millimolar. In certain embodiments, the polynucleotide compositions can comprise sodium phosphate at a concentration of about 5 millimolar, about 10 millimolar, or about 20 millimolar. In certain embodiments, the polynucleotide compositions will comprise a sodium phosphate salt in a range of about 10 mM to about 160 mM or in a range of about 20 mM to about 40 mM. In certain embodiments, the polynucleotide compositions can comprise a sodium phosphate buffer at a pH of about 6.8.

In certain embodiments, other useful transfer agents or adjuvants to transfer agents that can be used in polynucleotide compositions provided herein include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the polynucleotide compositions that comprise a transfer agent are formulated with counter-ions or other molecules that are known to associate with nucleic acid molecules. Illustrative examples include, but are not limited to, tetraalkyl ammonium ions, trialkyl ammonium ions, sulfonium ions, lithium ions, and polyamines such as spermine, spermidine, or putrescine. In certain embodiments, the polynucleotide compositions are formulated with a non-polynucleotide herbicide. Non-polynucleotide herbicidal molecules include, but are not limited to, glyphosate, auxin-like benzoic acid herbicides including dicamba, chloramben and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrionogen oxidase inhibitors, and 4-hydroxyphenyl-pyruvate-dioxygenase inhibiting herbicides.

In certain embodiments, the polynucleotides used in the compositions that are essentially identical or essentially complementary to the MLO target gene or transcript will comprise the predominant nucleic acid in the composition. Thus in certain embodiments, the polynucleotides that are essentially identical or essentially complementary to the target gene or transcript will comprise at least about 50%, 75%, 95%, 98%, or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

Polynucleotides comprising ssDNA, dsDNA, ssRNA, dsRNA, or RNA/DNA hybrids that are essentially identical or complementary to certain plant target genes or transcripts and that can be used in compositions containing transfer agents that include, but are not limited to, organosilicone preparations, to suppress those target genes when topically applied to plants are disclosed in co-assigned U.S. patent application Ser. No. 13/042,856. Various polynucleotide herbicidal molecules, compositions comprising those polynucleotide herbicidal molecules and transfer agents that include, but are not limited to, organosilicone preparations, and methods whereby herbicidal effects are obtained by the topical application of such compositions to plants are also disclosed in co-assigned U.S. patent application Ser. No. 13/042,856, and those polynucleotide herbicidal molecules, compositions, and methods are incorporated herein by reference in their entireties. Genes encoding proteins that can provide tolerance to an herbicide and/or that are targets of a herbicide are collectively referred to herein as "herbicide target genes". Herbicide target genes include, but are not limited to, a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase, a cellulose synthase, a beta tubulin, and a serine hydroxymethyltransferase gene. The effects of applying certain compositions comprising polynucleotides that are essentially identical or complementary to certain herbicide target genes and transfer agents on plants containing the herbicide target genes was shown to be potentiated or enhanced by subsequent application of an herbicide that targets the same gene as the polynucleotide in co-assigned U.S. patent application Ser. No. 13/042,856. For example, compositions comprising polynucleotides targeting the EPSPS herbicide target gene were potentiated by glyphosate in experiments disclosed in co-assigned U.S. patent application Ser. No. 13/042,856.

In certain embodiments of the compositions and methods disclosed herein, the composition comprising a polynucleotide and a transfer agent can thus further comprise a second polynucleotide comprising at least 19 contiguous nucleotides that are essentially identical or essentially complementary to a transcript to a protein that confers resistance to a herbicide. In certain embodiments, the second polynucleotide does not comprise a polynucleotide that is essentially identical or essentially complementary to a transcript encoding a protein of a target plant that confers resistance to said herbicidal molecule. Thus, in an exemplary and non-limiting embodiment, the second polynucleotide could be essentially identical or essentially complementary to a transcript encoding a protein that confers resistance to a herbicide in a weed (such as an EPSPS encoding transcript) but would not be essentially identical or essentially complementary to a transcript encoding a protein that confers resistance to that same herbicide in a crop plant.

In certain embodiments, the polynucleotide compositions that comprise a transfer agent can comprise glycerin. Glycerin can be provided in the composition at a concentration of about 0.1% to about 1% (w/v or v/v). A glycerin concentration of about 0.4% to about 0.6%, or about 0.5% (w/v or v/v) can also be used in the polynucleotide compositions that comprise a transfer agent.

In certain embodiments, the polynucleotide compositions that comprise a transfer agent can further comprise organic solvents. Such organic solvents include, but are not limited to, DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions).

In certain embodiments, the polynucleotide compositions that comprise a transfer agent can further comprise naturally derived or synthetic oils with or without surfactants or emulsifiers. Such oils include, but are not limited to, plant-sourced oils, crop oils (such as those listed in the 9th Compendium of Herbicide Adjuvants, publicly available on line at www.herbicide.adjuvants.com), paraffinic oils, polyol fatty acid esters, or oils with short-chain molecules modified with amides or polyamines such as polyethyleneimine or N-pyrrolidine.

In aspects of the invention, methods include one or more applications of the composition comprising a polynucleotide and a transfer agent or one or more effective components contained therein. In certain embodiments of the methods, one or more applications of a transfer agent or one or more effective components contained therein can precede one or more applications of the composition comprising a polynucleotide and a transfer agent. In embodiments where a transfer agent and/or one or more effective molecules contained therein is used either by itself as a pre-treatment or as part of a composition that includes a polynucleotide, embodiments of the polynucleotide molecules are double-stranded RNA polynucleotides, single-stranded RNA polynucleotides, double-stranded DNA polynucleotides, single-stranded DNA polynucleotides, chemically modified RNA or DNA polynucleotides or mixtures thereof.

Compositions and methods of the invention are useful for modulating or suppressing the expression of an endogenous Mildew Resistance Locus O (MLO) target gene or transgenic Mildew Resistance Locus O (MLO) target gene in a plant cell or plant. In certain embodiments of the methods and compositions provided herein, expression of MLO target genes can be suppressed completely, partially and/or transiently to result in an improvement in in fungal disease resistance and/or nematode resistance. In various embodiments, a Mildew Resistance Locus O (MLO) target gene includes coding (protein-coding or translatable) sequence, non-coding (non-translatable) sequence, or both coding and non-coding sequence. Compositions of the invention can include polynucleotides designed to target multiple Mildew Resistance Locus O (MLO) genes, or multiple segments of one or more Mildew Resistance Locus O (MLO) genes. The target gene can include multiple consecutive segments of a target Mildew Resistance Locus O (MLO) gene, multiple non-consecutive segments of a Mildew Resistance Locus O (MLO) target gene, multiple alleles of a target gene, or multiple Mildew Resistance Locus O (MLO) target genes from one or more species. Mildew Resistance Locus O (MLO) target genes include, but are not limited to, the endogenous Mildew Resistance Locus O (MLO) plant genes of SEQ ID NO: 29, 31, 33, 35, 37, 39, 41, 43, 45, 47, 49, 51, 53, 55, 57, 59, 61, 63, 65, 67, 69, 71, 73, 75, 77, or 79. Mildew Resistance Locus O (MLO) target genes include, but are not limited to, Mildew Resistance Locus O (MLO) plant genes that encode proteins that are orthologous to the proteins of SEQ ID NO: 1-28. Mildew Resistance Locus O (MLO) target genes include, but are not limited to, Mildew Resistance Locus O (MLO) plant genes that encode the proteins of SEQ ID NO: 1-28.

Target genes and plants containing those target genes can be obtained from: i) row crop plants including, but are not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e.g., an ornamental flowering plant or shrub or turf grass). The methods and compositions provided herein can also be applied to plants produced by a cutting, cloning, or grafting process (i.e., a plant not grown from a seed) include fruit trees and plants that include, but are not limited to, citrus, apples, avocados, tomatoes, eggplant, cucumber, melons, watermelons, and grapes as well as various ornamental plants. Such row crop, vegetable, culinary, fruit, tree, or ornamental plants exhibiting improvements in fungal disease resistance and/or nematode resistance that result from suppressing Mildew Resistance Locus O (MLO) gene expression are provided herein. Such row crop, vegetable, culinary, fruit, tree, or ornamental plant parts or processed plant products exhibiting improvements in fungal disease resistance and/or nematode resistance that result from suppressing Mildew Resistance Locus O (MLO) gene expression are also provided herein. Such plant parts can include, but are not limited to, flowers, stems, tubers, fruit, anthers, meristems, ovules, pollen, leaves, or seeds. Such processed plant products obtained from the plant parts can include, but are not limited to, a meal, a pulp, a feed, or a food product.

An aspect of the invention provides a method for modulating or suppressing expression of an Mildew Resistance Locus O (MLO) gene in a plant including (a) conditioning of a plant to permeation by polynucleotides and (b) treatment of the plant with the polynucleotide molecules, wherein the polynucleotide molecules include at least one segment of 18 or more contiguous nucleotides cloned from or otherwise identified from the Mildew Resistance Locus O (MLO) target gene in either anti-sense or sense orientation, whereby the polynucleotide molecules permeate the interior of the plant and induce modulation of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the Mildew Resistance Locus O (MLO) target gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches. In certain embodiments where the polynucleotide used in the composition comprises a promoter sequence essentially identical to, or essentially complementary to, at least 18 contiguous nucleotides of the promoter of the endogenous target gene, the promoter sequence of the polynucleotide is not operably linked to another sequence that is transcribed from the promoter sequence.

Compositions comprising a polynucleotide and a transfer agent provided herein can be topically applied to a plant or plant part by any convenient method, e.g., spraying or coating with a powder, or with a liquid composition comprising any of an emulsion, suspension, or solution. Such topically applied sprays or coatings can be of either all or of any a portion of the surface of the plant or plant part. Similarly, compositions that comprise a transfer agent or other pre-treatment can in certain embodiments be applied to the plant or plant part by any convenient method, e.g., spraying or wiping a solution, emulsion, or suspension. Compositions comprising a polynucleotide and a transfer agent provided herein can be topically applied to plant parts that include, but are not limited to, flowers, stems, tubers, meristems, ovules, fruit, anthers, pollen, leaves, or seeds.

Application of compositions comprising a polynucleotide and a transfer agent to seeds is specifically provided herein. Seeds can be contacted with such compositions by spraying, misting, immersion, and the like.

In certain embodiments, application of compositions comprising a polynucleotide and a transfer agent to plants, plant parts, or seeds in particular can provide for an improvement in fungal disease resistance and/or nematode resistance in progeny plants, plant parts, or seeds derived from those treated plants, plant parts, or seeds. In certain embodiments, progeny plants, plant parts, or seeds derived from those treated plants, plant parts, or seeds will exhibit an improvement in fungal disease resistance and/or nematode resistance that result from suppressing expression of an MLO gene. In certain embodiments, the methods and compositions provided herein can provide for an improvement in fungal disease resistance and/or nematode resistance in progeny plants or seeds as a result of epigenetically inherited suppression of MLO expression. In certain embodiments, such progeny plants exhibit an improvement in fungal disease resistance and/or nematode resistance from epigenetically inherited suppression of MLO gene expression that is not caused by a transgene where the polynucleotide is operably linked to a promoter, a viral vector, or a copy of the polynucleotide that is integrated into a non-native location in the chromosomal DNA of the plant. Without seeking to be limited by theory, progeny plants or seeds derived from those treated plants, plant parts, or seeds can exhibit an improvement in an improvement in fungal disease resistance and/or nematode resistance through an epigenetic mechanism that provides for propagation of an epigenetic condition where suppression of MLO gene expression occurs in the progeny plants, plant parts, or plant seeds. In certain embodiments, progeny plants or seeds exhibiting an improvement in fungal disease resistance and/or nematode resistance as a result of epigenetically inherited suppression of MLO gene expression can also exhibit increased methylation, and in particular, increased methylation of cytosine residues, in the endogenous MLO gene of the plant. Plant parts, including seeds, of the progeny plants that exhibit an improvement in an improvement in fungal disease resistance and/or nematode resistance as a result of epigenetically inherited suppression of MLO gene expression, can also in certain embodiments exhibit increased methylation, and in particular, increased methylation of cytosine residues, in the endogenous MLO gene. In certain embodiments, DNA methylation levels in DNA encoding the endogenous MLO gene can be compared in plants that exhibit an improvement in fungal disease resistance and/or nematode resistance and control plants that do not exhibit an improvement in fungal disease resistance and/or nematode resistance to correlate the presence of the an improvement in fungal disease resistance and/or nematode resistance to epigenetically inherited suppression of MLO gene expression and to identify plants that comprise the epigenetically inherited improvement in fungal disease resistance and/or nematode resistance.

Various methods of spraying compositions on plants or plant parts can be used to topically apply to a plant surface a composition comprising a polynucleotide that comprises a transfer agent. In the field, a composition can be applied with a boom that extends over the crops and delivers the composition to the surface of the plants or with a boomless sprayer that distributes a composition across a wide area. Agricultural sprayers adapted for directional, broadcast, or banded spraying can also be used in certain embodiments. Sprayers adapted for spraying particular parts of plants including, but not limited to, leaves, the undersides of leaves, flowers, stems, male reproductive organs such as tassels, meristems, pollen, ovules, and the like can also be used. Compositions can also be delivered aerially, such as by a crop dusting airplane. In certain embodiments, the spray can be delivered with a pressurized backpack sprayer calibrated to deliver the appropriate rate of the composition. In certain embodiments, such a backpack sprayer is a carbon dioxide pressurized sprayer with a 11015 flat fan or equivalent spray nozzle with a customized single nozzle assembly (to minimize waste) at a spray pressure of about 0.25 MPa and/or any single nozzle sprayer providing an effective spray swath of 60 cm above the canopy of 3 to 12 inch tall growing plants can be used. Plants in a greenhouse or growth chamber can be treated using a track sprayer or laboratory sprayer with a 11001XR or equivalent spray nozzle to deliver the sample solution at a determined rate. An exemplary and non-limiting rate is about 140 L/ha at about 0.25 MPa pressure.

In certain embodiments, it is also contemplated that a plant part can be sprayed with the composition comprising a polynucleotide that comprises a transfer agent. Such plant parts can be sprayed either pre- or post-harvest to provide for an improvement in fungal disease resistance and/or nematode resistance in the plant part that results from suppression of MLO gene expression. Compositions can be topically applied to plant parts attached to a plant by a spray as previously described. Compositions can be topically applied to plant parts that are detached from a plant by a spray as previously described or by an alternative method. Alternative methods for applying compositions to detached parts include, but are not limited to, passing the plant parts through a spray by a conveyor belt or trough, or immersing the plant parts in the composition.

Compositions comprising polynucleotides and transfer agents can be applied to plants or plant parts at one or more developmental stages as desired and/or as needed. Application of compositions to pre-germination seeds and/or to post-germination seedlings is provided in certain embodiments. Seeds can be treated with polynucleotide compositions provided herein by methods including, but not limited to, spraying, immersion, or any process that provides for coating, imbibition, and/or uptake of the polynucleotide composition by the seed. Seeds can be treated with polynucleotide compositions using seed batch treatment systems or continuous flow treatment systems. Seed coating systems are at least described in U.S. Pat. Nos. 6,582,516, 5,891,246, 4,079,696, and 4,023,525. Seed treatment can also be effected in laboratory or commercial scale treatment equipment such as a tumbler, a mixer, or a pan granulator. A polynucleotide composition used to treat seeds can contain one or more other desirable components including, but not limited to liquid diluents, binders to serve as a matrix for the polynucleotide, fillers for protecting the seeds during stress conditions, and plasticizers to improve flexibility, adhesion and/or spreadability of the coating. In addition, for oily polynucleotide compositions containing little or no filler, drying agents such as calcium carbonate, kaolin or bentonite clay, perlite, diatomaceous earth or any other adsorbent material can be added. Use of such components in seed treatments is described in U.S. Pat. No. 5,876,739. Additional ingredients can be incorporated into the polynucleotide compositions used in seed treatments. Such ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like that can be combined with compositions comprising a polynucleotide and a transfer agent. Further ingredients used in compositions that can be applied to seeds can be found in McCutcheon's, vol. 1, "Emulsifiers and Detergents," MC Publishing Company, Glen Rock, N.J., U.S.A., 1996 and in McCutcheon's, vol. 2, "Functional Materials," MC Publishing Company, Glen Rock, N.J., U.S.A., 1996. Methods of applying compositions to seeds and pesticidal compositions that can be used to treat seeds are described in US Patent Application publication 20080092256, which is incorporated herein by reference in its entirety.

Application of the compositions in early, mid-, and late vegetative stages of plant development is provided in certain embodiments. Application of the compositions in early, mid- and late reproductive stages is also provided in certain embodiments. Application of the compositions to plant parts at different stages of maturation is also provided.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1. Polynucleotides of the Invention Related to the MLO Target Gene Sequences The amino acid sequences of proteins encoded by targeted MLO genes and transcripts are provided in Table 2 with reference to SEQ ID NOs. 1-27 of the sequence listing. Such protein sequences can be used to identify orthologous MLO genes and transcripts from other plants not provided herewith. Such orthologous genes and their transcripts can then serve as targets of polynucleotides provided herein or as a source of polynucleotides that are specifically designed to target the orthologous genes or transcripts.

The target MLO polynucleotide molecule at least occurs in the genome of plants provided in Table 2. The MLO genes provided in Table 3, or their corresponding transcripts, can be used as targets of polynucleotide compositions comprising a polynucleotide of at least 18 contiguous nucleotides that are essentially identical or essentially complementary to those genes or transcripts. The proteins and genes respectively provided in Tables 2 and 3, or sequences contained within those proteins or genes can also be used to identify orthologous MLO genes from plants not listed in Tables 2 and 3. Such orthologous genes and their transcripts can then serve as targets of polynucleotides provided herein or as a source of polynucleotides that are specifically designed to target the orthologous genes or transcripts.

TABLE 2

Target MLO gene protein sequences

| | | |
|---|---|---|
| SEQ ID NO: 1 | Hordeum vulgare 1 | MLO-like protein from barley |
| SEQ ID NO: 2 | Sorghum bicolor 2 | MLO-like protein from sorghum |
| SEQ ID NO: 3 | Zea mays 3 | MLO-like protein from corn |
| SEQ ID NO: 4 | Gossypium hirsutum | MLO-like protein from cotton |
| SEQ ID NO: 5 | Glycine max 3 | MLO-like protein from soybeans |
| SEQ ID NO: 6 | Glycine max 4 | MLO-like protein from soybeans |
| SEQ ID NO: 7 | Cucumis sativus 2 | MLO-like protein from cucumber |
| SEQ ID NO: 8 | Cucumis sativus 4 | MLO-like protein from cucumber |
| SEQ ID NO: 9 | Cucumis sativus 5 | MLO-like protein from cucumber |
| SEQ ID NO: 10 | Cucumis sativus 6 | MLO-like protein from cucumber |
| SEQ ID NO: 11 | Vitis vinifera 1 | MLO-like protein from grape |
| SEQ ID NO: 12 | Vitis vinifera 7 | MLO-like protein from grape |
| SEQ ID NO: 13 | Arabidopsis thaliana 3 | MLO-like protein from *Arabidopsis* |
| SEQ ID NO: 14 | Arabidopsis thaliana 9 | MLO-like protein from *Arabidopsis* |
| SEQ ID NO: 15 | Arabidopsis thaliana 4 | MLO-like protein from *Arabidopsis* |
| SEQ ID NO: 16 | Arabidopsis thaliana 8 | MLO-like protein from *Arabidopsis* |
| SEQ ID NO: 17 | Arabidopsis thaliana 7 | MLO-like protein from *Arabidopsis* |
| SEQ ID NO: 18 | Arabidopsis thaliana 2 | MLO-like protein from *Arabidopsis* |
| SEQ ID NO: 19 | Arabidopsis thaliana 10 | MLO-like protein from *Arabidopsis* |
| SEQ ID NO: 20 | Arabidopsis thaliana 11 | MLO-like protein from *Arabidopsis* |
| SEQ ID NO: 21 | Arabidopsis thaliana 6 | MLO-like protein from *Arabidopsis* |
| SEQ ID NO: 22 | Arabidopsis thaliana 13 | MLO-like protein from *Arabidopsis* |
| SEQ ID NO: 23 | Arabidopsis thaliana 14 | MLO-like protein from *Arabidopsis* |
| SEQ ID NO: 24 | Arabidopsis thaliana 12 | MLO-like protein from *Arabidopsis* |
| SEQ ID NO: 25 | Arabidopsis thaliana 1 | MLO-like protein from *Arabidopsis* |
| SEQ ID NO: 26 | Arabidopsis thaliana 15 | MLO-like protein from *Arabidopsis* |
| SEQ ID NO: 27 | Arabidopsis thaliana 5 | MLO-like protein from *Arabidopsis* |

TABLE 3

Target gene sequences

| | | |
|---|---|---|
| SEQ ID NO: 28 | Hordeum vulgare | MLO protein from barley |
| SEQ ID NO: 29 | Hordeum vulgare | MLO cDNA from barley |
| SEQ ID NO: 30 | Cucumis sativus 1 | MLO-like protein from cucumber |
| SEQ ID NO: 31 | Cucumis sativus 1 | MLO-like cDNA from cucumber |
| SEQ ID NO: 32 | Cucumis sativus 3 | MLO-like protein from cucumber |
| SEQ ID NO: 33 | Cucumis sativus 3 | MLO-like cDNA from cucumber |
| SEQ ID NO: 34 | Cucumis sativus 7 | MLO-like protein from cucumber |
| SEQ ID NO: 35 | Cucumis sativus 7 | MLO-like cDNA from cucumber |
| SEQ ID NO: 36 | Cucumis sativus 8 | MLO-like protein from cucumber |
| SEQ ID NO: 37 | Cucumis sativus 8 | MLO-like cDNA from cucumber |
| SEQ ID NO: 38 | Lactuca sativa | MLO-like protein from lettuce |
| SEQ ID NO: 39 | Lactuca sativa | MLO-like cDNA from lettuce |
| SEQ ID NO: 40 | Pisum sativum 1 | MLO-like protein from pea |
| SEQ ID NO: 41 | Pisum sativum 1 | MLO-like cDNA from pea |
| SEQ ID NO: 42 | Medicago truncatula | MLO-like protein from barrel clover |
| SEQ ID NO: 43 | Medicago truncatula | MLO-like cDNA from barrel clover |
| SEQ ID NO: 44 | Glycine max 1 | MLO-like protein from soybean |
| SEQ ID NO: 45 | Glycine max 1 | MLO-like cDNA from soybean |
| SEQ ID NO: 46 | Glycine max 2 | MLO-like protein from soybean |
| SEQ ID NO: 47 | Glycine max 2 | MLO-like cDNA from soybean |
| SEQ ID NO: 48 | Capsicum annuum | MLO-like protein from pepper |
| SEQ ID NO: 49 | Capsicum annuum | MLO-like cDNA from pepper |
| SEQ ID NO: 50 | Solanum lycopersicum 1 | MLO-like protein from tomato |
| SEQ ID NO: 51 | Solanum lycopersicum 1 | MLO-like cDNA from tomatos |
| SEQ ID NO: 52 | Solanum lycopersicum 2 | MLO-like protein from tomato |
| SEQ ID NO: 53 | Solanum lycopersicum 2 | MLO-like cDNA from tomato |
| SEQ ID NO: 54 | Triticum aestivum | MLO-like protein from wheat |
| SEQ ID NO: 55 | Triticum aestivum | MLO-like cDNA from wheat |
| SEQ ID NO: 56 | Triticum aestivum 1 | MLO-like protein from wheat |
| SEQ ID NO: 57 | Triticum aestivum 1 | MLO-like cDNA from wheat |
| SEQ ID NO: 58 | Triticum aestivum 2 | MLO-like protein from wheat |
| SEQ ID NO: 59 | Triticum aestivum 2 | MLO-like cDNA from wheat |
| SEQ ID NO: 60 | Vitis vinifera 17 | MLO-like protein from grape |
| SEQ ID NO: 61 | Vitis vinifera 17 | MLO-like cDNA from grape |
| SEQ ID NO: 62 | Vitis vinifera 13 | MLO-like protein from grape |
| SEQ ID NO: 63 | Vitis vinifera 13 | MLO-like cDNA from grape |
| SEQ ID NO: 64 | Vitis vinifera 6 | MLO-like protein from grape |

TABLE 3-continued

Target gene sequences

| | | |
|---|---|---|
| SEQ ID NO: 65 | Vitis vinifera 6 | MLO-like cDNA from grape |
| SEQ ID NO: 66 | Vitis vinifera 3 | MLO-like protein from grape |
| SEQ ID NO: 67 | Vitis vinifera 3 | MLO-like cDNA from grape |
| SEQ ID NO: 68 | Zea mays 1 | MLO-like protein from corn |
| SEQ ID NO: 69 | Zea mays 1 | MLO-like cDNA from corn |
| SEQ ID NO: 70 | Sorghum bicolor 1 | MLO-like protein from sorghum |
| SEQ ID NO: 71 | Sorghum bicolor 1 | MLO-like cDNA from sorghum |
| SEQ ID NO: 72 | Oryza sativa japonica 1 | MLO-like protein from rice |
| SEQ ID NO: 73 | Oryza sativa japonica 1 | MLO-like cDNA from rice |
| SEQ ID NO: 74 | Oryza sativa japonica 2 | MLO-like protein from rice |
| SEQ ID NO: 75 | Oryza sativa japonica 2 | MLO-like cDNA from rice |
| SEQ ID NO: 76 | Oryza sativa japonica 3 | MLO-like protein from rice |
| SEQ ID NO: 77 | Oryza sativa japonica 3 | MLO-like cDNA from rice |
| SEQ ID NO: 78 | Oryza sativa indica | MLO-like protein from rice |
| SEQ ID NO: 79 | Oryza sativa indica | MLO-like cDNA from rice |

The sequence listing contains the target MLO DNA sequences from the indicated plant species of Table 3. For each gene having a DNA sequence provided in the sequence listing and listed in Table 3, polynucleotides such as single stranded or double stranded DNA or RNA fragments in sense and/or antisense orientation will be mixed with an organosilicone preparation. These compositions will be topically applied to plants to effect expression of the target genes in the specified plant to obtain the plants that exhibit disease resistance. In particular, plants that are resistant to powdery mildew, downy mildew, and/or rust infection and/or nematodes will be obtained through the application of such compositions.

Example 2. Identification of Orthologous MLO Genes

A bootstrapped phylogenetic tree is provided in FIG. 1. The phylogenetic tree shown in FIG. 1 was generated with ClustalX version 2.0.12 using default parameters. First, a multiple sequence alignment was generated with ClustalX using the default parameters, except that iteration at each alignment step was done. The bootstrapped phylogenetic tree was then assembled using the Neighbor-Joining method. The protein sequences disclosed in SEQ ID NOS: 1-27 are a useful basis set for determining whether MLO-like proteins are functional orthologs and likely to be useful targets for suppression in order to control fungal diseases such as powdery mildew, downy mildew and rust infections. Specifically, MLO homologs useful for the control of powdery mildews fall into one of two clades: 1) the clade with A. thaliana MLO2 (SEQ ID NO: 18), such as A. thaliana MLO6 (SEQ ID NO: 21), A. thaliana MLO12 (SEQ ID NO: 24) and Pisum sativum MLO1 (SEQ ID NO: 40) but not A. thaliana MLO11 (SEQ ID NO: 20) or 2) in the clade with Hordeum vulgare MLO (SEQ ID NO: 28), Zea mays MLO1 (SEQ ID NO: 68) and Sorghum bicolor MLO1 (SEQ ID NO: 70) but not Sorghum bicolor MLO2 (SEQ ID NO: 2)

The sequences disclosed in SEQ ID NO: 1 through 79, along with the phylogentic method for functional assignment described above, can be used to efficiently identify and clone MLO homologs useful for the control of pathogens causing powdery mildews, downy mildews or rusts, from other plant species not explicitly described herein.

Example 3. Polynucleotides that can be Used to Reduce MLO Expression in Various Plants Examples of polynucleotides that can be used to reduce expression of MLO genes in various plants is provided herewith as SEQ ID NOS: 80-195. The SEQ ID NOS: 80-195 describe sense/antisense double stranded RNA targeted to the coding regions of Mildew Resistance Locus O (MLO) sequences from a variety of dicot and monocot plants and are useful for downregulating MLO expression using methods described herein. Other regions of MLO genes can also be targeted to modify expression including coding regions and/or promoter regions. Polynucleotides that can be used to reduce MLO expression include sense/antisense dsRNA, antisense RNA, sense or antisense ssDNA as well as sense/antisense double stranded DNA. For example, a polynucleotide that comprises at least 18 contiguous nucleotides that are essentially identical or essentially complementary to SEQ ID NO: 29, 31, 33, 35, 37, 39, 41, 43, 45, 47, 49, 51, 53, 55, 57, 59, 61, 63, 65, 67, 69, 71, 73, 75, 77, or 79 can be used to downregulate expression of those MLO genes.

Example 4. Topical Polynucleotide Application and Powdery Mildew Testing Methods Barley seeds are planted in 2 inch pots in the greenhouse. Five days later, barley seedlings are sprayed with polynucleotides such as ssDNA and/or dsRNA polynucleotides directed to the promoter and/or the coding region of a target gene of interest. For example, polynucleotides directed to MLO include polynucleotides that comprise at least 18 contiguous nucleotides that are essentially identical or complementary to SEQ ID NO:28 or 29. Other examples of polynucleotides that target MLO for down regulation include polynucleotides of SEQ ID NO:80 to 83. A nucleotide solution of 6-20 nm of each ssDNA or 0.5-4 nm dsRNA, 0.1 to 0.3% L77 silwet, 50 mM $NaPO_4$ in a final volume of 40 microliters of water is applied. Two to 4 days post spraying, seedlings will be infected with dry spores of barley powdery mildew (Blumeria graminis f. sp. hordei) and 7 days post infection, disease development is determined by scoring for the percentage of leaf area covered with powdery mildew.

Cucumber seeds are planted in 3-inch square pots and thinned to one plant per pot after emergence. When the first true leaf is fully expanded and the second leaf is opening, a polynucleotide solution, such as ssDNA and/or dsRNA polynucleotides directed to the promoter and/or the coding region of a target gene of interest, is applied to the first true leaf or the cotyledons. For example, polynucleotides directed to MLO include polynucleotides that comprise at least 18 contiguous nucleotides that are essentially identical or complementary to SEQ ID NO:38 or 39. Examples of polynucleotides also include polynucleotides of SEQ ID NO:100 to 103. A nucleotide solution of 6-20 nm of each ssDNA or 0.5-4 nm dsRNA, 0.1 to 0.3% L77 Silwet, 50 mM $NaPO_4$ in a final volume of 40 microliters of water is applied. Two days later the entire cucumber plant is inoculated with a shower of dry spores of cucumber powdery mildew (*Sphaerotheca fuliginea*) shaken off diseased plants. Disease severity will be evaluated on the treated leaf and succeeding leaves 10 days later and at subsequent intervals.

Tomato seeds are planted in a 3-inch square pots and thinned to one plant per pot after emergence. Two weeks old tomato seedlings are treated with 6-20 nm of each ssDNA or 0.5-4 nm dsRNA, 0.2-0.5% L77 silwet, 50 mM $NaPO_4$, 1% ammonium sulfate in a final volume of 30 microliters of water. For example, polynucleotides directed to MLO include polynucleotides that comprise at least 18 contiguous nucleotides that are essentially identical or complementary to SEQ ID NO:50, 51, 52, or 53. Examples of polynucleotides also include polynucleotides of SEQ ID NO:126 to 131. Two to 4 days post spraying plants are inoculated with dry spores of tomato powdery mildew (*Oidium neolycopersici*) and 13 days post infection, disease development is scored for the percentage of leaf area covered with powdery mildew.

Figure 2:
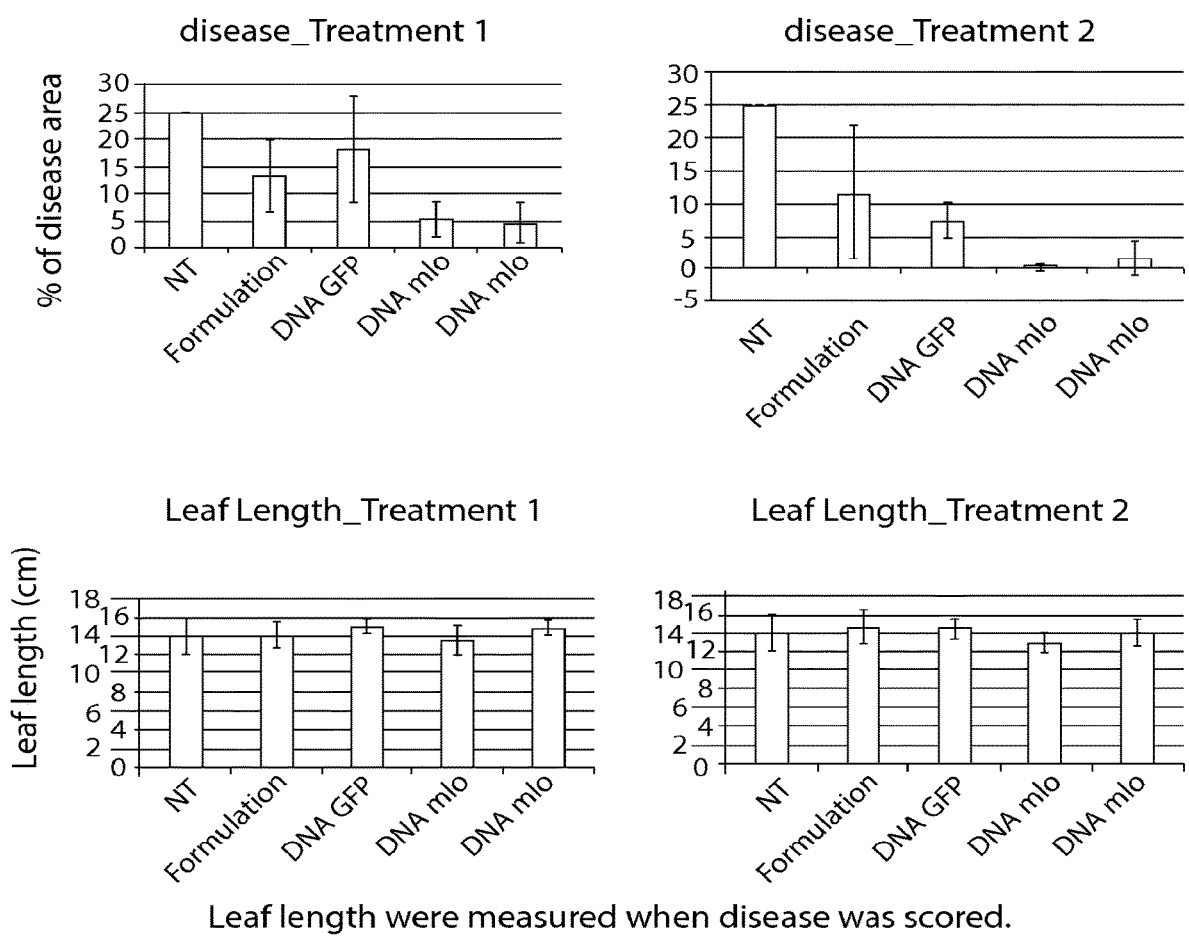
FIG. 2 presents graphs showing % disease area and leaf length measurements in untreated barley plants (NT) and barley plants treated with various liquid formulations as described in Table 6.

Example 5. Protection of Barley from Powdery Mildew by Topical Polynucleotide Application Barley seeds were planted in 2 inch pots in the greenhouse. Five days later, barley seedlings were sprayed with the indicated polynucleotides or a control formulation according to either the Treatment 1 or Treatment 2 methods of Tables 4 and 5, respectively. The liquids applied to the plants are provided in Table 6 and the description of nucleic acid sequences of the ssDNA polynucleotides used is provided in Table 7. Post spraying, the seedlings were infected with dry spores of barley powdery mildew (*Blumeria graminis* f sp. *hordei*) and 7 days post infection, disease development was scored for the percentage of leaf area covered with powdery mildew. The average leaf length was also scored. Results of this analysis are shown in FIG. 2.

TABLE 4

| Treatment 1 | |
| --- | --- |
| Treatment 1 | 5 mM NaPO4 |
| | 0.3% Silwet |
| | 2 × 5 ul/leaf |
| | Disease infection 3 days later |

TABLE 5

| Treatment 2 | |
| --- | --- |
| Treatment 2 | 5 mM NaPO4 |
| | 1% AMS |
| | 0.2% Silwet |
| | 2 × 7.5 ul/leaf |
| | Disease infection 2 day later |

TABLE 6

| Liquids Tested | | | | | | |
| --- | --- | --- | --- | --- | --- | --- |
| Liquid | trigger type | nucleotide ID # | | conc | silwet | Treatment # |
| S | Formulation | | | | 0.30% | first leaf Treatment 1 |
| C | DNA GFP | GFP_as | | 1 × 12 nmol | 0.30% | first leaf Treatment 1 |
| 1 | DNA mlo | T4213as, T4214as, T4215as | | 3 × 12 nmol | 0.30% | first leaf Treatment 1 |
| 2 | DNA mlo | T4216as, T4217as, T4218as | | 3 × 12 nmol | 0.30% | first leaf Treatment 1 |
| 3 | DNA mlo | T4211as, T4219as, T4220as | | 3 × 36 nmol | 0.20% | first leaf Treatment 2 |
| 4 | DNA mlo | T4212as, T4214as, T4222as | | 3 × 36 nmol | 0.20% | first leaf Treatment 2 |
| 5 | Formulation | | | | 0.20% | first leaf Treatment 2 |
| 6 | DNA GFP | GFP_as | | 1 × 36 nmol | 0.20% | first leaf Treatment 2 |

TABLE 7

| Polynucleotides used | | | | | | |
| --- | --- | --- | --- | --- | --- | --- |
| Target Plant and Gene | Type | Name | Sequence | SEQ ID | Length | Target |
| barley MLO | antisense DNA | T4211_AS | GGGGTGCTGGAGAGGCCCAGGTGG | 184 | 24 | ORF |
| barley MLO | antisense DNA | T4212_AS | CGACGTCTGGTGCGTGAACCGGA | 185 | 23 | ORF |
| barley MLO | antisense DNA | T4213_AS | CTGGTATTCCAAGGAGGTGGTCT | 186 | 23 | ORF |
| barley MLO | antisense DNA | T4214_AS | GATGAGGAGCAGGGATATGAAGC | 187 | 23 | ORF |
| barley MLO | antisense DNA | T4215_AS | ATGAGCTCCGCCTTCATCTTCTC | 188 | 23 | ORF |

TABLE 7-continued

Polynucleotides used

| Target Plant and Gene | Type | Name | Sequence | SEQ ID | Length | Target |
|---|---|---|---|---|---|---|
| barley MLO | antisense DNA | T4216_AS | GGCCTTCTTGTGCCGGTGCTGGA | 189 | 23 | ORF |
| barley MLO | antisense DNA | T4217_AS | CTGTCCACACAAAATGCGCCATC | 190 | 23 | ORF |
| barley MLO | antisense DNA | T4218_AS | GTTCTGGAACAACGTCAGGTGT | 191 | 22 | ORF |
| barley MLO | antisense DNA | T4219_AS | GTCGGGCGGTGGAACCAGAAG | 192 | 22 | ORF |
| barley MLO | antisense DNA | T4220_AS | AAAAATCTGCACTGGGGATGT | 193 | 21 | ORF |
| barley MLO | antisense DNA | T4221_AS | GATTTAGTCTGTGCACCGGGTGCG | 194 | 24 | ORF |
| barley MLO | antisense DNA | T4222_AS | AACCGGGTACATGTCCCTAGCCTC | 195 | 24 | ORF |

FIG. 2 shows that the percentage disease area was significantly deceased in plants treated with Silwet formulations containing the barley MLO antisense DNA polynucleotides relative to both the Silwet formulation alone or the Silwet formulation combined with a control GFP (Green Fluorescent Protein) polynucleotide (SEQ ID NO:196).

Example 6. Protection of Barley from Powdery Mildew by Topical Polynucleotide Application Barley seeds were planted in 2 inch pots in the greenhouse. Five days later, barley seedlings were sprayed with the indicated polynucleotides or a control formulation according to either the Treatment 1 or Treatment 2 methods of Tables 8 and 9, respectively. The liquids applied to the plants are provided in Table 10 and the description of nucleic acid sequences of the ssDNA polynucleotides used is provided in Table 7. Post spraying, the seedlings were infected with dry spores of barley powdery mildew (*Blumeria graminis* f sp. *hordei*) and 7 days post infection, disease development was scored for the percentage of leaf area covered with powdery mildew. The average leaf length was also scored. Results of this analysis are shown in Table 11.

TABLE 8

| Treatment 1 | |
|---|---|
| Treatment 1 | 5 mM NaPO4 |
| | 1% AMS |
| | 0.25% Silwet |
| | 2 × 5 ul |
| | Disease infection 2 days later |

TABLE 9

| Treatment 2 | |
|---|---|
| Treatment 2 | 5 mM NaPO4 |
| | 1% AMS |

TABLE 9-continued

| Treatment 2 | |
|---|---|
| | 0.25% Silwet |
| | 2 × 6 ul |
| | Disease infection 1 day later |

TABLE 10

Liquids Tested

| Liquid | trigger type | polynucleotide ID # | Concentration of polynucleotides | Treatment # |
|---|---|---|---|---|
| 0 | 0 | | | Treatment 1 |
| 7 | DNA GFP | GFP_as | 40 nmol | Treatment 1 |
| 8 | DNA GFP | GFP_as | 80 nmol | Treatment 1 |
| 9 | DNA mlo antisense | T4211as, 13, 15, 22 | 4 × 10 nmol | Treatment 1 |
| 10 | DNA mlo, antisense | T4212as, T4219as, T4220as, T4221as | 4 × 20 nmol | Treatment 1 |
| 11 | DNA GFP | GFP_as | 48 nmol | Treatment 2 |
| 12 | DNA GFP | GFP_as | 96 nmol | Treatment 2 |
| 13 | DNA mlo, antisense | T4211as, T4215as, T4216as, T4218as | 4 × 12 nmol | Treatment 2 |
| 14 | DNA mlo, antisense | T4219as, T4220as, T4221as, T4222as | 4 × 24 nmol | Treatment 2 |
| 15 | 0 | | | Treatment 2 |

Table 11 shows that the percentage disease area was significantly decreased in plants treated with Silwet formulations containing the barley MLO antisense DNA polynucleotides relative to both the non-treated control or the Silwet formulation combined with a control GFP (Green Fluorescent Protein) polynucleotide.

TABLE 11

Percentage of disease area

| Liquid | trigger type | R1 | R2 | R3 | R4 | R5 | R6 | avr | stdev |
|---|---|---|---|---|---|---|---|---|---|
| NT | NT | 10 | 25 | 10 | 5 | | | 13 | 8.7 |
| 15 | Blank | 25 | 5 | 5 | 5 | | | 10 | 10 |
| 11 | DNA GFP | 5 | 5 | 10 | 5 | 1 | 10 | 6 | 3.5 |
| 12 | DNA GFP | 5 | 1 | 1 | 5 | 5 | | 3.4 | 2.2 |
| 13 | DNA MLO | 1 | 1 | 1 | 1 | 1 | 5 | 1.7 | 1.6 |
| 14 | DNA MLO | 1 | 1 | 1 | 5 | 1 | | 1.8 | 1.8 |
| 7 | DNA GFP | 25 | 10 | 10 | 10 | 10 | 10 | 12.5 | 7.1 |
| 8 | DNA GFP | 10 | 5 | 5 | 5 | 10 | | 5 | 3.5 |
| 9 | DNA MLO | 5 | 1 | 1 | 5 | 1 | | 2.6 | 2.1 |
| 10 | DNA MLO | 5 | 5 | 5 | 5 | 1 | | 4.1 | 1.7 |

R1-R6 are replicates 1 through 6.

Example 7. Topical Polynucleotide Application and Nematode Testing Methods

Application of Polynucleotides to Leaves for Nematode Control

Ten day old cucumber plants grown in sand are spotted with nucleotides, either ssDNA and/or dsRNA polynucleotides, directed to the promoter and/or the coding region of a target gene of interest. A nucleotide solution of 6-20 nm of each ssDNA or 0.5-1 nm dsRNA, 0.1% L77 silwet, 50 mM NaPO4 in a final volume of 40 uL water is applied. Two cotyledon or leaves are spotted with 20 uL of the nucleotide solution for a total of 40 uL per plant. After 6-24 hours, 1000 vermiform eggs or 1000 J2 Meloidogyne incognita (RKN) are inoculated into each pot. Watering of the test plants is then restricted to only water as needed to prevent wilt for a period of 24 hours. After the 24 hour restricted watering, normal sub-irrigation watering is done for the duration of the test. Cucumber plants are harvested approximately 14 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. Visual phytotoxicity scale is also assigned (Vis. tox; visual reduction in root mass compared to the control): rs1=mild stunting; rs2=moderate stunting; rs3=severe stunting.

Experiments in soybeans using soy cyst nematodes (SCN) are similar to the cucumber RKN assay except for the following changes. Soybean seeds are planted in 100% sand in two inch square plastic pots. The polynucleotide solution is applied when the soybeans show the first trifoliate beginning to emerge, about 10 to 12 days after planting. At least six hours after application of the polynucleotide solution, the nematode soybean cyst nematode (SCN) inoculum (1000 vermiform eggs or 1000 J2s) is applied to the pots. Watering of the test plants is then restricted to only water as needed to prevent wilt for a period of 24 hours. After the 24 hour restricted watering, normal sub-irrigation watering is done for the duration of the test. Twenty eight days after inoculation the plants are harvested and cysts counted.

Experiments in corn using lesion nematodes are similar to above except for the following changes. Corn plants growing in a sand:Turface mix 2:1 in 4 inch deep pots (Turface™ MVP, Profile Products, LLC., Buffalo Grove, Ill.). Treatment with polynucleotide solution is done when the plants are approximately 8-10 days old. At least six hours after inoculation of the polynucleotide solution, plants are inoculated with 2 gm of P. scribneri infested corn roots which are then removed from the pot after 7 days. Watering of the test plants is then restricted to only water as needed to prevent wilt for a period of 24 hours after inoculation. After the 24 hour restricted watering, normal sub-irrigation watering as needed is done for the duration of the test. 12-14 days post inoculation, plants are harvested and nematodes extracted for 6 days from the cut up roots in a mist tent.

Application of Polynucleotides to Seeds for Nematode Control

Cucumber seeds are soaked approximately 5-72 hours in nucleotides, either ssDNA and/or dsRNA polynucleotides directed to the promoter and/or targeting the coding region of a target of interest. Seeds can also be soaked in water for a few hours prior to soaking in polynucleotide solution. Soaking solution consists of 20 nm of each ssDNA or 0.03-1 nm dsRNA, 0.1% silwet L77, 50 mM NaPO4 in a final volume 200 uL in water. The radicals of the cucumber seeds emerge within 72 hours, after which the seeds are placed on germination paper until root length is approximately 2 inches. Seedlings are transplanted to sand vials for RKN inoculation 24 hours later. Ten mL dry sand is added to each vial and seedlings are planted by tilting the vial and laying the seedling in the correct orientation so that the cotyledons are just above the sand and then tilting back to cover the radicles with sand. 3.3 ml water is added to each vial and the vials placed in racks under fluorescent light banks. 500 vermiform eggs or 300 J2 RKN are inoculated in each tube in 50 uL of deionized or spring water. Harvest of the cucumber plants is performed 10 to 12 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. The average of the triplicate gall rating is then calculated: green=0.00-0.33 (no galls); yellow=0.67-1.33 (mild galling); orange=1.67-2.33 (moderate galling); red=2.67-3.00 (severe galling). Visual phytotoxicity scale is also assigned (Vis. tox; visual reduction in root mass compared to the control): rs1=mild stunting; rs2=moderate stunting; rs3=severe stunting.

Experiments in soybeans using soy cyst nematodes (SCN) are similar to RKN assays except for the following changes. After 5-72 hours of soaking soybean seeds are planted in 100% sand in two inch square plastic pots. Seeds can also be soaked in water for a few hours prior to soaking in polynucleotide solution. Seven days after planting the soybean seed, the nematode soybean cyst nematode (SCN) inoculum (1000 vermiform eggs or 1000 J2s) are applied to the pot. Watering of the test plants is then restricted to only water as needed to prevent wilt for a period of 24 hours. After the 24 hour restricted watering, normal sub-irrigation watering is done for the duration of the test. Twenty eight days after inoculation the test is harvested and cysts counted.

Experiments in corn using lesion nematodes are similar to above except for the following changes. After 5-72 hours of soaking corn seeds are planted in a sand:turface mix 2:1 in 4 inch deep pots. Seeds can also be soaked in water for a few hours prior to soaking in polynucleotide solution. Inoculum of 2 gm of roots P. scribneri infested corn roots are applied at seeding and removed from the pot after 7 days. Watering of the test plants is then restricted to only water as needed to prevent wilt for a period of 24 hours after inoculation. After the 24 hour restricted watering, normal sub-irrigation watering as needed is done for the duration of the test. 12-14 days post inoculation, plants are harvested and nematodes extracted for 6 days from the cut up roots in a mist tent.

RKN and SCN J2s are prepared from hatchbowls using the following solutions: RKN solution: 1 L aerated tap water, 1 ml of 50 mg/ml kanamycin, 0.5 ml of 20 mg/ml imazalil sulfate; SCN solution: 1 L aerated tap water, 1 ml of 50 mg/ml kanamycin, 0.5 ml of 20 mg/ml imazalil sulfate, 1430 mg zinc sulfate.

Hatchbowls are autoclaved 6 oz bowls, lined with screen mesh and paper filter. Approximately 20 ml of appropriate hatch solution is poured into each bowl. Eggs are then place in the bowls and covered with foil. The bowls are then placed in a 25° C. incubator overnight. The next day the hatched J2's are extracted, additional solution added as needed and replaced in the incubator. Each bowl is used for 2 weeks and then disposed.

Figure 3:
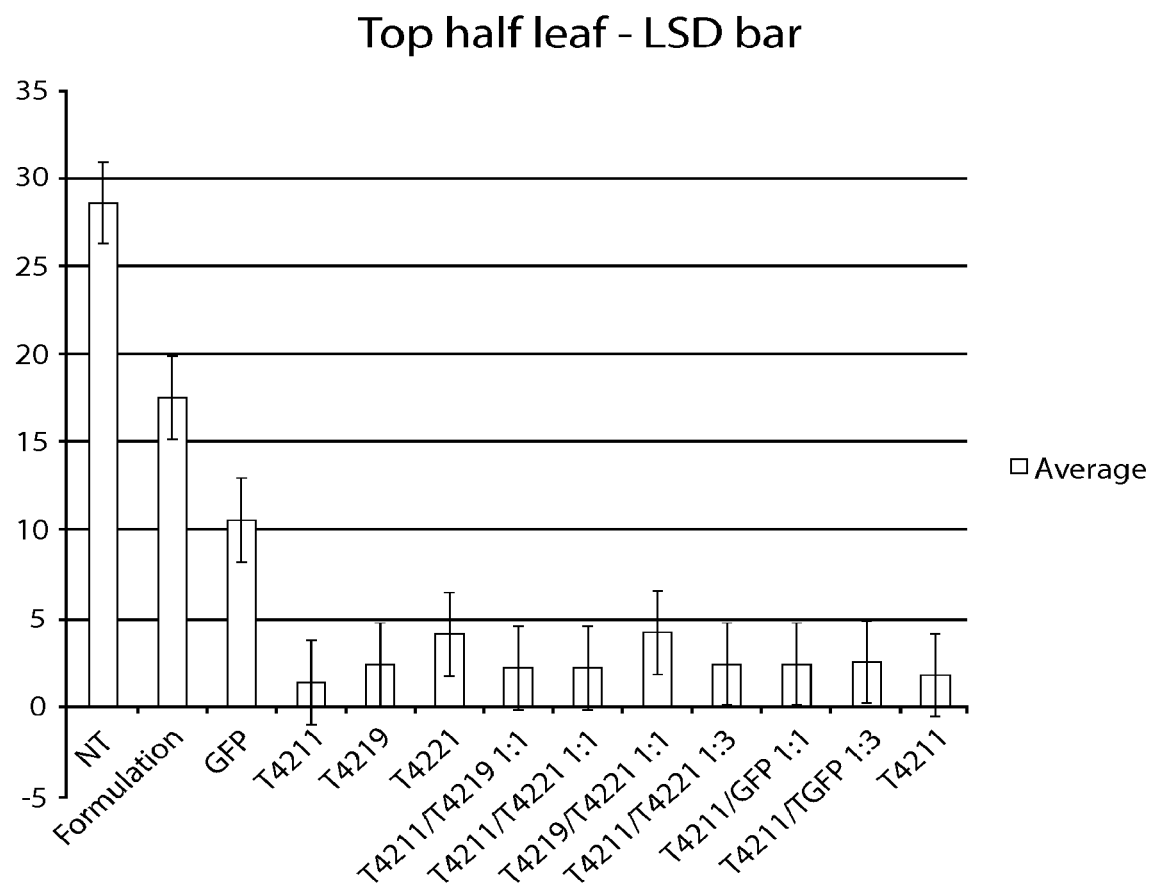
FIG. 3 presents a graph showing disease control measurements (percentage leaf area infected) in untreated barley plants (NT) and barley plants treated with various liquid formulations as described in Table 12.

Example 8. Protection of Barley from Powdery Mildew by Topical Polynucleotide Application Barley seeds were planted in 2 inch pots in the greenhouse. Five days later, barley seedlings were sprayed with the indicated polynucleotides or a control formulation according to the methods of Table 12. The description of nucleic acid sequences of the ssDNA polynucleotides used is provided in Table 13. Post spraying, the seedlings were infected with dry spores of barley powdery mildew (*Blumeria graminis* f sp. *hordei*) and 7 days post infection, disease development was scored for the percentage of leaf area covered with powdery mildew. Results of these experiments are shown in Table 14, ANOVA statistical calculations are shown in Table 15 and a corresponding graph with LSD bar is shown in FIG. 3.

TABLE 12

Treatment Protocols

| Trt | trigger type | nucleotide ID # | ratio | nmol/plant* |
|---|---|---|---|---|
| 1 | DNA GFP | GFP | | 13.4 |
| 2 | DNA mlo | T4211 | | 13.4 |
| 3 | DNA mlo | T4219 | | 13.4 |
| 4 | DNA mlo | T4221 | | 13.4 |
| 5 | DNA mlo | T4211/T4219 | 1 to 1 | 6.7/6.7 |
| 6 | DNA mlo | T4211/T4221 | 1 to 1 | 6.7/6.7 |
| 7 | DNA mlo | T4219/T4221 | 1 to 1 | 6.7/6.7 |
| 8 | DNA mlo | T4211/19as/21 | 1 to 1 to 1 | 4.5 each |
| 9 | DNA mlo | T4211/T4221 | 1 to 3 | 3.3/10 |
| 10 | DNA mlo | T4211/GFP | 1 to 1 | 6.7/6.7 |
| 11 | DNA mlo | T4211/TGFP | 1 to 3 | 3.3/10 |
| 12 | DNA mlo | T4211 | | 3.3/11 |

*The indicated amounts of polynucleotides were provided in 5 mM NaPO₄, 1% Ammonium Sulfate, and 0.25% Silwet ™ (wt percent).

TABLE 13

Polynucleotides used

| Seq Name | Sequence Composition | # nucleotides | SEQ ID NO | Organism |
|---|---|---|---|---|
| T4211 | GGGGTGCTGGAGAGGCCCAGGTGG | 24 | 184 | barley |
| T4212 | CGACGTCTGGTGCGTGAACCGGA | 23 | 185 | barley |
| T4213 | CTGGTATTCCAAGGAGGTGGTCT | 23 | 186 | barley |

TABLE 13-continued

Polynucleotides used

| Seq Name | Sequence Composition | # nucleotides | SEQ ID NO | Organism |
|---|---|---|---|---|
| T4214 | GATGAGGAGCAGGGATATGAAGC | 23 | 187 | barley |
| T4215 | ATGAGCTCCGCCTTCATCTTCTC | 23 | 188 | barley |
| T4216 | GGCCTTCTTGTGCCGGTGCTGGA | 23 | 189 | barley |
| T4217 | CTGTCCACACAAAATGCGCCATC | 23 | 190 | barley |
| T4218 | GTTCTGGAACAACGTCAGGTGT | 22 | 191 | barley |
| T4219 | GTCGGGGCGGTGGAACCAGAAG | 22 | 192 | barley |
| T4220 | AAAAATCTGCACTGGGGATGT | 21 | 193 | barley |
| T4221 | GATTTAGTCTGTGCACCGGGTGCG | 24 | 194 | barley |
| T4222 | AACCGGGTACATGTCCCTAGCCTC | 24 | 195 | barley |
| GFP | GTTGTAGTTGTACTCCATCTTATTG | 25 | 196 | *A. victoria* |

TABLE 14

Percent Leaf Infection Area Results

| Treatment No. | nucleotide ID # | Average Percent Infection Area | STDEV | N | Variance |
|---|---|---|---|---|---|
| | NT | 28.6 | 9.45 | 7 | 89.29 |
| | Formulation | 17.5 | 8.22 | 6 | 67.50 |
| 1 | GFP | 10.6 | 6.23 | 8 | 38.84 |
| 2 | T4211 | 1.38 | 2.26 | 8 | 5.13 |
| 4 | T4219 | 2.33 | 2.07 | 6 | 14.17 |
| 5 | T4221 | 4.16 | 2.04 | 6 | 4.27 |
| 6 | T4211/T4219 1:1 | 2.2 | 2.59 | 6 | 4.17 |
| 7 | T4211/T4221 1:1 | 2.2 | 2.59 | 5 | 6.70 |
| 8 | T4219/T4221 1:1 | 4.2 | 1.79 | 5 | 6.70 |
| 10 | T4211/T4221 1:3 | 2.4 | 2.4 | 5 | 3.20 |
| 11 | T4211/GFP 1:1 | 2.4 | 2.4 | 5 | 4.30 |
| 12 | T4211/TGFP 1:3 | 2.6 | 2.19 | 5 | 5.80 |
| | T4211 | 1.75 | 2.22 | 5 | 5.80 |

TABLE 15

| | ANOVA | | | | | |
|---|---|---|---|---|---|---|
| | ANOVA | | | | | |
| Source of Variation | SS | df | MS | F | P-value | F crit |
| Between Groups | 5351.475 | 15 | 356.765 | 17.96064 | 7.29E-19 | 1.581213 |
| Within Groups | 1469.914 | 74 | 19.86371 | | | |
| Total | 6821.389 | 89 | | | | |

Figure 4:
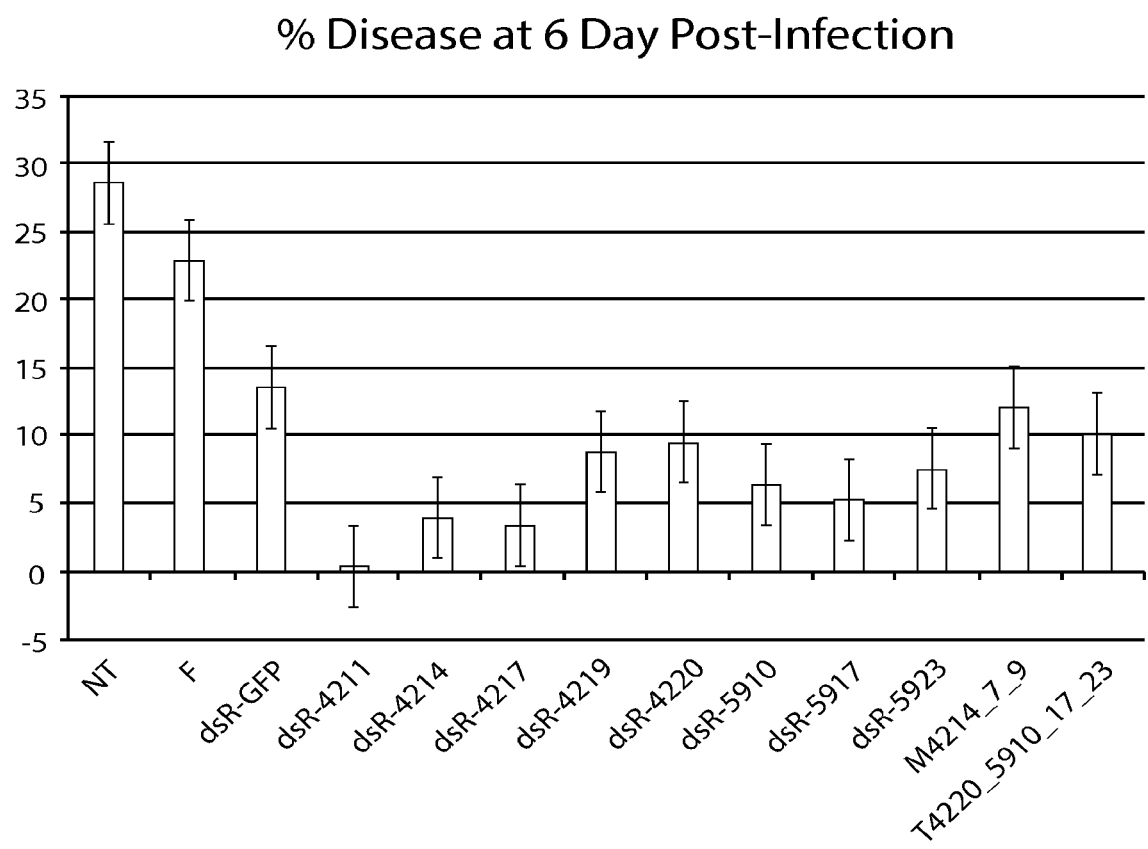
FIG. 4 presents a graph showing disease control measurements (percentage leaf area infected) in barley plants treated with short dsRNA polynucleotides at 6 day post-infection.
Figure 5:
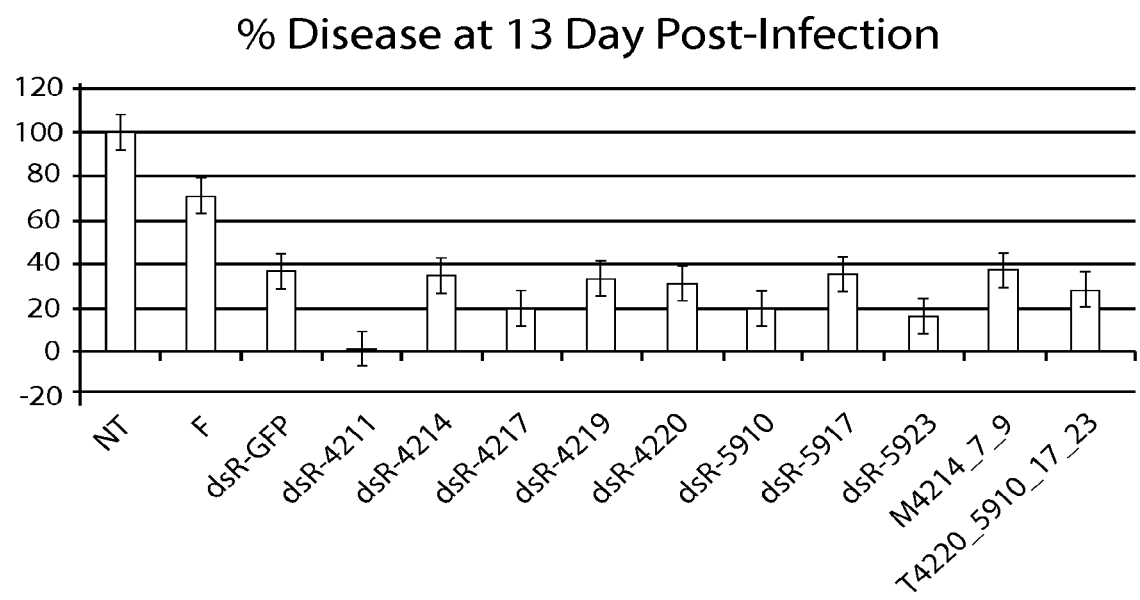
FIG. 5 presents a graph showing disease control measurements (percentage leaf area infected) in barley plants treated with short dsRNA polynucleotides at 13 day post-infection.
Figure 6:
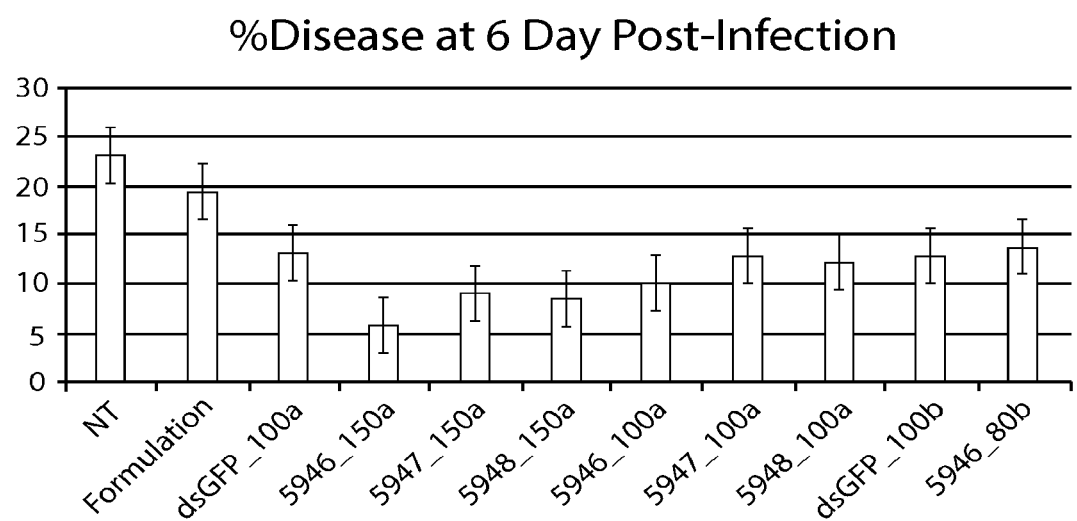
FIG. 6 presents a graph showing disease control measurements (percentage leaf area infected) in barley plants treated with long dsRNA polynucleotides at 6 day post-infection.

Example 9. Topical Application of Short dsRNA Polynucleotides Provides Protection of Barley from Powdery Mildew Barley seeds were planted in 2 inch pots in the greenhouse. Five days later, barley seedlings were treated by hand application of dsRNA polynucleotides or a control formulation as indicated in Table 16. 1.7-6.7 nm of the dsRNA polynucleotide, as indicated in Table 16, was provided in 5 mM $NaPO_4$, 1% Ammonium Sulfate, and 0.25% L77-Silwet™ (wt percent). Two cotyledon or leaves were spotted with 20 uL of the nucleotide solution for a total of 40 uL per plant. The nucleotide sequence of the dsRNA polynucleotides is provided in Table 17. Post application, the seedlings were infected with dry spores of barley powdery mildew (*Blumeria graminis* f sp. *hordei*) and disease development was scored at both 7 days and 14 days post infection for the percentage of leaf area covered with powdery mildew. Results of these experiments are shown in Table 18, ANOVA statistical calculations are shown in Table 19 and corresponding graph with LSD bar is shown in FIG. 4. FIG. 5 shows the results in graph format for 14 days post-infection.

TABLE 16

Treatment Protocols for dsRNA polynucleotides

| Trt | Trigger type | Nucleotide ID# | nmol/plant* |
|---|---|---|---|
| NT | None | | |
| F | None | | |
| 1 | dsRNA | T4211_dsRNA | 6.7 |
| 2 | dsRNA | T4114_dsRNA | 6.7 |
| 3 | dsRNA | T4217_dsRNA | 6.7 |
| 4 | dsRNA | T4219_dsRNA | 6.7 |
| 5 | dsRNA | T4220_dsRNA | 6.7 |
| 6 | dsRNA | T5910_dsRNA | 6.7 |
| 7 | dsRNA | T5917_dsRNA | 6.7 |
| 8 | dsRNA | T5923_dsRNA | 6.7 |
| 9 | dsRNA | M4214_7_9: a mix of T4214, T4217, T4219 | 2.2 each |
| 10 | dsRNA | T4220_5910_17_23: a mix of T4220, T5910, T5917, and T5923 | 1.7 each |
| 11 | dsRNA | GFP_dsRNA | 6.7 |

*The indicated amounts of polynucleotides were provided in 5 mM $NaPO_4$, 1% Ammonium Sulfate, and 0.25% Silwet ™ (wt percent).

TABLE 17 dsRNA polynucleotides used

| Seq Name | Sequence Composition | # nucleotides | SEQ ID NO | Organism |
|---|---|---|---|---|
| T4211_dsRNA | GGGGUGCUGGAGA GGCCCAGGUGG | 24 | 197 | barley |
| T4114_dsRNA | GAUGAGGAGCAGG GAUAUGAAGC | 23 | 198 | barley |
| T4217_dsRNA | CUGUCCACACAAA AUGCGCCAUC | 23 | 199 | barley |
| T4219_dsRNA | GUCGGGGCGGUGG AACCAGAAG | 22 | 200 | barley |
| T4220_dsRNA | AAAAAUCUGCACU GGGGAUGU | 21 | 201 | barley |
| T5910_dsRNA | CGCCUUCAUCUUC UCCAGCGCCUCC | 25 | 202 | barley |
| T5917_dsRNA | GUCGUCCUCCAUC GACCUCUUGAUG | 25 | 203 | barley |
| T5923_dsRNA | UCAGCCCGAUCUG CGUGUGGUAGCA | 25 | 204 | barley |
| GFP_dsRNA | GUUGUAGUUGUAC UCCAUCUUAUUG | 25 | 205 | *A. victoria* |

TABLE 18

Percent Infection Area on treated plants

| Treatment No. | nucleotide ID # | Average Percent Infection Area | STDEV | N | Variance (LSD) |
|---|---|---|---|---|---|
| 1 | T4211_dsRNA | 0.285714286 | 0.487950036 | 7 | 3 |
| 2 | T4114_dsRNA | 3.857142857 | 3.484660262 | 7 | 3 |
| 3 | T4217_dsRNA | 3.285714286 | 2.138089935 | 7 | 3 |
| 4 | T4219_dsRNA | 8.71428571 | 7.846746368 | 7 | 3 |
| 5 | T4220_dsRNA | 9.428571429 | 7.678045386 | 7 | 3 |

TABLE 18-continued

Percent Infection Area on treated plants

| Treatment No. | nucleotide ID # | Average Percent Infection Area | STDEV | N | Variance (LSD) |
|---|---|---|---|---|---|
| 6 | T5910_dsRNA | 6.285714286 | 8.920281866 | 7 | 3 |
| 7 | T5917_dsRNA | 5.142857143 | 2.60950643 | 7 | 3 |
| 8 | T5923_dsRNA | 7.428571429 | 8.323804075 | 7 | 3 |
| 9 | T4214, T4217, T4219 all dsRNA | 12 | 7.582875444 | 5 | 3 |
| 10 | T4220, T5910, T5917, T5923 all dsRNA | 10 | 7.745966692 | 6 | 3 |
| 11 | GFP_dsRNA | 13.57142857 | 8.017837257 | 7 | 3 |

Table 18 shows the percentage disease area was significantly reduced in plants treated with the Silwet formulation containing the barley MLO dsRNA triggers.

TABLE 19

ANOVA

| Source of Variation | SS | df | MS | F | P-value | F crit |
|---|---|---|---|---|---|---|
| Between Groups | 5242.448052 | 12 | 436.870671 | 9.63 | 5.29233E−11 | 1.63 |
| Within Groups | 3403.142857 | 75 | 45.3752381 | | | |
| Total | 8645.590909 | 87 | | | | |

FIG. 4 shows that at six days post infection, of the eight dsRNA triggers tested, six showed a significant reduction in the percent disease area when compared to the GFP dsRNA control (dsR-4211, dsR-4217, dsR-4219, dsR5910, dsR-5917, and dsR5923). Similarly, as shown in FIG. 5, at thirteen days post infection, four dsRNA treatments showed significant disease reduction when compared to the GFP dsRNA trigger (dsR-4211, dsR-4217, dsR-5910 and dsR-5923). The most efficacious trigger appeared to be T4211 dsRNA, similar to the results obtained using T4211 ssDNA, the dsRNA form of this polynucleotide reduced mildew infection by about 96%.

Example 10. Topical Application of Long dsRNA Polynucleotides Provides Protection of Barley from Powdery Mildew Barley seeds were planted in 2 inch pots in the greenhouse. Five days later, barley seedlings were treated by hand application with dsRNA polynucleotides or a control formulation as indicated in Table 20. 13.5-28 pmol of dsRNA polynucleotide as indicated in Table 20 was provided in 5 mM NaPO$_4$, 1% Ammonium Sulfate, and 0.25% L77-Silwet™ (wt percent). Two cotyledon or leaves were spotted with 20 uL of the nucleotide solution for a total of 40 uL per plant. The description of the nucleotide sequences of the dsRNA polynucleotides is provided in Table 21. Following application of the dsRNA polynucleotides, the seedlings were infected with dry spores of barley powdery mildew (*Blumeria graminis* f sp. *hordei*) and disease development was scored at 6 days post infection for the percentage of leaf area covered with powdery mildew. Results of these experiments are shown in Table 22, ANOVA statistical calculations are shown in Table 23 and corresponding graph with LSD bar is shown in FIG. 5.

TABLE 20

Treatment Protocol for long dsRNA polynucleotides

| Trt | Trigger type | Nucleotide ID# | pmol/plant* |
|---|---|---|---|
| NT | None | | |
| F | None | | |
| 1 | Long dsRNA | 5946_150a | 18.6 |
| 2 | Long dsRNA | 5947_150a | 18.6 |
| 3 | Long dsRNA | 5948_150a | 18.6 |
| 4 | Long dsRNA | 5946_100a | 28 |
| 5 | Long dsRNA | 5947_100a | 28 |
| 6 | Long dsRNA | 5948_100a | 28 |
| 7 | Long dsRNA | 5946_80b | 16.9 |
| 8 | Long dsRNA | dsGFP_100b | 28 |
| 9 | Long dsRNA | dsGFP_100b | 13.5 |

TABLE 21

Polynucleotides used

| Seq Name | Seq Composition | # nucleotides | SEQ ID NO | Organism |
|---|---|---|---|---|
| 5946_150a | AUGUCGGACAAAAAAGGGGUGCCGGCGCGGGA GCUGCCGGAGACGCCGUCGUGGGCGGUGGCGG UGGUCUUCGCCGCCAUGGUGCUCGUGUCCGUC CUCAUGGAACACGGCCUCCACAAGCUCGGCCA UUGGUUCCAGCACCGGCACAAG | 150 | 206 | Barley |
| 5947_150a | CGUCGUCGGCCCUCGAAGCCGACAUCCCCAGU GCAGAUUUUCCUUCAGCCAGGGAUGAGACAA GUUUCUGUAUUCAUGUUAGUCCCAAUGUAUAG CCAACAUAGGAUGUGAUGAUUCGUACAAUAAG AAAUACAAUUUUUUACUGAGUC | 150 | 207 | Barley |
| 5948_150a | UGGUGGUGGGGCUAGCUCUCCAGUUCCUCUGC AGCUAUAUGACCUUCCCCCUCUACGCGCUCGU CACACAGAUGGGAUCAAACAUGAAGAGGUCCA UCUUCGACGAGCAGACGUCCAAGGCGCUCACC AACUGGCGGAACACGGCCAAGG | 150 | 208 | Barley |
| 5946_100a | GUGGGCGGUGGCGGUGGUCUUCGCCGCCAUGG UGCUCGUGUCCGUCCUCAUGGAACACGGCCUC CACAAGCUCGGCCAUUGGUUCCAGCACCGGCA CAAG | 100 | 209 | Barley |
| 5947_100a | CAGGGAUGAGACAAGUUUCUGUAUUCAUGUUA GUCCCAAUGUAUAGCCAACAUAGGAUGUGAUG AUUCGUACAAUAAGAAAUACAAUUUUUUACUG AGUC | 100 | 210 | Barley |
| 5948_100a | CUCUACGCGCUCGUCACACAGAUGGGAUCAAA CAUGAAGAGGUCCAUCUUCGACGAGCAGACGU CCAAGGCGCUCACCAACUGGCGGAACACGGCC AAGG | 100 | 211 | Barley |
| 5946_80b | UCGCCGCCAUGGUGCUCGUGUCCGUCCUCAUG GAACACGGCCUCCACAAGCUCGGCCAUUGGUU CCAGCACCGGCACAAG | 80 | 212 | Barley |
| dsGFP_100a | UCAAGGAGGAUGGCAACAUCCUGGGCAAUAAG AUGGAGUACAACUACAACGCCCACAAUGUGUA CAUCAUGACCGACAAGGCCAAGAAUGGCAUCA AGGUGAACUUCAAGAUCCGCCACAACAUCGAG GAUGGCAGCGUGCAGCUGGCCGAC | 100 | 213 | A. victoria |

TABLE 22

Percent Leaf Infection Area Results

| Trt No. | Nucleotide ID | N | Avg Percent Infection | STDEV | LSD |
|---|---|---|---|---|---|
|  | NT | 8 | 23.125 | 5.303301 | 2.82 |
|  | Formulation | 8 | 19.375 | 7.763238 | 2.82 |
| 1 | dsGFP__100a | 8 | 13.125 | 7.529703 | 2.82 |
| 2 | 5946__150a | 9 | 5.777778 | 3.562926 | 2.82 |
| 3 | 5947__150a | 9 | 9 | 6.819091 | 2.82 |
| 4 | 5948__150a | 9 | 8.444444 | 6.930208 | 2.82 |
| 5 | 5946__100a | 8 | 10 | 6.546537 | 2.82 |
| 6 | 5947__100a | 9 | 12.77778 | 7.120003 | 2.82 |
| 7 | 5948__100a | 9 | 12.22222 | 7.546154 | 2.82 |
| 8 | dsGFP__100b | 9 | 12.77778 | 7.120003 | 2.82 |
| 9 | 5946__80b | 8 | 13.75 | 6.943651 | 2.82 |

TABLE 23

ANOVA

| Source of Variation | SS | df | MS | F | P-value | F crit |
|---|---|---|---|---|---|---|
| Between Groups | 2013.068853 | 10 | 201 | 4.4 | 0 | 1.7 |
| Within Groups | 3777.569444 | 83 | 46 |  |  |  |
| Total | 5790.638298 | 93 |  |  |  |  |

FIG. 5 shows that at six days post infection of the eight dsRNAs tested, T5946 (150-mer) had significantly lower infection compared to the GFP dsRNA control. The other two 150-mer dsRNAs (T5947 and T5948) also trended lower compared to the control.

What is claimed is:

1. A method for producing a tomato plant exhibiting an improvement in fungal disease resistance, the method comprising topically applying to a plant surface a composition that comprises:
   a. at least one dsRNA molecule of 24 to about 95 nucleotides in length, wherein the dsRNA molecule comprises a segment of at least 24 contiguous nucleotides that are identical or complementary to SEQ ID NO: 51 or SEQ ID NO: 53, wherein the dsRNA molecule is not operably linked to a promoter or to a viral vector and wherein the dsRNA molecule does not become integrated into the plant chromosome; and
   b. a transfer agent comprising an organosilicone preparation that conditions the tomato plant surface to permeation by the dsRNA molecule into plant cells, wherein said tomato plant exhibits an improvement in fungal disease resistance that results from suppression of an endogenous tomato Mildew Resistance Locus 0 (MLO) gene.

2. The method of claim 1, wherein said dsRNA molecule comprises a segment of at least 24 contiguous nucleotides that are identical or complementary to SEQ ID NO: 51.

3. The method of claim 1, wherein said dsRNA molecule comprises a segment of at least 24 contiguous nucleotides that are identical or complementary to SEQ ID NO: 53.

4. The method of claim 1, wherein the dsRNA molecule comprises a segment of at least 24 contiguous nucleotides that are identical or complementary to SEQ ID NO: 124-130 or 131.

5. The method of claim 1, wherein said composition comprises two or more of said dsRNA molecules.

6. The method of claim 1, wherein said composition further comprises a non-polynucleotide herbicidal molecule, a polynucleotide herbicidal molecule, a polynucleotide that suppresses an herbicide target gene, an insecticide, a fungicide, a nematocide, or a combination thereof.

7. The method of claim 1, wherein said composition further comprises a non-polynucleotide herbicidal molecule and said plant is resistant to said herbicidal molecule.

8. A tomato plant obtained by the method of claim 1; wherein the plant comprises the dsRNA molecule.

9. A processed product of said plant of claim 8, wherein said processed product comprises the dsRNA and exhibits an improved attribute relative to a processed product of an untreated control plant and wherein said improved attribute results from said fungal disease resistance.

10. A composition comprising a dsRNA molecule of 24 to about 95 nucleotides in length, wherein the dsRNA molecule comprises a segment of at least 24 contiguous nucleotides that are identical or complementary to SEQ ID NO: 51 or 53, wherein said dsRNA is not operably linked to a promoter or to a viral vector; and,
    a transfer agent comprising an organosilicone preparation that conditions a plant surface to permeation by the dsRNA molecule into plant cells.

11. The composition of claim 10, wherein said dsRNA molecule comprises a segment of at least 24 contiguous nucleotides that are identical or complementary to SEQ ID NO: 51.

12. The composition of claim 10, wherein the dsRNA molecule comprises a segment of at least 24 contiguous nucleotides that are identical or complementary to SEQ ID NO: 124-130 or 131.

13. The composition of claim 10, wherein said composition further comprises a non-polynucleotide herbicidal molecule, a polynucleotide herbicidal molecule, a polynucleotide that suppresses an herbicide target gene, an insecticide, a fungicide, a nematocide, or a combination thereof.

14. The composition of claim 10, wherein said dsRNA molecule is not physically bound to a biolistic particle.

15. A method of making a composition comprising the step of combining at least:
    a) a dsRNA molecule of 24 to about 95 nucleotides in length, wherein the dsRNA molecule comprises a segment of at least 24 contiguous nucleotides that are identical or complementary to SEQ ID NO: 51 or 53, wherein said dsRNA is not operably linked to a promoter or a viral vector; and,
    b) a transfer agent, wherein the transfer agent is an organosilicone preparation that conditions a plant surface to permeation by the dsRNA molecule into plant cells.

16. The composition of claim 10, wherein said dsRNA molecule comprises a segment of at least 24 contiguous nucleotides that are identical or complementary to SEQ ID NO: 53.

17. The method of claim 15, wherein said dsRNA molecule comprises a segment of at least 24 contiguous nucleotides that are identical or complementary to SEQ ID NO: 51.

18. The method of claim 15, wherein said dsRNA molecule comprises a segment of at least 24 contiguous nucleotides that are identical or complementary to SEQ ID NO: 53.

19. The method of claim 15, wherein the dsRNA molecule comprises a segment of at least 24 contiguous nucleotides that are identical or complementary to SEQ ID NO: 124-130 or 131.

\* \* \* \* \*